US009169304B2

(12) United States Patent
Allen et al.

(10) Patent No.: US 9,169,304 B2
(45) Date of Patent: Oct. 27, 2015

(54) **PROCESS FOR PURIFYING RECOMBINANT *PLASMODIUM FALCIPARUM* CIRCUMSPOROZOITE PROTEIN**

(71) Applicant: Pfenex Inc., San Diego, CA (US)

(72) Inventors: Jeffrey Allen, Poway, CA (US); Greg Cantin, Encinitas, CA (US); Ryan Haverstock, Encinitas, CA (US)

(73) Assignee: PFENEX INC., San Diego, CA (US)

( * ) Notice: Subject to any disclaimer, the term of this patent is extended or adjusted under 35 U.S.C. 154(b) by 0 days.

(21) Appl. No.: 13/844,261

(22) Filed: Mar. 15, 2013

(65) Prior Publication Data

US 2014/0051841 A1 Feb. 20, 2014

Related U.S. Application Data

(60) Provisional application No. 61/641,105, filed on May 1, 2012.

(51) Int. Cl.

| | |
|---|---|
| *A23J 1/10* | (2006.01) |
| *C07K 1/10* | (2006.01) |
| *C07K 14/445* | (2006.01) |
| *A61K 39/00* | (2006.01) |

(52) U.S. Cl.
CPC ..... *C07K 14/445* (2013.01); *A61K 2039/55566* (2013.01)

(58) Field of Classification Search
None
See application file for complete search history.

(56) References Cited

U.S. PATENT DOCUMENTS

| | | | |
|---|---|---|---|
| 4,551,433 | A | 11/1985 | DeBoer |
| 4,695,455 | A | 9/1987 | Barnes et al. |
| 4,709,017 | A | 11/1987 | Collier et al. |
| 4,755,465 | A | 7/1988 | Gray et al. |
| 4,830,962 | A | 5/1989 | Gelfand et al. |
| 4,861,595 | A | 8/1989 | Barnes et al. |
| 4,892,827 | A | 1/1990 | Pastan et al. |
| 4,925,792 | A | 5/1990 | Rappuoli |
| 5,055,294 | A | 10/1991 | Gilroy |
| 5,085,862 | A | 2/1992 | Klein et al. |
| 5,114,713 | A | 5/1992 | Sinigaglia |
| 5,128,130 | A | 7/1992 | Gilroy et al. |
| 5,169,760 | A | 12/1992 | Wilcox |
| 5,178,861 | A | 1/1993 | Vergara et al. |
| 5,281,532 | A | 1/1994 | Rammler et al. |
| 5,389,540 | A | 2/1995 | Makoff et al. |
| 5,427,788 | A | 6/1995 | Rappuoli et al. |
| 5,443,966 | A | 8/1995 | Fairweather et al. |
| 5,571,694 | A | 11/1996 | Makoff et al. |
| 5,614,382 | A | 3/1997 | Metcalf |
| 5,652,348 | A | 7/1997 | Burton et al. |
| 5,700,906 | A | 12/1997 | Arnot et al. |
| 5,750,110 | A | 5/1998 | Prieels et al. |
| 5,773,600 | A | 6/1998 | Burnette, III |
| 5,785,971 | A | 7/1998 | Rappuoli et al. |
| 5,792,458 | A | 8/1998 | Johnson et al. |
| 5,935,580 | A | 8/1999 | Ladant et al. |
| 6,010,871 | A | 1/2000 | Takahara et al. |
| 6,043,057 | A | 3/2000 | Holmgren et al. |
| 6,140,082 | A | 10/2000 | Loosmore et al. |
| 6,579,524 | B1 | 6/2003 | Corradin et al. |
| 7,015,036 | B2 | 3/2006 | Prachumsri et al. |
| 7,169,399 | B2 | 1/2007 | Roberts |
| 7,226,597 | B2 | 6/2007 | Ballard et al. |
| 7,232,671 | B2 | 6/2007 | Cieplak |
| 7,273,728 | B2 | 9/2007 | Wolfe et al. |
| 7,273,963 | B2 | 9/2007 | Kneteman et al. |
| 7,427,404 | B1 | 9/2008 | Pizza et al. |
| 7,575,891 | B2 | 8/2009 | Wolfe et al. |
| 7,618,799 | B2 | 11/2009 | Coleman et al. |
| 7,666,436 | B1 | 2/2010 | Pizza et al. |
| 7,722,889 | B2 | 5/2010 | Duffy et al. |
| 7,749,519 | B2 | 7/2010 | Sim et al. |
| 7,759,109 | B2 | 7/2010 | Studier |
| 7,781,186 | B2 | 8/2010 | Prachumsri et al. |
| 7,790,186 | B2 | 9/2010 | Yadava et al. |
| 7,985,564 | B2 | 7/2011 | Retallack et al. |
| 8,021,834 | B2 | 9/2011 | O'Hagan et al. |
| 8,058,407 | B2 | 11/2011 | Sun et al. |
| 8,097,453 | B2 | 1/2012 | Pau et al. |
| 8,138,306 | B2 | 3/2012 | Maloisel |
| 8,232,255 | B2 | 7/2012 | Hoffman et al. |
| 8,287,877 | B2 | 10/2012 | Plebanski |
| 8,288,127 | B2 | 10/2012 | Schneider et al. |
| 8,318,183 | B2 | 11/2012 | Duffy et al. |
| 8,318,897 | B2 | 11/2012 | Birkenmeyer et al. |
| 8,530,171 | B2 | 9/2013 | Retallack et al. |
| 8,603,824 | B2 | 12/2013 | Ramseier et al. |
| 2003/0039963 | A1 * | 2/2003 | Brahmachari et al. ............ 435/6 |

(Continued)

FOREIGN PATENT DOCUMENTS

| | | | |
|---|---|---|---|
| EP | 0207459 | A2 | 1/1987 |
| EP | 0278941 | A1 | 8/1988 |

(Continued)

OTHER PUBLICATIONS

Matthew et al. JBC vol. 284, pp. 26951-26963, 2009.*

Altschul et al., Basic Local Alignment Search Tool, J Mol Biol, 215(3):403-410 (1990).

Ancsin et al., A binding site for highly sulfated heparan sulfate is identified in the N terminus of the circumsporozoite protein: significance for malarial sporozoite attachment to hepatocytes, J. Biol. Chem, 279:21824-32 (2004).

Anders et al., Polymorphic antigens in *Plasmodium falciparum*, Blood, 74:1865-1875 (1989).

(Continued)

*Primary Examiner* — Gary Nickol
*Assistant Examiner* — Khatol Shahnan Shah
(74) *Attorney, Agent, or Firm* — Wilson Sonsini Goodrich & Rosati

(57) ABSTRACT

The present invention relates to processes for purifying high-quality recombinant *Plasmodium falciparum* circumsporozoite protein at high yields.

53 Claims, 36 Drawing Sheets

(56) References Cited

U.S. PATENT DOCUMENTS

| | | |
|---|---|---|
| 2004/0067880 A1 | 4/2004 | Kuo |
| 2004/0185050 A1 | 9/2004 | Mota et al. |
| 2005/0208068 A1 | 9/2005 | Milich et al. |
| 2006/0040352 A1 | 2/2006 | Retallack et al. |
| 2006/0110747 A1 | 5/2006 | Ramseier et al. |
| 2006/0188527 A1 | 8/2006 | Hoffman et al. |
| 2006/0234346 A1 | 10/2006 | Retallack et al. |
| 2007/0292918 A1 | 12/2007 | Stelman et al. |
| 2008/0057085 A1 | 3/2008 | Sim et al. |
| 2008/0102091 A1 | 5/2008 | Cohen et al. |
| 2008/0269070 A1 | 10/2008 | Ramseier et al. |
| 2009/0053265 A1 | 2/2009 | Corradin et al. |
| 2009/0196883 A1 | 8/2009 | Yadava et al. |
| 2009/0325230 A1 | 12/2009 | Schneider et al. |
| 2010/0137162 A1 | 6/2010 | Retallack et al. |
| 2011/0217784 A1 | 9/2011 | Allen et al. |
| 2011/0287443 A1 | 11/2011 | Retallack |
| 2013/0259890 A1* | 10/2013 | Dutta, Sheetij ............ 424/191.1 |

FOREIGN PATENT DOCUMENTS

| | | |
|---|---|---|
| EP | 0329257 A2 | 8/1989 |
| EP | 0329257 A3 | 8/1989 |
| EP | 0193585 B1 | 2/1992 |
| EP | 0134242 B1 | 6/1993 |
| EP | 0957933 B1 | 5/2008 |
| EP | 1326633 B1 | 3/2011 |
| EP | 2298900 A1 | 3/2011 |
| EP | 2385107 | 11/2011 |
| EP | 2258850 B1 | 7/2013 |
| WO | WO87/06939 | 11/1978 |
| WO | WO86/00911 | 2/1986 |
| WO | WO90/00402 | 1/1990 |
| WO | WO90/07006 | 6/1990 |
| WO | WO90/09444 | 8/1990 |
| WO | WO90/11775 | 10/1990 |
| WO | WO92/15677 | 9/1992 |
| WO | WO92/17204 | 10/1992 |
| WO | WO95/26982 | 10/1995 |
| WO | WO96/00735 | 1/1996 |
| WO | WO96/09116 | 3/1996 |
| WO | WO97/29825 | 8/1997 |
| WO | WO00/49146 | 8/2000 |
| WO | WO2005/052151 | 6/2005 |
| WO | WO2005/063805 | 7/2005 |
| WO | WO2005/069913 | 8/2005 |
| WO | WO2005/089093 | 9/2005 |
| WO | WO2006/014899 | 2/2006 |
| WO | WO2006/029887 | 3/2006 |
| WO | WO2006/088597 | 8/2006 |
| WO | WO2008/094986 | 8/2008 |
| WO | WO2008/134461 | 11/2008 |
| WO | WO2009/021931 | 2/2009 |
| WO | WO2009/114202 | 9/2009 |
| WO | WO2010/008764 | 1/2010 |
| WO | WO2011/139718 | 11/2011 |
| WO | WO02/22164 | 3/2012 |
| WO | WO2012/154199 | 11/2012 |

OTHER PUBLICATIONS

Bergey'S Manual of Determinative Bacteriology, R.E. Buchanan and N.E. Gibbons eds., pp. 217-289, 8th ed., The Williams & Wilkins Co., Baltimore, MD, (1974).
Birren et al. Analyzing DNA, Genome Analysis 1:543-559 (1997).
Bongfen et al., The N-terminal domain of *Plasmodium falciparum* circumsporozoite protein represents a target of protective immunity, The N-terminal domain of *Plasmodium falciparum* circumsporozoite protein represents a target of protective immunity, Vaccine, 27(2):328-35 (2009).
Carrillo et al., The Multiple Sequence Alignment Problem in Biology, SIAM J Applied Math, 48:1073-1082 (1988).
Coulson, High-performance searching of biosequence databases, Trends in Biotechnology, 12:76-80 (1994).
Davis et al., Mutants of *Escherichia coli* requiring methionine or Vitamin B12, Bact, 60:17-28 (1950).
Folena-Wasserman et al, Assay, purification and characterization of a recombinant malaria circumsporozoite fusion protein by high-performance liquid chromatography, J Chromatogr, 411:345-54 (1987).
Frishman et al., Starts of Bacterial Genes: Estimating the Reliability of Computer Predictions, Gene 234(20):257-265 (1999).
Grabski, Advances in preparation of biological extracts for protein purification, Methods Enzymol., 463:285-303 (2009).
Hall et al., Sequence of Plasmodium falciparum chromosomes 1, 3-9 and 13., Nature, 419(6906):527-531 (2002).
Harrison, Bacterial cell disruption: a key unit operation in the recovery of intracellular products, Biotechnology Advances, 9(2):217-240 (1991).
Hopkins, Physical and chemical cell disruption for the recovery of intracellular proteins, Bioprocess technology 12:57-83 (1991).
Ikehata et al., Primary structure of nitrile hydratase deduced from the nucleotide sequence of a *Rhodococcus* species and its expression in *Escherichia coli*, Eur J Biochem, 181(3):563-570 (1989).
Kastenmuller et al, Full-length *Plasmodium falciparum* circumsporozoite protein administered with long-chain Poly-ICLC or GLA/SE Elicits potent antibody and CD4+ T cell immunity and protection in mice, Infect Immun, doi:10.1128/IAI.0108-12, Dec. 2012.
Kolodny et al, Two-step chromatographic purification of recombinant *Plasmodium falciparum* circumsporozoite protein from *Escherichia coli*, J Chromatogr B, 762:77-86 (2001).
Ophorst et al., Expression and immunogenicity of the *Plasmodium falciparum* circumsporozoite protein: the role of GPI signal sequence, Vaccine, 25(8):1426-36 (2007).
PCT/US2013/037656 International Search Report and Written Opinion dated Aug. 28, 2013.
Plassmeyer et al., Structure of the *Plasmodium falciparum* Circumsporozoite Protein, a Leading Malaria Vaccine Candidate, JBC 284 (39):26951-26963 (2009).
Rathore et al., An immunologically cryptic epitope of *Plasmodium falciparum* circumsporozoite protein facilitates liver cell recognition and induces protective antibodies that block liver cell invasion, J. Biol. Chem. 280:20524-9 (2005).
Rathore et al., Binding and invasion of liver cells by *Plasmodium falciparum* sporozoites. Essential involvement of the amino terminus of circumsporozoite protein, J. Biol. Chem., 277:7092-7098 (2002).
Rathore et al., Role of cysteines in *Plasmodium falciparum* circumsporozoite protein: interactions with heparin can rejuvenate inactive protein mutants., Proc. Nat. Acad. Sci., 97(15):8530-35 (2000).
Riesenberg et al., High cell density cultivation of *Escherichia coli* at controlled specific growth rate, J Biotechnol 20(1):17-27 (1991).
Sanchez-Romero et al, Manual of Industrial Microbiology and Biotechnology, A. Demain & J. Davies, eds., pp. 460-474 (1999).
Sandberg et al. New chemical descriptors relevant for the design of biologically active peptides. A multivariate characterization of 87 amino acids, J. Med. Chem. 41:2481-2491 (1998).
Schneider et al., Auxotropic markers pyrF and proC can replace antibiotic markers in protein productions plasmids in high-cell-density *Pseudomonas* fluorescens fermentation. Biotechnol. Progress 21(2):343-8 (2005).
Schneider, Enabling Biodefense Countermeasures through Next Generation Vaccines, Presented at/Published in Phacilitate Vaccine Forum, Jan. 28, 2014.
Schweizer, Vectors to express foreign genes and techniques to monitor gene expression in *Pseudomondas*, Curr Op Biotech 12:439-445 (2001).

Slater et al, Molecular Biology and Biotechnology, J. Walker & R. Rapley, eds., pp. 125-154, The Royal Society of Chemistry, Cambridge, UK (2000).

Suzek et al., A Probabilistic Method for Identifying Start Codons in Bacterial Genomes. Bioinformatics, Oxford University Press, 17(12):1123-1130, (2001).

Welch et al., PLoS One, Design Parameters to Control Synthetic Gene Expression in *Escherichia coli*, 4(9):e7002 (10 pgs) (2009).

Winram, Development and Preclinical Optimization of a Circumsporozoite Protein (rCSP) Vaccine Candidate Against

(56) References Cited

OTHER PUBLICATIONS

Malaria Via a Virtual Pharmaceutical Approach, Presented at/Published in BioProcess International 2011, Nov. 3, 2011.
Winram, rCSP Expression Project Utilizing Pfenex Technology rCSP Expression Project Utilizing Pfenex Technology, Presented at/published in Vaccine Production Summit, San Diego, Jun. 14, 2010.
Noe et al., A full length *Plasmodium falciparum* recombinant circumsporozoite protein expressed by *Pseudomonas fluorescens* platform as a malaria vaccine candidate. PLOS ONE, 9(9):1-15 (2014).
PCT/US2013/037656 International Preliminary Report on Patentability dated Nov. 4, 2014.

Gutierrez et al, a full length *Plasmodium falciparum* recombinent circumsporozoite protein expressed by *Pseudomonas fluorescens* platform as a malaria vaccine candidate. A Poster Session Presentation at the 63$^{rd}$ Annual Meeting of the American Society of Tropical Medicine and Hygiene, New Orleans, LA, Nov. 5, 2014, Abstract 1606, 1 page.
Espinosa et al., A monoclonal antibody against the N-terminal region of the *Plasmodium falciparum* circumsporozoite protein strongly inhibits sporozoite invasion of hepatocytes. A Poster Session Presentation at the 63$^{rd}$ Annual Meeting of the American Society of Tropical Medicine and Hygiene, New Orleans, LA, Nov. 5, 2014, Abstract 1607, 1 page.

\* cited by examiner

FIG. 2A

A. *P. falciparum* 3D7 CS protein Genbank entry CAB38998 (SEQ ID NO: 1)

```
        predicted signal peptide
        ~~~~~~~~~~~~~~~~~~~~
   1    MMRKLAILSV SSFLFVEALF QEYQCYGSSS NTRVLNELNY DNAGTNLYNE
  51    LEMNYYGKQE NWYSLKKNSR SLGENDDGNN EDNEKLRKPK HKKLKQPADG
 101    NPDPNANPNV DPNANPNVDP NANPNVDPNA NPNANPNANP NANPNANPNA
 151    NPNANPNANP NANPNANPNA NPNANPNANP NANPNANPNA NPNANPNVDP
 201    NANPNANPNA NPNANPNANP NANPNANPNA NPNANPNANP NANPNANPNA
 251    NPNANPNANP NANPNANPNA NPNKNNQGNG QGHNMPNDPN RNVDENANAN
                                         Thrombospondin type 1 domain
                                         ~~~~~~~~~~~~~~~~~~~~~~~~~~
 301    SAVKNNNNEE PSDKHIKEYL NKIQNSLSTE WSPCSVTCGN GIQVRIKPGS
        Thrombospondin type 1 domain          putative GPI anchor
        ~~~~~~~~~~~~~~~~~~~~~~~~~~~           ~~~~~~~~~~~~~~~~~
 351    ANKPKDELDY ANDIEKKICK MEKCSSVFNV VNSSIGLIMV LSFLFLN
```

FIG. 2B

B. Cytoplasmic CSP (SEQ ID NO: 2):

```
   1    MQEYQCYGSS SNTRVLNELN YDNAGTNLYN ELEMNYYGKQ ENWYSLKKNS
  51    RSLGENDDGN NEDNEKLRKP KHKKLKQPAD GNPDPNANPN VDPNANPNVD
 101    PNANPNVDPN ANPNANPNAN PNANPNANPN ANPNANPNAN PNANPNANPN
 151    ANPNANPNAN PNANPNANPN ANPNANPNVD PNANPNANPN ANPNANPNAN
 201    PNANPNANPN ANPNANPNAN PNANPNANPN ANPNANPNAN PNANPNANPN
 251    ANPNKNNQGN GQGHNMPNDP NRNVDENANA NSAVKNNNNE EPSDKHIKEY
                Thrombospondin type 1 domain
                ~~~~~~~~~~~~~~~~~~~~~~~~~~~~~~~~~~~~~~~~~~~~
 301    LNKIQNSLST EWSPCSVTCG NGIQVRIKPG SANKPKDELD YANDIEKKIC
        Thrombospondin type 1 domain
        ~~~~~
 351    KMEKCSSVFN VVN
```

FIG. 2C

C. Periplasmic CSP (SEQ ID NO: 3):

```
   1    QEYQCYGSSS NTRVLNELNY DNAGTNLYNE LEMNYYGKQE NWYSLKKNSR
  51    SLGENDDGNN EDNEKLRKPK HKKLKQPADG NPDPNANPNV DPNANPNVDP
 101    NANPNVDPNA NPNANPNANP NANPNANPNA NPNANPNANP NANPNANPNA
 151    NPNANPNANP NANPNANPNA NPNANPNVDP NANPNANPNA NPNANPNANP
 201    NANPNANPNA NPNANPNANP NANPNANPNA NPNANPNANP NANPNANPNA
 251    NPNKNNQGNG QGHNMPNDPN RNVDENANAN SAVKNNNNEE PSDKHIKEYL
              Thrombospondin type 1 domain
              ~~~~~~~~~~~~~~~~~~~~~~~~~~~~~~~~~~~~~~~~~~~~~
 301    NKIQNSLSTE WSPCSVTCGN GIQVRIKPGS ANKPKDELDY ANDIEKKICK
        Thrombospondin type 1 domain
        ~~~~
 351    MEKCSSVFNV VN
```

FIG. 3A

A. *P. Falciparum* 3D7 CS nucleotide Genbank entry XM_001351086.1 (SEQ ID NO: 4)

```
 1141 atgatgagaa aattagctat tttatctgtt tcttcctttt tatttgttga ggccttattc
   61 caggaatacc agtgctatgg aagttcgtca acacaaggg ttctaaatga attaaattat
  121 gataatgcag gcactaattt atataatgaa ttagaaatga attattatgg gaaacaggaa
  181 aattggtata gtcttaaaaa aaatagtaga tcacttggag aaaatgatga tggaaataac
  241 gaagacaacg agaaattaag gaaaccaaaa cataaaaaat aaagcaacc agcggatggt
  301 aatcctgatc caaatgcaaa cccaaatgta gatccaatg ccaacccaaa tgtagatcca
  361 aatgcaaacc caatgtaga tccaaatgca aacccaaatg caaacccaaa tgcaaaccca
  421 aatgcaaacc caatgcaaa cccaaatgca aacccaaatg caaacccaaa tgcaaaccca
  481 aatgcaaacc caatgcaaa cccaaatgca aacccaaatg caaacccaaa tgcaaaccca
  541 aatgcaaacc ccatgcaaa tcctaatgca aacccaaatg caaacccaaa cgtagatcct
  601 aatgcaaatc caatgcaaa cccaaacgca aaccccaatg caaatcctaa tgcaaacccc
  661 aatgcaaatc ctaatgcaaa tcctaatgcc aatccaaatg caaatccaaa tgcaaaccca
  721 aacgcaaacc ccaatgcaaa tcctaatgcc aatccaaatg caaatccaaa tgcaaaccca
  781 aatgcaaacc caatgcaaa ccccaatgca atcctaata aaaacaatca aggtaatgga
  841 caaggtcaca atatgccaaa tgacccaaac cgaaatgtag atgaaaatgc taatgccaac
  901 agtgctgtaa aaaataataa taacgaagaa ccaagtgata agcacataaa agaatattta
  961 aacaaaatac aaaattctct ttcaactgaa tggtccccat gtagtgtaac ttgtggaaat
 1021 ggtattcaag ttagaataaa gcctggctct gctaataaac ctaaagacga attagattat
 1081 gcaaatgata ttgaaaaaaa aatttgtaaa atggaaaaat gttccagtgt gtttaatgtc
 1141 gtaaatagtt caataggatt aataatggta ttatccttct gttccttaa ttag
```

FIG. 3B

B. (SEQ ID NO: 5) Optimized CSP Nucleic Acid Sequence 1 Encoding Amino Acid Sequence of Fig. 2C (SEQ ID NO: 3)

```
    1 caggagtatc aatgctatgg tagctcaagc aacacccgcg tcctgaatga gctgaactat
   61 gacaacgccg ggacgaacct gtacaacgag ttggagatga actactacgg caaacaggag
  121 aactggtact cgcttaagaa gaacagccgg agtctcggtg aaaacgacga tggaaacaac
  181 gaggacaacg aaaaactgcg caagccgaaa cataagaaac tgaaacagcc ggctgacggc
  241 aacccggacc cgaacgcaaa cccgaacgtg gacccgaatg caacccgaa tgtggatccc
  301 aatgcaaacc cgaatgttga ccccaacgct aacccgaacg cgaatccgaa tgccaacccg
  361 aacgccaacc ccaacgccaa tccaaacgcc aatcctaacg caacccgaa cgcgaatccc
  421 aatgctaacc ccaacgctaa ccctaacgcc aatccgaacg cgaacccgaa cgctaaccca
  481 aacgcgaacc ctaacgccaa cccgaacgcc aaccctaacg ctaatcctaa tgtagacccc
  541 aacgcgaacc cgaacgccaa cccgaacgcg aaccccaacg cgaacccgaa cgcgaatccg
  601 aacgccaatc cgaatgcgaa tccaaacgcc aacccaaacg caacccgaa cgcgaatccc
  661 aacgccaatc ccaatgcgaa ccctaacgcc aatccaaatg caatccgaa cgcgaacccc
  721 aacgccaatc cgaacgccaa tccgaacgcg aaccccaata gaacaacca aggcaacggc
  781 caggccaca acatgccgaa cgacccaaac cgtaacgtcg atgaaaacgc taatgccaac
  841 tccgccgtga agaataacaa taacgaagaa cccagcgaca acacatcaa agagtacctg
  901 aacaagatcc aaaacagtct ctcgaccgaa tggtcgccct gctccgtgac ctgcgggaac
  961 ggtattcagg tgcgcatcaa gcccggcagc gccaacaagc cgaaggatga attggattac
 1021 gcgaacgaca tcgaaaagaa gatctgtaag atggagaagt gctccagcgt gttcaacgtc
 1081 gtcaac
```

FIG. 3C

C.   (SEQ ID NO: 6) Optimized CSP Nucleic Acid Sequence 2 Encoding Amino Acid Sequence of Fig. 2C (SEQ ID NO: 3)

```
   1  caagaatacc agtgttatgg cagctccagt aacactcgcg tgctcaatga gcttaactat
  61  gacaacgcag gcaccaactt gtataacgaa ctggagatga attactacgg taaacaggag
 121  aactggtaca gtctgaaaaa gaactcccgt tcactcggcg aaaatgatga cggcaataac
 181  gaggataacg aaaagttgcg caagccgaag cataagaaac tgaaacagcc agccgacggc
 241  aacccggacc caaatgccaa tccgaacgtg gaccccaacg cgaatccaaa cgtggacccc
 301  aacgccaacc caacgtgga ccccaacgct aaccccaatg ctaatcccaa tgccaatccc
 361  aatgccaatc ccaacgcgaa ccccaacgct aacccgaatg ccaaccccaa cgccaacccg
 421  aacgcaaacc cgaacgcgaa cccgaacgct aacccgaatg ccaacccgaa cgccaaccca
 481  aacgcaaacc caaatgccaa tcctaacgcc aacccgaacg cgaatcctaa tgtggaccct
 541  aatgcgaacc cgaatgcgaa cccgaatgcc aacccgaacg ccaacccgaa cgcaaacccg
 601  aatgcgaacc ctaacgcaaa cccgaatgcg aacccaaacg cgaaccccaa cgcaaacccg
 661  aacgcgaacc cgaacgccaa ccctaacgct aacccaaacg ccaacccgaa cgccaacccc
 721  aacgcgaatc cgaacgcgaa ccctaacgcc aacccgaaca agaataacca aggtaacggg
 781  caaggacaca acatgccgaa cgacccgaac cggaacgtcg atgagaacgc caatgcgaac
 841  tcggccgtta agaacaacaa caatgaagaa cccagcgata aacacatcaa agaatacctg
 901  aacaaaatcc agaattcgtt gagcaccgag tggtcgcctt gcagcgttac ctgcgggaac
 961  ggcattcagg tccgcatcaa gccgggctcc gccaataagc caaggatga gctggactac
1021  gccaacgata tcgagaagaa gatctgcaag atggaaaagt gcagctcggt attcaacgtg
1081  gtcaac
```

FIG. 11A
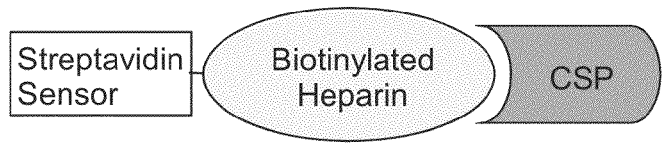
FIG. 11B
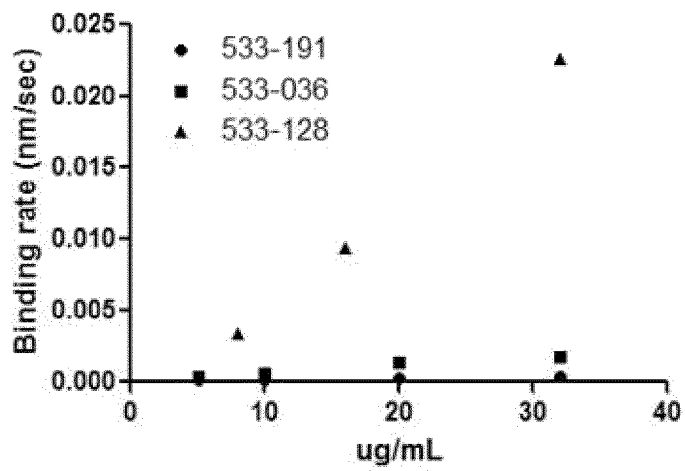
FIG. 11C
Comparison of CSP binding rates
| CSP batch | CSP µg/mL | Binding rate (nm/sec) | StDev | |
|---|---|---|---|---|
| 533-036 | 5 | 3.70E-04 | 1.41E-05 | |
| | 10 | 7.00E-04 | | 10 mg batch |
| | 20 | 1.41E-03 | 1.13E-04 | [low level of aggregation] |
| | 32 | 1.74E-03 | 1.41E-05 | |
| 533-191 | 5 | 1.00E-04 | 2.83E-05 | 30 mg batch |
| | 10 | 1.25E-04 | 2.12E-05 | [no aggregation] |
| | 20 | 2.20E-04 | 5.66E-05 | |
| | 32 | 3.85E-04 | 6.36E-05 | |
| 533-128 | 8 | 3.39E-03 | 1.84E-04 | |
| | 16 | 9.38E-03 | 2.12E-04 | 3 g batch |
| | 32 | 2.27E-02 | 6.36E-05 | [very high aggregation] |

FIG. 17A

```
  1    QEYQCYGSSS   NTRVLNELNY   DNAGTNLYNE   LEMNYYGKQE   NWYSLKKNSR
 51    SLGENDDGNN   EDNEKLRKPK   HKKLKQPADG   NPDPNANPNV   DPNANPNVDP
101    NANPNVDPNA   NPNANPNANP   NANPNANPNA   NPNANPNANP   NANPNANPNA
151    NPNANPNANP   NANPNANPNA   NPNANPNVDP   NANPNANPNA   NPNANPNANP
201    NANPNANPNA   NPNANPNANP   NANPNANPNA   NPNANPNANP   NANPNANPNA
251    NPNKNNQGNG   QGHNMPNDPN   RNVDENANAN   SAVKNNNNEE   PSDKHIKEYL
301    NKIQNSLSTE   WSPCSVTCGN   GIQVRIKPGS   ANKPKDELDY   ANDIEKKICK
351    MEKCSSVFNV   VN
```

FIG. 17B

```
  1    QEYQCYGSSS   NTRVLNELNY   DNAGTNLYNE   LEMNYYGKQE   NWYSLKKNSR
 51    SLGENDDGNN   EDNEKLRKPK   HKKLKQPADG   NPDPNANPNV   DPNANPNVDP
101    NANPNVDPNA   NPNANPNANP   NANPNANPNA   NPNANPNANP   NANPNANPNA
151    NPNANPNANP   NANPNANPNA   NPNANPNVDP   NANPNANPNA   NPNANPNANP
201    NANPNANPNA   NPNANPNANP   NANPNANPNA   NPNANPNANP   NPNANPNA
251    NPNKNNQGNG   QGHNMPNDPN   RNVDENANAN   SAVKNNNNEE   PSDKHIKEYL
301    NKIQNSLSTE   WSPCSVTCGN   GIQVRIKPGS   ANKPKDELDY   ANDIEKKICK
351    MEKCSSVFNV   VN
```

SEQUENCE LISTING

<160> NUMBER OF SEQ ID NOS: 111

<210> SEQ ID NO 1
<211> LENGTH: 397
<212> TYPE: PRT
<213> ORGANISM: Plasmodium falciparum

<400> SEQUENCE: 1

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
            115                 120                 125

Asn Ala Asn Pro Asn Ala Asn Pro Asn Ala Asn Pro Asn Ala Asn Pro
        130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Lys Asn Asn Gln Gly Asn Gly Gln Gly His Asn Met Pro Asn Asp
        275                 280                 285

Pro Asn Arg Asn Val Asp Glu Asn Ala Asn Ala Asn Ser Ala Val Lys
    290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
                325                 330                 335

Thr Cys Gly Asn Gly Ile Gln Val Arg Ile Lys Pro Gly Ser Ala Asn
            340                 345                 350

Lys Pro Lys Asp Glu Leu Asp Tyr Ala Asn Asp Ile Glu Lys Lys Ile
        355                 360                 365
```

```
Cys Lys Met Glu Lys Cys Ser Ser Val Phe Asn Val Asn Ser Ser
    370                 375                 380

Ile Gly Leu Ile Met Val Leu Ser Phe Leu Phe Leu Asn
385                 390                 395
```

<210> SEQ ID NO 2
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Gln Glu Tyr Gln Cys Tyr Gly Ser Ser Ser Asn Thr Arg Val Leu
1               5                   10                  15

Asn Glu Leu Asn Tyr Asp Asn Ala Gly Thr Asn Leu Tyr Asn Glu Leu
            20                  25                  30

Glu Met Asn Tyr Tyr Gly Lys Gln Glu Asn Trp Tyr Ser Leu Lys Lys
        35                  40                  45

Asn Ser Arg Ser Leu Gly Glu Asn Asp Asp Gly Asn Asn Glu Asp Asn
    50                  55                  60

Glu Lys Leu Arg Lys Pro Lys His Lys Lys Leu Lys Gln Pro Ala Asp
65                  70                  75                  80

Gly Asn Pro Asp Pro Asn Ala Asn Pro Asn Val Asp Pro Asn Ala Asn
                85                  90                  95

Pro Asn Val Asp Pro Asn Ala Asn Pro Asn Val Asp Pro Asn Ala Asn
            100                 105                 110

Pro Asn Ala Asn Pro Asn Ala Asn Pro Asn Ala Asn Pro Asn Ala Asn
        115                 120                 125

Pro Asn Ala Asn Pro Asn Ala Asn Pro Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Val Asp Pro Asn Ala Asn Pro Asn Ala Asn Pro Asn Ala Asn
            180                 185                 190

Pro Asn Ala Asn Pro Asn Ala Asn Pro Asn Ala Asn Pro Asn Ala Asn
        195                 200                 205

Pro Asn Ala Asn Pro Asn Ala Asn Pro Asn Ala Asn Pro Asn Ala Asn
    210                 215                 220

Pro Asn Ala Asn Pro Asn Ala Asn Pro Asn Ala Asn Pro Asn Ala Asn
225                 230                 235                 240

Pro Asn Ala Asn Pro Asn Ala Asn Pro Asn Ala Asn Pro Asn Lys Asn
                245                 250                 255

Asn Gln Gly Asn Gly Gln Gly His Asn Met Pro Asn Asp Pro Asn Arg
            260                 265                 270

Asn Val Asp Glu Asn Ala Asn Ala Asn Ser Ala Val Lys Asn Asn Asn
        275                 280                 285

Asn Glu Glu Pro Ser Asp Lys His Ile Lys Glu Tyr Leu Asn Lys Ile
    290                 295                 300

Gln Asn Ser Leu Ser Thr Glu Trp Ser Pro Cys Ser Val Thr Cys Gly
305                 310                 315                 320

Asn Gly Ile Gln Val Arg Ile Lys Pro Gly Ser Ala Asn Lys Pro Lys
                325                 330                 335
```

```
Asp Glu Leu Asp Tyr Ala Asn Asp Ile Glu Lys Lys Ile Cys Lys Met
            340                 345                 350

Glu Lys Cys Ser Ser Val Phe Asn Val Val Asn
        355                 360

<210> SEQ ID NO 3
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Glu Tyr Gln Cys Tyr Gly Ser Ser Asn Thr Arg Val Leu Asn
1               5                   10                  15

Glu Leu Asn Tyr Asp Asn Ala Gly Thr Asn Leu Tyr Asn Glu Leu Glu
            20                  25                  30

Met Asn Tyr Tyr Gly Lys Gln Glu Asn Trp Tyr Ser Leu Lys Lys Asn
        35                  40                  45

Ser Arg Ser Leu Gly Glu Asn Asp Asp Gly Asn Asn Glu Asp Asn Glu
50                  55                  60

Lys Leu Arg Lys Pro Lys His Lys Lys Leu Lys Gln Pro Ala Asp Gly
65                  70                  75                  80

Asn Pro Asp Pro Asn Ala Asn Pro Asn Val Asp Pro Asn Ala Asn Pro
                85                  90                  95

Asn Val Asp Pro Asn Ala Asn Pro Asn Val Asp Pro Asn Ala Asn Pro
            100                 105                 110

Asn Ala Asn Pro Asn Ala Asn Pro Asn Ala Asn Pro Asn Ala Asn Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Val Asp Pro Asn Ala Asn Pro Asn Ala Asn Pro Asn Ala Asn Pro
            180                 185                 190

Asn Ala Asn Pro Asn Ala Asn Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Lys Asn Asn
                245                 250                 255

Gln Gly Asn Gly Gln Gly His Asn Met Pro Asn Asp Pro Asn Arg Asn
            260                 265                 270

Val Asp Glu Asn Ala Asn Ala Asn Ser Ala Val Lys Asn Asn Asn Asn
        275                 280                 285

Glu Glu Pro Ser Asp Lys His Ile Lys Glu Tyr Leu Asn Lys Ile Gln
    290                 295                 300

Asn Ser Leu Ser Thr Glu Trp Ser Pro Cys Ser Val Thr Cys Gly Asn
305                 310                 315                 320

Gly Ile Gln Val Arg Ile Lys Pro Gly Ser Ala Asn Lys Pro Lys Asp
```

```
                         325                 330                 335
        Glu Leu Asp Tyr Ala Asn Asp Ile Glu Lys Lys Ile Cys Lys Met Glu
                340                 345                 350

Lys Cys Ser Ser Val Phe Asn Val Val Asn
                355                 360

<210> SEQ ID NO 4
<211> LENGTH: 1194
<212> TYPE: DNA
<213> ORGANISM: Plasmodium falciparum

<400> SEQUENCE: 4
atgatgagaa aattagctat tttatctgtt tcttcctttt tatttgttga ggccttattc      60
caggaatacc agtgctatgg aagttcgtca aacacaaggg ttctaaatga attaaattat     120
gataatgcag gcactaattt atataatgaa ttagaaatga attattatgg gaaacaggaa     180
aattggtata gtcttaaaaa aaatagtaga tcacttggag aaaatgatga tggaaataac     240
gaagacaacg agaaattaag gaaaccaaaa cataaaaaat taaagcaacc agcggatggt     300
aatcctgatc caaatgcaaa cccaaatgta gatcccaatg ccaacccaaa tgtagatcca     360
aatgcaaacc caaatgtaga tccaaatgca acccaaatg caaacccaaa tgcaaaccca     420
aatgcaaacc caaatgcaaa cccaaatgca acccaaatg caaacccaaa tgcaaaccca     480
aatgcaaacc caaatgcaaa cccaaatgca acccaaatg caaacccaaa tgcaaaccca     540
aatgcaaacc ccaatgcaaa tcctaatgca acccaaatg caaacccaaa cgtagatcct     600
aatgcaaatc caaatgcaaa cccaaacgca aaccccaatg caaatcctaa tgcaaacccc     660
aatgcaaatc ctaatgcaaa tcctaatgcc aatccaaatg caaatccaaa tgcaaaccca     720
aacgcaaacc ccaatgcaaa tcctaatgcc aatccaaatg caaatccaaa tgcaaaccca     780
aatgcaaacc caaatgcaaa ccccaatgca atcctaata aaaacaatca aggtaatgga     840
caaggtcaca atatgccaaa tgacccaaac cgaaatgtag atgaaaatgc taatgccaac     900
agtgctgtaa aaaataataa taacgaagaa ccaagtgata agcacataaa agaatattta     960
aacaaaatac aaaattctct ttcaactgaa tggtccccat gtagtgtaac ttgtggaaat    1020
ggtattcaag ttagaataaa gcctggctct gctaataaac ctaaagacga attagattat    1080
gcaaatgata ttgaaaaaaa aatttgtaaa atggaaaaat gttccagtgt gtttaatgtc    1140
gtaaatagtt caataggatt aataatggta ttatccttct tgttccttaa ttag          1194

<210> SEQ ID NO 5
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
caggagtatc aatgctatgg tagctcaagc aacacccgcg tcctgaatga gctgaactat      60
gacaacgccg ggacgaacct gtacaacgag ttggagatga actactacgg caaacaggag     120
aactggtact cgcttaagaa gaacagccgg agtctcggtg aaaacgacga tggaaacaac     180
gaggacaacg aaaaactgcg caagccgaaa cataagaaac tgaaacagcc ggctgacggc     240
aacccggacc cgaacgcaaa cccgaacgtg gacccgaatg caaacccgaa tgtggatccc     300
aatgcaaacc cgaatgttga ccccaacgct aacccgaacg cgaatccgaa tgccaacccg     360
```

```
aacgccaacc ccaacgccaa tccaaacgcc aatcctaacg caaacccgaa cgcgaatccc      420
aatgctaacc ccaacgctaa ccctaacgcc aatccgaacg cgaacccgaa cgctaaccca      480
aacgcgaacc ctaacgccaa cccgaacgcc aaccctaacg ctaatcctaa tgtagacccc      540
aacgcgaacc cgaacgccaa ccctaacgcg aaccccaacg cgaacccgaa cgcgaatccg      600
aacgccaatc cgaatgcgaa tccaaacgcc aacccaaacg caaacccgaa cgcgaatccc      660
aacgccaatc ccaatgcgaa ccctaacgcc aatccaaatg caaatccgaa cgcgaaccccc    720 aacgccaatc cgaacgccaa tccgaacgcg aaccccaata agaacaacca aggcaacggc     780
cagggccaca acatgccgaa cgacccaaac cgtaacgtcg atgaaaacgc taatgccaac     840
tccgccgtga agaataacaa taacgaagaa cccagcgaca aacacatcaa agagtacctg     900
aacaagatcc aaaacagtct ctcgaccgaa tggtcgccct gctccgtgac ctgcgggaac     960
ggtattcagg tgcgcatcaa gcccggcagc gccaacaagc cgaaggatga attggattac    1020
gcgaacgaca tcgaaaagaa gatctgtaag atggagaagt gctccagcgt gttcaacgtc    1080
gtcaac                                                               1086
```

<210> SEQ ID NO 6
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
caagaatacc agtgttatgg cagctccagt aacactcgcg tgctcaatga gcttaactat       60
gacaacgcag gcaccaactt gtataacgaa ctggagatga attactacgg taaacaggag      120
aactggtaca gtctgaaaaa gaactcccgt tcactcggcg aaaatgatga cggcaataac      180
gaggataacg aaaagttgcg caagccgaag cataagaaac tgaaacagcc agccgacggc      240
aacccggacc caaatgccaa tccgaacgtg gaccccaacg cgaatccaaa cgtggacccc      300
aacgccaacc ccaacgtgga ccccaacgct aaccccaatg ctaatcccaa tgccaatccc      360
aatgccaatc ccaacgcgaa ccccaacgct aacccgaatg ccaaccccaa cgccaacccg      420
aacgcaaacc cgaacgcgaa cccgaacgct aacccgaatg ccaacccgaa cgccaaccca      480
aacgcaaacc caaatgccaa tcctaacgcc aacccgaacg cgaatcctaa tgtggaccct      540
aatgcgaacc cgaatgcgaa cccgaatgcc aacccgaacg ccaacccgaa cgcaaacccg      600
aatgcgaacc ctaacgcaaa cccgaatgcg aacccaaacg cgaacccaa cgcaaacccg       660 aacgcgaacc cgaacgccaa ccctaacgct aacccaaacg ccaacccgaa cgccaacccc      720
aacgcgaatc cgaacgcgaa ccctaacgcc aacccgaaca agaataacca aggtaacggg      780
caaggacaca acatgccgaa cgacccgaac cggaacgtcg atgagaacgc caatgcgaac      840
tcggccgtta agaacaacaa caatgaagaa cccagcgata aacacatcaa agaatacctg      900
aacaaaatcc agaattcgtt gagcaccgag tggtcgcctt gcagcgttac ctgcgggaac      960
ggcattcagg tccgcatcaa gccgggctcc gccaataagc ccaaggatga gctggactac     1020
gccaacgata tcgagaagaa gatctgcaag atggaaaagt gcagctcggt attcaacgtg    1080
gtcaac                                                               1086
```

<210> SEQ ID NO 7
<211> LENGTH: 21
<212> TYPE: PRT

```
<213> ORGANISM: Plasmodium falciparum

<400> SEQUENCE: 7

Glu Asn Asp Asp Gly Asn Asn Glu Asp Asn Glu Lys Leu Arg Lys Pro
1               5                   10                  15

Lys His Lys Lys Leu
            20

<210> SEQ ID NO 8
<211> LENGTH: 21
<212> TYPE: PRT
<213> ORGANISM: Plasmodium falciparum

<400> SEQUENCE: 8

Asp Lys Arg Asp Gly Asn Asn Glu Asp Asn Glu Lys Leu Arg Lys Pro
1               5                   10                  15

Lys His Lys Lys Leu
            20

<210> SEQ ID NO 9
<211> LENGTH: 22
<212> TYPE: PRT
<213> ORGANISM: Unknown
<220> FEATURE:
<223> OTHER INFORMATION: Description of Unknown: DsbA secretion leader
      peptide

<400> SEQUENCE: 9

Met Arg Asn Leu Ile Leu Ser Ala Ala Leu Val Thr Ala Ser Leu Phe
1               5                   10                  15

Gly Met Thr Ala Gln Ala
            20

<210> SEQ ID NO 10
<211> LENGTH: 20
<212> TYPE: PRT
<213> ORGANISM: Unknown
<220> FEATURE:
<223> OTHER INFORMATION: Description of Unknown: Azu secretion leader
      peptide

<400> SEQUENCE: 10

Met Phe Ala Lys Leu Val Ala Val Ser Leu Leu Thr Leu Ala Ser Gly
1               5                   10                  15

Gln Leu Leu Ala
            20

<210> SEQ ID NO 11
<211> LENGTH: 31
<212> TYPE: PRT
<213> ORGANISM: Unknown
<220> FEATURE:
<223> OTHER INFORMATION: Description of Unknown: Ibp-S31A secretion
      leader polypeptide

<400> SEQUENCE: 11

Met Ile Arg Asp Asn Arg Leu Lys Thr Ser Leu Leu Arg Gly Leu Thr
1               5                   10                  15

Leu Thr Leu Leu Ser Leu Thr Leu Leu Ser Pro Ala Ala His Ala
            20                  25                  30

<210> SEQ ID NO 12
<211> LENGTH: 21
<212> TYPE: PRT
```

```
<213> ORGANISM: Unknown
<220> FEATURE:
<223> OTHER INFORMATION: Description of Unknown: Tpr secretion leader
      peptide

<400> SEQUENCE: 12

Met Asn Arg Ser Ser Ala Leu Leu Leu Ala Phe Val Phe Leu Ser Gly
1               5                   10                  15

Cys Gln Ala Met Ala
            20

<210> SEQ ID NO 13
<211> LENGTH: 24
<212> TYPE: PRT
<213> ORGANISM: Unknown
<220> FEATURE:
<223> OTHER INFORMATION: Description of Unknown: CupB2 secretion leader
      peptide

<400> SEQUENCE: 13

Met Leu Phe Arg Thr Leu Leu Ala Ser Leu Thr Phe Ala Val Ile Ala
1               5                   10                  15

Gly Leu Pro Ser Thr Ala His Ala
            20

<210> SEQ ID NO 14
<211> LENGTH: 25
<212> TYPE: PRT
<213> ORGANISM: Unknown
<220> FEATURE:
<223> OTHER INFORMATION: Description of Unknown: CupA2 secretion leader
      peptide

<400> SEQUENCE: 14

Met Ser Cys Thr Arg Ala Phe Lys Pro Leu Leu Leu Ile Gly Leu Ala
1               5                   10                  15

Thr Leu Met Cys Ser His Ala Phe Ala
            20                  25

<210> SEQ ID NO 15
<211> LENGTH: 21
<212> TYPE: PRT
<213> ORGANISM: Unknown
<220> FEATURE:
<223> OTHER INFORMATION: Description of Unknown: NikA secretion leader
      peptide

<400> SEQUENCE: 15

Met Arg Leu Ala Ala Leu Pro Leu Leu Leu Ala Pro Leu Phe Ile Ala
1               5                   10                  15

Pro Met Ala Val Ala
            20

<210> SEQ ID NO 16
<211> LENGTH: 24
<212> TYPE: PRT
<213> ORGANISM: Unknown
<220> FEATURE:
<223> OTHER INFORMATION: Description of Unknown: Pbp A20V secretion
      leader peptide

<400> SEQUENCE: 16

Met Lys Leu Lys Arg Leu Met Ala Ala Met Thr Phe Val Ala Ala Gly
1               5                   10                  15

Val Ala Thr Val Asn Ala Val Ala
```

20

<210> SEQ ID NO 17
<211> LENGTH: 21
<212> TYPE: PRT
<213> ORGANISM: Unknown
<220> FEATURE:
<223> OTHER INFORMATION: Description of Unknown: DsbC secretion leader
      peptide

<400> SEQUENCE: 17

Met Arg Leu Thr Gln Ile Ile Ala Ala Ala Ala Ile Ala Leu Val Ser
1               5                   10                  15

Thr Phe Ala Leu Ala
            20

<210> SEQ ID NO 18
<211> LENGTH: 21
<212> TYPE: PRT
<213> ORGANISM: Unknown
<220> FEATURE:
<223> OTHER INFORMATION: Description of Unknown: TolB secretion leader
      peptide

<400> SEQUENCE: 18

Met Arg Asn Leu Leu Arg Gly Met Leu Val Val Ile Cys Cys Met Ala
1               5                   10                  15

Gly Ile Ala Ala Ala
            20

<210> SEQ ID NO 19
<211> LENGTH: 24
<212> TYPE: PRT
<213> ORGANISM: Unknown
<220> FEATURE:
<223> OTHER INFORMATION: Description of Unknown: Pbp secretion leader
      peptide

<400> SEQUENCE: 19

Met Lys Leu Lys Arg Leu Met Ala Ala Met Thr Phe Val Ala Ala Gly
1               5                   10                  15

Val Ala Thr Ala Asn Ala Val Ala
            20

<210> SEQ ID NO 20
<211> LENGTH: 23
<212> TYPE: PRT
<213> ORGANISM: Unknown
<220> FEATURE:
<223> OTHER INFORMATION: Description of Unknown: Lao secretion leader
      peptide

<400> SEQUENCE: 20

Met Gln Asn Tyr Lys Lys Phe Leu Leu Ala Ala Ala Val Ser Met Ala
1               5                   10                  15

Phe Ser Ala Thr Ala Met Ala
            20

<210> SEQ ID NO 21
<211> LENGTH: 23
<212> TYPE: PRT
<213> ORGANISM: Unknown
<220> FEATURE:
<223> OTHER INFORMATION: Description of Unknown: CupC2 secretion leader
      peptide

```
<400> SEQUENCE: 21

Met Pro Pro Arg Ser Ile Ala Ala Cys Leu Gly Leu Leu Gly Leu Leu
1               5                   10                  15

Met Ala Thr Gln Ala Ala Ala
            20

<210> SEQ ID NO 22
<211> LENGTH: 21
<212> TYPE: PRT
<213> ORGANISM: Unknown
<220> FEATURE:
<223> OTHER INFORMATION: Description of Unknown: PorE secretion leader
      peptide

<400> SEQUENCE: 22

Met Lys Lys Ser Thr Leu Ala Val Ala Val Thr Leu Gly Ala Ile Ala
1               5                   10                  15

Gln Gln Ala Gly Ala
            20

<210> SEQ ID NO 23
<211> LENGTH: 24
<212> TYPE: PRT
<213> ORGANISM: Unknown
<220> FEATURE:
<223> OTHER INFORMATION: Description of Unknown: Pbp secretion leader
      peptide

<400> SEQUENCE: 23

Met Lys Leu Lys Arg Leu Met Ala Ala Met Thr Phe Val Ala Ala Gly
1               5                   10                  15

Val Ala Thr Ala Asn Ala Val Ala
            20

<210> SEQ ID NO 24
<211> LENGTH: 21
<212> TYPE: PRT
<213> ORGANISM: Unknown
<220> FEATURE:
<223> OTHER INFORMATION: Description of Unknown: FlgI secretion leader
      peptide

<400> SEQUENCE: 24

Met Lys Phe Lys Gln Leu Met Ala Met Ala Leu Leu Leu Ala Leu Ser
1               5                   10                  15

Ala Val Ala Gln Ala
            20

<210> SEQ ID NO 25
<211> LENGTH: 33
<212> TYPE: PRT
<213> ORGANISM: Unknown
<220> FEATURE:
<223> OTHER INFORMATION: Description of Unknown: ttg2C secretion leader
      polypeptide

<400> SEQUENCE: 25

Met Gln Asn Arg Thr Val Glu Ile Gly Val Gly Leu Phe Leu Leu Ala
1               5                   10                  15

Gly Ile Leu Ala Leu Leu Leu Ala Leu Arg Val Ser Gly Leu Ser
            20                  25                  30

Ala
```

```
<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Gln Asn Ser Leu Ser Thr Glu Trp Ser Pro Cys Ser
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Cys Gly Asn Gly Ile Gln Val Arg
1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Ser Ser Val
1

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Glu Tyr Gln Cys Tyr Gly Ser Ser Ser Asn Thr Arg Val Leu Asn
1               5                   10                  15

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Glu Tyr Gln Cys Tyr Gly Ser Ser Ser Asn Thr Arg Val Leu Asn
1               5                   10                  15

Glu Leu Asn Tyr
            20

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 31

Tyr Gly Ser Ser Ser Asn Thr Arg Val Leu Asn Glu Leu Asn Tyr
1               5                   10                  15

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Thr Arg Val Leu Asn Glu Leu Asn Tyr Asp Asn Ala Gly Thr Asn
1               5                   10                  15

Leu Tyr Asn

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Leu Asn Tyr
1

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Tyr Asp Asn Ala Gly Thr Asn Leu Tyr Asn
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Asn Ala Gly Thr Asn Leu Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Asn Ala Gly Thr Asn Leu Tyr Asn Glu Leu
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Asp Asn Ala Gly Thr Asn Leu Tyr Asn Glu Leu Glu Met Asn Tyr Tyr
1               5                   10                  15

Gly

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Asp Asn Ala Gly Thr Asn Leu Tyr Asn Glu Leu Glu Met Asn Tyr Tyr
1               5                   10                  15

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Thr Asn Leu Tyr Asn
1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Asn Glu Leu Glu Met Asn Tyr Tyr Gly Lys Gln
1               5                   10

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Glu Leu Glu Met Asn Tyr Tyr Gly Lys Gln Glu Asn Trp Tyr Ser Leu
1               5                   10                  15

Lys Lys Asn

<210> SEQ ID NO 42
<211> LENGTH: 24
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 42

Glu Met Asn Tyr Tyr Gly Lys Gln Glu Asn Trp Tyr Ser Leu Lys Lys
1               5                   10                  15

Asn Ser Arg Ser Leu Gly Glu Asn
            20

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Met Asn Tyr Tyr Gly Lys Gln Glu Asn Trp Tyr
1               5                   10

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Lys Gln Glu Asn Trp Tyr Ser Leu Lys Lys Asn Ser Arg Ser Leu
1               5                   10                  15

Gly

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Lys Gln Glu Asn Trp Tyr Ser Leu Lys Lys Asn Ser Arg Ser Leu
1               5                   10                  15

Gly Glu Asn

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Asn Trp Tyr Ser Leu Lys Lys Asn Ser Arg Ser Leu Gly Glu Asn
1               5                   10                  15

Asp

<210> SEQ ID NO 47
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 47

Glu Asn Trp Tyr Ser Leu Lys Lys Asn Ser Arg Ser Leu Gly Glu Asn
1               5                   10                  15

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Asn Trp Tyr Ser Leu Lys Lys Asn Ser Arg
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Leu Lys Lys Asn Ser Arg Ser Leu Gly Glu Asn Asp
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Leu Lys Lys Asn Ser Arg Ser Leu Gly Glu Asn
1               5                   10

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Arg Ser Leu Gly Glu Asn Asp
1               5

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Asn Glu Lys Leu Arg Lys Pro Lys His Lys Lys Leu Lys Gln Pro
1               5                   10                  15
```

Ala

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Gly Asn Pro Asp Pro Asn Ala Asn Pro Asn Val
1               5                   10

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Pro Asn Ala Asn Pro Asn Val
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Pro Asn Ala Asn Pro Asn
1               5

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Pro Asn Ala Asn Pro Asn Val Asp Pro Asn Ala Asn Pro Asn Ala
1               5                   10                  15

Asn Pro Asn Ala
            20

<210> SEQ ID NO 57
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Ala Asn Pro Asn Ala Asn Pro Asn Ala Asn Pro Asn Ala Asn Pro Asn
1               5                   10                  15

Ala Asn Pro Asn Ala Asn Pro Asn Ala Asn Pro Asn Ala Asn Pro Asn
            20                  25                  30

Val

<210> SEQ ID NO 58
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asn Pro Asn Ala Asn Pro Asn Ala Asn Pro Asn Ala Asn Pro Asn Ala
1               5                   10                  15

Asn Pro Asn Lys Asn Asn Gln Gly Asn Gly Gln Gly His Asn Met Pro
            20                  25                  30

Asn

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ala Asn Pro Asn Ala Asn Pro Asn Ala Asn Pro Asn Lys Asn Asn Gln
1               5                   10                  15

Gly Asn Gly Gln Gly His Asn Met Pro Asn Asp Pro Asn Arg Asn Val
            20                  25                  30

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asn Gly Gln Gly His Asn Met Pro Asn
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Pro Asn Arg Asn Val
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Pro Asn Arg Asn Val Asp Glu Asn
1               5

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Pro Asn Arg Asn Val Asp Glu Asn Ala Asn Ala Asn Ser Ala Val
1               5                   10                  15

Lys Asn

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Glu Asn Ala Asn Ala Asn Ser Ala
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Glu Asn Ala Asn Ala Asn
1               5

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Asn Ala Asn Ala Asn Ser Ala Val Lys Asn Asn
1               5                   10

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Ala Val Lys Asn Asn Asn Asn
1               5

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 68

Glu Pro Ser Asp Lys His Ile Lys Glu Tyr Leu Asn Lys
1               5                   10

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Pro Ser Asp Lys His Ile Lys Glu Tyr Leu Asn Lys Ile Gln Asn
1               5                   10                  15

Ser Leu Ser Thr
            20

<210> SEQ ID NO 70
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Lys His Ile Lys Glu Tyr Leu Asn Lys Ile Gln Asn Ser Leu Ser
1               5                   10                  15

Thr Glu Trp Ser Pro Cys Ser Val Thr Cys Gly
            20                  25

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Lys His Ile Lys Glu Tyr Leu Asn Lys Ile Gln Asn Ser Leu Ser
1               5                   10                  15

<210> SEQ ID NO 72
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Lys His Ile Lys Glu Tyr Leu Asn Lys Ile Gln Asn Ser Leu Ser
1               5                   10                  15

Thr Glu Trp Ser Pro Cys Ser Val Thr Cys Gly Asn Gly Ile Gln Val
            20                  25                  30

Arg Ile Lys Pro Gly Ser Ala Asn Lys Pro Lys
            35                  40

<210> SEQ ID NO 73
<211> LENGTH: 28
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 73

Asp Lys His Ile Lys Glu Tyr Leu Asn Lys Ile Gln Asn Ser Leu Ser
1               5                   10                  15
Thr Glu Trp Ser Pro Cys Ser Val Thr Cys Gly Asn
            20                  25

<210> SEQ ID NO 74
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Lys His Ile Lys Glu Tyr Leu Asn Lys Ile Gln Asn Ser Leu Ser Thr
1               5                   10                  15
Glu Trp Ser Pro Cys Ser Val Thr Cys Gly Asn Gly Ile Gln Val Arg
            20                  25                  30
Ile Lys Pro Gly Ser Ala Asn Lys Pro Lys
        35                  40

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys His Ile Lys Glu Tyr Leu Asn Lys Ile Gln Asn Ser Leu Ser Thr
1               5                   10                  15

<210> SEQ ID NO 76
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Tyr Leu Asn Lys Ile Gln Asn Ser Leu Ser Thr Glu Trp Ser Pro
1               5                   10                  15
Cys Ser Val Thr Cys Gly Asn Gly Ile Gln Val Arg Ile Lys Pro Gly
            20                  25                  30
Ser Ala Asn Lys Pro Lys
        35

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Glu Tyr Gln Cys Tyr Gly Ser Ser Ser Asn Thr Arg
```

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Val Leu Asn Glu Leu Asn Tyr Asp Asn Ala Gly Thr Asn Leu Tyr Asn
1               5                   10                  15

Glu Leu Glu Met Asn Tyr Tyr Gly Lys
            20                  25

<210> SEQ ID NO 79
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Val Leu Asn Glu Leu Asn Tyr Asp Asn Ala Gly Thr Asn Leu Tyr Asn
1               5                   10                  15

Glu Leu Glu Met Asn Tyr Tyr Gly Lys Gln
            20                  25

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Leu Asn Tyr Asp Asn Ala Gly Thr Asn Leu Tyr Asn Glu Leu Glu
1               5                   10                  15

Met Asn Tyr Tyr Gly Lys
            20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Asn Tyr Asp Asn Ala Gly Thr Asn Leu Tyr Asn Glu Leu Glu Met
1               5                   10                  15

Asn Tyr Tyr Gly Lys
            20

<210> SEQ ID NO 82
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 82

Tyr Asp Asn Ala Gly Thr Asn Leu Tyr Asn Glu Leu Glu Met Asn Tyr
1               5                   10                  15

Tyr Gly Lys Gln Glu Asn Trp Tyr Ser Leu Lys
            20                  25

<210> SEQ ID NO 83
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Asn Leu Tyr Asn Glu Leu Glu Met Asn Tyr Tyr Gly Lys Gln Glu
1               5                   10                  15

Asn Trp Tyr Ser Leu Lys
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr Asn Glu Leu Glu Met Asn Tyr Tyr Gly Lys Gln Glu Asn Trp Tyr
1               5                   10                  15

Ser Leu Lys Lys
            20

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Glu Asn Trp Tyr Ser Leu Lys
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Glu Asn Trp Tyr Ser Leu Lys Lys
1               5

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 87

Ser Leu Gly Glu Asn Asp Asp Gly Asn Asn Glu Asp Asn Glu Lys Leu
1               5                   10                  15

Arg

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Leu Gly Glu Asn Asp Asp Gly Asn Asn Glu Asp Asn Glu Lys
1               5                   10                  15

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Gly Glu Asn Asp Asp Gly Asn Asn Glu Asp Asn Glu Lys
1               5                   10

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Asn Glu Lys Leu Arg Lys Pro Lys
1               5

<210> SEQ ID NO 91
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Leu Lys Gln Pro Ala Asp Gly Asn Pro Asp Pro Asn Ala Asn Pro Asn
1               5                   10                  15

Val Asp Pro Asn Ala Asn Pro Asn Val Asp
            20                  25

<210> SEQ ID NO 92
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Pro Asn Ala Asn Pro Asn Ala Asn Pro Asn Lys Asn Asn Gln Gly Asn
1               5                   10                  15
```

Gly Gln Gly His Asn Met Pro Asn Asp Pro Asn Arg
            20                  25

<210> SEQ ID NO 93
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Pro Asn Ala Asn Pro Asn Lys Asn Asn Gln Gly Asn Gly Gln Gly His
1               5                   10                  15

Asn Met Pro Asn Asp Pro Asn Arg
            20

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asn Asn Gln Gly Asn Gly Gln Gly His Asn Met Pro Asn Asp Pro Asn
1               5                   10                  15

Arg

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asn Asn Gln Gly Asn Gly Gln Gly His Asn Met Pro Asn
1               5                   10

<210> SEQ ID NO 96
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly His Asn Met Pro Asn Asp Pro Asn Arg Asn Val Asp Glu Asn Ala
1               5                   10                  15

Asn Ala Asn Ser Ala Val Lys
            20

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Val Asp Glu Asn Ala Asn Ala Asn Ser Ala Val Lys
1               5                   10

<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asn Val Asp Glu Asn Ala Asn Ala Asn Ser Ala Val Lys Asn Asn Asn
1               5                   10                  15

Asn Glu

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asn Asn Asn Asn Glu Glu Pro Ser Asp Lys
1               5                   10

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

His Ile Lys Glu Tyr Leu Asn Lys Ile Gln Asn Ser Leu Ser Thr Glu
1               5                   10                  15

Trp

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu Tyr Leu Asn Lys
1               5

<210> SEQ ID NO 102
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Gln Asn Ser Leu Ser Thr Glu Trp Ser Pro Cys Ser Val Thr Cys
1               5                   10                  15

Gly Asn Gly Ile Gln Val Arg
            20

<210> SEQ ID NO 103
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ile Gln Asn Ser Leu Ser Thr Glu Trp Ser Pro Cys Ser Val Thr Cys
1               5                   10                  15

Gly Asn Gly Ile Gln Val Arg Ile Lys Pro Gly
            20                  25

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Lys Pro Gly Ser Ala Asn Lys Pro Lys Asp Glu Leu Asp Tyr Ala
1               5                   10                  15

Asn Asp Ile Glu Lys Lys
            20

<210> SEQ ID NO 105
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Lys Pro Gly Ser Ala Asn Lys Pro Lys Asp Glu Leu Asp Tyr Ala
1               5                   10                  15

Asn Asp Ile Glu Lys
            20

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Glu Leu Asp Tyr Ala Asn Asp Ile Glu Lys
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Glu Leu Asp Tyr Ala Asn Asp Ile Glu Lys Lys
1               5                   10

```
<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Cys Ser Ser Val Phe Asn Val Val Asn
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Ser Ser Val Phe Asn Val Val
1               5

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Alkylated-Cys

<400> SEQUENCE: 110

Tyr Gln Cys Tyr Gly Ser Ser Ser Asn Thr Arg Val Leu Asn Glu
1               5                   10                  15

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Glu Tyr Gln Cys Tyr Gly Ser Ser Ser Asn Thr Arg Val Leu Asn
1               5                   10                  15

Glu
```

US 9,169,304 B2

PROCESS FOR PURIFYING RECOMBINANT *PLASMODIUM FALCIPARUM* CIRCUMSPOROZOITE PROTEIN

CROSS-REFERENCE TO RELATED APPLICATION

This application claims the benefit of U.S. Provisional Patent Application Ser. No. 61/641,105, filed on May 1, 2012, and incorporated herein by reference in its entirety.

SEQUENCE LISTING

The instant application contains a Sequence Listing which has been submitted in ASCII format via EFS-Web and is incorporated by reference in its entirety herein. Said ASCII copy, created on Apr. 8, 2013, is named 38194-739.201_SL.txt and is 46,753 bytes in size.

GOVERNMENT SUPPORT

This invention was made with Government support under contract AI-N01-054210 awarded by (Division of Microbiology and Infectious Diseases/National Institute of Allergy and Infectious Diseases). The Government has certain rights in the invention.

FIELD OF THE INVENTION

The invention is in the field of protein purification, in particular, purification of recombinantly-expressed *Plasmodium falciparum* circumsporozoite protein.

BACKGROUND OF THE INVENTION

Malaria is caused by parasites of the genus *Plasmodium*. According to the Centers for Disease Control, malaria ranks second in Africa as the greatest cause of death from infectious diseases, after HIV/AIDS. It ranks fifth worldwide, after respiratory infections, HIV/AIDS, diarrheal diseases, and tuberculosis. *Plasmodium falciparum*, one of at least eleven known *Plasmodium* parasites that attack humans, causes a particularly severe infection characterized by sequestration of the parasite in vital organs and deep tissues where it can evade the immune system.

There is no effective malaria vaccine available. Recent strategies target the *Plasmodium falciparum* circumsporozoite protein (CSP), which is critical for the pathogenesis of the parasite. Currently, a vaccine called RTS,S (GlaxoSmithKline), composed of a portion of CSP, is in Phase III clinical trials. CSP is a protein monomer that can be broadly described as having three regions—the N-terminal region, the central repeat region, and the C-terminal region. The N and C-terminal regions contain crucial protective regions important for parasite invasion, and the central region contains highly conserved immunodominant tetrapeptide repeats. The vaccine RTS,S does not include the N-terminal region of CSP. It is composed of a portion of the CSP central repeat and the C-terminal region, linked to hepatitis B surface antigen. Recent reports indicating that the N-terminal region of CSP is immunogenic suggest that a vaccine strategy utilizing a CSP molecule having the N-terminal region would be superior.

Development of a manufacturing scale purification process to make recombinant CSP in amounts that meet the needs for vaccine research and production presents challenges. The N-terminal region of CSP is highly susceptible to degradation. Furthermore, CSP dimerizes due to the formation of covalent intermolecular disulfide bonds that involve a free cysteine near the monomer's N-terminus. CSP also forms higher molecular weight aggregates. Present purification schemes provide recombinant CSP monomer lacking the N-terminal region, or they generate low yields of intact CSP. Denaturation to eliminate dimers and aggregates has required refolding, which is complicated by the presence of two disulfide bonds involving four cysteine residues in the C-terminal region of CSP. These disulfide bonds are critical for the structure and function of the C-terminal protective region; disrupting them has been shown to destroy CSP's ability to bind to liver cells. Furthermore, additional denaturing and refolding steps are burdensome, costly, reduce yield, and are challenging to scale up for use with large fermentation batches. Therefore, scalable purification methods for obtaining high quality recombinant CSP at high yields are needed.

SUMMARY OF THE INVENTION

The invention relates to a process for purifying recombinant *P. falciparum* circumsporozoite protein (rCSP) made in a bacterial host cell expression system. This process provides rCSP at high yields without the need for denaturing and refolding the protein. The present invention overcomes obstacles previously encountered in the field, including dimerization, aggregation, and N-terminal degradation of rCSP. The process provided by the invention is scalable, and can be applied to large fermentation batches.

In embodiments, the present invention provides a process for purifying recombinant *P. falciparum* circumsporozoite protein, said process comprising (a) obtaining a bacterial cell lysate preparation comprising recombinant *P. falciparum* circumsporozoite protein dimers; (b) separating the bacterial cell lysate preparation of step (a) into a soluble fraction comprising the *P. falciparum* circumsporozoite protein dimers, and an insoluble fraction; (c) separating the recombinant *P. falciparum* circumsporozoite protein dimers in the soluble fraction of step (b) from host cell proteins in the soluble fraction; and (d) subjecting the recombinant *P. falciparum* circumsporozoite protein dimers obtained in step (c) to preferential reducing conditions; thereby obtaining purified recombinant *P. falciparum* circumsporozoite protein.

In related embodiments, the purified recombinant *P. falciparum* circumsporozoite protein is obtained at an overall purification yield of about 10% to about 75%, about 10% to about 70%, about 10% to about 65%, about 10% to about 60%, 10% to about 55%, about 10% to about 50%, about 10% to about 45%, about 10% to about 40%, about 10% to about 35%, about 10% to about 30%, about 10% to about 25%, about 10% to about 20%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 25% to about 75%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%, about 30% to about 75%, about 30% to about 70%, about 30% to about 65%, about 30% to about 60%, about 30% to about 55%, about 30% to about 50%, about 30% to about 45%, or about 30% to about 40%. In embodiments, not more than about 10% of the purified recombinant *P. falciparum* circumsporozoite protein obtained is degraded at the N-terminus. In embodiments, not more than about 10% of the purified recombinant *P. falciparum* circumsporozoite protein obtained is dimerized. In embodiments, not more than about 5% of the purified recombinant *P. falciparum* circumsporozoite protein obtained is present as high molecular weight aggregates. In embodiments, not more than about 10% of the purified recombinant *P. falciparum* circumsporozoite protein obtained is denatured. In related embodiments, the purified recombinant *P. falciparum* circumsporozoite protein obtained comprises at least about 90% *P. falciparum* circumsporozoite protein monomer.

In embodiments of the invention, the bacterial cell lysate is a Pseudomonad cell lysate. In related embodiments, the Pseudomonad cells are *Pseudomonas* cells, and in other related embodiments the *Pseudomonas* cells are *Pseudomonas fluorescens.*

In embodiments, the separating of step (b) above comprises disk-stack centrifugation and/or depth filtration. The separating of step (c) can comprise chromatography. In embodiments, the chromatography comprises one or more of the following: anion-exchange chromatography, cation exchange chromatography, hydrophobic interaction chromatography, size exclusion chromatography, affinity chromatography, and mixed mode chromatography. The use of hydroxyapetite chromatography as mixed mode chromatography is contemplated. In certain embodiments, the separating of step (b) comprises disk-stack centrifugation and depth filtration, and the separating of step (d) comprises anion exchange chromatography and mixed-mode chromatography.

In embodiments of the invention, the preferential reducing conditions comprise DTT, cysteine, glutathione, monothioglycerol, thioglycolate, dithiothreitol, dithioerythritol, acetylcysteine, 2-Mercaptoethanol (B-mercaptoethanol), TCEP-HCl (pure, crystalline Tris(2-carboxyethyl)phosphine hydrochloride), or 2-Mercaptoethylamine-HCl (2-MEA). In certain related embodiments, the preferential reducing conditions comprise DTT at a concentration of about 0.010 to about 0.030 mM. The buffer exchange can comprises tangential flow filtration carried out using a membrane having a pore size of about 4 kDa to about 8 kDa. In embodiments, the preferential reducing conditions comprise an ingredient that meets the standards of the United States Pharmacopeial Convention (Rockville, Md.), as published in the United States Pharmacopeia-National Formulary (USP-NF), or analogous standards in countries outside the United States, e.g., as published in The International Pharmacopeia (World Health Organization).

The process as claimed is scalable to a bacterial cell lysate preparation comprising about 1 gram to about 2000 grams rCSP. In related embodiments, the amount of rCSP in the bacterial lysate preparation is about 1 gram to about 2000 grams.

The invention further relates to a process for purifying recombinant *P. falciparum* circumsporozoite protein, the process comprising: (a) obtaining a culture of bacterial host cells, wherein the bacterial host cells are transformed with an expression vector comprising a nucleic acid sequence encoding a *P. falciparum* circumsporozoite protein; (b) growing the culture of bacterial host cells, thereby expressing *P. falciparum* circumsporozoite protein from the expression vector; (c) disrupting the bacterial host cells from the culture of bacterial host cells grown in step (b) to generate a bacterial cell lysate preparation, wherein the bacterial cell lysate preparation comprises *P. falciparum* circumsporozoite protein dimers; (d) separating the bacterial cell lysate preparation of step (c) into a soluble fraction comprising the *P. falciparum* circumsporozoite protein dimers, and an insoluble fraction; (e) separating the recombinant *P. falciparum* circumsporozoite protein dimers in the soluble fraction of step (d) from host cell proteins; (f) subjecting the recombinant *P. falciparum* circumsporozoite protein dimers obtained in step (e) to preferential reducing conditions, thereby obtaining *P. falciparum* circumsporozoite protein monomer; and (g) removing reducing reagents used in the preferential reducing conditions of step (f) by buffer exchange; thereby obtaining purified recombinant *P. falciparum* circumsporozoite protein.

In related embodiments, the purified recombinant *P. falciparum* circumsporozoite protein is obtained at an overall purification yield of about 10% to about 75%, about 10% to about 70%, about 10% to about 65%, about 10% to about 60%, about 20% to about 75%, about 20% to about 70%, about 20% to about 65%, about 25% to about 75%, about 25% to about 70%, about 25% to about 65%, about 25% to about 60%, about 30% to about 75%, about 30% to about 70%, about 30% to about 65%, or about 30% to about 60%. In embodiments, not more than about 10% of the purified recombinant *P. falciparum* circumsporozoite protein obtained is degraded at the N-terminus. In embodiments, not more than about 10% of the purified recombinant *P. falciparum* circumsporozoite protein obtained is dimerized. In embodiments, not more than about 5% of the purified recombinant *P. falciparum* circumsporozoite protein obtained is present as high molecular weight aggregates. In embodiments, not more than about 10% of the purified recombinant *P. falciparum* circumsporozoite protein obtained is denatured. In related embodiments, the purified recombinant *P. falciparum* circumsporozoite protein obtained comprises at least about 90% *P. falciparum* circumsporozoite protein monomer.

In embodiments of the invention, the bacterial cell lysate is a Pseudomonad cell lysate. In related embodiments, the Pseudomonad cells are *Pseudomonas* cells, and in further related embodiments the *Pseudomonas* cells are *Pseudomonas fluorescens*. In certain embodiments, the nucleic acid sequence encoding the *P. falciparum* circumsporozoite protein is fused to a periplasmic secretion signal sequence. The periplasmic secretion signal sequence can be a *P. fluorescens* secretion signal sequence, for example, LAO, pbp, pbpA20V, or cupA2. The expression of any CSP is contemplated, as described further herein. In certain embodiments, the rCSP is encoded by a nucleic acid sequence having an amino acid sequence as set forth in SEQ ID NO: 3, or an amino acid sequence having at least 90% identity to the amino acid sequence set forth in SEQ ID NO: 3.

In embodiments, the separating of step (d) above comprises disk-stack centrifugation and/or depth filtration. The separating of step (e) can comprise chromatography. In embodiments, the chromatography comprises one or more of the following: anion-exchange chromatography, cation exchange chromatography, hydrophobic interaction chromatography, size exclusion chromatography, affinity chromatography, and mixed mode chromatography. The use of hydroxyapetite chromatography as mixed mode chromatography is contemplated. In certain embodiments, the separating of step (d) comprises disk-stack centrifugation and depth filtration, and the separating of step (e) comprises anion exchange chromatography and mixed-mode chromatography.

In embodiments of the invention, the preferential reducing conditions comprise DTT, cysteine, glutathione, monothioglycerol, thioglycolate, dithiothreitol, dithioerythritol, acetylcysteine, 2-Mercaptoethanol (B-mercaptoethanol), TCEP-HCl (pure, crystalline Tris(2-carboxyethyl)phosphine hydrochloride), or 2-Mercaptoethylamine-HCl (2-MEA). In certain related embodiments, the preferential reducing conditions comprise DTT at a concentration of about 0.010 to about 0.030 mM. The buffer exchange can comprises tangential flow filtration carried out using a membrane having a pore size of about 4 kDa to about 8 kDa.

The process as claimed is scalable to a bacterial cell lysate preparation comprising about 1 gram to about 2000 grams rCSP. In related embodiments, the amount of rCSP in the bacterial lysate preparation is about 1 gram to about 2000 grams. In embodiments of the invention, the culture of bacterial host cells grown in step (b) is about 10 liters to about 500 liters.

In embodiments, the present invention relates to a process for purifying recombinant *P. falciparum* circumsporozoite protein, said process comprising: (a) obtaining a bacterial cell lysate preparation comprising recombinant *P. falciparum* circumsporozoite protein dimer; (b) separating the bacterial cell lysate preparation of step (a) into a soluble fraction comprising the *P. falciparum* circumsporozoite protein dimer, and an insoluble fraction; (c) separating the recombinant *P. falciparum* circumsporozoite protein dimer in the soluble fraction of step (b) from host cell proteins in the soluble fraction; and (d) subjecting the recombinant *P. falciparum* circumsporozoite protein dimer obtained in step (c) to preferential reducing conditions to obtain *P. falciparum* circumsporozoite protein; thereby obtaining purified recombinant *P. falciparum* circumsporozoite protein. In these embodiments, the method further comprises stably maintaining the purified recombinant *P. falciparum* circumsporozoite protein in a stable liquid formulation, the method comprising providing a formulation comprising about 1 to about 5, about 1 to about 10, about 1 to about 20, about 1 to about 30, about 1 to about 40, or about 1 to about 50 mg/ml rCSP, about 0.5 to about 1.5 mM MTG and about 1% to about 20% arginine in 0.5× or 1×PBS at a pH of about 6.0 to about 7.5, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In embodiments, the process further comprises: (e) separating the recombinant *P. falciparum* circumsporozoite protein obtained in step (d) from host cell proteins. In these embodiments, the method further comprises stably maintaining the purified recombinant *P. falciparum* circumsporozoite protein in a stable liquid formulation, the method comprising providing a formulation comprising about 1 to about 5, about 1 to about 10, about 1 to about 20, about 1 to about 30, about 1 to about 40, or about 1 to about 50 mg/ml rCSP, about 0.5 to about 1.5 mM MTG and about 1% to about 20% arginine in 0.5× or 1×PBS at a pH of about 6.0 to about 7.5, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In related embodiments, the purified recombinant *P. falciparum* circumsporozoite protein is obtained at an overall purification yield of about 10% to about 75%. In certain embodiments, recombinant *P. falciparum* circumsporozoite protein is obtained at an overall purification yield of: about 10% to about 75%, about 10% to about 70%, about 10% to about 60%, about 10% to about 50%, about 10% to about 40%, about 10% to about 30%, about 20% to about 75%, about 20% to about 50%, about 20% to about 40%, or about 20% to about 30%. In embodiments, not more than about 10% of the purified recombinant *P. falciparum* circumsporozoite protein obtained is degraded at the N-terminus. In embodiments, not more than about 10% of the purified recombinant *P. falciparum* circumsporozoite protein obtained is dimerized. In embodiments, not more than about 5% of the purified recombinant *P. falciparum* circumsporozoite protein obtained is present as high molecular weight aggregates. In embodiments, not more than about 10% of the purified recombinant *P. falciparum* circumsporozoite protein obtained is denatured. In embodiments, the purified recombinant *P. falciparum* circumsporozoite protein obtained comprises at least about 90% *P. falciparum* circumsporozoite protein monomer. In embodiments, the bacterial cell lysate is a Pseudomonad cell lysate. In related embodiments, the Pseudomonad cells are *Pseudomonas* cells. In specific embodiments, the *Pseudomonas* cells are *Pseudomonas fluorescens*.

In embodiments of the invention, the separating of step (b) comprises disk-stack centrifugation. In embodiments, the separating of step (b) comprises depth filtration. In embodiments, the separating of step (c) comprises chromatography, and wherein the chromatography comprises anion-exchange chromatography and mixed mode chromatography. In embodiments, the separating of step (c) comprises mixed mode chromatography, and wherein the mixed mode chromatography is hydroxyapetite chromatography.

In embodiments, the separating of step (e) comprises hydrophobic interaction chromatography. In these embodiments, the method further comprises stably maintaining the purified recombinant *P. falciparum* circumsporozoite protein in a stable liquid formulation, the method comprising providing a formulation comprising about 1 to about 5, about 1 to about 10, about 1 to about 20, about 1 to about 30, about 1 to about 40, or about 1 to about 50 mg/ml rCSP, about 0.5 to about 1.5 mM MTG and about 1% to about 20% arginine in 0.5× or 1×PBS at a pH of about 6.0 to about 7.5, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In embodiments, the stable liquid formulation comprises about 1.0 mM MTG and about 10% arginine in 1×PBS at a pH of about 6.4 to 7.0, at a temperature of about 3° C. to 5° C., wherein the rCSP is stably maintained for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In embodiments, the preferential reducing conditions comprise a mild reducing agent. In embodiments of the invention, the mild reducing agent is DTT, cysteine, acetylcysteine, glutathione, monothioglycerol (MTG), thioglycolate, dithothiothreitol, dithioerythritol, acetylcysteine, 2-Mercaptoethanol (B-mercaptoethanol), TCEP-HCl (pure, crystalline Tris(2-carboxyethyl)phosphine hydrochloride), or 2-Mercaptoethylamine-HCl (2-MEA). In specific embodiments, the mild reducing agent is DTT, MTG, acetylcysteine, glutathione, thioglycolate, or cysteine. In certain embodiments, the mild reducing agent is DTT at a concentration of about 0.01 to about 0.03 mM, or MTG at a concentration of about 0.5 mM to about 1.5 mM. In embodiments, the preferential reducing conditions further comprise a disaggregating agent. In embodiments, the preferential reducing conditions further comprise a disaggregating agent is urea, arginine, guanidine HCl, or a detergent. In certain embodiments, the disaggregating agent is about 1.5 to 2.5M urea. In specific embodiments, the mild reducing conditions comprise about 0.05 to about 1 mM MTG and about 2M urea.

In embodiments, the methods of the invention further comprise preparing a stable liquid *P. falciparum* circumsporozoite protein formulation, comprising diafiltering about 1 mg/ml to about 50 mg/ml, about 1 mg/ml to about 25 mg/ml, about 1 mg/ml to about 10 mg/ml, about 1 mg/ml to about 5 mg/ml, about 5 mg/ml to about 50 mg/ml, about 5 mg/ml to about 25 mg/ml, or about 5 mg/ml to about 10 mg/ml recombinant *P. falciparum* circumsporozoite protein into a formulation buffer comprising about 0.5 mM to about 1.5 mM MTG and about 10% to about 20% arginine. In these embodiments, the storage temperature can be about 4° C. to about 15° C., about 4° C. to about 10° C., about 4° C. to about 9° C., about 4° C. to about 8° C., about 4° C. to about 7° C., about 4° C. to about 6° C., about 4° C. to about 5° C., about 5° C. to about 10° C., about 5° C. to about 9° C., about 5° C. to about 8° C., about 5° C. to about 7° C., or about 5° C. to about 6° C. In these embodiments, the formulation buffer can have a pH of about 6.0 to about 7.5, about 6.4 to about 7.2, about 6.4 to about 7.0, about 6.6 to about 6.8, or about 6.7.

In embodiments, the formulation buffer comprises 0.5× or 1×PBS. In these embodiments, the storage temperature can be about 4° C. to about 15° C., about 4° C. to about 10° C., about 4° C. to about 9° C., about 4° C. to about 8° C., about 4° C. to about 7° C., about 4° C. to about 6° C., about 4° C. to about 5° C., about 5° C. to about 10° C., about 5° C. to about 9° C., about 5° C. to about 8° C., about 5° C. to about 7° C., or about 5° C. to about 6° C. In these embodiments, the formulation buffer can have a pH of about 6.0 to about 7.5, about 6.4 to about 7.2, about 6.4 to about 7.0, about 6.6 to about 6.8, or about 6.7.

In certain embodiments, the formulation buffer comprises about 1.0 mM MTG, about 10% to about 20% arginine, 1×PBS, has a pH of about 6.4 to about 6.0, and wherein the storage temperature is about 4° C. to about 6° C.

In embodiments, the stable liquid *P. falciparum* circumsporozoite protein formulation contains at least one of the following: not more than about 1%, not more than about 2%, not more than about 3%, not more than about 4%, not more than about 5%, not more than about 6%, not more than about 7%, not more than about 8%, not more than about 9%, or not more than about 10% *P. falciparum* circumsporozoite protein dimer; not more than about 1%, not more than about 2%, not more than about 3%, not more than about 4%, not more than about 5%, not more than about 6%, not more than about 7%, not more than about 8%, not more than about 9%, or not more than about 10% high *P. falciparum* circumsporozoite protein molecular weight aggregates; not more than about 1%, not more than about 2%, not more than about 3%, not more than about 4%, not more than about 5%, not more than about 6%, not more than about 7%, not more than about 8%, not more than about 9%, or not more than about 10% denatured *P. falciparum* circumsporozoite protein; not more than about 1%, not more than about 2%, not more than about 3%, not more than about 4%, not more than about 5%, not more than about 6%, not more than about 7%, not more than about 8%, not more than about 9%, or not more than about 10% pyroglutamate-containing *P. falciparum* circumsporozoite protein species, and; not more than about 1%, not more than about 2%, not more than about 3%, not more than about 4%, not more than about 5%, not more than about 6%, not more than about 7%, not more than about 8%, not more than about 9%, or not more than about 10% *P. falciparum* circumsporozoite protein degradation products. In embodiments, the process is scalable to a bacterial cell lysate preparation comprising about 1 gram to about 2000 grams rCSP. In embodiments, the amount of rCSP in the bacterial lysate preparation is about 1 gram to about 2000 grams. In embodiments, the bacterial cell lysate is prepared from host cells transformed with an expression vector comprising a nucleic acid sequence encoding the recombinant *P. falciparum* circumsporozoite protein. In embodiments, the Pseudomonad cells are *Pseudomonas* cells. In specific embodiments, the *Pseudomonas* cells are *Pseudomonas fluorescens*.

In embodiments of the invention, the recombinant *P. falciparum* circumsporozoite protein encoded by the nucleic acid sequence has an amino acid sequence as set forth in SEQ ID NO: 3, or an amino acid sequence having at least 90% identity to the amino acid sequence set forth in SEQ ID NO: 3. In embodiments, the *P. fluorescens* cells are a PyrF production host strain having the genotype ΔpyrF, lacIQ, and ΔhtpX. In embodiments, the nucleic acid sequence encoding the recombinant *P. falciparum* circumsporozoite protein is fused to a periplasmic secretion signal sequence. In embodiments, the periplasmic secretion signal sequence is a *P. fluorescens* secretion signal sequence. In certain embodiments, the *P. fluorescens* periplasmic secretion signal sequence is LAO, pbp, pbpA20V, or cupA2. In specific embodiments, the *P. fluorescens* periplasmic secretion signal sequence is LAO.

The invention also relates to a stable liquid formulation of recombinant *P. falciparum* circumsporozoite protein, comprising about 1 to about 5, about 1 to about 10, about 1 to about 20, about 1 to about 30, about 1 to about 40, or about 1 to about 50 mg/ml recombinant *P. falciparum* circumsporozoite protein in a formulation buffer comprising about 0.5 to about 1.5 mM MTG and about 10% to about 20% arginine. In these embodiments, the formulation buffer can have a pH of about 6.0 to about 7.5, 6.4 to about 7.2, about 6.4 to about 7.0, about 6.6 to about 6.8, about 6.4 to about 6.7, or about 7.0. In these embodiments, the formulation buffer can comprise comprises 0.5× or 1×PBS. In these embodiments, the formulation buffer can have a pH of about 6.0 to about 7.5, 6.4 to about 7.2, about 6.4 to about 7.0, about 6.6 to about 6.8, about 6.4, about 6.7, or about 7.0.

In any of these embodiments, the stable liquid formulation can be stored at a storage temperature of about 4° C. to about 15° C., about 4° C. to about 10° C., about 4° C. to about 9° C., about 4° C. to about 8° C., about 4° C. to about 7° C., about 4° C. to about 6° C., about 4° C. to about 5° C., about 5° C. to about 10° C., about 5° C. to about 9° C., about 5° C. to about 8° C., about 5° C. to about 7° C., or about 5° C. to about 6° C.

In embodiments the stable liquid formulation comprises about 1 to about 5 mg/ml rCSP, about 1.0 mM MTG, about 10% arginine, 1×PBS, has a pH of about 6.0 to about 7.5, and wherein the storage temperature is about 4° C. to about 6° C. In embodiments the stable liquid P. falciparum circumsporozoite protein formulation contains at least one of the following: not more than about 1%, not more than about 2%, not more than about 3%, not more than about 4%, not more than about 5%, not more than about 6%, not more than about 7%, not more than about 8%, not more than about 9%, or not more than about 10% P. falciparum circumsporozoite protein dimer; not more than about 1%, not more than about 2%, not more than about 3%, not more than about 4%, not more than about 5%, not more than about 6%, not more than about 7%, not more than about 8%, not more than about 9%, or not more than about 10% high P. falciparum circumsporozoite protein molecular weight aggregates, and; not more than about 1%, not more than about 2%, not more than about 3%, not more than about 4%, not more than about 5%, not more than about 6%, not more than about 7%, not more than about 8%, not more than about 9%, or not more than about 10% P. falciparum circumsporozoite protein degradation products.

The invention further relates to a method for stably maintaining rCSP in a stable liquid formulation, the method comprising providing a formulation comprising about 1 to about 5, about 1 to about 10, about 1 to about 20, about 1 to about 30, about 1 to about 40, or about 1 to about 50 mg/ml rCSP, about 0.5 to about 1.5 mM MTG and about 1% to about 20% arginine in 0.5× or 1×PBS at a pH of about 6.0 to about 7.5, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In embodiments, the method for stably maintaining rCSP in a stable liquid formulation comprises providing a formulation comprising about 1 to about 5, about 1 to about 10, about 1 to about 20, about 1 to about 30, about 1 to about 40, or about 1 to about 50 mg/ml rCSP, about 0.5 to about 1.5 mM MTG and about 10% to about 20% arginine in 1×PBS at a pH of about 6.4 to about 7.2, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In embodiments, the method for stably maintaining rCSP in a stable liquid formulation, comprises providing a formulation comprising about 1 to about 5, about 1 to about 10, about 1 to about 20, about 1 to about 30, about 1 to about 40, or about 1 to about 50 mg/ml rCSP, about 0.5 to about 1.5 mM MTG and about 10% to about 20% arginine in 1×PBS at a pH of about 6.4 to about 7.0, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 2. P. falciparum CSP Amino Acid Sequences. A. Plasmodium falciparum 3D7 CS Amino acid sequence; GenBank entry CAB38998 (SEQ ID NO: 1) with putative native secretion leader and GPI anchor. B. Amino acid sequence of cytoplasmic CSP (SEQ ID NO: 2) with the N-terminal methionine, and without the native leader and GPI anchor, shown as a non-limiting example. C. Amino acid sequence of periplasmic CSP (SEQ ID NO: 3) without the native leader, N-terminal methionine and GPI anchor, shown as a non-limiting example.

FIG. 3. P. falciparum CSP Nucleic Acid Sequences. A. The P. falciparum 3D7 CS nucleotide sequence; GenBank entry XM_001351086.1 (SEQ ID NO: 4). B. An optimized nucleotide sequence (SEQ ID NO: 5) encoding the CSP amino acid sequence of SEQ ID NO: 3 fused to a periplasmic secretion leader, shown as a non-limiting example. C. An optimized nucleotide sequence (SEQ ID NO: 6) encoding CSP fused to a periplasmic secretion leader, shown as a non-limiting example.

A. SE-HPLC chromatogram of rCSP sample after centrifugal concentration. B. SE-HPLC chromatogram of aggregated batch 533-128.

FIG. 11. Biolayer Interferometry (BLI) Analysis of rCSP for Heparin Binding. A. Heparin biosensor configuration. B. BLI analysis of heparin binding for various preparations of rCSP. C. Comparison of rCSP binding rates.

Figure 12A:
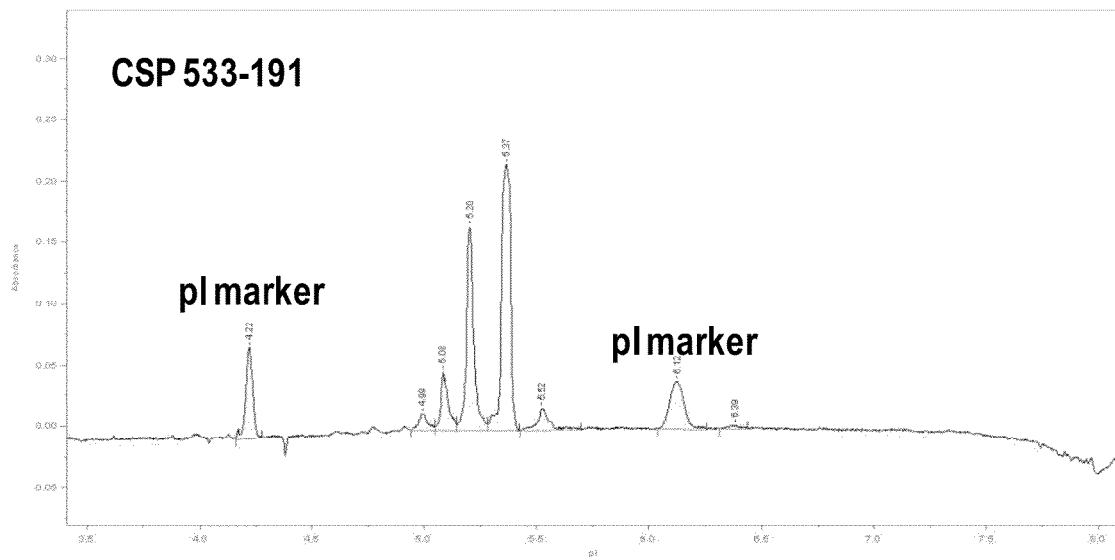
Figure 12B:
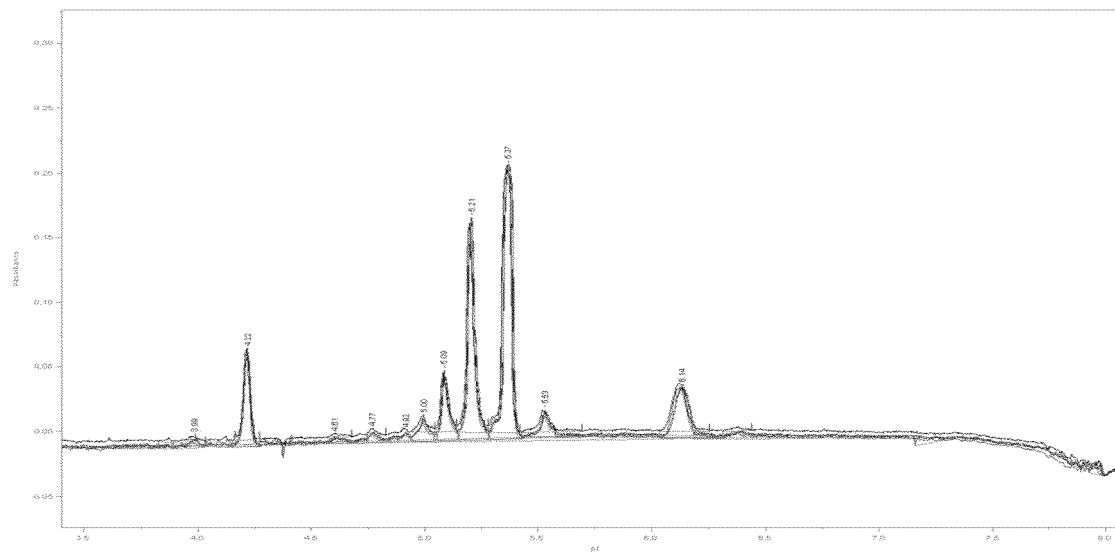

FIG. 12. Capillary Isoelectric Focusing (cIEF) Analysis of rCSP. Samples were incubated for 1 h in the presence of 2M urea and 10 mM DTT and then concentrated to ~1.5 mg/mL. A. Analysis of rCSP 533-191 internal reference. B. cIEF precision assessment; electropherogram overlays of five repeat injections of batch 533-191.

Figure 13A:
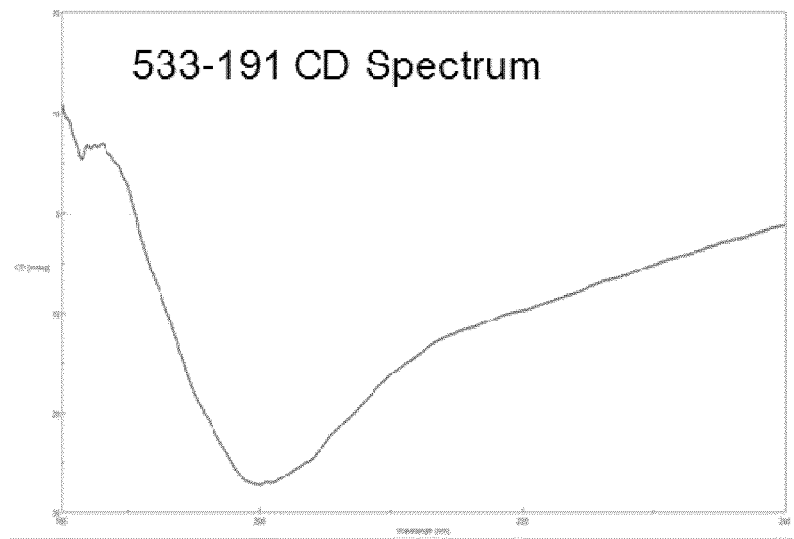
Figure 13B:
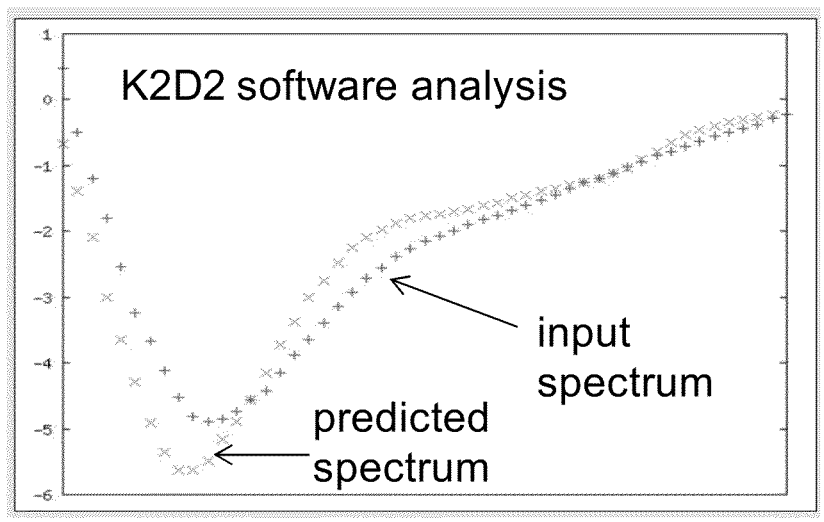
Figure 14A:
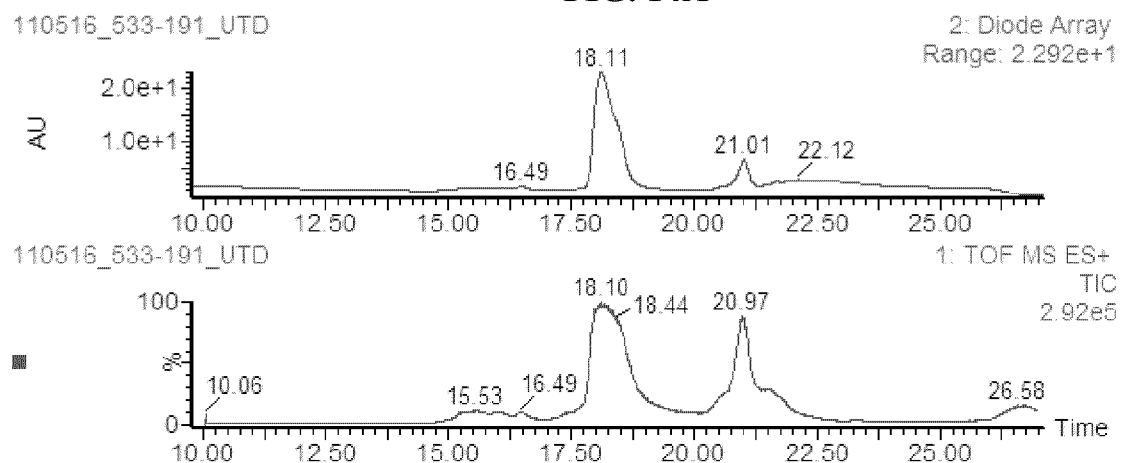
Figure 14B:
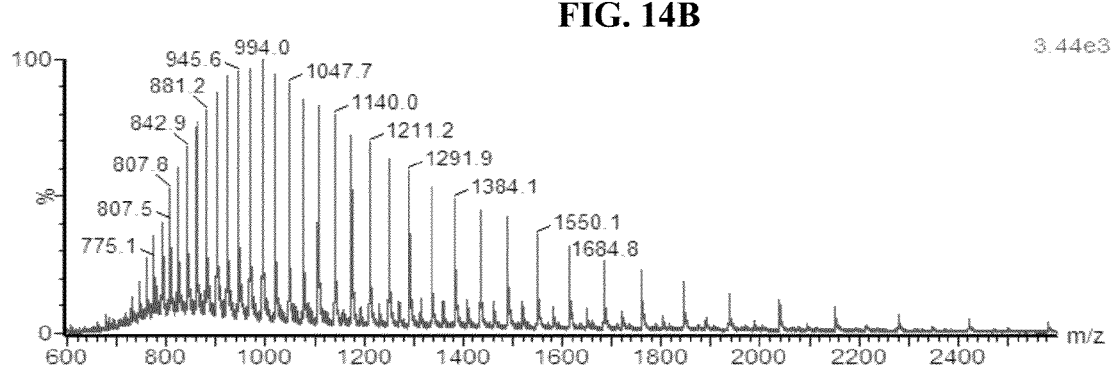
Figure 14C:
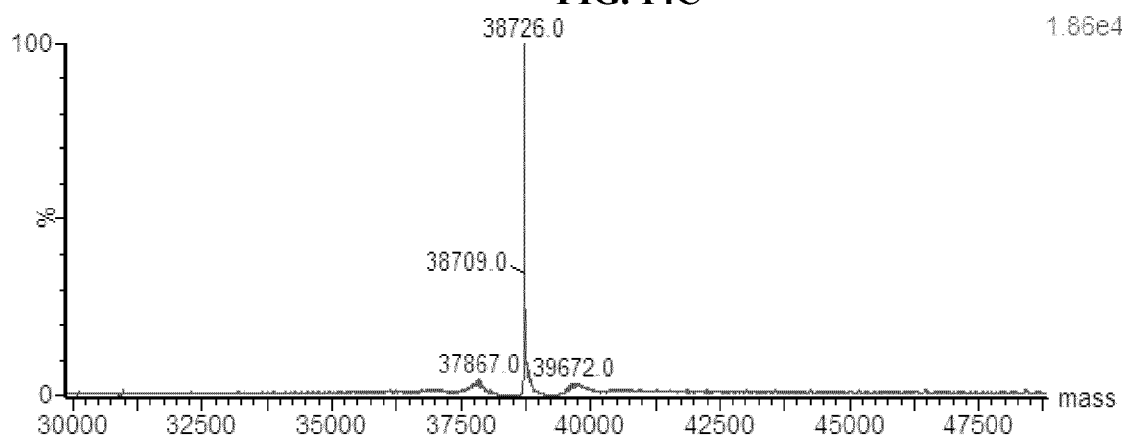
Figure 14D:
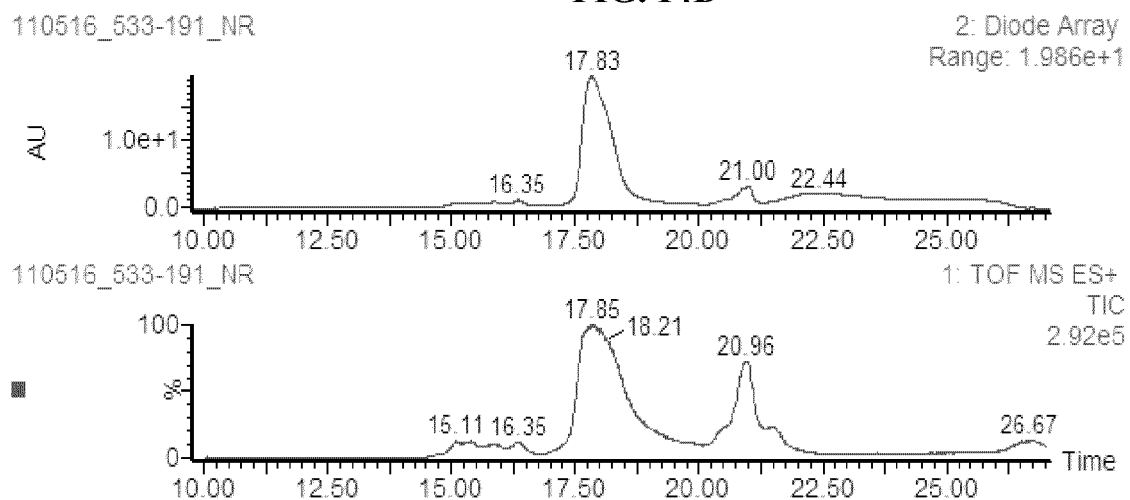
Figure 14E:
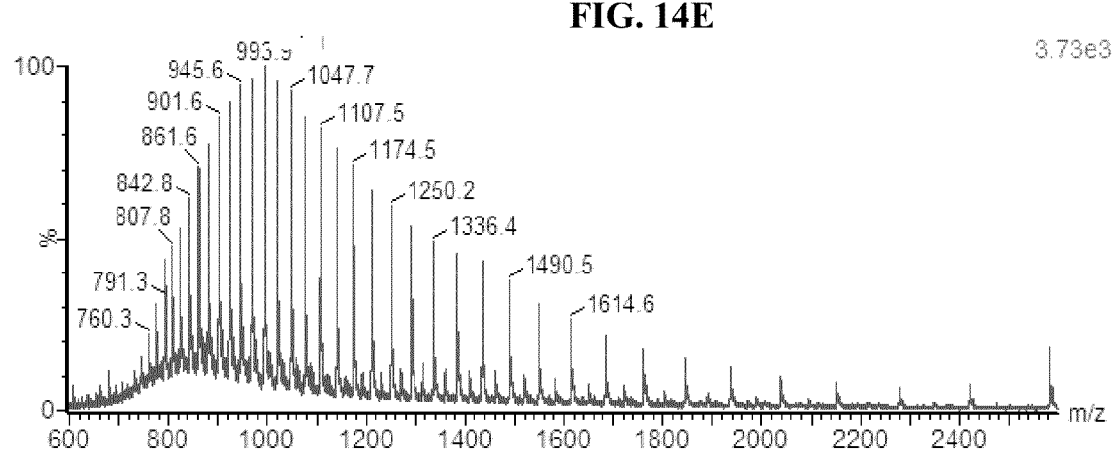
Figure 14F:
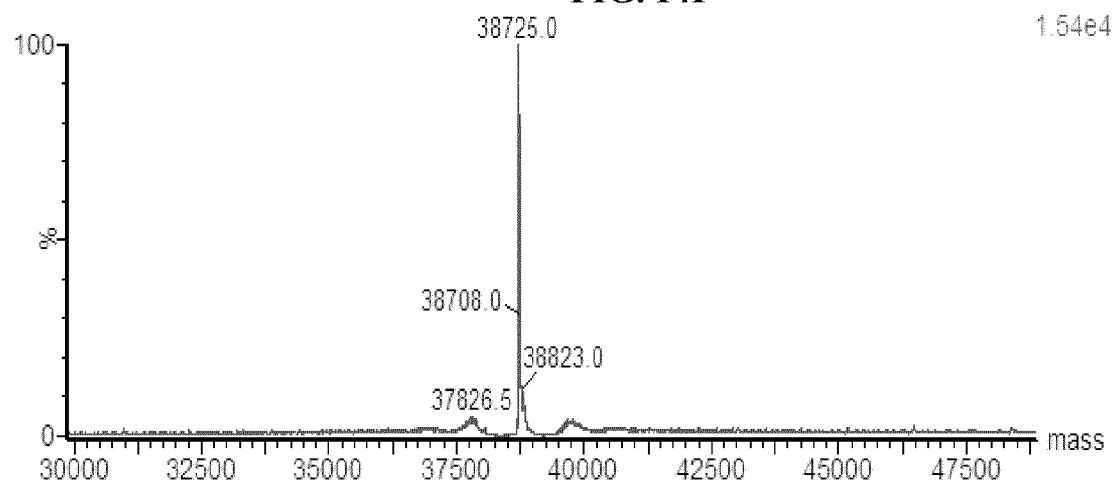

FIG. 13. Far UV Circular Dichroism Analysis of rCSP. Instrument: JASCO 815; Temperature=20 C; Scan speed=100 nm/min; D.I.T.=1 sec; Data pitch=1 nm; Accumulations=5. A. CD spectrum of 533-191 internal reference standard. B. Software analysis: Input spectrum vs. predicted spectrum.

FIG. 14. Intact Mass Analysis of Preparation 533-191 by LC-MS, Reduced (A-C) and Non-reduced (D-F). A. Chromatograms (UV, upper panel; and MS TIC (mass spectra total ion current, lower panel)) of the reduced sample. B. The summed mass spectra from the target peak region of 18.1 min. C. Deconvoluted spectrum derived from the summed mass spectra of the 18.1 min. region. D. Chromatograms of the non-reduced sample. E. The summed mass spectra from the target peak region of 17.8 min. F. Deconvoluted spectrum derived from the summed mass spectra of the 17.8 min. region. The difference between the observed and theoretical MW (delta MW) was 1 and 4 Da for the reduced and non-reduced samples, respectively.

FIG. 15. Intact Mass Analysis of Alkylated 533 Samples by LC-MS. Deconvoluted spectra for alkylated samples are shown. A. Alkylated non-reduced 533-191 was observed to have a delta of 6.0 Da compared to the theoretical MW of 533 with one cysteine alkylation. B. Reduced and alkylated 533-191 was observed to have a delta of 3.9 Da compared to the theoretical MW of 533 with five cysteine alkylations. There was an additional species that correlates with 533 containing four cysteine alkylations, and was present at ~43% total abundance. This observation was most likely due to incomplete alkylation.

Figure 16A:
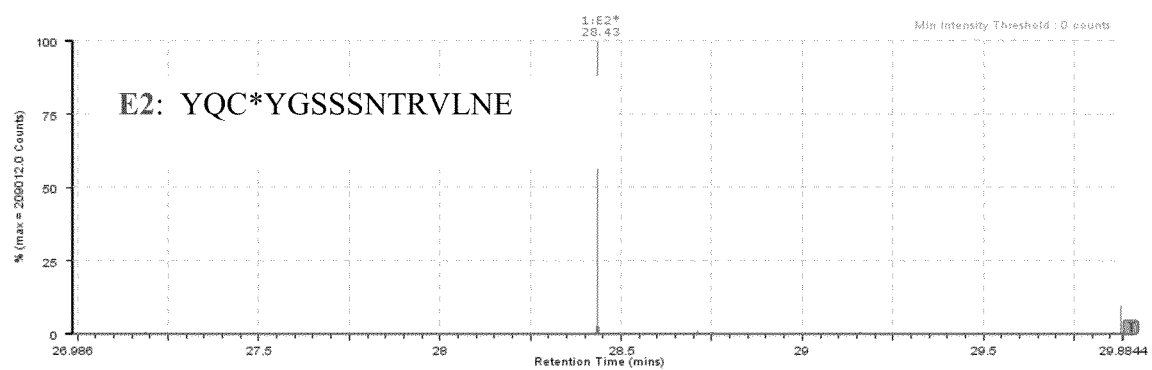
Figure 16B:
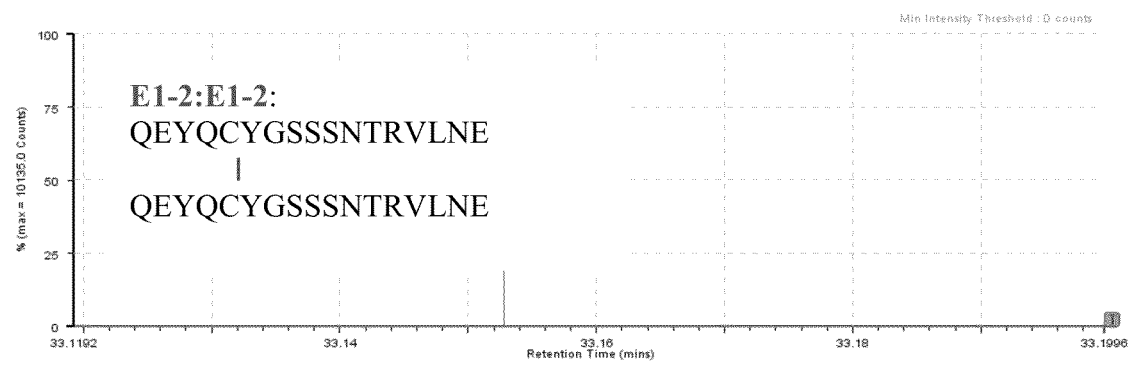

FIG. 16. Analysis of the N-terminal Cysteine of 533-191 by Non-reduced Glu-C Digestion Followed by LC-MS/MS. A. The resulting data was processed with BiopharmaLynx as described in the methods section. A zoomed in portion of a centroided MS chromatogram shows the identification of the Glu-C peptide E2* (containing the first, most N-terminal, cysteine C1) (SEQ ID NO: 110) and that it is alkylated (denoted by *). B. A different zoomed in portion of the same centroided MS chromatogram shows the identification of the Glu-C generated disulfide-bonded E1-E2:E1-E2 dipeptide (core sequence disclosed as SEQ ID NO: 111). E1-E2 signifies a missed cleavage at a glutamic acid residue within the peptide.

FIG. 17. Peptide Mapping of Reduced and Alkylated 533-128. A. Sequence (SEQ ID NO: 3) coverage (75.4%) for the BiopharmaLynx analysis of the Asp-N digest. B. Sequence (SEQ ID NO: 3) coverage (56.9%) for the BiopharmaLynx analysis of the trypsin digest. Amino acids in purple text indicate identification. Light gray text indicates no identification. Turquoise highlighted cysteines indicate in vitro cysteine alkylated residues identified. Yellow highlighted N/Q residues indicate deamidations identified. These deamidations were searched for variably, thus identification alone does not indicate at what level each of these residues is deamidated. Some may in fact be false identifications, and further analysis is required to confirm these deamidations. C. LC-MS chromatogram showing the peaks associated with the peptides identified for the Asp-N digest. D. LC-MS chromatogram showing the peaks associated with the peptides identified for the Asp-N digest.

Figure 18A:
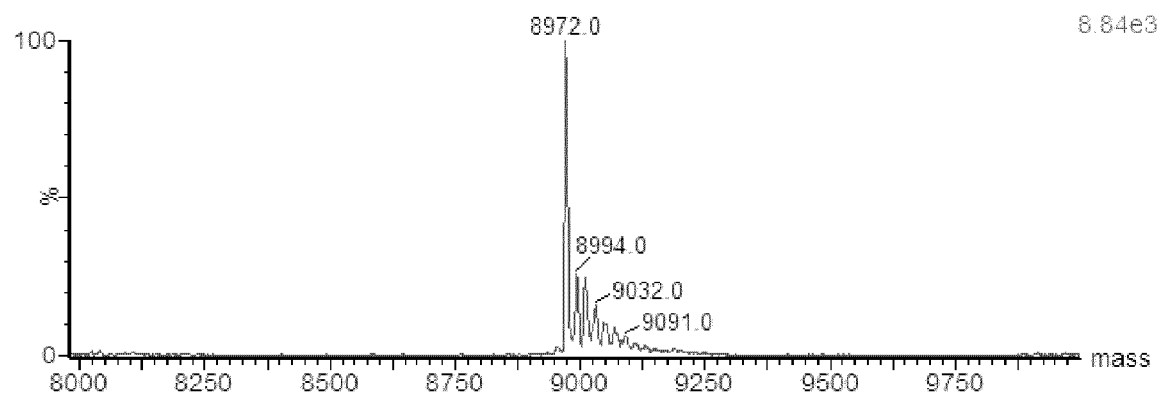
Figure 18B:
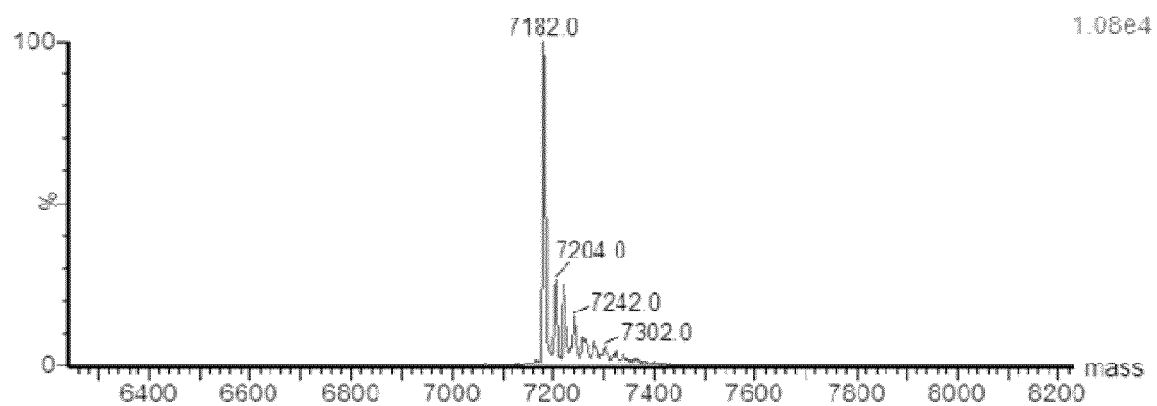

FIG. 18. Manual Identification of Large Peptides Not Identified by BiopharmaLynx Software. MS spectra from the respective peaks were summed and deconvoluted using MaxEnt1. A. Deconvoluted spectra from the 29.1 min. peak. For the peptide 179-267 (a.a.), the observed MW was 0.9 Da from the theoretical MW (8,971.15 Da). B. Deconvoluted spectra from the 30.5 min. peak. For the peptide 107-178 (aa), the observed MW was 3.8 Da from the theoretical MW (7,178.19 Da).

Figure 19A:
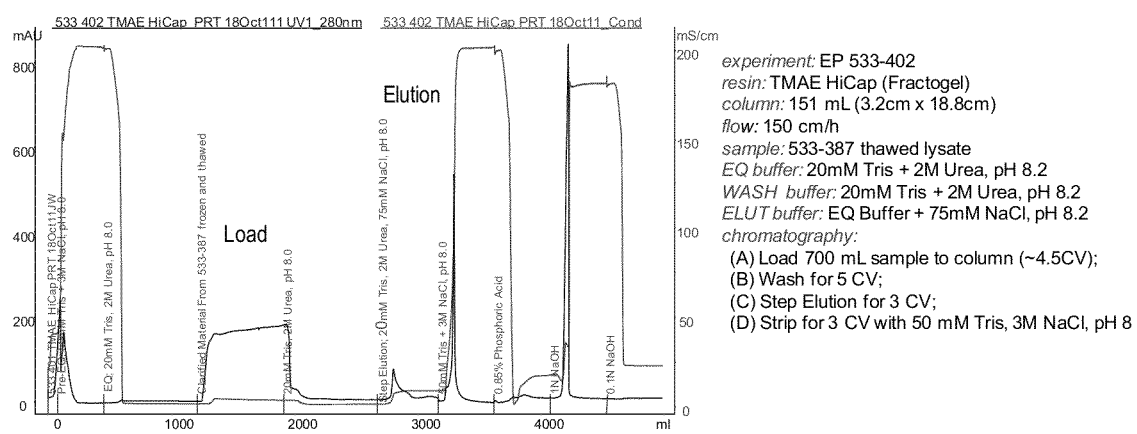
Figure 19B:
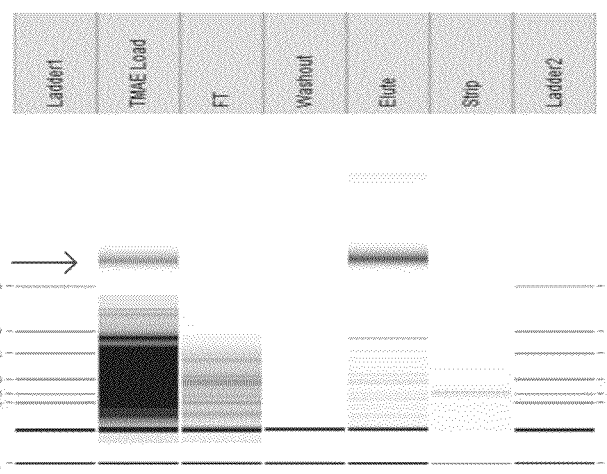

FIG. 19. TMAE HiCap Chromatography for Batch 533-406. A. Chromatogram and column run conditions. B. SDS-CGE gel-like image analysis of fractions.

Figure 20A:
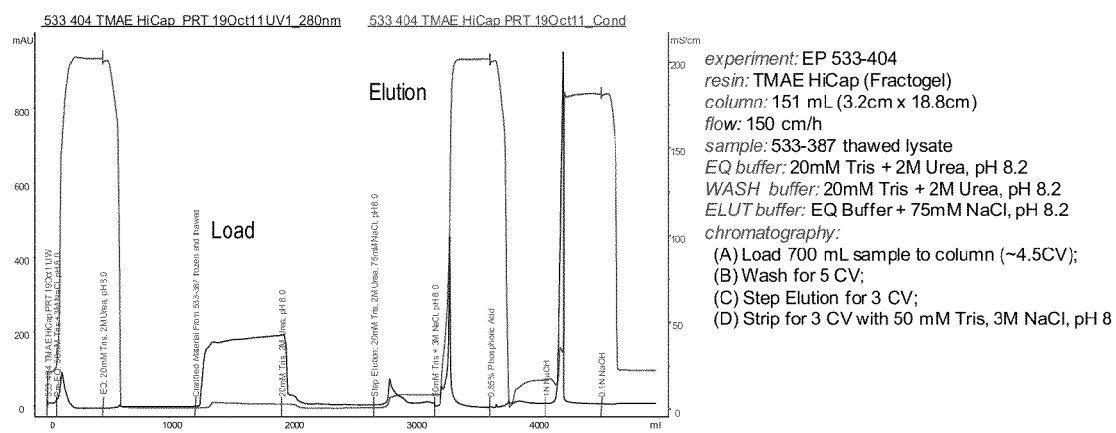
Figure 20B:
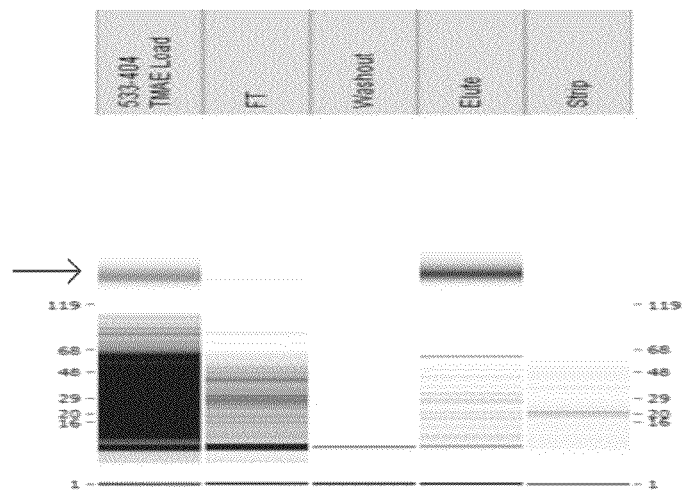

FIG. 20. TMAE HiCap Chromatography for Batch 533-407. A. Chromatogram and column run conditions. B. SDS-CGE gel-like image analysis of fractions.

Figure 21A:
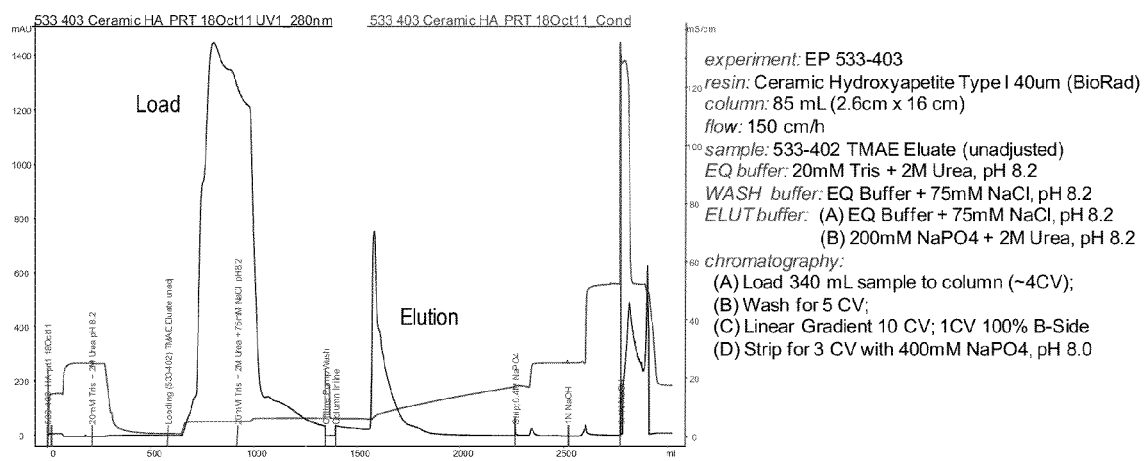
Figure 21B:
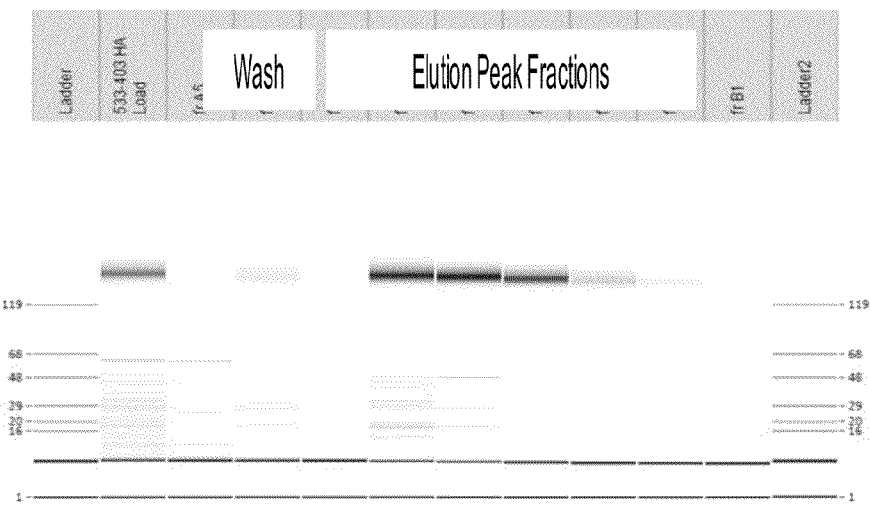

FIG. 21. Ceramic HA Type I Chromatography for Batch 533-406. A. Chromatogram and column run conditions. B. SDS-CGE gel-like image analysis of fractions.

Figure 22A:
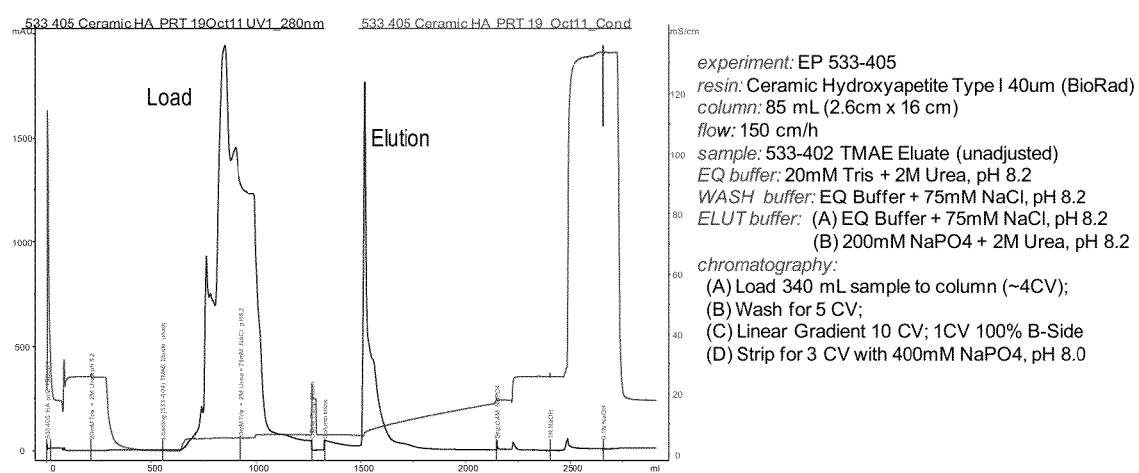
Figure 22B:
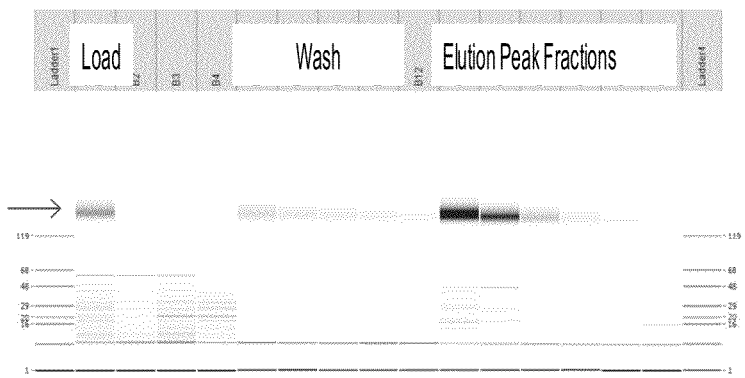

FIG. 22. Ceramic HA Type I Chromatography for Batch 533-407. A. Chromatogram and column run conditions. B. SDS-CGE gel-like image analysis of fractions.

Figure 23:
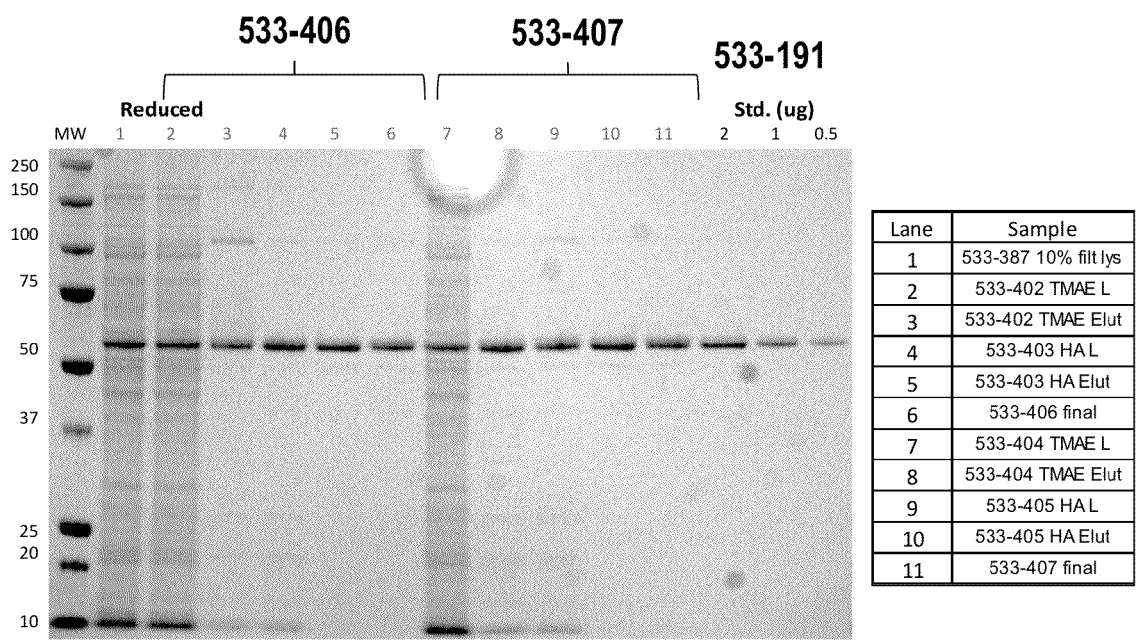

FIG. 23. SDS-PAGE of Integrated Purification Runs. Recombinant CSP batches 533-406 and 533-407 were analyzed by SDS-PAGE using a 10% Bis-Tris gel with MOPS buffer; MW=molecular weight markers; L=column load; Elut=column elution sample; Final=final purified rCSP.

Figure 24:
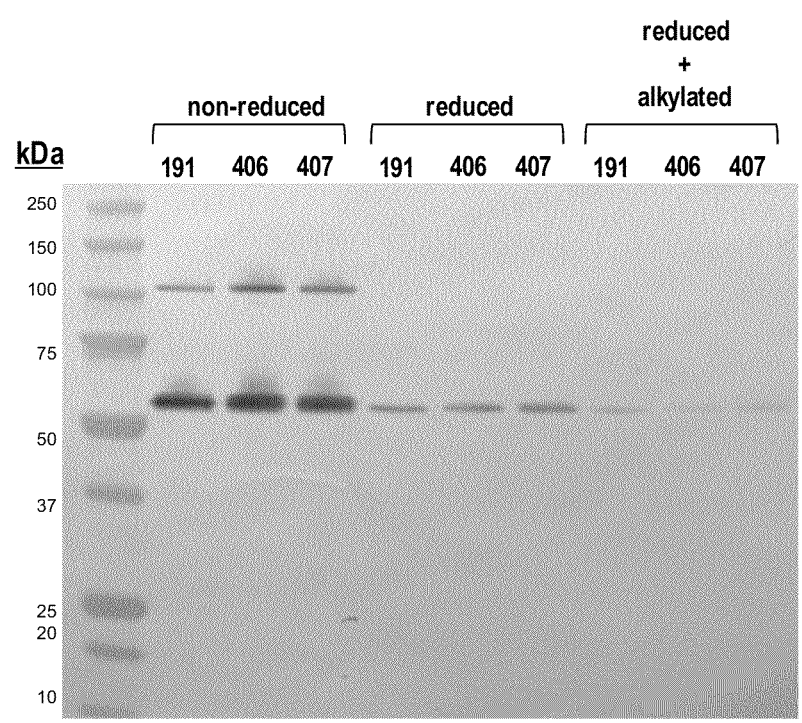

FIG. 24. Western Blot Analysis of Integrated Purification Runs. Recombinant CSP, batch 533-406, 533-407 and 533-191 analyzed by Western blot using conformation-specific 4C2 antibody.

Figure 25A:
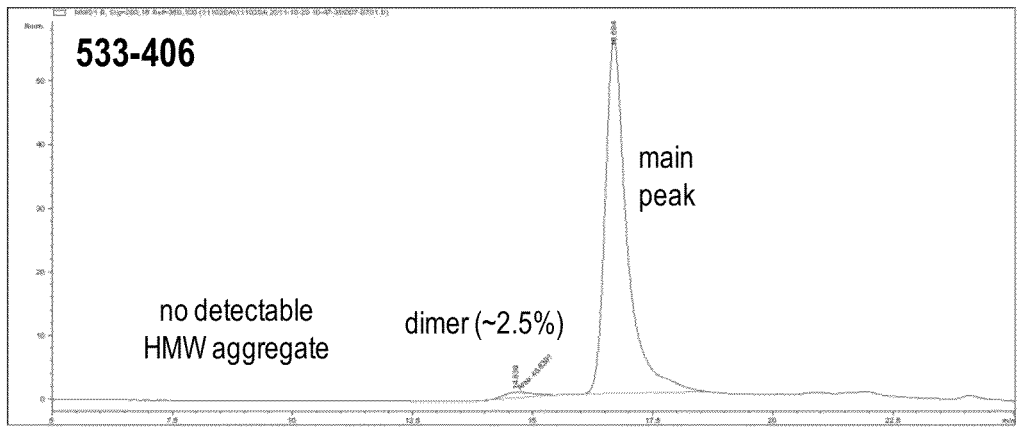
Figure 25B:
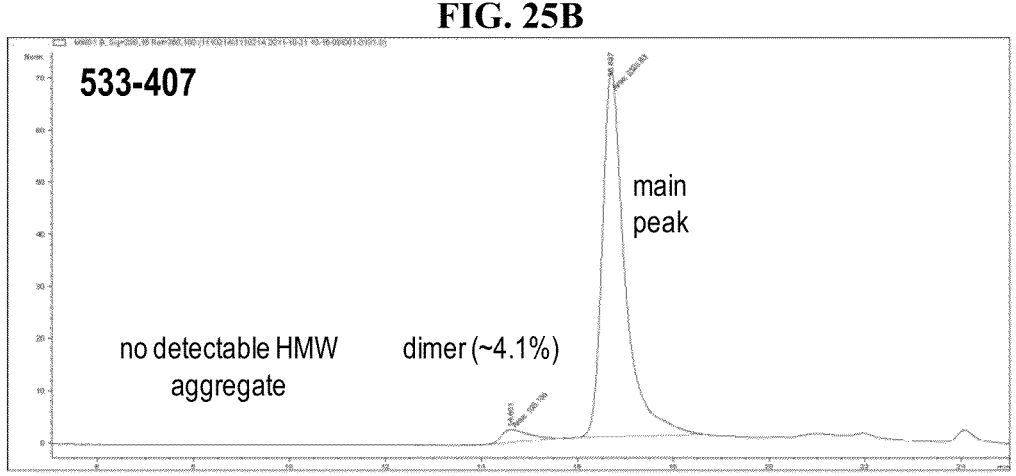
Figure 25C:
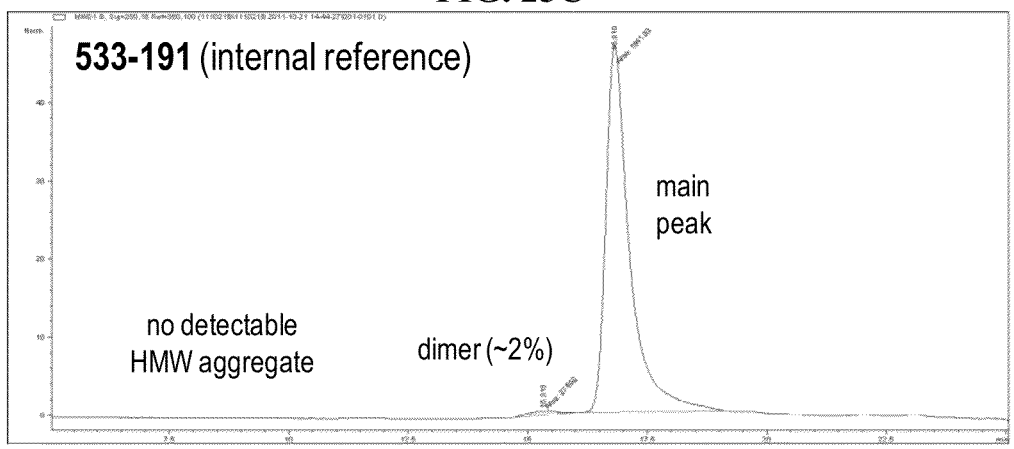

FIG. 25. Size Exclusion HPLC Analysis of rCSP. A. SE-HPLC chromatogram of rCSP batch 533-406. B. SE-HPLC chromatogram of rCSP batch 533-407. C. SE-HPLC chromatogram of rCSP reference 533-191.

Figure 26A:
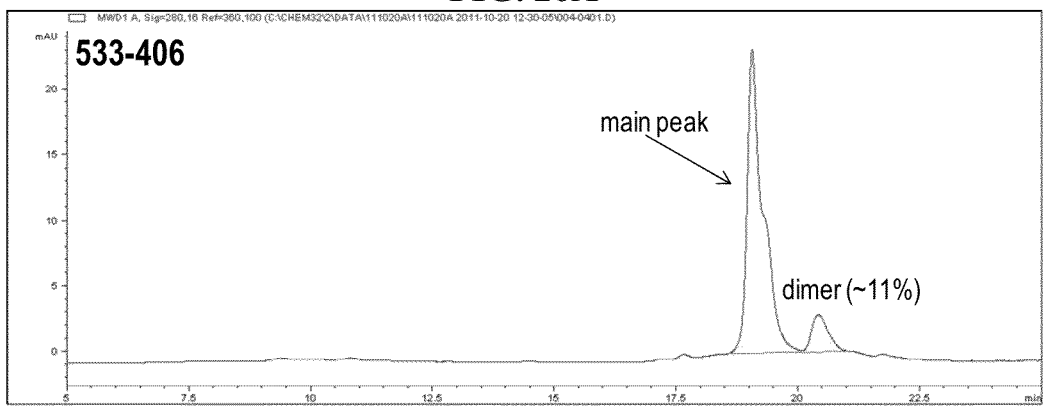
Figure 26B:
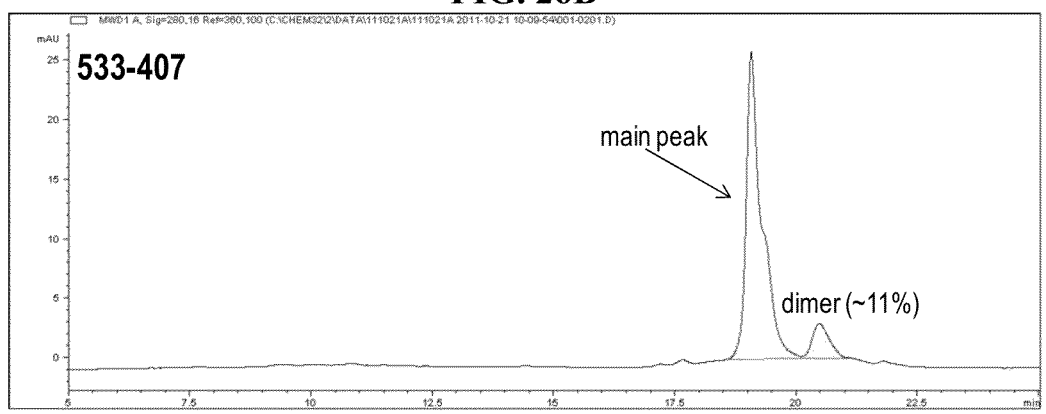
Figure 26C:
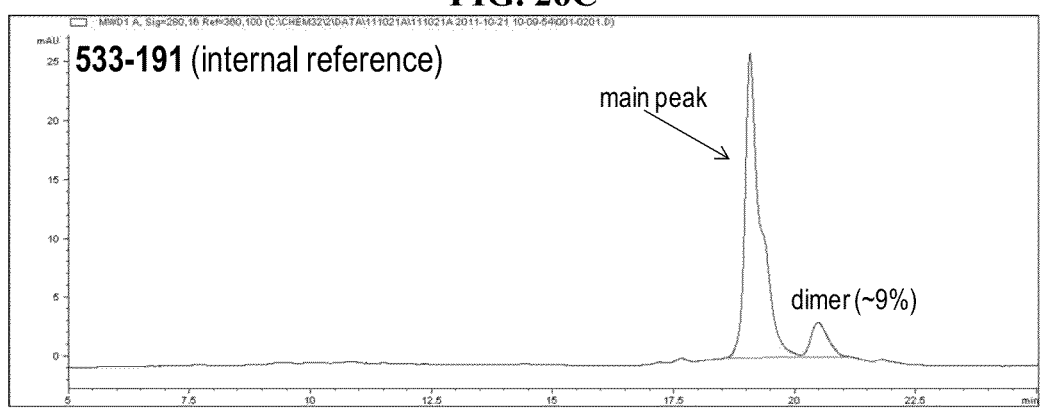

FIG. 26. RP-HPLC Analysis of rCSP. A. RP-HPLC chromatogram of rCSP batch 533-406. B. RP-HPLC chromatogram of rCSP batch 533-407. C. RP-HPLC chromatogram of rCSP reference 533-191.

Figure 27A:
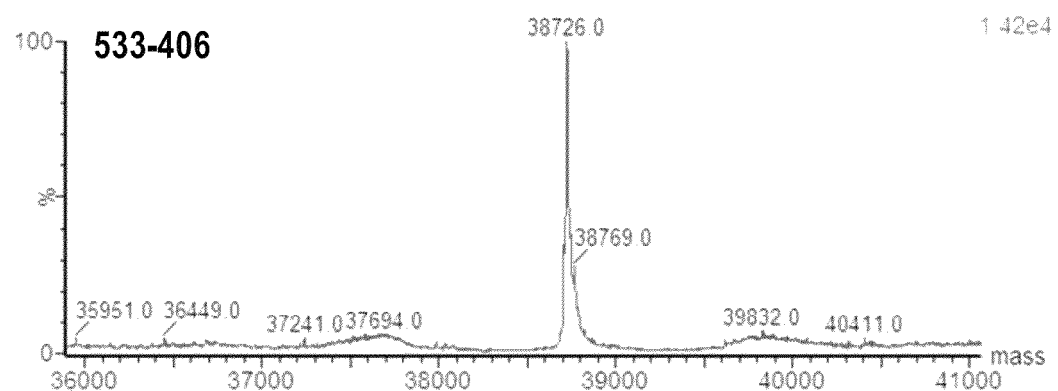
Figure 27B:
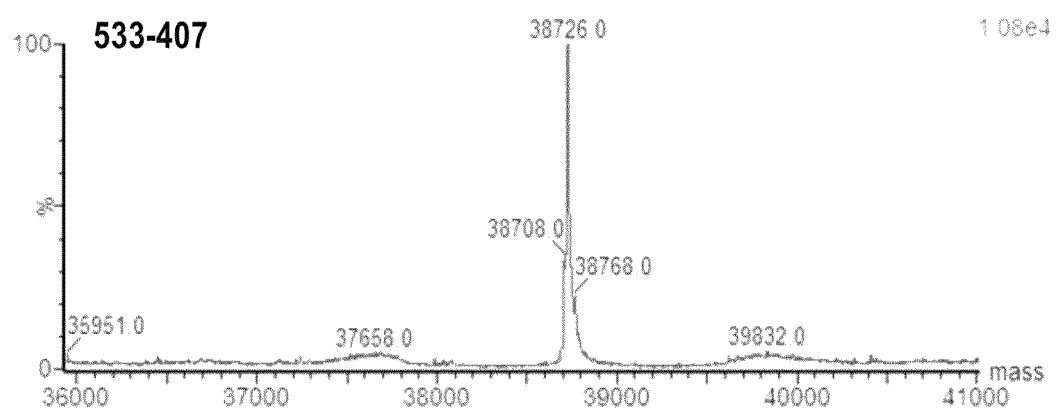
Figure 27C:
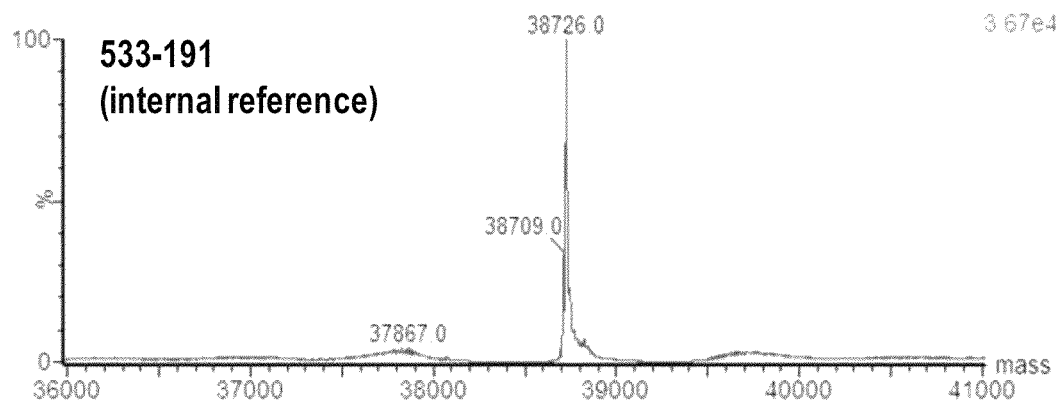

FIG. 27. Intact Mass Analysis of rCSP. A. Deconvoluted spectrum of rCSP batch 533-406. B. Deconvoluted spectrum of rCSP batch 533-407. C. Deconvoluted spectrum of rCSP reference 533-191.

Figure 28A:
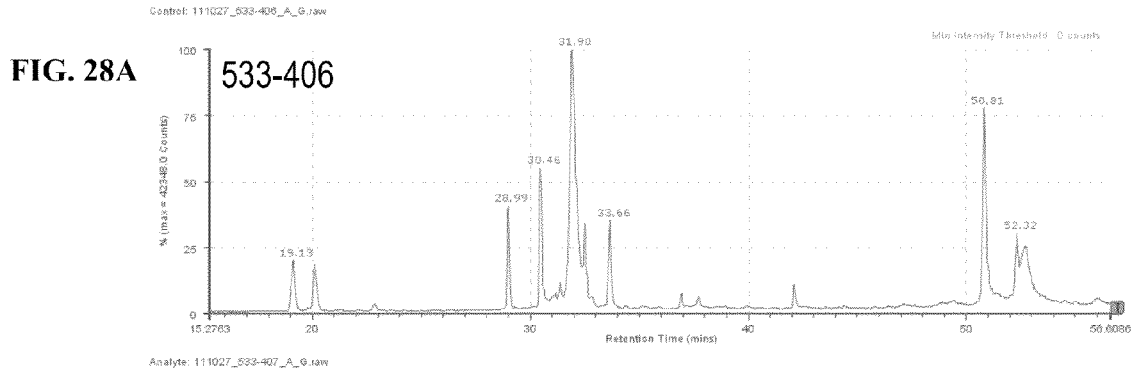
Figure 28B:
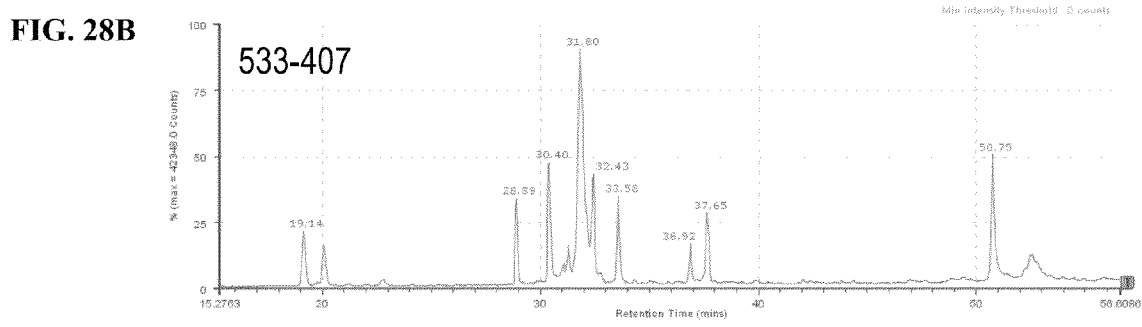
Figure 28C:
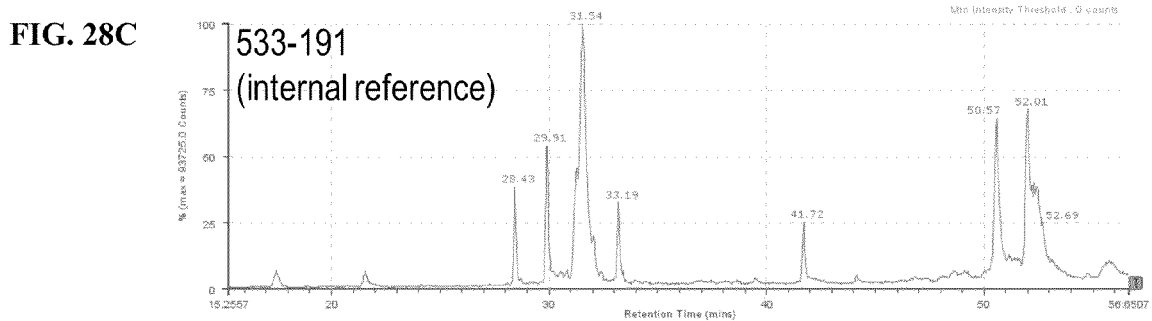

FIG. 28. Peptide Mapping Analysis of rCSP. A. LC/MS GluC peptide map of rCSP batch 533-406. B. LC/MS GluC peptide map of rCSP batch 533-407. C. LC/MS GluC peptide map of rCSP reference 533-191.

Figure 29A:
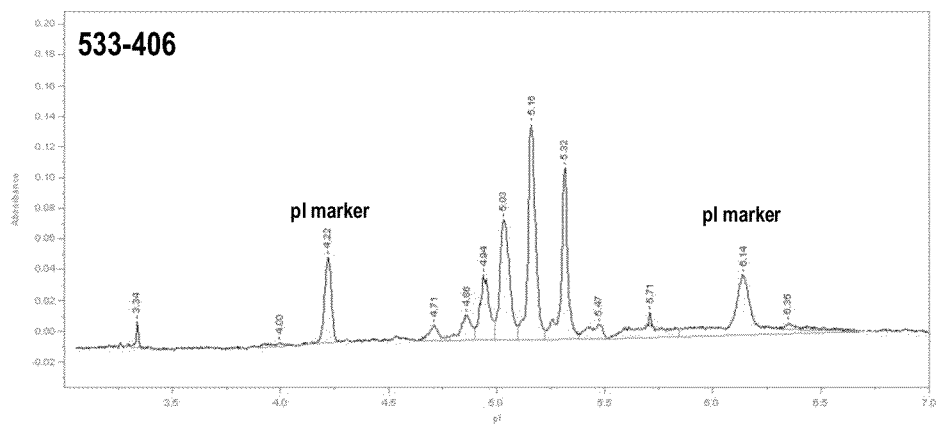
Figure 29B:
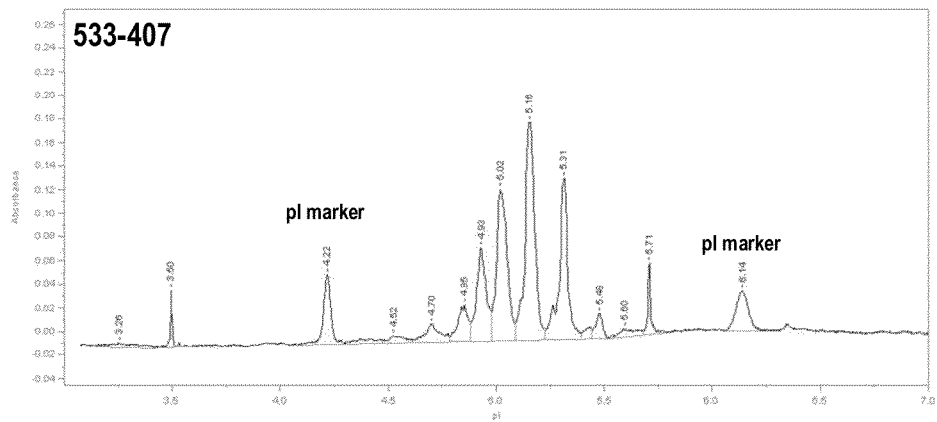
Figure 29C:
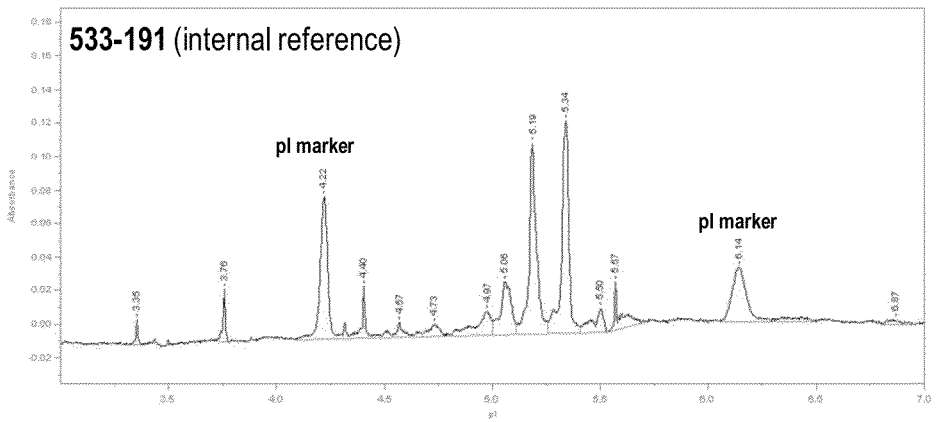

FIG. 29. Capillary Isoelectric-focusing (cIEF) Analysis of rCSP. A. cIEF analysis of rCSP batch 533-406. B. cIEF analysis of rCSP batch 533-407. C. cIEF analysis of rCSP reference 533-191.

FIG. 30. Far UV Circular Dichroism Analysis of rCSP and Intrinsic Fluorescence Analysis of rCSP. A. Far UV Circular Dichroism Analysis of rCSP. Instrument: JASCO 815; Temperature=20° C.; Scan speed=100 nm/min; D.I.T.=1 sec; Data pitch=0.1 nm; Accumulations=5; CD spectra of 533-191 (internal reference), 533-406, and 533-407 as indicated. B. Intrinsic Fluorescence Analysis of rCSP. Measure Mode: Em. Spectrum; Sensitivity=740 V; D.I.T.=1 sec; Bandwidth (Ex)2.00=nm; Bandwidth(Em)=10 nm; Ex. Wavelength=280 nm; Measure Range=295-395 nm; Data pitch=1 nm; Shutter Control=Auto; CD Detector=PMT; Accumulations=3; Solvent=PBS; Concentration 166 (w/v) %; Temperature increment 20° C. Savitzky-Golay smoothing with a convolution width of 25 was applied to the spectra. Fluorescence spectra of 533-191 (internal reference), 533-406, and 533-407 as indicated.

Figure 31:
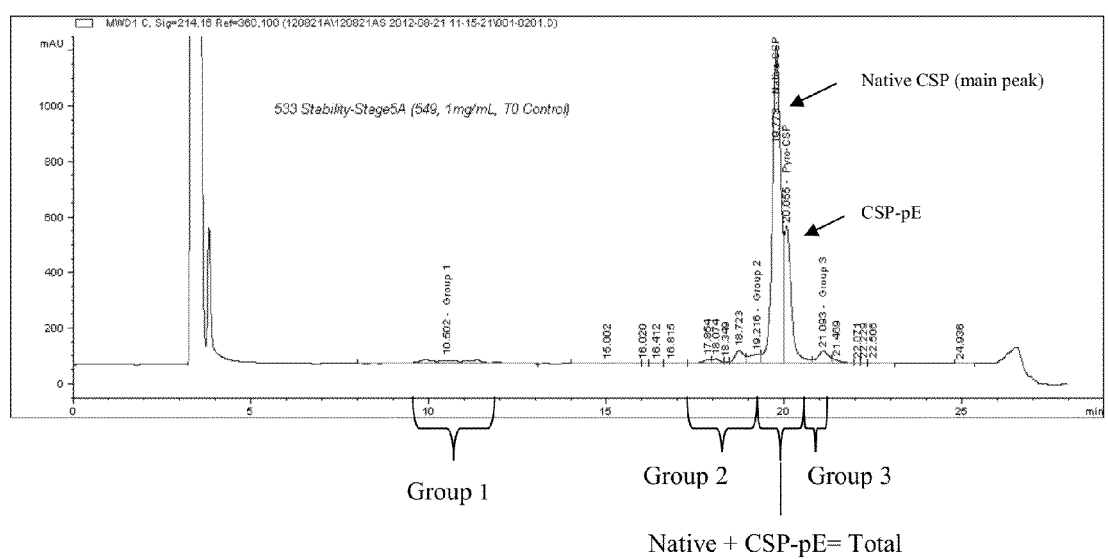

FIG. 31. RP-HPLC Analysis of rCSP. RP-HPLC of 1 mg/ml rCSP at 4° C., pH 7.5, at Time 0 indicating Group 1-3 peaks. pE=pyroglutamate-containing shoulder.

Figure 32A:
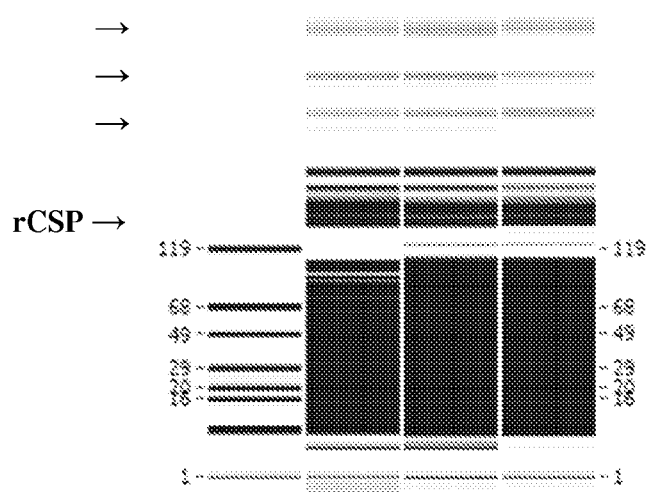
Figure 32B:
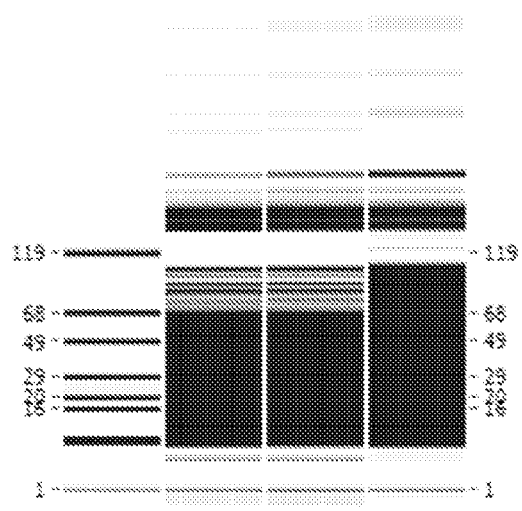
Figure 32C:
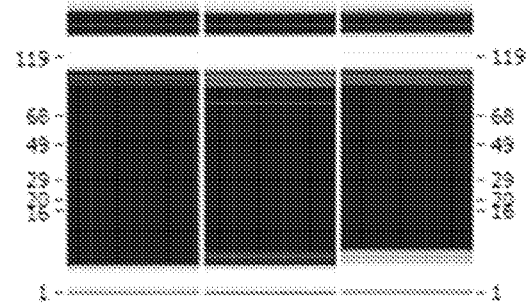

FIG. 32. Effect of Post-freeze Hold Time on High Molecular Weight Species. Frozen and thawed bulk filtrates from Engineering Run 1 paste and Process Run Through paste were showing effect on laddering of post-freeze-thaw hold time (T). A. Samples not held post-thaw (T=0). High molecular weight species "laddering" indicated by upper three arrows. rCSP indicated by lower arrow. B. Samples held at room temperature for 2.5 hours post-thaw (T=2.5). C. Samples held at room temperature for 6 hours post-thaw (T=6). All Panels: Lane 1=MW markers; Lane 2=PRT (−252) pre-2 µm filtration; Lane 3=PRT (−445) post-2 µm filtration; Lane 3=ER1 (−445) post 2-µm filtration.

DETAILED DESCRIPTION OF THE INVENTION

The present invention provides a scalable, novel process for purifying recombinant *P. falciparum* circumsporozoite protein (CSP). In the methods of the present invention, rCSP is obtained at high yields without the need for denaturing and refolding the protein. This achievement is significant for at least the following reasons: full-length CSP tends to form dimers and higher aggregates, and the N-terminus of CSP monomer is frequently degraded. Dimerization is associated with the presence of an unpaired cysteine residue near the N-terminus of the monomer. Previous attempts to eliminate the dim er required discarding it, or denaturing and refolding the protein. The methods of the present invention overcome the above obstacles using a novel process that makes use of dimerized CSP, without the need for denaturation and refolding. In the present methods, the CSP dimer is purified under non-denaturing conditions, then subjected to novel preferential reducing conditions. These preferential reducing conditions reduce the intermolecular disulfide bonds to separate the monomers, while preserving each monomer's intramolecular disulfide bonds. Therefore, refolding is not needed and output is vastly increased due to use of the dimer that otherwise would be discarded. A striking advantage of the claimed method is that the CSP monomer obtained from the rCSP that was maintained as a dimer during purification is not degraded at the N-terminus. Therefore, both the quality and quantity of the purified rCSP is vastly improved by the present invention.

In embodiments, the purification process of the present invention comprises:
1) Obtaining a bacterial cell lysate preparation, wherein the bacterial cell lysate preparation comprises rCSP dimers;
2) Purifying the rCSP dimers; and
3) Subjecting the purified rCSP dimers to preferential reducing conditions,
thereby obtaining high quality rCSP.

As described, the preferential reducing conditions reduce the intermolecular disulfide bonds to separate the monomers, while preserving each monomer's intramolecular disulfide bonds.

In embodiments, the purification process comprises further purification of the separated rCSP monomers. In embodiments, host cell proteins are removed from the rCSP monomers by chromatography, e.g., hydrophobic interaction chromatography.

In embodiments, the purification process further comprises removing reducing agents introduced by the preferential reducing conditions by buffer exchange. In these embodiments, the undegraded, rCSP monomer obtained is not aggregated.

In specific embodiments, the purification step comprises:
a) Separation of the cell lysate preparation into a soluble and insoluble fraction, wherein the soluble fraction comprises rCSP dimers; and
b) Separation of the rCSP dimers in the soluble fraction from host cell proteins.

In embodiments, the invention further provides methods for removing reducing agents, disaggregating agents and/or other unwanted reagents following the preferential reducing step, without resulting in the formation of rCSP HMW aggregates.

The present invention also provides rCSP stable liquid formulations, including high concentration rCSP stable liquid formulations.

Figure 1:
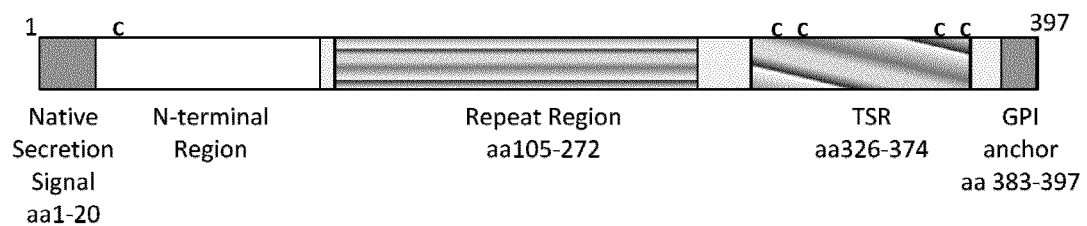
FIG. 1. P. falciparum CSP Protein Structure. The diagram shows the domains in the protein set forth in GenBank CAB38998, and the cysteines (each designated by C) at residues 25, 334, 338, 369 and 374.

*P. falciparum* Circumsporozoite Protein Expression
*P. falciparum* Circumsporozoite Protein The *P. falciparum* circumsporozoite protein (CSP) is a monomer composed of three major regions: an N terminus that binds heparin sulfate proteoglycans, a four-amino acid repeat region (NANP), and a thrombospondin-like type I repeat domain in the C-terminal portion of the protein (FIG. 1). Structural studies indicate that the repeat region forms a rod-like structure about 21-25 nm in length and 1.5 nm in width (Plassmeyer, et al., 25 Sep. 2009, J. Biol. Chem., vol. 284 no. 39: 26951-26963, incorporated herein by reference).

CSP amino acid and nucleotide sequences are set forth herein in SEQ ID NOS: 1-6, and in the published literature, e.g., at GenBank accession numbers CAB38998 (protein) and XM_001351086.1 (nucleotide); by Hall, N., et al., 2002, Nature 419(6906), 527-531; and in U.S. Pat. No. 7,722,889, "*Plasmodium* liver stage antigens," all incorporated herein by reference. A number of CSP polymorphisms having very similar sequences and the same structural features as described above and, e.g., by Plassmeyer, et al., 2009, been identified.

Vaccine development targeting CSP has focused on the central repeat region containing B-cell epitopes, and the C-terminus containing the TSR domain, T-cell epitopes, and B-cell epitopes (Plassmeyer, et al., 2009, and Rathore and McCutchan, 2000, Proc. Nat. Acad. Sci. vol. 97 no. 15: 8530-35). The N-terminal region has now been shown to play a role in liver cell attachment and immunogenicity, and to contain an epitope that interacts with liver cells through heparin sulfate. Antibodies raised to the N-terminal region epitope were found to be inhibitory in a sporozoite invasion assay. (See, e.g.: Plassmeyer, et al., 2009; Ancsin and Kisilevsky, 2004, J. Biol. Chem. 279: 21824-32; Rathore, et al., 2005, J. Biol. Chem. 280: 20524-9; and Rathore, et al., 2002, J. Biol. Chem. 277: 7092-7098.) Rathore, et al., 2002 reported the involvement of amino acid residues 28-33 in receptor binding, and recognition of residues 65-110, which potentially form a T-cell epitope, was reported by Bongfen, et al., 2009 (Vaccine 27(2):328-35) to be protective from disease. Therefore, it is a priority to obtain CSP having the N-terminal region for use in vaccine research and production.

CSP has five cysteine residues. One cysteine residue is located near the N-terminus, at position 25 of the full-length amino acid sequence (which includes the leader) as shown in FIGS. 1 and 2A. In the sequences without the leader shown in FIGS. 2B and 2C, this cysteine is at positions 25, 6 and 5, respectively, which can be referred to as "C25" or "Cys 25," "C6" or "Cys 6," or "C5" or "Cys 5." Cys 25 is implicated in the disulfide bonding between CSP monomers that produces CSP dimers. Typically, in non-denaturing CSP purification schemes, dimers comprise a large portion of the rCSP. Dimers previously have been observed to be present at up to about 40 percent of the CSP measured in recombinant bacterial lysate.

The N-terminal region of CSP is susceptible to clipping at several specific sites, including two major sites. Depending on the numbering used, one major site of proteolysis occurs between C5 and Y6, resulting in removal of residues 1-5 (referencing the numbering in SEQ ID NO: 3 in FIG. 2C), between C25 and Y26 resulting in removal of residues 1-25 (referencing the numbering in SEQ ID NO: 1 in FIG. 2A), or between C6 and Y7 resulting in removal of residues 1-6 (referencing the numbering in SEQ ID NO: 2 in FIG. 2B). The second major site is between V14 and L15, resulting in removal of residues 1-14 (referencing the numbering in SEQ ID NO: 3 in FIG. 2C), between V34 and L35 resulting in removal of residues 1-34 (referencing the numbering in SEQ ID NO: 1 in FIG. 2A), or between V15 and L16 resulting in removal of residues 1-15 (referencing the numbering in SEQ ID NO: 2 in FIG. 2B). In preparations wherein a high level of clipping is observed, additional clipping is noted between residues N29/E30 and S44/L45 (referencing the numbering in SEQ ID NO: 3 in FIG. 2C).

"Degradation" or "proteolysis" at the N-terminus refers to nonspecific degradation as well as specific clipping. The CSP that is unclipped, undegraded or unproteolyzed in the N-terminal region up to a certain residue is referred to herein as being intact to the most N-terminal residue present. For example, a CSP species that is either clipped or nonspecifically degraded to remove residues 1, 2, and 3, and includes residue 4, is referred to as being degraded to residue 4 and intact to residue 4. As a specific example, a species that is degraded to residue Glutamine 4 (Q4) and includes residue Q4 is said to be degraded to residue Q4 and intact from residue Q4. In embodiments of the present invention, not more than 10% of the purified rCSP obtained is degraded to a specified residue, e.g., a residue selected from residues 2-50. In related embodiments, at least 90% of the purified rCSP is intact to a residue selected from residues 1-50. In embodiments of the present invention, not more than 10%, 9%, 8%, 7%, 6%, 5%, 4%, 3%, 2%, 1% or none of the purified rCSP obtained is degraded, clipped, or proteolyzed to an amino acid selected from residues 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In embodiments, at least 90%, 91%, 92%, 93%, 94%, 95%, 96%, 97%, 98%, 99% or 100% of the purified rCSP obtained is intact to an amino acid selected from residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

The C-terminal region, which contains the thrombospondin-like type I repeat (TSR), has four cysteine residues. (See, e.g., position numbers 315, 319, 350, and 355 of the CSP sequence of FIG. 2A, positions 334, 338, 369, and 374 of the full sequence of FIG. 2A, positions 315, 319, 350, and 355 of FIG. 2B, and positions 314, 318, 349, and 354 of FIG. 2C). Disulfide bonds form between $C_{314}$ and $C_{349}$, and $C_{318}$ and $C_{354}$ using the numbering in FIG. 3C, or between $C_{315}$ and $C_{350}$, and $C_{319}$ and $C_{355}$ using the numbering in FIG. 3B. Disruption of disulfide bonding between C-terminal region cysteine residues was reported to affect the binding of CSP to target HepG2 cells (Rathore, D., and McCutchan, T., 2000, Proc. Nat. Acad. Sci. vol. 97 no. 15: 8530-35). Purification schemes that require denaturing and refolding the substantial proportion of dimerized or aggregated rCSP typically obtained face the challenge of restoring proper disulfide bonding in the C-terminal region (intact disulfide bonds).

In the methods of the present invention, the undesirable CSP dimer is preferentially reduced to generate CSP monomer, without denaturing the protein. In embodiments of the present invention, the undenatured purified rCSP obtained comprises less than about 5% CSP having improper disulfide bonding. Improper disulfide bonding occurs when one or both of the two disulfide bonds in the C-terminal region is improperly paired (e.g., a cysteine is paired with the wrong cysteine or is not paired). Improper disulfide bonding can be evaluated using any method known to those of skill in the art or described herein.

In embodiments, the purified rCSP obtained comprises less than about 10%, less than about 9%, less than about 8%, less than about 7%, less than about 6%, less than about 5%, less than about 4%, less than about 3%, less than about 2%, or less than about 1% denatured rCSP, e.g., having improper disulfide bonding. Improper disulfide bonding is identified when at least one of the two native disulfide bonds in the C-terminal region is mispaired or unpaired. In embodiments, at least about 90%, 91%, 92%, 93%, 94%, 95%, 96%, 97%, 98%, 99% or 100%, respectively, of the purified rCSP has intact disulfide bonds.

FIG. 2A shows the full-length protein as provided at GenBank CAB38998, comprising the putative native secretory signal peptide (not present in the mature form of the protein), and the GPI anchor region. In embodiments, the purified rCSP obtained using the methods of the present invention does not comprise the GPI anchor. According to Ophorst, et al., deleting the GPI anchor region improves the immunogenicity of P. falciparum CSP without altering expression or secretion of the protein (Ophorst, et al., 9 Feb. 2007, Vaccine 25(8): 1426-36). In embodiments, the GPI anchor region is included. In embodiments, the GPI anchor region is truncated, i.e., part of it is present. Examples of amino acid sequences of CSP contemplated for purification using the methods of the present invention are shown in FIGS. 2B and 2C. FIG. 2B depicts a cytoplasmic species having the N-terminal methionine in addition to amino acids 21 to 382 of GenBank CAB38998. FIG. 2C depicts the periplasmic species corresponding to the species in FIG. 2B, also comprising amino acids 21 to 382 of GenBank CAB38998. In embodiments, a secretion leader is fused to the N-terminus of the protein for periplasmic secretion of the CSP.

The CSP of FIG. 2A is a monomer of 397 amino acids in length, having a molecular weight of about 42.6 kDa and an isoelectric point of 5.37. The mature form (i.e., without the secretion leader, amino acids 1-20) of FIG. 2C is a protein having a molecular weight of about 38.7 kDa and an isoelectric point of 5.21. The molecular weight has been observed to be 38725.0 Da when fully reduced, and 38721.0 Da when non-reduced (with two native intramolecular disulfide bonds).

CSP Variants and Modifications

As described, the methods of the present invention provides overcome obstacles to rCSP purification previously encountered, including the tendency of rCSP to dimerize and aggregate due to the presence of an unpaired cysteine in the N-terminal region of the protein.

In embodiments, the methods of the invention are used to purify any sequence variant or modification of CSP. In embodiments, purification of any CSP variant or polymorph is contemplated, provided that it dimerizes due to interactions between monomers involving an unpaired thiol residue, e.g., cysteine, in the N-terminal region of the protein. CSP polymorphisms have been described by, e.g., Rathore, et al., 2005, referenced above, and Anders, et al., 1989, Polymorphic antigens in *Plasmodium falciparum*," Blood 74: 1865. Sequences disclosed in the published literature include, for example, the protein sequences at GenBank accession no. AAA29555, AAN87594, AAA29554.1, AAA29524.1, AAA63421.1 ACO49545.1, and AAA63422.1.

In embodiments, the dimerizing variants or modifications of CSP that can be purified using the methods of the present invention comprise an unpaired thiol residue in the N-terminal region, and an N-terminal region epitope at positions 93-113, as described by Rathore, et al., 2005 (numbering as used in report). In related embodiments, these dimerizing variants or modifications of CSP comprise an unpaired thiol residue in the N-terminal region, and the N-terminal region epitope sequence ENDDGNNEDNEKLRKPKHKKL (SEQ ID NO: 7) or DKRDGNNEDNEKLRKPKHKKL (SEQ ID NO: 8).

The invention contemplates purification of engineered rCSP modifications as well as naturally-occurring polymorphisms. Modifications include substitutions, insertions, elongations, deletions, and derivatizations, alone or in combination. In embodiments, the rCSP may include one or more modifications of a non-essential amino acid residue. A non-essential amino acid residue is a residue that can be altered, e.g., deleted or substituted, in the novel amino acid sequence without abolishing or substantially reducing the activity or function of the protein, e.g., the protein's immunogenicity or its ability to bind to a specific antibody. In embodiments, the rCSP can include one or more modifications of an essential amino acid residue. An essential amino acid residue is a residue that when altered, e.g., deleted or substituted, in the novel amino acid sequence the activity of the reference peptide is substantially reduced or abolished. The substitutions, insertions and deletions can be in any region of the rCSP. For example, the rCSP can include 1, 2, 3, 4, 5, 6, 7, 8, 9, 10, or more substitutions, both in a consecutive manner or spaced throughout the molecule. Alone or in combination with the substitutions, the rCSP can include 1, 2, 3, 4, 5, 6, 7, 8, 9, 10, or more insertions, again either in consecutive manner or spaced throughout the peptide molecule. The rCSP, alone or in combination with the substitutions and/or insertions, can include 1, 2, 3, 4, 5, 6, 7, 8, 9, 10, or more deletions, again either in consecutive manner or spaced throughout the peptide molecule. The rCSP, alone or in combination with the substitutions, insertions and/or deletions, can include 1, 2, 3, 4, 5, 6, 7, 8, 9, 10, or more amino acid additions.

Substitutions include conservative amino acid substitutions. A conservative amino acid substitution is one wherein the amino acid residue is replaced with an amino acid residue having a similar side chain, or similar physicochemical characteristics (e.g., electrostatic, hydrogen bonding, isosteric, hydrophobic features). The amino acids may be naturally or unnaturally occurring. Families of amino acid residues having similar side chains are known in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), .beta.-branched side chains (e.g., threonine, valine, isoleucine) and aromatic side chains (e.g., tyrosine, phenylalanine, tryptophan, histidine). Substitutions may also include non-conservative changes.

The terms "amino acid" or "amino acid residue" refer to natural amino acids, unnatural amino acids, and modified amino acids. Unless otherwise specified, reference to an amino acid includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to, homolysine, homoarginine, homoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid, pyroglutamate, and thioproline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine. Additional residues that can be incorporated are described in Sandberg et al. (1998) J. Med. Chem. 41:2481-2491.

Sequence identity, as is understood in the art, is a relationship between two or more polypeptide sequences or two or more polynucleotide sequences, as determined by comparing the sequences. In the art, identity also can refer to the degree of sequence relatedness between polypeptide or polynucleotide sequences, as determined by the match between strings of such sequences. Identity can be calculated by known methods including, but not limited to, those described in Computational Molecular Biology, Lesk, A. M., ed., Oxford University Press, New York (1988); Biocomputing: Informatics and Genome Projects, Smith, D. W., ed., Academic Press, New York, 1993; Computer Analysis of Sequence Data, Part I, Griffin, A. M. and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., Stockton Press, New York (1991); and Carillo, H., and Lipman, D., SIAM J Applied Math, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux et al. (1984) Nucleic Acids Research 12:387; suite of five BLAST programs, three designed for nucleotide sequences queries (BLASTN, BLASTX, and TBLASTX) and two designed for protein sequence queries (BLASTP and TBLASTN) (Coulson (1994) Trends in Biotechnology 12:76-80; Birren et al. (1997) Genome Analysis 1:543-559). The BLAST X program is publicly available from NCBI and other sources (BLAST Manual, Altschul, S., et al., NCBI NLM NIH, Bethesda, Md. 20894; Altschul et al. (1990) J. Mol. Biol. 215:403-410). The Smith Waterman algorithm also can be used to determine identity.

In embodiments, a variant rCSP has an amino acid sequence that is at least about 90%, at least about 91%, at least about 92%, at least about 93%, at least about 94%, at least about 95%, at least about 96%, at least about 97%, at least about 98% or at least about 99% identical to the sequence as set forth in SEQ ID NO: 1 (shown in FIG. 2A), SEQ ID NO: 2 (shown in FIG. 2B), or SEQ ID NO: 3 (shown in FIG. 2C). In embodiments, the variant rCSP is encoded by a nucleic acid sequence that is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the sequence as set forth in SEQ ID NO: 4 (shown in FIG. 3A) or SEQ ID NO: 5 (shown in FIG. 3B).

Expression of *P. falciparum* Circumsporozoite Protein

The methods of the present invention contemplate the purification of recombinant *P. falciparum* circumsporozoite protein produced in a bacterial overexpression system. Methods for cloning a gene encoding a recombinant protein into an expression vector, transforming a bacterial host cell with the expression vector, and growing the transformed host cells under conditions suitable for expressing recombinant CSP, are well within the knowledge of those having skill in the art. Suitable methods are also described herein and have been described in the literature.

Methods for expressing heterologous proteins, including useful regulatory sequences (e.g., promoters, secretion leaders, and ribosome binding sites), in *Pseudomonas* host cells, as well as other host cells useful in the methods of the present invention, are described, e.g., in U.S. Pat. App. Pub. No. 2008/0269070 and 2010/0137162, both titled "Method for Rapidly Screening Microbial Hosts to Identify Certain Strains with Improved Yield and/or Quality in the Expression of Heterologous Proteins," U.S. Pat. App. Pub. No. 2006/0040352, "Expression of Mammalian Proteins in *Pseudomonas Fluorescens*," and U.S. Pat. App. Pub. No. 2006/0110747, "Process for Improved Protein Expression by Strain Engineering," all incorporated herein by reference in their entirety. These publications also describe bacterial host strains useful in practicing the methods of the invention, wherein the host strains have been engineered to overexpress folding modulators or wherein protease mutations have been introduced, in order to increase heterologous protein expression.

Regulatory Elements

An expression construct useful in practicing the methods of the present invention can include, in addition to the protein coding sequence, any of the following regulatory elements operably linked thereto: a promoter, a ribosome binding site (RBS), a transcription terminator, and translational start and stop signals, transcriptional enhancer sequences, translational enhancer sequences, other promoters, activators, cistronic regulators, polycistronic regulators, tag sequences, such as nucleotide sequence "tags" and "tag" polypeptide coding sequences, which facilitate identification, separation, purification, and/or isolation of an expressed polypeptide.

Useful RBSs can be obtained from any of the species useful as host cells in expression systems according to, e.g., U.S. Pat. App. Pub. No. 2008/0269070 and U.S. Pat. App. Pub. No. 2010/0137162. Many specific and a variety of consensus RBSs are known, e.g., those described in and referenced by D. Frishman et al., Gene 234(2):257-65 (8 Jul. 1999); and B. E. Suzek et al., Bioinformatics 17(12):1123-30 (December 2001). In addition, either native or synthetic RBSs may be used, e.g., those described in: EP 0207459 (synthetic RBSs); O. Ikehata et al., Eur. J. Biochem. 181(3):563-70 (1989) (native RBS sequence AAGGAAG). Further examples of methods, vectors, and translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox, incorporated herein by reference in their entirety.

Leaders

In embodiments, a sequence encoding a secretion leader is fused to the sequence encoding the CSP. In embodiments, the secretion leader is a periplasmic secretion leader. In embodiments, the secretion leader is the native secretion leader.

In embodiments, soluble proteins are present in either the cytoplasm or periplasm of the cell during production. Methods for selecting and using secretion signal peptides or leaders in optimizing heterologous protein expression are described in detail in, e.g., U.S. Pat. No. 7,618,799, "Bacterial leader sequences for increased expression," and U.S. Pat. No. 7,985,564, "Expression systems with Sec-secretion," both incorporated herein by reference in their entirety, as well as in U.S. Pat. App. Pub. Nos. 2008/0269070 and 2010/0137162, referenced above. Table 1 below provides nonlimiting examples of secretion leader sequences contemplated for use in association with the methods of the present invention.

In embodiments, a secretion leader used is LAO, pbp, pbpA20V, or cupA2. In a specific embodiment, the LAO secretion leader is used.

TABLE 1

Example Secretion Leader Sequences

| Secretion Leader | Amino Acid Sequence | SEQ ID NO: |
|---|---|---|
| DsbA | MRNLILSAALVTASLFGMTAQA | 9 |
| Azu | MFAKLVAVSLLTLASGQLLA | 10 |
| Ibp-S31A | MIRDNRLKTSLLRGLTLTLLSLTLLSPAAHA | 11 |
| Tpr | MNRSSALLLAFVFLSGCQAMA | 12 |
| CupB2 | MLFRTLLASLTFAVIAGLPSTAHA | 13 |

TABLE 1-continued

Example Secretion Leader Sequences

| Secretion Leader | Amino Acid Sequence | SEQ ID NO: |
|---|---|---|
| CupA2 | MSCTRAFKPLLLIGLATLMCSHAFA | 14 |
| NikA | MRLAALPLLLAPLFIAPMAVA | 15 |
| Pbp A20V | MKLKRLMAAMTFVAAGVATVNAVA | 16 |
| DsbC | MRLTQIIAAAAIALVSTFALA | 17 |
| TolB | MRNLLRGMLVVICCMAGIAAA | 18 |
| Pbp | MKLKRLMAAMTFVAAGVATANAVA | 19 |
| Lao | MQNYKKFLLAAAVSMAFSATAMA | 20 |
| CupC2 | MPPRSIAACLGLLGLLMATQAAA | 21 |
| PorE | MKKSTLAVAVTLGAIAQQAGA | 22 |
| Pbp | MKLKRLMAAMTFVAAGVATANAVA | 23 |
| FlgI | MKFKQLMAMALLLALSAVAQA | 24 |
| ttg2C | MQNRTVEIGVGLFLLAGILALLLLALRVSGLSA | 25 |

Promoters

The promoters used in expressing rCSP purified in accordance with the present invention may be constitutive promoters or regulated promoters. Methods for selection of a useful promoter for regulating expression of a heterologous protein are well known in the art and described extensively in the literature. Common examples of useful regulated promoters include those of the family derived from the lac promoter (i.e., the lacZ promoter), including the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In embodiments, the promoter is derived from an E. coli organism.

Inducible promoter sequences can be used to regulate expression of CSP in accordance with the methods of the invention. In embodiments, inducible promoters useful in the methods of the present invention include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an E. coli organism.

Common examples of non-lac-type promoters useful in expression systems according to the present invention include, e.g., those listed in Table 2.

TABLE 2

Examples of non-lac Promoters

| Promoter | Inducer |
|---|---|
| $P_R$ | High temperature |
| $P_L$ | High temperature |
| Pm | Alkyl- or halo-benzoates |

TABLE 2-continued

Examples of non-lac Promoters

| Promoter | Inducer |
|---|---|
| Pu | Alkyl- or halo-toluenes |
| Psal | Salicylates |

See, e.g.: J. Sanchez-Romero & V. De Lorenzo (1999) Manual of Industrial Microbiology and Biotechnology (A. Demain & J. Davies, eds.) pp. 460-74 (ASM Press, Washington, D.C.); H. Schweizer (2001) Current Opinion in Biotechnology, 12:439-445; and R. Slater & R. Williams (2000 Molecular Biology and Biotechnology (J. Walker & R. Rapley, eds.) pp. 125-54 (The Royal Society of Chemistry, Cambridge, UK)). A promoter having the nucleotide sequence of a promoter native to the selected bacterial host cell also may be used to control expression of the transgene encoding the target polypeptide, e.g., a Pseudomonas anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., E. coli catabolite activator protein, MalT protein; AraC family transcriptional activators; repressor proteins, e.g., E. coli LacI proteins; and dual-function regulatory proteins, e.g., E. coli NagC protein. Many regulated-promoter/promoter-regulatory-protein pairs are known in the art. In one embodiment, the expression construct for the target protein(s) and the heterologous protein of interest are under the control of the same regulatory element.

Promoter regulatory proteins interact with an effector compound, i.e., a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

In embodiments wherein a lac family promoter is utilized, a lacI gene can also be present in the system. The lacI gene, which is normally a constitutively expressed gene, encodes the Lac repressor protein LacI protein, which binds to the lac operator of lac family promoters. Thus, where a lac family promoter is utilized, the lacI gene can also be included and expressed in the expression system.

Promoter systems useful in *Pseudomonas* are described in the literature, e.g., in U.S. Pat. App. Pub. No. 2008/0269070, also referenced above.

Host Cells

The methods of the present invention can be used to purify rCSP expressed in any bacterial host cell expression system, including, but not limited to, Pseudomonad and *E. coli* host cells. In embodiments, the rCSP is expressed in Pseudomonads or closely related bacterial organisms. In certain embodiments, the Pseudomonad host cell is *Pseudomonas fluorescens*. In embodiments, the host cell is *E. coli*, *Bacillus subtilus*, or *Pseudomonas putida*.

Bacterial host cells and constructs useful in practicing the methods of the invention can be identified or made using reagents and methods known in the art and described in the literature, e.g., in U.S. Pat. App. Pub. No. 2009/0325230, "Protein Expression Systems," incorporated herein by reference in its entirety. This publication describes production of a recombinant polypeptide by introduction of a nucleic acid construct into an auxotrophic *Pseudomonas fluorescens* host cell comprising a chromosomal lacI gene insert. The nucleic acid construct comprises a nucleotide sequence encoding the recombinant polypeptide operably linked to a promoter capable of directing expression of the nucleic acid in the host cell, and also comprises a nucleotide sequence encoding an auxotrophic selection marker. The auxotrophic selection marker is a polypeptide that restores prototrophy to the auxotrophic host cell. In embodiments, the cell is auxotrophic for proline, uracil, or combinations thereof. In embodiments, the host cell is derived from MB101 (ATCC deposit PTA-7841) using methods known to those of skill in the art and described in the scientific literature. For example, U.S. Pat. App. Pub. No. 2009/0325230, and Schneider, et al., 2005, "Auxotrophic markers pyrF and proC can replace antibiotic markers on protein production plasmids in high-cell-density *Pseudomonas fluorescens* fermentation," Biotechnol. Progress 21(2): 343-8, both incorporated herein by reference in their entirety, describe a production host strain auxotrophic for uracil, that was made by deleting the pyrF gene in strain MB101. The pyrF gene was cloned from strain MB214 (ATCC deposit PTA-7840) to generate a plasmid that can complement the pyrF deletion to restore prototrophy.

In particular embodiments, a dual PyrF-ProC dual auxotrophic selection marker system in a *P. fluorescens* host cell is used. A PyrF production host strain as described can be used as the background for introducing other desired genomic changes, including those described herein as useful in practicing the methods of the invention. In embodiments, the *P. fluorescens* host strain is a PyrF production host strain having the genotype ΔpyrF, lacI$^Q$, and ΔhtpX. In embodiments, the lacI$^Q$ is inserted in the lvs gene (lvs:lacIQ1).

In embodiments, *P. fluorescens* host strain DC469 (ΔpyrF, lacI$^Q$, ΔhtpX) which is derived from biovar 1 strain MB101, is used for producing rCSP useful in the methods of the invention. In strain DC469, the lacI$^Q$ is inserted in the lvs gene (lvs:lacIQ1). LacI$^Q$ insertions commonly are made in any of various appropriate locations, as known to those of skill in the art.

In embodiments, the host cell is of the order Pseudomonadales. Where the host cell is of the order Pseudomonadales, it may be a member of the family Pseudomonadaceae, including the genus *Pseudomonas*. Gamma Proteobacterial hosts include members of the species *Escherichia coli* and members of the species *Pseudomonas fluorescens*.

Other *Pseudomonas* organisms may also be useful. Pseudomonads and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA). Table 3 presents these families and genera of organisms.

TABLE 3

Families and Genera Listed in the Part, "Gram-Negative Aerobic Rods and Cocci" (Bergey, 1974)

| | |
|---|---|
| Family I. Pseudomonaceae | *Gluconobacter* |
| | *Pseudomonas* |
| | *Xanthomonas* |
| | *Zoogloea* |
| Family II. Azotobacteraceae | *Azomonas* |
| | *Azotobacter* |
| | *Beijerinckia* |
| | *Derxia* |
| Family III. Rhizobiaceae | *Agrobacterium* |
| | *Rhizobium* |
| Family IV. Methylomonadaceae | *Methylococcus* |
| | *Methylomonas* |
| Family V. Halobacteriaceae | *Halobacterium* |
| | *Halococcus* |
| Other Genera | *Acetobacter* |
| | *Alcaligenes* |
| | *Bordetella* |
| | *Brucella* |
| | *Francisella* |
| | *Thermus* |

*Pseudomonas* and closely related bacteria are generally part of the group defined as "Gram(−) Proteobacteria Subgroup 1" or "Gram-Negative Aerobic Rods and Cocci" (Buchanan and Gibbons (eds.) (1974) Bergey's Manual of Determinative Bacteriology, pp. 217-289). *Pseudomonas* host strains are described in the literature, e.g., in U.S. Pat. App. Pub. No. 2006/0040352, cited above.

"Gram-negative Proteobacteria Subgroup 1" also includes Proteobacteria that would be classified in this heading according to the criteria used in the classification. The heading also includes groups that were previously classified in this section but are no longer, such as the genera *Acidovorax*, *Brevundimonas*, *Burkholderia*, *Hydrogenophaga*, *Oceanimonas*, *Ralstonia*, and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey (1974). In addition hosts can include cells from the genus *Pseudomonas*, *Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis*, *Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus;* 2) Pseudomonadaceae family bacteria of the genera *Cellvibrio, Oligella,* and *Teredinibacter;* 3) Rhizobiaceae family bacteria of the genera *Chelatobacter, Ensifer, Liberibacter* (also called "*Candidatus Liberibacter*"), and *Sinorhizobium;* and 4) Methylococcaceae family bacteria of the genera *Methylobacter, Methylocaldum, Methylomicrobium, Methylosarcina,* and *Methylosphaera.*

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas filva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis;* and *Pseudomonas xiamenensis.* In one embodiment, the host cell is *Pseudomonas fluorescens.*

The host cell can also be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii;* and *Pseudomonas veronii.*

In other embodiments, the *Pseudomonas* host cell overexpresses DsbA, DsbB, DsbC, and DsbD. DsbA, B, C, and D are disulfide bond isomerases, described, e.g., in U.S. Pat. App. Pub. Nos. 2008/0269070 and 2010/0137162.

In other embodiments, the *Pseudomonas* host cell is wild-type, i.e., having no protease expression defects and not overexpressing any folding modulator.

A host cell that is defective in the expression of a protease can have any modification that results in a decrease in the normal activity or expression level of that protease relative to a wild-type host. For example, a missense or nonsense mutation can lead to expression of protein that not active, and a gene deletion can result in no protein expression at all. A change in the upstream regulatory region of the gene can result in reduced or no protein expression. Other gene defects can affect translation of the protein. The expression of a protease can also be defective if the activity of a protein needed for processing the protease is defective.

Examples of proteases and folding modulators useful for generating Pseudomonad host cells useful in association with the methods of the present invention, and methods for identifying host cells, are described in, e.g., U.S. Pat. App. Pub. Nos. 2008/0269070 and 2010/0137162, referenced above.

Codon Optimization

Methods for optimizing codons to improve expression of heterologous proteins in bacterial hosts are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety. Codon optimization for expression in *E. coli* is described, e.g., by Welch, et al., 2009, PLoS One, "Design Parameters to Control Synthetic Gene Expression in *Escherichia coli,* 4(9): e7002, incorporated by reference herein.

TABLE 4

Codons occurring at less than 5% in *P. flourescens* MB214

| Amino Acid(s) | Codon(s) Used | % Occurrence |
|---|---|---|
| G Gly | GGA | 3.26 |
| I Ile | ATA | 3.05 |
| L Leu | CTA | 1.78 |
|  | CTT | 4.57 |
|  | TTA | 1.89 |
| R Arg | AGA | 1.39 |
|  | AGG | 2.72 |
|  | CGA | 4.99 |
| S Ser | TCT | 4.28 |

The present invention contemplates the use of any coding sequence for the CSP, including any sequence that has been optimized for expression in the host cell being used. Sequences contemplated for use can be optimized to any degree as desired, including, but not limited to, optimization to eliminate: codons occurring at less than 5% in the *Pseudomonas* host cell, codons occurring at less than 10% in the *Pseudomonas* host cell, a rare codon-induced translational pause, a putative internal RBS sequence, an extended repeat of G or C nucleotides, an interfering secondary structure, a restriction site, or combinations thereof.

Furthermore, the amino acid sequence of any secretion leader useful in practicing the methods of the present invention can be encoded by any appropriate nucleic acid sequence.

Fermentation Format

Expression of recombinant proteins for purification according to the methods of the present invention can be carried in any fermentation format. For example, batch, fed-batch, semi-continuous, and continuous fermentation modes may be employed herein. Fermentation conditions that result in production of a recombinant protein, e.g., CSP, in a bacterial expression system can be optimized as deemed appropriate by one of skill in the art, using methods described in the literature. For example, methods for optimizing production of toxin proteins are described in U.S. Pat. App. Pub. No. 2011/0287443, "High Level Expression of Recombinant Toxin Proteins," incorporated by reference herein in its entirety. In embodiments, the fermentation medium may be selected from among rich media, minimal media, and mineral salts media. In other embodiments either a minimal medium or a mineral salts medium is selected. In certain embodiments, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium (see, B D Davis & E S Mingioli (1950) J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media can also contain mineral salts and a carbon source, but can be supplemented with, e.g., low levels of amino acids, vitamins, peptones, or other ingredients, though these are added at very minimal levels. Media can be prepared using the methods described in the art, e.g., in U.S. Pat. App. Pub. No. 2006/0040352, referenced and incorporated by reference above. Details of cultivation procedures and mineral salts media useful in the methods of the present invention are described by Riesenberg, D et al., 1991, "High cell density cultivation of *Escherichia coli* at controlled specific growth rate," J. Biotechnol. 20 (1):17-27.

Fermentation Scale

The purification methods of the present invention are particularly useful because they can be scaled up to process large amounts of protein. Scaling up production of rCSP typically results in rCSP aggregates. The present methods are compatible with large-scale processing and are contemplated for use when the starting material comprises large amounts of rCSP. The purification methods of the present invention also are contemplated for use in obtaining protein from bacterial cell lysate produced at any smaller scale. Thus, e.g., microliter-scale, centiliter scale, and deciliter scale fermentation volumes can be used. In embodiments, 1 Liter scale and larger fermentation volumes are used.

In embodiments, the fermentation volume is about 1 Liter to about 100 Liters. In certain embodiments, the fermentation volume is at least about 2 Liters, at least about 3 Liters, at least about 4 Liters, at least about 5 Liters, at least about 6 Liters, at least about 7 Liters, at least about 8 Liters, at least about 9 Liters, at least about 10 Liters, at least about 20 Liters, at least about 25 Liters, at least about 50 Liters, at least about 75 Liters, at least about 100 Liters, at least about 200 Liters, at least about 500 Liters, at least about 1,000 Liters, at least about 2,000 Liters, at least about 5,000 Liters, at least about 10,000 Liters, or at least about 50,000 Liters. In embodiments, the fermentation volume is about 1 Liter to about 5 Liters, about 1 Liter to about 10 Liters, about 1 Liter to about 20 Liters, about 1 Liter to about 25 Liters, about 1 Liter to about 50 Liters, about 1 Liter to about 75 Liters, about 10 Liters to about 25 Liters, about 25 Liters to about 50 Liters, or about 50 Liters to about 100 Liters.

High Throughput Screens

In some embodiments, a high throughput screen can be conducted to determine optimal conditions for expressing rCSP. The conditions that can be varied in the screen include, for example, the host cell, genetic background of the host cell (e.g., deletions of different protease genes or overexpression of folding modulators), type of promoter in an expression construct, type of secretion leader fused to the sequence encoding the recombinant protein, growth temperature, OD at induction when an inducible promoter is used, concentration of inducing agent used (e.g., IPTG when a lacZ promoter is used), duration of protein induction, growth temperature following addition of an inducing agent to a culture, rate of agitation of culture, method of selection for plasmid maintenance, volume of culture in a vessel, etc.

Methods of screening microbial hosts to identify strains with improved yield and/or quality in the expression of heterologous proteins are described, for example, in U.S. Pat. App. Pub. No. 2008/0269070.

Induction

As described elsewhere herein, inducible promoters can be used in the expression construct to control expression of the recombinant protein, e.g., a lac promoter. In the case of the lac promoter derivatives or family members, e.g., the tac promoter, the effector compound is an inducer, such as a gratuitous inducer, e.g., IPTG (isopropyl-β-D-1-thiogalactopyranoside, also called "isopropylthiogalactoside"), lactose, or allolactose. In embodiments, a lac promoter derivative is used, and recombinant protein expression is induced by the addition of IPTG to a final concentration of about 0.01 mM to about 1.0 mM, when the cell density has reached a level identified by an $OD_{575}$ of about 80 to about 160. In embodiments wherein a non-lac type promoter is used, as described herein and in the literature, other inducers or effectors can be used. In one embodiment, the promoter is a constitutive promoter. Methods for inducing promoters are described in the art, e.g., in U.S. Pat. No. 7,759,109, "High Density Growth of T7 Expression Strains with Auto-induction Option," and U.S. Pat. App. Pub. No. 2011/0217784, "Method for Producing Soluble Recombinant Interferon Protein without Denaturing," both incorporated herein by reference in their entirety.

In specific embodiments, the rCSP is expressed in *Pseudomonas fluorescens* and expression is regulated by a lac promoter. In these embodiments the fermentation culture is induced at 100-160 AU (absorbence units) at 575 nm induction cell density, with 0.1 to 0.2 mM IPTG, at pH 6.5 to 7.2, at a temperature of 27 to 32° C.

Protein Purification

In the methods of the present invention, dimers of recombinant *P. falciparum* CSP are purified from a bacterial cell lysate prepared from cells expressing rCSP. In embodiments, purification includes separation of the CSP dimer from the host cell debris and proteins and other impurities to generate a soluble fraction containing the CSP dimer and an insoluble fraction. The CSP dimer in the soluble fraction is separated from host cell proteins and any other undesired impurities. Separation from host cell debris, separation from host cell proteins, and separation from any other impurities, can be carried out in distinct process steps or in the same step(s), depending on the separation method used. Separation methods useful in accordance with the methods of the invention for purifying the rCSP are described in the literature, e.g., in Methods in Enzymology (1990) volume 182. A Guide to Protein Purification. Edited by M. P. Deutscher. Academic Press; and Ausubel, F. M., Brett, R., Kingston, R. E., Moore, D. D., Seidman, J. G., Smith, J. A., and Struhl, L. 1991. Current Protocols in Molecular Biology, Vol. 1. Wiley. New York, both incorporated herein by reference in their entirety.

Scalable Process

Scaling up production of rCSP typically results in protein aggregation. The purification process of the present invention is scalable and can be used to purify rCSP at high overall purification process yields from starting material, e.g., cell culture or bacterial cell lysate, comprising large amounts of rCSP. In embodiments, the process is scalable up to a starting amount or initial load of rCSP comprising about 100 mg to about 3000 grams rCSP. In embodiments, the starting amount of rCSP comprises about 1 gram to about 3000 grams, about 100 grams to about 3000 grams, about 250 grams to about 3000 grams, about 500 grams to about 3000 grams, about 750 grams to about 3000 grams, about 1000 grams to about 3000 grams, about 100 grams to about 2000 grams, about 250 grams to about 2000 grams, about 500 grams to about 2000 grams, about 750 grams to about 2000 grams, about 1000 grams to about 2000 grams, about 100 grams to about 1000 grams, about 150 grams to about 1000 grams, about 200 grams to about 1000 grams, about 250 grams to about 1000 grams, about 300 grams to about 1000 grams, about 400 grams to about 1000 grams, about 500 grams to about 1000 grams, or about 750 grams to about 1000 grams. In embodiments, the methods of the present invention are used to obtain any of the above starting amounts of rCSP at an overall purification process yield of at least about 10%, at least about 15%, at least about 20%, at least about 25%, at least about 30%, at least about 35%, at least about 40%, at least about 50%, at least about 60%, at least about 70%, about 10% to about 75%, about 10% to about 70%, about 10% to about 65%, about 10% to about 60%, about 20% to about 75%, about 20% to about 70%, about 20% to about 65%, about 25% to about 75%, about 25% to about 70%, about 25% to about 65%, about 25% to about 60%, about 30% to about 75%, about 30% to about 70%, about 30% to about 65%, or about 30% to about 60%. In embodiments, the above purification process yields comprise not more than 10% denatured rCSP, not more than 10% degraded rCSP, and/or 10% dimerized rCSP. In embodiments, the above purification process yields comprise not more than 5% denatured rCSP, not more than 5% degraded rCSP, and/or not more than 5% dimerized rCSP.

Preferential Reducing Conditions

In the methods of the present invention, the rCSP dimers separated from host cell proteins in the methods of the invention are subjected to preferential reducing conditions. These preferential reducing conditions selectively reduce certain disulfide bonds while leaving others intact. When the rCSP is subjected to the preferential reducing conditions, the intermolecular disulfide bond of the rCSP dimer is reduced to separate the dimer into two monomers. The structure, for example, as represented by the two intramolecular disulfide bonds in the C-terminal region, remains intact. Therefore, the preferential reducing conditions are critical to the high overall process yield (due to dimer utilization), and decreased complexity (due to lack of a refolding step and the need to separate the dimer from the monomer) relative to previously used methods. A further advantage of this strategy is that a greater proportion of the rCSP maintained as a dimer during purification is obtained with an intact N-terminus. Therefore, the quality and quantity of the recovered rCSP is vastly improved. In embodiments, the preferential reducing conditions comprise a mild reducing agent. In embodiments, the mild reducing agent is DTT, cysteine, acetylcysteine, glutathione, monothioglycerol (MTG), thioglycolate, dithothiothreitol, dithioerythritol, acetylcysteine, 2-Mercaptoethanol (B-mercaptoethanol), TCEP-HCl (pure, crystalline Tris(2-carboxyethyl)phosphine hydrochloride), or 2-Mercaptoethylamine-HCl (2-MEA), or any other appropriate reducing agent known in the art. In certain embodiments, the mild reducing agent is dithiothreitol (DTT) at a final concentration of about 0.001 to about 0.1 mM. In embodiments, the mild reducing agent comprises DTT at a final concentration of about 0.010 mM to about 0.030 mM, about 0.010 mM to about 0.020 mM, about 0.010 mM to about 0.025 mM, about 0.020 mM to about 0.025 mM, about 0.020 mM to about 0.030 mM, or about 0.025 mM to about 0.030 mM. In embodiments, the concentration of DTT is about 20 µM. In embodiments, the mild reducing agent is monothioglycerol (MTG) at a final concentration of about 0.5 mM to about 5 mM. In embodiments, the mild reducing agent comprises MTG or cysteine at a final concentration of about 0.5 mM to about 4 mM, about 0.5 mM to about 3 mM, about 0.5 mM to about 2 mM, about 0.5 mM to about 1 mM, about 0.6 mM to about 2 mM, about 0.6 mM to about 1.5 mM, about 0.6 mM to about 1.4 mM, about 0.6 mM to about 1.3 mM, about 0.6 mM to about 1.2 mM, about 0.6 mM to about 1.1 mM, about 0.6 mM to about 1.05 mM, about 0.6 mM to about 1 mM, about 0.7 mM to about 2 mM, about 0.7 mM to about 1.5 mM, about 0.7 mM to about 1.4 mM, about 0.7 mM to about 1.3 mM, about 0.7 mM to about 1.2 mM, about 0.7 mM to about 1.1 mM, about 0.7 mM to about 1.05 mM, about 0.7 mM to about 1 mM, about 0.8 mM to about 2 mM, about 0.8 mM to about 1.5 mM, about 0.8 mM to about 1.4 mM, about 0.8 mM to about 1.3 mM, about 0.8 mM to about 1.2 mM, about 0.8 mM to about 1.1 mM, about 0.8 mM to about 1.05 mM, about 0.8 mM to about 1 mM, about 0.9 mM to about 2 mM, about 0.9 mM to about 1.5 mM, about 0.9 mM to about 1.4 mM, about 0.9 mM to about 1.3 mM, about 0.9 mM to about 1.2 mM, about 0.9 mM to about 1.1 mM, about 0.9 mM to about 1.05 mM, about 0.9 mM to about 1 mM, about 1 mM to about 1.5 mM, about 1 mM to about 1.4 mM, about 1 mM to about 1.3 mM, about 1 mM to about 1.2 mM, about 1 mM to about 1.1 mM, about 0.5 mM, about 0.6 mM, about 0.7 mM, about 0.8 mM, about 0.9 mM, about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 3.0 mM, about 4.0 mM, or about 5.0 mM. In embodiments, the mild reducing agent comprises MTG or cysteine at a final concentration of about 1 mM.

In embodiments, the mild reducing agent and a disaggregation agent are added to the purified dimerized CSP, or aggregated CSP, in buffer (e.g., PBS, Tris, or Hepes) and mixed at room temperature (about 21° C.). In embodiments, the disaggregation agent is arginine, guanidine HCl, a detergent, or any other known disaggregation agent. In embodiments, the mild reducing agent is MTG and the disaggregating agent is urea. In embodiments, the preferential reducing conditions comprise MTG and urea in a buffer. In embodiments, the buffer is Hepes, PBS, Tris, or any other appropriate buffer. In embodiments, the preferential reducing conditions comprise 1.0 mM MTG and 2M urea in Hepes. In embodiments, the disaggregating agent is added earlier in the purification process, e.g., prior to cell disruption, as described elsewhere herein. In these embodiments, the disaggregating agent already is present at sufficient concentration when the mild reducing agent is added to initiate preferential reduction of the rCSP dimers. For example, the disaggregating agent is urea present at a concentration of about 0.5 M to about 4 M. In embodiments, the concentration of urea is about 2.5 M, about 3 M, about 1 to about 2 M, about 1 to about 2.5 M, about 1 to about 3 M, about 1.5 to about 2 M, about 1.5 to about 2.5 M, about 1.5 to about 3 M, about 2 to about 2.5 M, about 2 to about 3 M, or about 2.5 to about 3 M.

In embodiments, the mixing is carried out at about 21° C. for about 8 to about 48 hours. In embodiments, the mixing is carried out for about 12 to about 24 hours, or for about 16 to about 18 hours. Mixing can be carried out by, e.g., rapid stirring with a magnetic stir bar and stir plate, rocking platform, overhead mixer, or in a bag recirculating dimerized CSP and reducing agent using a peristaltic pump. In embodiments, the preferential reducing conditions are carried out in a total volume of about 1 mL to about 25 L. In embodiments, the volume is about 100 mL to about 1 L. In embodiments, the preferential reducing conditions are carried out in a volume of about 200-600 mL.

In certain embodiments, the preferential reducing conditions are carried out using dimeric rCSP purified from Butyl 650S chromatography. In other embodiments, the preferential reducing conditions are carried out on rCSP dimer fractions eluting from ceramic hydroxyapatite chromatography.

Bacterial Cell Lysate

A bacterial cell lysate preparation is obtained by disrupting bacterial cells expressing recombinant protein using any appropriate known cell disruption method, including physical or mechanical cell disruption methods and non-mechanical cell disruption methods. Disruption methods vary in the severity of the disruption process, the equipment and/or reagents needed, and in ease of use. Cell disruption methods are selected based on, e.g., the difficulty in disrupting the particular cells and the amount of material being processed. Preferred methods for disrupting bacterial cells are methods that produce a bacterial cell lysate that can be used in the downstream purification steps to obtain undenatured, undegraded recombinant protein.

Cell Culture Provided for Disruption

In embodiments of the present invention, the bacterial cells from a culture expressing the recombinant protein are provided for disruption as, e.g., a whole cell broth, a cell suspension, a cell slurry, or a cell paste. In embodiments, the cells are present in a solution comprising a disaggregation agent sufficient to prevent CSP aggregate formation. In these embodiments, the CSP is not denatured, therefore the C-terminal region disulfide bonds of CSP are intact. In embodiments, the bacterial cells are diluted to adjust the volume of cells:medium or cells:diluents.

In embodiments, the culture of bacterial host cells is used to make a cell paste for disruption according to the methods of the present invention. The cell paste can be prepared from the culture according to methods known in the art and described in the literature. For example, a cell paste can be made by harvesting a whole fermentation broth by centrifugation, and separating the resulting cell pellet and cell free broth. In embodiments, for fermentation harvest, the whole fermentation broth is harvested by centrifugation at 10,000×g for 90 min. The cell paste can be frozen at −70 to −80° C. In embodiments, the cell paste is reconstituted prior to disruption in a solution containing a concentration of a disaggregation agent sufficient to prevent CSP aggregation without denaturing the CSP. In undenatured CSP, the C-terminal region disulfide bonds are intact. In embodiments, the disaggregation agent is urea. In embodiments, the disaggregation agent is, e.g., arginine, guanidine HCl, a detergent, or any other appropriate disaggregation agent known in the art. In embodiments, the disaggregation agent is an ingredient that meet the standards of the United States Pharmacopeial Convention (Rockville, Md.), as published in the United States Pharmacopeia-National Formulary (USP-NF), or analogous standards in countries outside the United States, e.g., as published in The International Pharmacopeia (World Health Organization). In certain embodiments, the disaggregation agent is 2 M urea. In embodiments the disaggregation agent comprises urea at a final concentration of about 0.5 M to about 4 M. In embodiments, the concentration of urea is about 2.5 M, about 3 M, about 1 to about 2 M, about 1 to about 2.5 M, about 1 to about 3 M, about 1.5 to about 2 M, about 1.5 to about 2.5 M, about 1.5 to about 3 M, about 2 to about 2.5 M, about 2 to about 3 M, or about 2.5 to about 3 M. In certain embodiments, a solution of 2 M urea and 20 mM tris, pH 8.1±0.2 is used for reconstitution of the cell paste. In embodiments, the cell paste is reconstituted to 20% solids (w/v). In embodiments, the cell paste is reconstituted to less than 20% solids (w/v). The use of a disaggregation agent throughout the process of the present invention is contemplated.

As described herein in the Examples, the cell paste and disaggregation agent buffer solution can be stirred, e.g., with a stainless-steel impeller (Barnant Mixer Series 20, Barnant Co., Barrington, Ill. or LabMaster, 0-1800 rpm, Lightnin, Rochester, N.Y.) without allowing the solution to vortex, until all cells are thawed and the solution is homogeneous. It is within the skill of a person working in the art to identify reconstitution conditions that suitably prepare the cells for the desired method of cell disruption. In embodiments wherein the cells will be mechanically disrupted using a microfluidizer, particulate size is to prevent potential clogging of the microfluidizer channels.

In embodiments, the culture of bacterial host cells expressing CSP is present as whole cell broth. In embodiments, the broth is diluted to create a 20% (v/v) mixture. In embodiments, the dilution buffer comprises a disaggregation agent. In certain embodiments, the dilution buffer comprising a disaggregation agent is 3.1 M urea, 31 mM tris, pH 8.1±0.2, and is added to yield 2 M urea and 20 mM tris at 20% (v/v) cells.

Cell Disruption

A bacterial cell lysate preparation can be made by disrupting cells using any appropriate method known in the art. Identification of a method can be made by one of skill in the art, based on, e.g., the processing scale, reproducibility, potential damage to the recombinant protein due to the disruption, and particular lysate characteristics required for planned separation steps. One of skill in the art can establish the minimum force of the disruption method that will yield the highest quality product. Aspects of protein quality include but are not limited to protein dimerization or higher-order aggregation, protein degradation, or protein denaturation. These aspects can be evaluated by methods described herein and known in the art. Characteristics of the cell lysate preparation required for downstream separation steps can be identified using guidance in the published literature on the particular separation method. In embodiments, for methods including disk-stack centrifugation, e.g., as described herein, solids are not more than 10%. In embodiments, solids are not more than 11%, 12%, 13%, 14%, 15%, 16%, 17%, 18%, 19% or 20%. Other lysate characteristics potentially important in separation steps include, but are not limited to, buffer composition, solution viscosity, temperature of lysate (as they affect separation in centrifuge).

Cultures can be OD-normalized prior to disruption. For example, cells can be normalized to an $OD_{600}$ of about 10, about 11, about 12, about 13, about 14, about 15, about 16, about 17, about 18, about 19, or about 20.

Methods for disrupting cells include physical disruption (e.g., mechanical cell lysis, liquid homogenization, sonication, freeze/thaw, and manual grinding), and permeabilization (e.g., chemical disruption, disruption by osmotic shock, enzymatic disruption, and heat disruption). A bacterial cell lysate useful in the methods of the invention can be made using any appropriate method for disrupting cells to release the soluble fraction, e.g., as described by: Grabski, A. C., 2009, "Advances in preparation of biological extracts for protein purification," Methods Enzymol. 463:285-303; Hopkins, T. R., 1991, "Physical and chemical cell disruption for the recovery of intracellular proteins," Bioprocess technology 12: 57-83; and Harrison, S. T., 1991, "Bacterial cell disruption: a key unit operation in the recovery of intracellular products," Biotechnology Advances 9 (2): 217-240, all incorporated by reference herein in their entirety. It is within the capabilities of one of skill in the art to select an appropriate method based on the cells and scale of purification, knowing the advantages and disadvantages of the available methods. For example, vigorous mechanical treatments reduce cell lysate viscosity but can result in the inactivation of labile proteins by heat or oxidation, while non-mechanical treatments, e.g., cell permeabilization, may not release the target protein from the cells, and can produce viscous cell lysates. Depending on the cell type used to express the recombinant protein, cellular extracts can contain varying amounts of nucleic acid, ribosomal material, lipids, dispersed cell wall polysaccharide, carbohydrates, chitin, small molecules, and unwanted proteins (e.g., host proteins). Production of a bacterial cell lysate that can be efficiently manipulated in downstream purification processes without inactivation or degradation of the recombinant protein is critical.

Mechanical cell disruption methods include, e.g., use of a blender or mixer, beadmilling, or beadbeating. Liquid homogenization methods include microfluidization, as well as homogenization using, e.g., a Constant Cell Disruptor, Niro-Soavi homogenizer, APV-Gaulin homogenizer, Dounce Homogenizer, Potter-Elvehjem Homogenizer, or French Press. Other physical disruption procedures include sonication, freeze/thaw, and manual grinding. Equipment useful for physical disruption is commercially available.

In specific embodiments, cells are disrupted mechanically using a microfluidizer, e.g., according to methods described herein in the Examples and as known in the art and published in the literature. In these embodiments, a Microfluidics M-110Y microfluidizer operating at 10,000±1,000 psi can be used to disrupt the cells. The lysate from the microfluidizer can be passed through a shell-and-tube heat exchanger, which cools the solution to ≤12° C., and collected according to any method known in the art.

In embodiments, any appropriate microfluidizer is used. In embodiments, at least one agent is added to aid the cell disruption process. For example, cells can be suspended in a hypotonic buffer. Lysozyme added at, e.g., 200 µg/ml, digests the polysaccharide component of bacterial cell walls. In embodiments, cells are treated with glass beads to facilitate the crushing of cell walls. In embodiments, a protease inhibitor is added at any time during the purification process. In certain embodiments, a protease inhibitor is added before or during lysis.

Periplasmic Release by Osmotic Shock

In embodiments, the rCSP is directed to the periplasm using a periplasmic leader as described herein, and a bacterial cell lysate is generated by permeabilizing the cell wall. For example, in embodiments, chemical and/or enzymatic cell lysis reagents, such as cell-wall lytic enzyme and EDTA, can be used. Use of frozen or previously stored cultures is also contemplated in the methods of the invention. The cells can be permeabilized by osmotic shock, e.g., as described herein in the Examples or as known in the art and reported in the literature.

Purifying Recombinant CSP Dimers

In the methods of the invention, rCSP dimers in the bacterial cell lysate preparation are separated from impurities including host cell debris and host cell proteins. In embodiments, purification is performed to sequentially separate the rCSP from the cell debris and the host cell proteins. For example, the lysate first can be separated into soluble and insoluble fractions, then the rCSP dimers present in the soluble fraction can be separated from host cell proteins and other impurities. In other embodiments, the rCSP dimers are separated from the cell debris and the host cell proteins in the same step or series of steps. In embodiments, Expanded Bed Chromatography, where the lysate is passed over a chromatographic bed that both separates out cell debris and host cell proteins, is used. Additional purification steps may follow Expanded Bed Chromatography to remove remaining contaminants.

Separating the Bacterial Cell Lysate Preparation into Soluble and Insoluble Fractions In the purification methods of the present invention, the bacterial cell lysate preparation comprising recombinant protein is separated into a soluble and an insoluble fraction. This process removes debris to clarify the soluble fraction containing the recombinant protein. In embodiments, the bacterial cell lysate preparation to be separated into soluble and insoluble fractions comprises freshly lysed cells. In other embodiments, the bacterial cell lysate preparation is subjected to one or more manipulations or treatments prior to being separated into a soluble and an insoluble fraction. These manipulations, or clarification pre-treatments, can include treatment to facilitate future manipulations or enhance recombinant protein recovery or quality as desired.

For example, the bacterial cell lysate preparation can be diluted, or treated at least one reagent, e.g., a flocculent or coagulant. Flocculents, including ammonium sulfate and PEG, enhance precipitation of the insoluble fraction of the bacterial cell lysate preparation thereby enhancing separation of the insoluble fraction from the soluble fraction. In embodiments, a nuclease, e.g., DNase (25-50 μg/ml) and/or RNase (50 μg/ml), is added to the bacterial cell lysate preparation to reduce its viscosity.

Methods for separating a bacterial cell lysate into a soluble fraction, comprising soluble proteins, and an insoluble fraction, comprising cell debris, are well known in the art. Any method or combination of methods for separation of liquids and solids deemed appropriate by one of skill in the art is contemplated for use in association with the methods of the present invention. Useful methods include, but are not limited to, centrifugation, filtration, sedimentation, and other clarification methods, and combinations thereof. In certain embodiments, centrifugation is carried out to separate larger cell debris particles from the recombinant protein, followed by a filtration method which separates smaller debris particles. In certain embodiments, microfiltration is performed in the absence of centrifugation or other methods.

Separation Methods—Soluble and Insoluble Fraction
Centrifugation

One or more centrifugation methods can be used to separate the bacterial cell lysate into a soluble (liquid) and insoluble (solid) fraction. Centrifugation methods useful for separating a bacterial cell lysate into a soluble and insoluble fraction include, e.g., fixed angle centrifugation, disk-stack centrifugation, tubular bowl centrifugation, and batch centrifugation using a floor centrifuge.

Centrifugation can be performed using any appropriate equipment and method. Centrifugation of cell culture or lysate for the purposes of separating a soluble fraction from an insoluble fraction is well-known in the art and described extensively in the literature, e.g., in Methods in Enzymology (1990), edited by M. P. Deutscher, and by Ausubel, F. M., et al., 1991. For example, lysed cells can be centrifuged at 20,800×g for 20 minutes (at 4° C.), and the supernatants removed using manual or automated liquid handling. The pellet (insoluble) fraction can be resuspended in a buffered solution, e.g., phosphate buffered saline (PBS), pH 7.4. Resuspension can be carried out using, e.g., equipment such as impellers connected to an overhead mixer, magnetic stir-bars, rocking shakers, etc.

In embodiments of the present invention, the bacterial cell lysate is separated into soluble and insoluble fractions using a series of procedures, e.g., centrifugation followed by one or more additional centrifugation procedures or one or more filtration or sedimentation procedures. Each procedure further clarifies the soluble fraction.

In embodiments, the separation is carried out using disk-stack centrifugation as described herein. In disk stack centrifugation a disk stack centrifuge separates solids and one or two liquid phases from each other in a continuous process. The denser solids are forced outwards by centrifugal forces while the less dense liquid phases form inner concentric layers. Special plates are inserted where liquid phases meet to attain maximum separation efficiency. The solids can be removed manually, intermittently or continuously. Clarified liquids overflow in the outlet area on top of the bowl. Different liquid phases can be directed to separate chambers and sealed off from each other to prevent cross contamination. Disk stack centrifuges can be used to separate phases with minimum density differences.

In embodiments of the invention wherein disk stack centrifugation is used to separate the bacterial cell lysate preparation into soluble and insoluble fractions, 20 percent (w/v or v/v) lysates are diluted 1:1 with Super Q purified water or 2 M urea, 20 mM Tris, pH 8.0 and thoroughly mixed by recirculation with a peristaltic pump or by a stainless steel impeller, to create homogeneous 10% (w/v or v/v) lysates. A disc stack centrifuge, e.g., an SC-6 centrifuge (GEA Westfalia, Olede, Germany) is operated at 15,000×g. Using peristaltic pumps and platinum-cured silicone tubing, 10% and 20% lysates are fed to the centrifuge at flow rates of 0.3 to 1.0 L/min at temperatures of 15 to 22° C. Centrate backpressure is maintained at 75 to 85 psig. Centrates are allowed to exit the SC-6, with and without heat-exchange, at 12 to 30° C., and can be collected into polypropylene vessels or Flexboy® bags. The insoluble fractions/particles are intermittently discharged at determined intervals and the cycle repeats. Real-time, in-line turbidity can be collected on the centrate via an AF16 single-channel near infrared (NIR) absorption meter (Optek-Danulat, Germantown, Wis.) and reported as a percentage concentration unit (CU) of a calibrated range. Instantaneous and bulk samples of centrate can be taken for nephelometric turbidity unit (NTU) measurement with a Hach 2100p (Loveland, Colo.). Turbidity reduction (1−NTUcentrate/NTUfeed) is useful for assessing centrifuge performance, with >90% reduction being a good level for beginning further optimization.

Depth Filtration

In embodiments, the bacterial cell lysate preparation is clarified or further clarified following centrifugation using depth filtration. In embodiments, separation of the soluble and insoluble fractions is carried out by disk-stack centrifugation followed by depth filtration. In embodiments wherein depth filtration is used, particles down to 0.2 μm are removed using a combination of depth and sterile filters. In certain embodiments, depth and membrane filters are evaluated for their suitability in filtering supernatants and centrates. In embodiments, supernatants and centrates (e.g., lysates of 10% cell pastes or whole cell broth) are pumped through depth filters at 18 to 28° C. at 50 to 100 LMH. In embodiments, the soluble fraction of a bacterial cell lysate preparation that has been separated using a centrifugation method, e.g., disk stack centrifugation, is pumped through membrane filters at 10 psig to establish a $V_{max}$ value.

Nonlimiting examples of depth filters useful in methods of the invention wherein the bacterial cell lysate preparation is separated into soluble and insoluble fractions using depth filtration are: Millipore C0HC, A1HC, B1HC and X0HC depth filters, CUNO 60ZA and CUNO 90ZA. The filters can be evaluated based on, e.g., pressure limitations at a feed load of <20 L/m² or reduction in turbidity. In embodiments, a depth filter useful in practicing depth filtration in accordance with the methods of the invention has a matrix having small pores and high charge density, and does not have a 0.1 μm nominal membrane, which often plugs and leads to pressure failure. In embodiments, the filter used displays a pressure drop of ≤30 psi and/or a turbidity reduction to a feed load of 40 L/m². In embodiments, the depth filter used in practicing depth filtration in accordance with the methods of the invention is a Millipore X0HC filter.

Microfiltration

Microfiltration (MF) is a scalable process that in one unit operation removes solids and provides a feedstream that can be used directly for chromatography. In embodiments, separation of the soluble and insoluble fractions is carried out using microfiltration without prior centrifugation. In embodiments, microfiltration includes tangential-flow filtration (TFF) using membranes with pores in the micron to submicron range. In embodiments, the pores are 0.22 to 0.45 µm. Ideally, particles larger than the membrane pore size, such as cell debris, are retained (retentate), while those smaller than the pore size diffuse through the membrane with other solutes and solvents (permeate). For recovery of rCSP, it is desired to retain cell debris in the retentate and collect the rCSP in the permeate through concentration and buffer exchange.

Bacterial cell lysate preparations of 5 to 20% (w/v) solids can be concentrated to 40% (w/v) solids via tangential flow filtration and diafiltered for 1 to 3 DVs (diavolumes) with 2 M urea, 20 mM Tris/20 mM MES/20 mM Bis-Tris pH 6-8.

Freeze-Thaw Process

In embodiments, the lysate is frozen and thawed prior to further processing steps, e.g., steps to remove host cell proteins. Depending on the volume, the lysate can be divided into aliquots for more efficient freezing. In embodiments, each lysate aliquot is 100% solid in about 19 hours or less. In embodiments, each lysate aliquot is 100% solid in about 18 hours or less, about 18.1 hours or less, about 18.2 hours or less, about 18.3 hours or less, about 18.4 hours or less, about 18.5 hours or less, about 18.6 hours or less, about 18.7 hours or less, about 18.8 hours or less, or about 18.9 hours or less. In embodiments, each lysate aliquot is at least about 65% solid in about 7 hours or less, about 6.9 hours or less, about 6.8 hours or less, about 6.7 hours or less, about 6.6 hours or less, about 6.5 hours or less, about 6.4 hours or less, about 6.3 hours or less, about 6.2 hours or less, about 6.1 hours or less, or about 6 hours or less. In embodiments, each lysate aliquot is at least about 25% solid in about 5 hours or less, about 4.9 hours or less, about 4.8 hours or less, about 4.7 hours or less, about 4.6 hours or less, about 4.5 hours or less, about 4.4 hours or less, about 4.3 hours or less, about 4.2 hours or less, about 4.1 hours or less, or about 4 hours or less. In embodiments, the lysate aliquots are about 1 L to about 2 L. In embodiments, the lysate is frozen in 1 L or 2 L PETG bottles.

In embodiments, the freeze thaw process includes a room temperature hold after the lysate is thawed. In embodiments, the lysate is held at room temperature for at least about 4 to at least about 7 hours, at least about 4.5 to at least about 7 hours, at least about 5 to at least about 7 hours, or at least about 5.5 to at least about 7 hours, or at least about 6 to at least about 7 hours, or at least about 6.5 to at least about 7 hours, at least about 4 to at least about 6 hours, at least about 4.5 to at least about 6 hours, at least about 5 to at least about 6 hours, or at least about 5.5 to at least about 6 hours. In embodiments, the lysate is held at room temperature for about 6 hours after thawing.

In embodiments, the freeze-thaw process significantly reduces the presence of high molecular weight protein species, or "laddering," in the lysate. The presence of laddering can predict a low rCSP yield in subsequent chromatography steps.

In embodiments, precipitation levels are reduced after the freeze-thaw process, and prior to further processing steps, by a treatment that reduces precipitation to a level that allows successful completion of chromatography steps, e.g., TMAE chromatography. For example, the precipitation level should be low enough to allow normal chromatography. In embodiments, the method used to reduce the precipitation to an acceptable level does not result in increased N-terminal clipping when compared to the use of no treatment to reduce precipitation. In embodiments, lysate precipitate levels are reduced by membrane filtration after thawing, or after a room temperature hold following thawing. In embodiments, Sartobran P (0.45 µm/0.2 µm) Membrane Filters are used for the membrane filtration of the lysate. In embodiments, such a filtration procedure is carried out at any step during the purification process. In embodiments, the rCSP is subjected to membrane filtration after the last column and before the buffer exchange step.

Separating rCSP from Host Cell Proteins in the Soluble Fraction

Methods for separating recombinant proteins from host cell proteins, and the use of one or more separation methods selected based on characteristics of the recombinant protein, are known in the art and described at length in the literature, e.g., in Methods in Enzymology (1990), edited by M. P. Deutscher. Separation methods can be selected based on differences in properties of the recombinant protein and contaminants, e.g., size, charge, binding properties, and solubility. Protocols based on these parameters can include affinity chromatography, ion exchange chromatography, size exclusion chromatography, hydrophobic interaction chromatography, and mixed-mode chromatography. In embodiments, separation methods serve to concentrate the recombinant protein.

Exemplary separation methods are described herein, however in embodiments any known method or combination of methods for separating rCSP from host cell proteins or other impurities, and/or for concentrating the recombinant protein, is utilized as deemed appropriate. Desirable separation methods result in the purification of undegraded, nondenatured CSP monomer following preferential reduction of the rCSP dimer as described herein. In embodiments, the rCSP (monomer) obtained is further separated from remaining impurities, including host cell proteins.

Chromatography

In embodiments, chromatography is used to separate the rCSP dimer from host cell proteins present in the soluble fraction obtained by separating the bacterial cell lysate preparation. In embodiments, a low concentration of disaggregation agent is present during chromatography, to prevent aggregation without reducing the intermolecular disulfide bond in the dimer (which joins the monomers), and further without denaturing the intramolecular disulfide bonds of CSP. In embodiments, the low concentration of disaggregation agent is about 2M urea. In certain embodiments, the bacterial cell lysate soluble fraction is present in 20 mM Tris, pH 8.0, and 2M urea.

Many types of chromatography are known in the art and described in the literature, e.g., in Methods in Enzymology (1990), edited by M. P. Deutscher.

In embodiments, ion exchange chromatography is used. In ion exchange chromatography, e.g., anion exchange or cation exchange chromatography, the recombinant protein is bound to fixed charges, e.g., on a substrate such as a column. While the recombinant protein is immobilized, unmobilized contaminants are eliminated. The recombinant protein is later eluted or displaced from the fixed charges. Substrates or ion exchangers useful in carrying out the methods of the present invention are known in the art and include but are not limited to cellulose, dextrans, agarose, and polystyrene. A column of any size, or any other appropriate known system useful for ion exchange chromatography, e.g., batch ion exchange chromatography, is contemplated for use in the methods of the invention. In embodiments, anion exchange chromatography, cation exchange chromatography, or both, are used.

Hydrophobic interaction chromatography (HIC) is based on a hydrophobic interaction between the stationary phase and the component to be separated. HIC methods include a hydrophobic stationary phase and a polar mobile phase. Polar components prefer the mobile phase and elute first. As the hydrophobic character of a compound increases, retention becomes longer. Generally, the lower the polarity of the mobile phase, the higher is its eluent strength. Adsorption and desorption are supported by increasing or decreasing, respectively, the salt concentration of the liquid or changing the charge on the ligand and/or the substance to be adsorbed/desorbed by changing pH. HIC methods are described in the literature, e.g., in WO 96/00735, "Hydrophobic Chromatographic Resins with Ionizable Groups," WO 96/09116 and U.S. Pat. No. 5,652,348, "Chromatographic Resins and Methods for Using Same," all incorporated by reference herein in their entirety. A hydrophobic interaction separation method can be based on thiophilic adsorbents, as described in, e.g., U.S. Pat. No. 8,138,306, "Separation Method," incorporated herein by reference in its entirety. U.S. Pat. No. 8,138,306 also describes use of a separation matrix including uncharged ligands that possess a quadrupole or dipole moment.

In embodiments of the present invention, HIC of rCSP dimer or monomer is performed using any appropriate hydrophobic group, e.g., hexyl, phenyl, octyl, or butyl. Hydrophobic resins are commercially available, and include, e.g., Hexyl 650C (Tosoh USA), Phenyl HP (GE, 17-5195-01), Butyl HP (GE, 28-4110-01), PPG 600M (Tosoh USA), and MEP HyperCel (Pall). In embodiments, HIC is carried out after initiating the mild reduction step (under the preferential reducing conditions). In embodiments, the HIC purification step successfully reduces the level of host cell proteins to at most 500 ppm, at most 450 ppm, at most 400 ppm, at most 350 ppm, at most 300 ppm, at most 250 ppm, at most 200 ppm, at most 150 ppm, at most 100 ppm, at most 50 ppm, at most 40 ppm, at most 30 ppm, at most 20 ppm, at most 10 ppm, at most 5 ppm, or to a nondetectable level. In embodiments, the HIC purification step successfully reduces the level of host cell proteins to at most 50 ppm, at most 40 ppm, at most 30 ppm, at most 20 ppm, or at most 10 ppm, as detected by an ELISA. In embodiments, the N-terminal clipping of rCSP observed following the HIC purification step is at most 5%, at most 4%, at most 3%, at most 2%, at most 1.5%, at most 1%, at most 0.5%, or not detectable. In embodiments, the HIC purification step results in rCSP of at least 98%, at least 98.5%, at least 99%, or at least 99.5% purity. In embodiments, the HIC purification step results in an rCSP concentration of at least about 0.1 mg/ml to about 2 mg/ml. In embodiments, the HIC purification step results in an rCSP concentration of at least about 0.15 mg/ml to about 2 mg/ml, at least about 0.2 mg/ml to about 2 mg/ml, at least about 0.25 mg/ml to about 2 mg/ml, at least about 0.3 mg/ml to about 2 mg/ml, at least about 0.35 mg/ml to about 2 mg/ml, at least about 0.4 mg/ml to about 2 mg/ml, at least about 0.45 mg/ml to about 2 mg/ml, at least about 0.5 mg/ml to about 2 mg/ml, at least about 0.1 mg/ml to about 1 mg/ml, at least about 0.15 mg/ml to about 1 mg/ml, at least about 0.2 mg/ml to about 1 mg/ml, at least about 0.25 mg/ml to about 1 mg/ml, at least about 0.3 mg/ml to about 1 mg/ml, at least about 0.35 mg/ml to about 1 mg/ml, at least about 0.4 mg/ml to about 1 mg/ml, at least about 0.45 mg/ml to about 1 mg/ml, at least about 0.5 mg/ml to about 1 mg/ml. In certain embodiments, the HIC purification step reduces the level of host cell proteins to at most 50 ppm, and the N-terminal clipping is at most 1%.

In embodiments, HIC is used to separate N-terminally clipped species from full-length species. In embodiments, HIC increases the total rCSP by about 5 to about 15% as measured by RP-HPLC. In embodiments, the increase is about 8 to about 12%, about 9 to about 11%, at least about 8%, at least about 9%, about 10%, at least about 1%, or at least about 12%.

In embodiments, HIC is carried using a Hexyl 650C column with a gradient elution or a step elution. In embodiments, HIC is carried out following reduction with MTG, using a Hexyl 650C column with a 0.5 to 0M, or a 1.0 to 0M, ammonium sulfate gradient elution.

Chromatography methods also can be based on affinity between the ligand and compound to be separated. Examples of useful affinities are antibody-antigen affinity, metal ion affinity and receptor-ligand affinity. Proteins can be separated based on size, by size exclusion chromatography. Size exclusion methods include, e.g., gel filtration.

Mixed mode chromatography methods separate proteins based on a combination of separation parameters. For example, the combination of two or more of the known ion exchange separation principles has been denoted mixed mode ion-exchangers. See for example WO 97/29825, "Process for Chromatographic Separation of Peptides and Nucleic Acid, and New High Affinity Ion Exchange Matrix," describing mixed mode anion-exchangers.

High salt ligands (HSL) described in, e.g., U.S. Pat. No. 8,138,306, can function as mixed mode cation-exchange ligands and have been shown to be of interest in industrial applications such as protein purification since they can withstand high salt concentrations and accordingly do not require substantial dilution of the sample.

In embodiments of the present invention, mixed mode chromatography is used to separate rCSP from host cell proteins. In specific embodiments, hydroxyapatite chromatography is used. In embodiments, the host cell protease responsible for clipping the N-terminus of CSP is separated from the rCSP by hydroxyapatite chromatography. In embodiments, TMAE load is used in the hydroxyapatite chromatography.

Hydroxyapatite chromatography is a method of purifying proteins that utilizes an insoluble hydroxylated calcium phosphate [$Ca_{10}(PO_4)_6(OH)_2$], which forms both the matrix and ligand. Functional groups consist of pairs of positively charged calcium ions (C-sites) and clusters of negatively charged phosphate groups (P-sites). The interactions between hydroxyapatite and proteins are complex and multi-mode. In one method of interaction, positively charged amino groups on proteins associate with the negatively charged P-sites, and protein carboxyl groups interact by coordination complexation to C-sites. Acidic and basic proteins usually interact with cHA resin through different mechanisms: an acidic protein usually binds to C-sites via a coordination bond to carboxyl group, while a basic protein binds to P-sites through charge interaction with the amine group. Ceramic hydroxyapatite (cHA) chromatography overcome some difficulties associated with crystalline hydroxyapatite, such as limited flow rates. Ceramic hydroxyapatite has high durability, good protein binding capacity, and can be used at higher flow rates and pressures than crystalline hydroxyapatite. Chromatographic separation using cHA can be performed in several distinct modes, such as binding mode, flow-through mode, or a combination binding/flow-through mode. Methods of using ceramic hydroxyapatite chromatography are described in, e.g., U.S. Pat. No. 8,058,407, "Purification of acidic proteins using ceramic hydroxyapatite chromatography," incorporated by reference herein in its entirety.

Buffer Exchange

In embodiments, buffer exchange is carried out after initiation of the preferential reducing treatment. Buffer exchange can remove certain undesired reagents, e.g., undesired reducing reagents. In embodiments, buffer exchange removes salts, urea, and/or DTT. Any method of buffer exchange that does not allow the rCSP to readily form higher molecular weight aggregates (e.g., tetramers, hexamers, and oligomers) is useful in the methods of the invention. In embodiments, buffer exchange is carried out by diafiltration methods, e.g., gel filtration (desalting) chromatography, or tangential flow filtration (TFF) with a UF/DF membrane. In embodiments, buffer exchange is carried out using TFF with a UF/DF membrane of about 5 to about 10 kDa MWCO. In embodiments, the UF/DF membrane is about 5 to about 9 kDa MWCO, about 5 to about 8 kDa MWCO, about 5 to about 7 kDa MWCO, or about 5 to about 6 kDa MWCO. In certain embodiments, buffer exchange is carried out using TFF with a UF/DF membrane of about 5 kDa MWCO. In embodiments, membranes are equilibrated with 1×PBS prior to product introduction. In embodiments, the rCSP is exchanged into a buffer in which the rCSP is stable.

In embodiments, the mildly-reduced (monomerized) rCSP is recirculated across the membranes at 324 LMH (liters/m$^2$/hour) and 720 LMH at about 21° C. to 23° C. In embodiments, a formulation buffer that maintains rCSP stability is recirculated across the membranes. In embodiments, 1×PBS, 10% (w/v) arginine-HCl (0.5M arginine-HCl) (available from, e.g., J. T. Baker, part number 2067), 1 mM monothioglycerol (available from, e.g., MP BIOMEDICALS, Santa Ana, Calif., catalog number 155727, or Research Organic, Cleveland, Ohio, catalog number 0178M), pH 6.4 is recirculated across the membranes at 324 LMH at room temperature (21-23° C.). In embodiments, a TMP of 21-24 psi is applied to the retentate (diafiltered load) while over the 5 kDa membrane. In embodiments, TMPs of 10-15 psi and 21-24 psi are applied to the retentate while over the 5 kDa membranes. In embodiments, constant volume diafiltration is carried out for multiple, e.g., 5 to 10, retentate volumes (diavolumes). In embodiments, after several diavolumes, e.g., 3 to 10, the retentate is concentrated 2× and diafiltered for another several diavolumes, e.g., 3 to 10. The retentate is concentrated and diluted to 1.0 mg/mL. The final purified rCSP is stored frozen at −80° C.

rCSP Stable Liquid Formulation

The final purified rCSP can be diafiltered into a liquid formulation buffer to generate an rCSP stable liquid formulation. In embodiments, rCSP the stable liquid formulation allows rCSP to be stably maintained at high concentration. In embodiments, the rCSP in the liquid formulation buffer retains its physical and chemical stability during storage. Stability of the rCSP liquid formulation can be evaluated after selected time periods at a given temperature. Negative indicators of rCSP stability (or indicators of instability) include, for example, a decrease in the amount or percent of rCSP monomer (% total rCSP), an increase in the amount or percent of dimer, an increase in aggregates, an increase in degradation products, an increase in denaturation, a decrease in the percent or fraction of rCSP determined to be active. In embodiments, indicators of rCSP quality, as described herein, are used to indicate stability as stability can be considered a measure of quality over time. Similarly, indicators of rCSP stability also can be used to indicate rCSP quality. In embodiments, rCSP stability in a stable liquid formulation is indicated by the presence or maintenance of a minimum amount of rCSP monomer, e.g., at least about 80% to about 100% of the total protein. In embodiments, rCSP stability is indicated by the presence or maintenance of about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, about 99% to about 100%, about 80% to about 99%, about 81% to about 99%, about 82% to about 99%, about 83% to about 99%, about 84% to about 99%, about 85% to about 99%, about 86% to about 99%, about 87% to about 99%, about 88% to about 99%, about 89% to about 99%, about 90% to about 99%, about 91% to about 99%, about 92% to about 99%, about 93% to about 99%, about 94% to about 99%, about 95% to about 99%, about 96% to about 99%, about 97% to about 99%, about 98% to about 99%, about 80% to about 98%, about 81% to about 98%, about 82% to about 98%, about 83% to about 98%, about 84% to about 98%, about 85% to about 98%, about 86% to about 98%, about 87% to about 98%, about 88% to about 98%, about 89% to about 98%, about 90% to about 98%, about 91% to about 98%, about 92% to about 98%, about 93% to about 98%, about 94% to about 98%, about 95% to about 98%, about 96% to about 98%, about 97% to about 98%, about 80% to about 97%, about 81% to about 97%, about 82% to about 97%, about 83% to about 97%, about 84% to about 97%, about 85% to about 97%, about 86% to about 97%, about 87% to about 97%, about 88% to about 97%, about 89% to about 97%, about 90% to about 97%, about 91% to about 97%, about 92% to about 97%, about 93% to about 97%, about 94% to about 97%, about 95% to about 97%, about 96% to about 97%, about 80% to about 96%, about 81% to about 96%, about 82% to about 96%, about 83% to about 96%, about 84% to about 96%, about 85% to about 96%, about 86% to about 96%, about 87% to about 96%, about 88% to about 96%, about 89% to about 96%, about 90% to about 96%, about 91% to about 96%, about 92% to about 96%, about 93% to about 96%, about 94% to about 96%, about 95% to about 96%, about 80% to about 95%, about 81% to about 95%, about 82% to about 95%, about 83% to about 95%, about 84% to about 95%, about 85% to about 95%, about 86% to about 95%, about 87% to about 95%, about 88% to about 95%, about 89% to about 95%, about 90% to about 95%, about 91% to about 95%, about 92% to about 95%, about 93% to about 95%, about 94% to about 95%, about 80% to about 94%, about 81% to about 94%, about 82% to about 94%, about 83% to about 94%, about 84% to about 94%, about 85% to about 94%, about 86% to about 94%, about 87% to about 94%, about 88% to about 94%, about 89% to about 94%, about 90% to about 94%, about 91% to about 94%, about 92% to about 94%, about 93% to about 94%, about 80% to about 93%, about 81% to about 93%, about 82% to about 93%, about 83% to about 93%, about 84% to about 93%, about 85% to about 93%, about 86% to about 93%, about 87% to about 93%, about 88% to about 93%, about 89% to about 93%, about 90% to about 93%, about 91% to about 93%, about 92% to about 93%, about 80% to about 92%, about 81% to about 92%, about 82% to about 92%, about 83% to about 92%, about 84% to about 92%, about 85% to about 92%, about 86% to about 92%, about 87% to about 92%, about 88% to about 92%, about 89% to about 92%, about 90% to about 92%, about 91% to about 92%, about 80% to about 91%, about 81% to about 91%, about 82% to about 91%, about 83% to about 91%, about 84% to about 91%, about 85% to about 91%, about 86% to about 91%, about 87% to about 91%, about 88% to about 91%, about 89% to about 91%, about 90% to about 91%, about 80% to about 90%, about 81% to about 90%, about 82% to about 90%, about 83% to about 90%, about 84% to about 90%, about 85% to about 90%, about 86% to about 90%, about 87% to about 90%, about 88% to about 90%, about 89% to about 90%, about 80% to about 89%, about 81% to about 89%, about 82% to about 89%, about 83% to about 89%, about 84% to about 89%, about 85% to about 89%, about 86% to about 89%, about 87% to about 89%, about 88% to about 89%, about 80% to about 88%, about 81% to about 88%, about 82% to about 88%, about 83% to about 88%, about 84% to about 88%, about 85% to about 88%, about 86% to about 88%, about 87% to about 88%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% rCSP monomer, when stored for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year. The amount of rCSP monomer can be determined as described herein or by any appropriate method known in the art, e.g., SE-HPLC. The amount of rCSP monomer prior to storage can be used for comparison.

In embodiments, rCSP stability in a stable liquid formulation is indicated by a maximum rate of decrease in rCSP monomer, e.g., a decrease of less than or equal to about 10% over about 9 days to a year in storage. In embodiments, the amount of rCSP monomer in a stable liquid formulation decreases by not more than about 0%, 0.5%, 1%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, or 20%, when stored for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year. In certain embodiments, rCSP stability is indicated by a maximum rate of decrease in rCSP monomer of less than or equal to about 1% to about 3% or to about 5% when stored for about 9 days to about 25 days. In certain embodiments, rCSP stability is indicated by a maximum rate of decrease in rCSP monomer of less than or equal to about 1% when stored for about 9 days to about 25 days.

In embodiments, rCSP stability in a stable liquid formulation is indicated by, e.g., not more than a maximum increase in the amount of rCSP dimer, aggregated species, denatured species, or degradation products. In embodiments, the amount of rCSP dimer, aggregated species, denatured species, and/or degradation products in the stable liquid formulation increases by not more than about 0%, 0.5%, 1%, 1.5%, 2%, 2.5%, 3%, 3.5%, 4%, 4.5%, 5%, 6%, 7%, 8%, 9%, or 10%, when stored for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year. In certain embodiments, rCSP stability is indicated by a maximum rate of increase in rCSP dimer, aggregated species, denatured species, or degradation products of less than or equal to about 1% to about 3% or to about 5% when stored for at least about 20 or 25 days. In certain embodiments, rCSP stability is indicated by a maximum rate of increase in aggregated species of less than or equal to about 1% when stored for at least about 20 or 25 days. In certain embodiments, rCSP stability is indicated by a maximum rate of increase in degradation products of less than or equal to about 5% when stored for at least about 20 or 25 days. In embodiments, rCSP stability is indicated by the presence of less than 10% rCSP dimer, aggregated species, denatured species, or degradation products. In embodiments, rCSP stability is indicated by the presence of rCSP dimer, aggregated species, denatured species, or degradation products at not more than 10%, not more than 9%, not more than 8%, not more than 7%, not more than 6%, not more than 5%, not more than 4%, not more than 3%, not more than 2%, or not more than 1% of the total protein or purified CSP obtained. The amounts of rCSP dimer, aggregated species or degradation products can be determined by methods described herein or by any appropriate method known in the art, e.g., SE-HPLC. The amounts prior to storage (e.g., at T=0) can be used for comparison.

In embodiments, the rCSP is stably maintained in the stable liquid formulation at about 4° C. to about 25° C. In embodiments, the rCSP is maintained in the stable liquid formulation at about 4° C. to about 25° C., about 4° C. to about 24° C., about 4° C. to about 23° C., about 4° C. to about 22° C., about 4° C. to about 21° C., about 4° C. to about 20° C., about 4° C. to about 19° C., about 4° C. to about 18° C., about 4° C. to about 17° C., about 4° C. to about 16° C., about 4° C. to about 15° C., about 4° C. to about 14° C., about 4° C. to about 13° C., about 4° C. to about 12° C., about 4° C. to about 11° C., about 4° C. to about 10° C., about 4° C. to about 9° C., about 4° C. to about 8° C., about 4° C. to about 7° C., about 4° C. to about 6° C., or about 4° C. to about 5° C. In certain embodiments, the rCSP is stably maintained in the stable liquid formulation at about 4° C.

In embodiments, rCSP is maintained in the stable liquid formulation at a high concentration, e.g., at a concentration of at least about 1 mg/ml to about 50 mg/ml. In embodiments, rCSP is maintained in the stable formulation at a concentration of at least about 1 mg/ml, at least about 1.5 mg/ml, at least about 2 mg/ml, at least about 2.5 mg/ml, at least about 3 mg/ml, at least about 3.5 mg/ml, at least about 4 mg/ml, at least about 4.5 mg/ml, at least about 5 mg/ml, at least about 6 mg/ml, at least about 7 mg/ml, at least about 8 mg/ml, at least about 9 mg/ml, at least about 10 mg/ml, at least about 15 mg/ml, at least about 20 mg/ml, at least about 25 mg/ml, at least about 30 mg/ml, at least about 35 mg/ml, at least about 40 mg/ml, at least about 45 mg/ml, at least about 50 mg/ml, about 2 to about 50 mg/ml, about 3 to about 50 mg/ml, about 4 to about 50 mg/ml, about 5 to about 50 mg/ml, about 10 to about 50 mg/ml, about 15 to about 50 mg/ml, about 20 to about 50 mg/ml, about 30 to about 50 mg/ml, about 40 to about 50 mg/ml, about 2 to about 40 mg/ml, about 3 to about 40 mg/ml, about 4 to about 40 mg/ml, about 5 to about 40 mg/ml, about 10 to about 40 mg/ml, about 15 to about 40 mg/ml, about 20 to about 40 mg/ml, about 30 to about 40 mg/ml, about 2 to about 30 mg/ml, about 3 to about 30 mg/ml, about 4 to about 30 mg/ml, about 5 to about 30 mg/ml, about 10 to about 30 mg/ml, about 15 to about 30 mg/ml, about 20 to about 30 mg/ml, about 2 to about 20 mg/ml, about 3 to about 20 mg/ml, about 4 to about 20 mg/ml, about 5 to about 20 mg/ml, about 10 to about 20 mg/ml, about 15 to about 20 mg/ml, about 2 to about 15 mg/ml, about 3 to about 15 mg/ml, about 4 to about 15 mg/ml, about 5 to about 15 mg/ml, about 10 to about 15 mg/ml, about 2 to about 10 mg/ml, about 3 to about 10 mg/ml, about 4 to about 10 mg/ml, about 5 to about 10 mg/ml, about 6 to about 10 mg/ml, about 7 to about 10 mg/ml, about 8 to about 10 mg/ml, about 9 to about 10 mg/ml, about 1 to about 9 mg/ml, about 2 to about 9 mg/ml, about 3 to about 9 mg/ml, about 4 to about 9 mg/ml, about 5 to about 9 mg/ml, about 6 to about 9 mg/ml, about 7 to about 9 mg/ml, about 8 to about 9 mg/ml, about 1 to about 8 mg/ml, about 2 to about 8 mg/ml, about 3 to about 8 mg/ml, about 4 to about 8 mg/ml, about 5 to about 8 mg/ml, about 6 to about 8 mg/ml, about 7 to about 8 mg/ml, about 1 to about 7 mg/ml, about 2 to about 7 mg/ml, about 3 to about 7 mg/ml, about 4 to about 7 mg/ml, about 5 to about 7 mg/ml, about 6 to about 7 mg/ml, about 1 to about 6 mg/ml, about 2 to about 6 mg/ml, about 3 to about 6 mg/ml, about 4 to about 6 mg/ml, about 5 to about 6 mg/ml, about 1 to about 5 mg/ml, about 2 to about 5 mg/ml, about 3 to about 5 mg/ml, about 4 to about 5 mg/ml, about 1 to about 4 mg/ml, about 2 to about 4 mg/ml, about 3 to about 4 mg/ml, about 1 to about 3 mg/ml, about 2 to about 4 mg/ml, or about 1 to about 2 mg/ml.

In embodiments, the rCSP stable liquid formulation comprises a mild reducing agent, e.g., DTT, cysteine, acetylcysteine, glutathione, monothioglycerol (MTG), thioglycolate, dithothiothreitol, dithioerythritol, acetylcysteine, 2-Mercaptoethanol (B-mercaptoethanol), TCEP-HCl (pure, crystalline Tris(2-carboxyethyl)phosphine hydrochloride), or 2-Mercaptoethylamine-HCl (2-MEA), or any other appropriate reducing agent known in the art. In embodiments, the mild reducing agent is DTT, MTG, acetylcysteine, glutathione, thioglycolate, or cysteine. In embodiments, the mild reducing agent is MTG, cysteine, or acetylcysteine. In embodiments, the mild reducing agent is MTG at a final concentration of about 0.5 mM to about 4 mM, about 0.5 mM to about 3 mM, about 0.5 mM to about 2 mM, about 0.5 mM to about 1 mM, about 0.6 mM to about 2 mM, about 0.6 mM to about 1.5 mM, about 0.6 mM to about 1.4 mM, about 0.6 mM to about 1.3 mM, about 0.6 mM to about 1.2 mM, about 0.6 mM to about 1.1 mM, about 0.6 mM to about 1.05 mM, about 0.6 mM to about 1 mM, about 0.7 mM to about 2 mM, about 0.7 mM to about 1.5 mM, about 0.7 mM to about 1.4 mM, about 0.7 mM to about 1.3 mM, about 0.7 mM to about 1.2 mM, about 0.7 mM to about 1.1 mM, about 0.7 mM to about 1.05 mM, about 0.7 mM to about 1 mM, about 0.8 mM to about 2 mM, about 0.8 mM to about 1.5 mM, about 0.8 mM to about 1.4 mM, about 0.8 mM to about 1.3 mM, about 0.8 mM to about 1.2 mM, about 0.8 mM to about 1.1 mM, about 0.8 mM to about 1.05 mM, about 0.8 mM to about 1 mM, about 0.9 mM to about 2 mM, about 0.9 mM to about 1.5 mM, about 0.9 mM to about 1.4 mM, about 0.9 mM to about 1.3 mM, about 0.9 mM to about 1.2 mM, about 0.9 mM to about 1.1 mM, about 0.9 mM to about 1.05 mM, about 0.9 mM to about 1 mM, about 1 mM to about 1.5 mM, about 1 mM to about 1.4 mM, about 1 mM to about 1.3 mM, about 1 mM to about 1.2 mM, about 1 mM to about 1.1 mM, about 0.5 mM, about 0.6 mM, about 0.7 mM, about 0.8 mM, about 0.9 mM, about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 3.0 mM, about 4.0 mM, or about 5.0 mM.

In embodiments, the rCSP stable liquid formulation comprises a disaggregation agent. In embodiments, the disaggregation agent is arginine, guanidine HCl, a detergent, urea, or any other appropriate disaggregating agent known in the art. In embodiments, the formulation comprises at least about 1% to about 25% w/v arginine. In embodiments, the storage or formulation buffer comprises about 1% to about 24% w/v arginine, about 1% to about 23% w/v arginine, about 1% to about 22% w/v arginine, about 1% to about 21% w/v arginine, about 1% to about 20% w/v arginine, about 1% to about 19% w/v arginine, about 1% to about 18% w/v arginine, about 1% to about 17% w/v arginine, about 1% to about 16% w/v arginine, about 1% to about 15% w/v arginine, about 1% to about 14% w/v arginine, about 1% to about 13% w/v arginine, about 1% to about 12% w/v arginine, about 1% to about 11% w/v arginine, about 1% to about 10% w/v arginine, about 1% to about 9% w/v arginine, about 1% to about 8% w/v arginine, about 1% to about 7% w/v arginine, about 1% to about 6% w/v arginine, about 1% to about 5% w/v arginine, about 5% to about 24% w/v arginine, about 5% to about 23% w/v arginine, about 5% to about 22% w/v arginine, about 5% to about 21% w/v arginine, about 5% to about 20% w/v arginine, about 5% to about 19% w/v arginine, about 5% to about 18% w/v arginine, about 5% to about 17% w/v arginine, about 5% to about 16% w/v arginine, about 5% to about 15% w/v arginine, about 5% to about 14% w/v arginine, about 5% to about 13% w/v arginine, about 5% to about 12% w/v arginine, about 5% to about 11% w/v arginine, about 5% to about 10% w/v arginine, about 7% to about 24% w/v arginine, about 7% to about 23% w/v arginine, about 7% to about 22% w/v arginine, about 7% to about 21% w/v arginine, about 7% to about 20% w/v arginine, about 7% to about 19% w/v arginine, about 7% to about 18% w/v arginine, about 7% to about 17% w/v arginine, about 7% to about 16% w/v arginine, about 7% to about 15% w/v arginine, about 7% to about 14% w/v arginine, about 7% to about 13% w/v arginine, about 7% to about 12% w/v arginine, about 7% to about 11% w/v arginine, about 7% to about 10% w/v arginine, about 8% to about 24% w/v arginine, about 8% to about 23% w/v arginine, about 8% to about 22% w/v arginine, about 8% to about 21% w/v arginine, about 8% to about 20% w/v arginine, about 8% to about 19% w/v arginine, about 8% to about 18% w/v arginine, about 8% to about 17% w/v arginine, about 8% to about 16% w/v arginine, about 8% to about 15% w/v arginine, about 8% to about 14% w/v arginine, about 8% to about 13% w/v arginine, about 8% to about 12% w/v arginine, about 8% to about 11% w/v arginine, about 8% to about 10% w/v arginine, about 9% to about 24% w/v arginine, about 9% to about 23% w/v arginine, about 9% to about 22% w/v arginine, about 9% to about 21% w/v arginine, about 9% to about 20% w/v arginine, about 9% to about 19% w/v arginine, about 9% to about 18% w/v arginine, about 9% to about 17% w/v arginine, about 9% to about 16% w/v arginine, about 9% to about 15% w/v arginine, about 9% to about 14% w/v arginine, about 9% to about 13% w/v arginine, about 9% to about 12% w/v arginine, about 9% to about 11% w/v arginine, about 9% to about 10% w/v arginine, about 10% to about 24% w/v arginine, about 10% to about 23% w/v arginine, about 10% to about 22% w/v arginine, about 10% to about 21% w/v arginine, about 10% to about 20% w/v arginine, about 10% to about 19% w/v arginine, about 10% to about 18% w/v arginine, about 10% to about 17% w/v arginine, about 10% to about 16% w/v arginine, about 10% to about 15% w/v arginine, about 10% to about 14% w/v arginine, about 10% to about 13% w/v arginine, about 10% to about 12% w/v arginine, about 10% to about 11% w/v arginine, about 11% to about 24% w/v arginine, about 11% to about 23% w/v arginine, about 11% to about 22% w/v arginine, about 11% to about 21% w/v arginine, about 11% to about 20% w/v arginine, about 11% to about 19% w/v arginine, about 11% to about 18% w/v arginine, about 11% to about 17% w/v arginine, about 11% to about 16% w/v arginine, about 11% to about 15% w/v arginine, about 11% to about 14% w/v arginine, about 11% to about 13% w/v arginine, about 11% to about 12% w/v arginine, about 12% to about 24% w/v arginine, about 12% to about 23% w/v arginine, about 12% to about 22% w/v arginine, about 12% to about 21% w/v arginine, about 12% to about 20% w/v arginine, about 12% to about 19% w/v arginine, about 12% to about 18% w/v arginine, about 12% to about 17% w/v arginine, about 12% to about 16% w/v arginine, about 12% to about 15% w/v arginine, about 12% to about 14% w/v arginine, or about 12% to about 13% w/v arginine. In certain embodiments, the storage buffer comprises about 10% arginine.

In embodiments, the rCSP stable liquid formulation comprises a buffer. In embodiments, the buffer is PBS, Hepes, Histidine, or Tris buffer. In embodiments, the buffer is 1×PBS or 0.5×PBS. In embodiments, the stable rCSP formulation has a pH of about 6.0 to about pH 7.5. In embodiments, the stable rCSP formulation has a pH of about pH 6.0, about pH 6.1, about pH 6.2, about pH 6.3, about pH 6.4, about pH 6.5, about pH 6.6, about pH 6.7, about pH 6.8, about pH 6.9, about pH 7.0, about pH 7.1, about pH 7.2, about pH 7.3, about pH 7.4, or about pH 7.5. In embodiments, the stable rCSP formulation has a pH of about pH 6.0 to about pH 7.4, about pH 6.0 to about pH 7.3, about pH 6.0 to about pH 7.2, about pH 6.0 to about pH 7.1, about pH 6.0 to about pH 7.0, about pH 6.0 to about pH 7.5, about pH 6.0 to about pH 7.4, about pH 6.0 to about pH 7.3, about pH 6.0 to about pH 7.2, about pH 6.0 to about pH 7.1, about pH 6.0 to about pH 7.0, about pH 6.0 to about pH 6.9, about pH 6.0 to about pH 6.8, about pH 6.0 to about pH 6.7, about pH 6.0 to about pH 6.6, about pH 6.0 to about pH 6.5, about pH 6.1 to about pH 7.5, about pH 6.1 to about pH 7.4, about pH 6.1 to about pH 7.3, about pH 6.1 to about pH 7.2, about pH 6.1 to about pH 7.1, about pH 6.1 to about pH 7.0, about pH 6.1 to about pH 6.9, 6.1 to about pH 6.8, about pH 6.1 to about pH 6.7, about pH 6.1 to about pH 6.6, about pH 6.1 to about pH 6.5, about pH 6.2 to about pH 7.5, about pH 6.2 to about pH 7.4, about pH 6.2 to about pH 7.3, about pH 6.2 to about pH 7.2, about pH 6.2 to about pH 7.1, about pH 6.2 to about pH 7.0, 6.2 to about pH 6.9, about pH 6.2 to about pH 6.8, about pH 6.2 to about pH 6.7, about pH 6.2 to about pH 6.6, about pH 6.0 to about pH 6.5, about pH 6.3 to about pH 7.5, about pH 6.3 to about pH 7.4, about pH 6.3 to about pH 7.3, about pH 6.3 to about pH 7.2, about pH 6.3 to about pH 7.1, about pH 6.3 to about pH 7.0, 6.3 to about pH 6.9, about pH 6.3 to about pH 6.8, about pH 6.3 to about pH 6.7, about pH 6.3 to about pH 6.6, about pH 6.3 to about pH 6.5, about pH 6.4 to about pH 7.5, about pH 6.4 to about pH 7.4, about pH 6.4 to about pH 7.3, about pH 6.4 to about pH 7.2, about pH 6.4 to about pH 7.1, about pH 6.4 to about pH 7.0, 6.4 to about pH 6.9, about pH 6.4 to about pH 6.8, about pH 6.4 to about pH 6.7, about pH 6.4 to about pH 6.6, about pH 6.4 to about pH 6.5, about pH 6.5 to about pH 7.5, about pH 6.5 to about pH 7.4, about pH 6.5 to about pH 7.3, about pH 6.5 to about pH 7.2, about pH 6.5 to about pH 7.1, about pH 6.5 to about pH 7.0, 6.6 to about pH 6.9, about pH 6.6 to about pH 6.8, about pH 6.6 to about pH 6.7, about pH 6.6 to about pH 6.6, about pH 6.6 to about pH 6.5, about pH 6.6 to about pH 7.5, about pH 6.6 to about pH 7.4, about pH 6.6 to about pH 7.3, about pH 6.6 to about pH 7.2, about pH 6.6 to about pH 7.1, about pH 6.6 to about pH 7.0, 6.6 to about pH 6.9, about pH 6.6 to about pH 6.8, about pH 6.6 to about pH 6.7, about pH 6.7 to about pH 7.5, about pH 6.7 to about pH 7.4, about pH 6.7 to about pH 7.3, about pH 6.7 to about pH 7.2, about pH 6.7 to about pH 7.1, about pH 6.7 to about pH 7.0, 6.7 to about pH 6.9, about pH 6.7 to about pH 6.8, about pH 6.7 to about pH 6.7, about pH 6.7 to about pH 6.6, about pH 6.7 to about pH 6.5, about pH 6.8 to about pH 7.5, about pH 6.8 to about pH 7.4, about pH 6.8 to about pH 7.3, about pH 6.8 to about pH 7.2, about pH 6.8 to about pH 7.1, about pH 6.8 to about pH 7.0, 6.8 to about pH 6.9, about pH 6.8 to about pH 6.8, about pH 6.8 to about pH 6.7, about pH 6.9 to about pH 7.5, about pH 6.9 to about pH 7.4, about pH 6.9 to about pH 7.3, about pH 6.9 to about pH 7.2, about pH 6.9 to about pH 7.1, pH 6.9 to about pH 7.0, about pH 7.0 to about pH 7.5, about pH 7.0 to about pH 7.4, about pH 7.0 to about pH 7.3, about pH 7.0 to about pH 7.2, or about pH 7.0 to about pH 7.1.

In embodiments, the rCSP stable liquid formulation comprises about 1 to about 5, about 1 to about 10, about 1 to about 20, about 1 to about 30, about 1 to about 40, or about 1 to about 50 mg/ml rCSP, about 0.5 to about 1.5 mM MTG and about 10% to about 20% arginine in 1×PBS at a pH of about 6.4 to about 7.2. In certain embodiments, the stable rCSP formulation comprises 1 mM MTG and 10% arginine in 1×PBS at a pH of about 6.4 to about 7.2. In embodiments, the pH is about 6.4 to 7.0. In certain embodiments, the pH is about 6.7. In embodiments, the, the rCSP stable liquid formulation is stored at storage temperature of about 4° C.

In embodiments, the rCSP stable liquid formulation comprises about 1 to about 5, about 1 to about 10, about 1 to about 20, about 1 to about 30, about 1 to about 40, or about 1 to about 50 mg/ml rCSP, about 0.5 to about 1.5 mM MTG, and about 1% to about 20% arginine, in 0.5× or 1×PBS, at a pH of about 6.0 to about 7.5.

In embodiments, the rCSP stable liquid formulation comprises about 1 to about 5, about 1 to about 10, about 1 to about 20, about 1 to about 30, about 1 to about 40, or about 1 to about 50 mg/ml rCSP, about 0.5 to about 1.5 mM MTG, and about 10% to about 20% arginine, in 0.5× or 1×PBS, at a pH of about 6.4 to about 7.2.

In embodiments, the rCSP stable liquid formulation comprises about 1 to about 5, about 1 to about 10, about 1 to about 20, about 1 to about 30, about 1 to about 40, or about 1 to about 50 mg/ml rCSP, about 0.5 to about 1.5 mM MTG, and about 10% to about 20% arginine, in 0.5× or 1×PBS, at a pH of about 6.4 to about 7.0.

In embodiments, the rCSP stable liquid formulation comprises about 1 to about 5 or about 1 to about 10 mg/ml rCSP, about 0.8 to about 1.2 mM MTG, about 5% to about 15% arginine, in 1×PBS, at a pH of about 6.4 to about 7.0.

In embodiments, the rCSP stable liquid formulation comprises about 1 to about 5 mg/ml rCSP, about 1.0 mM MTG, and about 10% arginine, in 1×PBS, at a pH of about 6.4 to about 7.0.

In other embodiments, the rCSP stable liquid formulation comprises 10 mM Tris base, 4.2% Mannitol, 2% Arginine-HCl, 100 µM EDTA, and 1 mM MTG, pH 7.5. In embodiments, the stable rCSP formulation comprises 10 mM Histidine, 4.2% Mannitol, 2% Arginine-HCl, 100 µM EDTA, and 1 mM MTG, at pH 7.0.

In embodiments, the rCSP stable liquid formulation comprises about 0.5 mM MTG to about 1.5 mM MTG and about 0.3 to about 0.7 M arginine in PBS, at about pH 6.4 to about pH 7.0. In embodiments, the rCSP stable liquid formulation comprises about 1 mM MTG and about 0.2 to about 0.7 M arginine in PBS at about pH 6.4 to about pH 7.0. In embodiments, the rCSP stable liquid formulation comprise about 1 mM glutathione or 1 mM cysteine, and about 1% w/v arginine in PBS at about pH 6.4 to about pH 7.0. In embodiments, the rCSP stable liquid formulation comprises about 1 mM MTG and about 1% w/v arginine or about 0.5 M arginine in PBS at about pH 7.0.

In further embodiments, the stable liquid formulations of the present invention facilitate the use of the rCSP for the manufacturing of products, e.g., vaccines, to be administered to patients. In this regard, it is desirable that excipients used in the rCSP formulation meet the standards of the United States Pharmacopeial Convention (Rockville, Md.), as published in the United States Pharmacopeia-National Formulary (USP- NF), or analogous standards in countries outside the United States, e.g., as published in The International Pharmacopeia (World Health Organization).

The invention further relates to methods for stably maintaining rCSP in the rCSP stable liquid formulations over time. Stable maintenance of rCSP in an rCSP stable liquid formulation is evaluated over time, using the same indicators of stability described above, e.g., stable maintenance is positively indicated by the % total rCSP, and negatively indicated by the % rCSP dimer, the % aggregated rCSP, the % denatured rCSP, and/or the % degraded rCSP present after a given time in the formulation. In embodiments, the percent total rCSP is the percent of rCSP (the rCSP monomer) present after a given time. Therefore, stable maintenance can be indicated by the presence of a certain minimal amount of rCSP after a given time in the stable liquid formulation. In other embodiments, the percent total rCSP is the percent rCSP present after a given time in the formulation relative to the starting amount of rCSP in the formulation. In other embodiments, the percent total rCSP is the percent rCSP present after a given time. The amount of rCSP can be evaluated by known methods, as described elsewhere herein. The % total rCSP is equal to the % rCSP monomer, for example, as determined by RP-HPLC or SE-HPLC and described herein in the Examples.

In embodiments, the rCSP stably maintained in the rCSP stable liquid formulation is prepared according to the methods described and claimed herein, e.g., by a process for purifying recombinant *P. falciparum* circumsporozoite protein, said process comprising: (a) obtaining a bacterial cell lysate preparation comprising recombinant *P. falciparum* circumsporozoite protein dimer; (b) separating the bacterial cell lysate preparation of step (a) into a soluble fraction comprising the *P. falciparum* circumsporozoite protein dimer, and an insoluble fraction; (c) separating the recombinant *P. falciparum* circumsporozoite protein dimer in the soluble fraction of step (b) from host cell proteins in the soluble fraction; and (d) subjecting the recombinant *P. falciparum* circumsporozoite protein dimer obtained in step (c) to preferential reducing conditions to obtain *P. falciparum* circumsporozoite protein, and (e) separating the recombinant *P. falciparum* circumsporozoite protein obtained in step (d) from host cell proteins, thereby obtaining purified recombinant *P. falciparum* circumsporozoite protein. In embodiments, the separating of step (e) comprises hydrophobic interaction chromatography.

In these methods, the rCSP is stably maintained at a temperature of about 3 degrees C. to about 25° C. for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In embodiments, the invention relates to a method for stably maintaining rCSP in a stable liquid formulation, the method comprising providing or preparing a stable liquid formulation of rCSP, wherein the rCSP is stably maintained at a temperature of about 3° C. to about 25° C.

In embodiments, the invention relates to a method for stably maintaining rCSP in a stable liquid formulation, the method comprising providing a formulation comprising about 1 to about 5, about 1 to about 10, about 1 to about 20, about 1 to about 30, about 1 to about 40, or about 1 to about 50 mg/ml rCSP, about 0.5 to about 1.5 mM MTG and about 1% to about 20% arginine in 0.5× or 1×PBS at a pH of about 6.0 to about 7.5, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In embodiments, the invention relates to a method for stably maintaining rCSP in a stable liquid formulation, the method comprising providing a formulation comprising about 1 to about 5, about 1 to about 10, about 1 to about 20, about 1 to about 30, about 1 to about 40, or about 1 to about 50 mg/ml rCSP, about 0.5 to about 1.5 mM MTG and about 10% to about 20% arginine in 1×PBS at a pH of about 6.4 to about 7.2, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In embodiments, the invention relates to a method for stably maintaining rCSP in a stable liquid formulation, the method comprising providing a formulation comprising about 1 to about 5, about 1 to about 10, about 1 to about 20, about 1 to about 30, about 1 to about 40, or about 1 to about 50 mg/ml rCSP, about 0.5 to about 1.5 mM MTG and about 10% to about 20% arginine in 1×PBS at a pH of about 6.4 to about 7.0, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In embodiments, the invention relates to a method for stably maintaining rCSP in a stable liquid formulation, the method comprising providing a formulation comprising about 1 to about 5 or about 1 to about 10 mg/ml rCSP, about 0.8 to about 1.2 mM MTG, about 5% to about 15% arginine, in 1×PBS, at a pH of about 6.4 to about 7.0, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

In embodiments, the invention relates to a method for stably maintaining rCSP in a stable liquid formulation, the method comprising providing a formulation comprising about 1 to about 5 mg/ml rCSP, about 1.0 mM MTG and about 10% arginine, in 1×PBS, at a pH of about 6.4 to about 7.0, wherein the rCSP is stably maintained at a temperature of about 3° C. to about 25° C., for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year.

Process

In embodiments, the purification method is carried out using a *P. fluorescens* fermentation whole broth. The broth is diluted with buffer in the presence of a disaggregant to achieve a homogenization feed that is ≤20% solids, e.g., in 3.1 M urea, 31 mM Tris, pH 8.2. The diluted fermentation broth is lysed by microfluidization, generating cell lysate. The lysate is diluted 1:1 with 2 M urea, 20 mM Tris, pH 8.2, creating a 10% solids lysate. The *P. fluorescens* solids in the lysate are separated from the rCSP-containing buffer by disk-stack centrifugation and depth filtration. The rCSP-containing buffer is further 0.2-1 μm filtered and frozen. In embodiments, the filtered rCSP-containing buffer (lysate) is frozen in 1 L or 2 L bottles, e.g., Nalgene® PETG bottles. In embodiments, the lysates are frozen in 1 L PETG bottles at −72° C. for at least 7 hours. In embodiments, the lysates are frozen for at least about 7 hours to at least about 18 hours or any range of about 2 to about 6 hours falling between about 7 and 18 hours. In embodiments, the lysates are frozen for at least about 8 hours, at least about 9 hours, at least about 10 hours, at least about 11 hours, at least about 12 hours, at least about 13 hours, at least about 14 hours, at least about 15 hours, at least about 16 hours, or at least about 17 hours. The rCSP clarified cell extract is thawed, then purified by anion exchange chromatography (AEX). In embodiments, the thawed lysate is held at room temperature before the chromatography. In embodiments, the thawed lysate is subjected to filtration after thawing and prior to AEX. In embodiments, the filtration is membrane filtration. In embodiments, the filtration is 0.2 to 0.45 μm membrane filtration. The rCSP-containing AEX eluate is collected and further purified by hydroxyapatite chromatography (HA), and the rCSP-containing HA eluate is collected and stored at 2-8° C. The HA eluate is brought back to ambient temperature and 0.2-1 μm filtered, and the rCSP is subjected to preferential reducing conditions. Chromatography elution fractions containing dimerized CSP in buffer are pooled to a final volume of 200-600 mL. The pool is subjected to preferential reduction by addition of dithiothreitol reductant to a final concentration of 20 μM, or MTG reductant to a final concentration of 1 mM, and stirred rapidly with a magnetic stir bar and stir plate for 12-24 hours at room temperature. Alternatively, aggregated rCSP in PBS is subjected to the same process by first adding 2 M urea to the material before undergoing preferential reduction. In embodiments, the rCSP is then further purified by HIC.

After being subjected to preferential reducing conditions and/or after HIC purification, the rCSP is concentrated and diafiltered into formulation buffer by TFF.

Alternatively, the HA eluate is subjected to preferential reducing conditions at room temperature and held overnight before either diafiltering into formulation buffer or loaded to HIC, then concentrating and diafiltering.

In embodiments, the formulation buffer comprises 1 mM MTG and 10% arginine. The diafiltered rCSP in formulation buffer is passed through a final 0.2-μm filter to yield the bulk drug substance.

Analysis of Purified *P. Falciparum* Circumsporozoite Protein

Product Specifications

Numerous assay methods are known in the art for evaluating the yield and/or quality of proteins. Use of any appropriate method for characterizing the recombinant protein is contemplated herein.

Protein Yield

The overall purification yield or overall process yield of purified rCSP is the total amount of purified rCSP obtained using the methods of the invention relative to the amount of rCSP determined to be present in the starting material. It is generally expressed as a percent yield. It is understood that determination of the percent yield will depend not only on the amount of protein measured in the starting material, e.g., cell culture, the bacterial cell lysate preparation, or the soluble fraction (before or after clarification), but it also will depend on the load used for each step. In embodiments, wherein the full yield of a step, e.g., the harvest step, is not processed in the next step, e.g., the cell disruption step, the overall process yield must be calculated using the step loads and yields. Where the full yield of all steps is used, the overall process yield can be calculated by dividing the final yield by the amount of rCSP in the starting material. Any appropriate method for measuring protein known in the art or as described herein can be used, for example, SDS-PAGE, including SDS-CGE and Western blot analysis. SDS-PAGE can be carried out under reducing or non-reducing conditions. SDS-PAGE carried out under non-reducing conditions allows individual comparison of monomeric, dimeric and aggregated species (HMW aggregates). For example, such comparisons can be used to determine the yield of purified rCSP monomer relative to rCSP monomer in the starting material, or relative to rCSP dimer, monomer and aggregated species in the starting material. Evaluation under reducing conditions gives a measure of all rCSP species. Activity assays, e.g., binding assays, as described herein and known in the art also can provide information regarding protein yield.

Typically, the starting amount or initial rCSP load is determined by measuring protein concentration in an aliquot of the cell culture, bacterial cell lysate, soluble fraction or clarified lysate fraction. The total amount of protein put into the purification process is then calculated by extrapolation of the aliquot data to the volume of material processed in subsequent steps (the "load"). In embodiments, the initial load amount is used in the determination of overall process yield. In embodiments, the starting amount of rCSP comprises about 1 gram to about 3000 grams, about 100 grams to about 3000 grams, about 250 grams to about 3000 grams, about 500 grams to about 3000 grams, about 750 grams to about 3000 grams, about 1000 grams to about 3000 grams, about 100 grams to about 2000 grams, about 250 grams to about 2000 grams, about 500 grams to about 2000 grams, about 750 grams to about 2000 grams, about 1000 grams to about 2000 grams, about 100 grams to about 1000 grams, about 150 grams to about 1000 grams, about 200 grams to about 1000 grams, about 250 grams to about 1000 grams, about 300 grams to about 1000 grams, about 400 grams to about 1000 grams, about 500 grams to about 1000 grams, or about 750 grams to about 1000 grams.

Comparing the total amount of purified rCSP obtained, to the amount of rCSP measured in the starting material, gives the overall purification process yield as a percent yield (or fractional yield). In embodiments of the present invention, the overall purification process percent yield of purified rCSP obtained is about 10% to about 75%. In embodiments, the percent yield of purified rCSP obtained is at least about 10%, at least about 15%, at least about 20%, at least about 25%, at least about 30%, at least about 35%, at least about 40%, at least about 50%, at least about 60%, at least about 70%, about 10% to about 70%, about 10% to about 65%, about 10% to about 60%, about 20% to about 75%, about 20% to about 70%, about 20% to about 65%, about 25% to about 75%, about 25% to about 70%, about 25% to about 65%, about 25% to about 60%, about 30% to about 75%, about 30% to about 70%, about 30% to about 65%, about 30% to about 60%, about 30% to about 65%, or about 30% to about 60%. In embodiments, these process yields are the yields of rCSP that contain limited amounts of denatured, degraded, dimerized, or aggregated rCSP. In embodiments, these process yields comprise not more than 10% denatured rCSP, not more than 10% degraded rCSP, 10% aggregated rCSP, and/or 10% dimerized rCSP. In embodiments, these process yields comprise not more than 5% denatured rCSP, not more than 5% degraded rCSP, 5% aggregated rCSP, and/or not more than 5% dimerized rCSP.

Protein yield also can be expressed as the percent or fraction of total cell protein (tcp), the amount of protein/cell, or the percent or proportion of dry biomass. In embodiments wherein yield is expressed in terms of culture volume the culture cell density may be taken into account, particularly when yields between different cultures are being compared. It is understood that recovery yields also can be determined for each step, or for multiple steps, of the purification process (as opposed to describing overall purification yield).

Protein Quality

In related embodiments, the rCSP is described in terms of protein quality at any step of the purification process. In embodiments as described herein, protein quality can be described as a function of the amount or percentage of the rCSP that is dimerized or not dimerized, degraded or not degraded (or clipped) at the N-terminus, or denatured or not denatured, i.e., having intact disulfide bonds in the C-terminal region, or any combination thereof. Measures of quality also include the percent or fraction of CSP determined to be active, e.g., by binding assay. In these embodiments, activity can be expressed by comparing the amount of protein determined to be active to the total amount of protein assayed. The amount of protein at any step of purification that is determined to be, e.g., dimerized, not dimerized, aggregated, not aggregated, degraded, not degraded, denatured, not denatured, inactive, or active can be compared with the total amount of protein at the same step. For example, the amount of not dimerized, not aggregated, not degraded, not denatured, or active rCSP in the purified protein obtained can be compared with the total amount of purified rCSP obtained, to arrive at a percent or fractional value of the amount of not dimerized, not aggregated, not degraded, not denatured, or active rCSP, etc. Alternatively, the amount of not dimerized, not aggregated, not degraded, not denatured, or active rCSP, etc. in the purified protein obtained can be compared with the amount of not dimerized, not aggregated, not degraded, not denatured, or active rCSP, etc. in the starting material to arrive at a percent or fractional value of the recovered amount of rCSP that is not dimerized, not aggregated, not degraded, not denatured, or that is active, etc.

Any method for evaluating rCSP dimer formation as described herein or as known in the art can be used to determine the percent rCSP dimer formation. Methods can include, e.g., HPLC (including RP-HPLC and SE-HPLC). Methods for evaluating HMW aggregate formation can include, e.g., HPLC and SDS-PAGE.

In embodiments of the present invention, the purified rCSP obtained comprises less than about 12% dimer. In embodiments, the purified rCSP obtained comprises less than about 11%, less than about 10%, less than about 9%, less than about 8%, less than about 7%, less than about 6%, less than about 5%, less than about 4%, less than about 3%, less than about 2%, or less than about 1% dimer. In related embodiments, the purified rCSP obtained comprises at least 88% monomer. In embodiments, the purified rCSP obtained comprises at least 89%, at least 90%, at least 91%, at least 92%, at least 93%, at least 94%, at least 95%, at least 96%, at least 97%, at least 98%, at least 99%, at least 100% monomer.

Any method for evaluating rCSP degradation as described herein or as known in the art can be used to determine the percent rCSP degradation. Methods can include, e.g., LC-MS/intact mass, SDS-PAGE, HPLC (including RP-HPLC and SE-HPLC), and N-terminal sequencing.

In embodiments of the present invention, the purified rCSP obtained comprises less than about 10% total rCSP species degraded at the N-terminus. In embodiments, the purified rCSP obtained comprises less than about 9%, less than about 8%, less than about 7%, less than about 6%, less than about 5%, less than about 4%, less than about 3%, less than about 2%, or less than about 1% total rCSP species degraded at the N-terminus. In embodiments, none of the purified rCSP obtained is degraded at the N-terminus. In embodiments, the percent degradation is the percent clipped at C5/Y6 or V14/L15. In embodiments, the percent degradation is the percent clipped at both C5/Y6 and V14/L15. In embodiments, the percent degradation is the percent clipped at C5/Y6, V14/L15, and/or N29/E30. In other embodiments, the percent degradation is the percent clipped at C5/Y6, V14/L15, N29/E30, and/or S44/L45. In embodiments, the percent degradation is the percent of rCSP obtained that is nonspecifically degraded. In embodiments, the purified rCSP obtained comprises less than about 10%, less than about 9%, less than about 8%, less than about 7%, less than about 6%, less than about 5%, less than about 4%, less than about 3%, less than about 2%, or less than about 1% rCSP that is nonspecifically degraded at the N-terminus. In embodiments, none of the purified rCSP obtained is nonspecifically degraded at the N-terminus. In embodiments, the percent degradation is the percent of rCSP obtained that is clipped at C5/Y6, V14/L15, N29/E30, and/or S44/L45 combined with the percent of rCSP that is nonspecifically degraded at the N-terminus. In related embodiments, at least 90%, at least 91%, at least 92%, at least 93%, at least 94%, at least 95%, at least 96%, at least 97%, at least 98%, at least 99%, or 100% of the rCSP obtained is not degraded at the N-terminus, either nonspecifically or by clipping at C5/Y6, V14/L15, N29/E30, and/or S44/L45.

In embodiments of the present invention, not more than 10%, 9%, 8%, 7%, 6%, 5%, 4%, 3%, 2%, 1% or none of the purified rCSP obtained is degraded, clipped, or proteolyzed to an amino acid selected from residues 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 (where residue 1 is the first residue in the expressed protein not including the leader, e.g., Q in SEQ ID NO:2C and M in SEQ ID NO: 2B). In embodiments, at least 90%, 91%, 92%, 93%, 94%, 95%, 96%, 97%, 98%, 99% or 100% of the purified rCSP obtained is intact to an amino acid selected from residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

In specific embodiments, the purified rCSP is obtained at an overall purification process yield of about 10% to about 75%, wherein the purified rCSP comprises less than about 5% dimer, comprises less than about 10% total C5/Y6 and V14/L15 clipped species, and less than about 5% denatured rCSP.

Any method for evaluating rCSP denaturation as described herein or as known in the art can be used to determine the percent denatured protein. For example, methods for analyzing secondary structure, e.g., CD and intrinsic fluorescence, and methods for analyzing disulfide bonding, e.g., peptide mapping and alkylation/intact mass/Glu-C digest, can be used.

In embodiments, the purified rCSP obtained comprises less than about 10%, less than about 9%, less than about 8%, less than about 7%, less than about 6%, less than about 5%, less than about 4%, less than about 3%, less than about 2%, or less than about 1% denatured rCSP, e.g., rCSP having improper disulfide bonding. Improper disulfide bonding is identified when at least one of the two native disulfide bonds in the C-terminal region is mispaired or unpaired. In embodiments, at least about 90%, 91%, 92%, 93%, 94%, 95%, 96%, 97%, 98%, 99% or 100%, respectively, of the purified rCSP has intact disulfide bonds. In other embodiments, denaturation is determined by comparing one or more measures of secondary structure of the purified rCSP to a reference standard rCSP.

It is understood that the numbering used to describe the clipping sites or the cysteines and disulfide bonds can vary depending on the rCSP amino acid sequence.

Pyroglutamate-Containing Species

In certain embodiments, it may be desirable that pyroglutamate-containing rCSP species, e.g., rCSP wherein glutamine is deamidated to glutamate, and subsequently glutamate is cyclized to pyroglutamate (glutamine→glutamic acid→pyroglutamate), are limited. As described herein, the nonpyroglutamate-containing species of rCSP has been observed to decrease over time as the pyroglutamate-containing species increases over time. Pyroglutamate can be measured by any appropriate method known in the art, e.g., RP-HPLC.

In embodiments, the purified rCSP obtained comprises less than about 20%, less than about 18%, less than about 15%, less than about 10%, less than about 9%, less than about 8%, less than about 7%, less than about 6%, less than about 5%, less than about 4%, less than about 3%, less than about 2%, or less than about 1% pyroglutamate-containing rCSP.

In embodiments, process yields comprise not more than about 20%, 18%, 15%, 10%, 5%, or 1% pyroglutamate-containing rCSP.

In embodiments, the amount of pyroglutamate-containing species in a formulation of rCSP increases by not more than about 0%, 0.5%, 1%, 1.5%, 2%, 2.5%, 3%, 3.5%, 4%, 4.5%, 5%, 6%, 7%, 8%, 9%, or 10%, when stored for at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 30 days, at least about 60 days, at least about 70 days, at least about 80 days, at least about 90 days, at least about 6 months, or at least about 1 year. In certain embodiments, the maximum rate of increase in pyroglutamate-containing species is less than or equal to about 1% to about 3% or to about 5% when stored for about 9 days to about 25 days. The amounts prior to storage (e.g., at T=0) can be used for comparison.

In embodiments, rCSP quality is indicated by the presence of less than about 10% rCSP pyroglutamate-containing species. In embodiments, rCSP quality is indicated by the absence of pyroglutamate-containing species, wherein these species are present at not more than about 10%, not more than about 9%, not more than about 8%, not more than about 7%, not more than about 6%, not more than about 5%, not more than about 4%, not more than about 3%, not more than about 2%, or not more than about 1% of the total protein or purified CSP obtained.

Protein Purity

In embodiments, purity of the rCSP is evaluated by SDS-CGE and/or SDS-PAGE at any step in the purification process, and a purity value assigned accordingly. The purity can be calculated by the SDS-CGE instrument software, which divides the peak area of the target protein (e.g., rCSP monomer) in a electropherogram by the area of the other peaks. In embodiments the purity of the purified rCSP obtained using the methods of the invention is about 85% to 100%. In embodiments, the purity is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, about 85% to about 99%, about 85% to about 98%, about 85% to about 97%, about 85% to about 96%, about 90% to about 99%, about 90% to about 98%, about 90% to about 97%, about 90% to about 96%, or about 90% to about 95%.

In certain embodiments, the purified rCSP obtained has a purity of 96%, contains not more than 5% dimer, contains no detectable high molecular weight (HMW) aggregates, contains less than 10 EU/mg endotoxin, and has no detectable proteolytic clipping. In embodiments the endotoxin is present at not more than about 10 EU/mg, not more than about 25 EU/mg, not more than about 50 EU/mg, not more than about 100 EU/mg, not more than about 250 EU/mg, not more than about 400 EU/mg, or not more than about 500 EU/mg.

Product Analysis

In embodiments of the present invention, the recombinant CSP is evaluated at any step of the purification process of the invention for any of yield, purity, quality, and stability using methods as described herein, reported in the literature, and known in the art. Assays for evaluating rCSP are provided herein as non-limiting examples.

Determining Protein Yield

The present invention provides a process useful for obtaining purified rCSP at a high overall purification yield. SDS-PAGE methods, e.g., SDS-CGE or Western blot, can be used to determine yield and to monitor rCSP purity as appropriate at any step of the purification process. In embodiments, the protein included in the yield measurement includes monomeric rCSP and not dimeric or aggregated rCSP. In embodiments, step yields and/or overall yield is determined. In embodiments, subjecting the rCSP to preferential reducing conditions results in an increased step yield of rCSP monomer due to conversion of rCSP dimers into monomers.

Suitable methods for determining yield are known to those of skill in the art, for example, protein samples can be analyzed by HTP microchip SDS capillary gel electrophoresis (SDS-CGE) using a LabChip GXII instrument (Caliper Life-Sciences, Hopkinton, Mass.) with a HT Protein Express v2 chip and corresponding reagents (part numbers 760499 and 760328, respectively, Caliper LifeSciences). Samples are prepared following the manufacturer's protocol (Protein User Guide Document No. 450589, Rev. 3) and electrophoresed on polyacrylamide gels. After separation the gel is stained, destained, and digitally imaged.

Protein concentrations of purified rCSP samples can be determined by absorbance at 280 nm ($A_{280}$ for 1 mg/ml=0.61 AU as determined by Vector NTI Invitrogen) using an Eppendorf BioPhotometer (Eppendorf, Hamburg, Germany).

Western blot analysis to determine yield or purity can be carried out according to any appropriate method known in the art by transferring CSP separated on SDS-PAGE gels to a nitrocellulose membrane and incubating the membrane with a monoclonal anti-Pf CSP antibody.

CSP antibodies useful for any analytical methods described herein can be generated by suitable procedures known to those of skill in the art. Useful antibodies also have been described in the literature, and are commercially available. CSP conformation-specific monoclonal antibodies suitable have been described, for example, antibodies 4C2, 4B3, and 1G12 were characterized and reported to be sensitive to CSP denaturation by Plassmeyer, et al., 2009. CSP antibodies having desired binding characteristics can be generated and screened according to methods described in the literature, e.g., by Plassmeyer, et al., 2009.

Determining Protein Denaturation

In embodiments, the purification process of the present invention is used to obtain purified rCSP monomer that is not denatured, without the need for refolding. rCSP that is not denatured has a native structure that can be evaluated, e.g., by comparison to an internal reference standard. In embodiments, denaturation is analyzed based on the presence of proper disulfide bonding in the C-terminal region. Protein secondary or tertiary structure, and the presence of proper disulfide bonding in the C-terminal region, can be analyzed by methods known in the art or described herein.

Protein secondary structure can be analyzed using, e.g., circular dichroism (CD) or intrinsic fluorescence. CD can employ a spectropolarimeter (e.g., Jasco J-815, JASCO). The far UV-CD region from 185-250 nm monitors secondary structural differences (i.e., a-helices, b-sheets, and random coils). Far-UV CD spectroscopy (240-190 nm) can be carried out on the Jasco J-815 spectropolarimeter with the bandwidth set to 1 nm and scanning speed of 100 nm/min, Digital Integration Time (DIT)=1 sec, with 5× accumulations, using 0.1 mm path length cuvettes. Samples can be analyzed at 20° C. in ×5 mM tris (Sigma, catalog number T7818-250G)/16.7 mM sodium sulfate (Sigma, catalog number 59627-500G) pH, 7.5 buffer. Analysis software, e.g., K2D2, described by Perez-Iratxeta, et al., 2008, "K2D2: estimation of protein secondary structure from circular dichroism spectra," BMC Structural Biology 8:25 (doi:10.1186/1472-6807-8-25), can be used to evaluate percent alpha helix and beta strand in the protein. CSP is reported to contain 5% alpha helix and 27% beta strand (by, e.g., Plassmeyer, et al., 2009).

For intrinsic fluorescence, the initial spectropolarimeter temperature can be set to 20° C., followed by stepwise increases to 40, 45, 55, 65, and 75° C., followed by a return to 20° C. The fluorescence is read at each temperature setting with the fluorescence readings can be set as follows: Excitation at 280 nm; Emission at 295-395 nm; Sensitivity=790 V; Data pitch=1 nm; Digital Integtation Time (DIT)=1 sec; Band width emission=10 nm; Spectrum accumulations=3; Stir bar rpm=200.

Denaturation/conformation of the rCSP obtained can be evaluated using biolayer interferometry (BLI) which measures binding of rCSP to a selected target. In embodiments, binding to conformation-specific antibodies (e.g., antibodies that will not bind to denatured protein) and/or heparin is measured. Functional binding assays are useful to monitor differences in rCSP conformation and can be employed as surrogate potency assays. Examples of conformation-specific antibodies useful in these methods are described herein and by Plassmeyer, et al., 2009. Example biosensor configurations using heparin and conformation-specific antibodies are described herein in the Examples.

Globular folded structure can be analyzed using size-exclusion HPLC (SE-HPLC). Size exclusion separates proteins based on size with larger proteins eluting earlier than smaller ones. In embodiments, size exclusion (SE) HPLC is performed using a TSK-GEL G3000SWXL column. Notably, as described in the Examples, rCSP (which is ~38 kDa) has a shorter retention time than expected.

Disulfide bonding can be analyzed using peptide mapping as described herein in the Examples. The rCSP can be subjected to a double protease digestion, first with trypsin, then with elastase. The double digests are analyzed by LC-MS/MS, and the resulting data processed using BiopharmaLynx (Waters Corp., Milford, Mass.) to identify the two disulfide bonded dipeptides. As a negative control procedure, the same data can be processed using a method file containing the inverse of the above (i.e., incorrect) disulfide bonds, $C_{314}$-$C_{354}$ and $C_{318}$-$C_{349}$.

Determining Protein Degradation

The present invention provides a purification process useful for obtaining purified rCSP that is not degraded in the N-terminal region. In embodiments, LC-MS is used to monitor proteolytic clipping, deamidation, oxidation, and fragmentation, and to verify that the N-terminal region cysteine is unpaired.

In embodiments, the free N-terminal cysteine is identified by alkylation and peptide mapping, e.g., as described herein in the Examples.

In embodiments, RP-HPLC is used to detect fragmentation, deamidation, and oxidation.

HPLC can be used to characterize the rCSP, providing structural information including monomer and dimer content. In embodiments, Reverse Phase HPLC (RP-HPLC) is used to evaluate monomer and dimer content, fragmentation, deamidation, and oxidation. Addition of a reducing agent, e.g., 20 µM DTT, can aid in identification of species by shifting the dimer observed toward monomer, and aggregates to dimer or monomer. Methods for RP-HPLC, including appropriate reversed phase (RP) columns, are known in the art and described in the literature. In certain embodiments, a $C_4$ Jupiter column (Phenomenex) is used.

In embodiments, preparative hydrophobic chromatography is used to resolve monomer and dimer forms of rCSP.

In embodiments, protein charge heterogeneity is analyzed using, e.g., capillary isoelectric focusing (cIEF) or imaged capillary isoelectric focusing (icIEF). In these embodiments, a standard, e.g., an rCSP internal reference standard, may be used for comparison. As described in the Examples herein, an rCSP internal reference standard evaluated using cIEF shows main peaks at pI 5.20 and pI 5.76 and smaller peaks at pI 4.99, 5.08 and 5.52.

In embodiments, CSP microheterogeneity is analyzed using peptide mapping mass spectrometry.

Determining Protein Purity

In embodiments, contaminants including host cell proteins and nucleic acids are evaluated using methods well known in the art.

As described with regard to yield determination, SDS-PAGE methods are useful for identifying contaminating dimer and HMW aggregated species. In embodiments, SE-HPLC is used to identify aggregated species.

In embodiments, ELISA methods are used to measure host cell protein. For example, the host cell protein (HCP) ELISA can be performed using the "Immunoenzymetric Assay for the Measurement of *Pseudomonas fluorescens* Host Cell Proteins" kit from Cygnus Technologies, Inc., catalog number F450, according to the manufacturer's protocol. The plate can be read on a SPECTRAmax Plus (Molecular Devices), using Softmax Pro v3.1.2 software.

In embodiments, endotoxin is evaluated by a *Limulus amebocyte* lysate (LAL) test. LAL tests are well known in the art and have been approved by the FDA for testing drugs, devices, and other products that contact the blood. In embodiments, the amount of endotoxin in the elution fractions is analyzed using an Endosafe-PTS portable endotoxin analyzer (Charles River Laboratories (CHL)) following manufacturer-supplied operating procedures, using cartridges with sensitivity ranges of 1-0.01 EU/mL (CHL, part number PTS2001F) and 10-0.1 EU/mL (CHL, part number PTS201F).

In embodiments, host cell DNA is analyzed using Q-PCR. Host cell DNA can be evaluated using, e.g., oligonucleotide primers specific for the DNA Polymerase I gene. Expression plasmid backbone sequences of the expression strain are detected by real-time quantitative PCR. Real-time PCR can be performed with, e.g., a DNA Engine Opticon System PTC-200 DNA Engine Cycler (MJ Research, CFD-3200 Opticon).

Purification of rCSP Internal Reference Standard

In embodiments, an rCSP internal reference standard is used in analyses performed in association with the methods of the present invention. The reference standard can be made according to methods known in the art or as described herein. For example, cell paste from host cells expressing rCSP can be microfluidized, separated to remove solid cell debris, and separated to remove host cell proteins. The final purified rCSP can be buffer exchanged into PBS (pH 7.2) by gel filtration, filter-sterilized, and stored at −80° C. The purity of the internal reference standard can be analyzed by, e.g., SDS-PAGE. In embodiments, the purity of the rCSP internal reference standard is determined to be >90% by SDS-PAGE. In embodiments, the standard contains less than 10% dimer. Western blot analysis can be used to confirm identity of the rCSP and reveal the presence of fragmented species. A conformation-specific antibody assay can be carried out, e.g., using an antibody that is sensitive to the C-terminal domain wherein the two native disulfide bonds are intact and properly paired. Appropriate antibodies have been described in the literature, e.g., by Plassmeyer, et al., 2009. Reduced and alkylated samples can be analyzed for loss of signal indicating that the purified rCSP standard has the correct disulfide structure. In embodiments, the concentration of the rCSP standard is determined by absorbance at 280 nm. In embodiments, the reference material has demonstrated potency in animal studies.

In embodiments of the present invention, the primary recovery process has two options. Cells can be harvested by centrifuging and the cell paste frozen. The cell paste can then be thawed and micofluidized to produce cell homogenate. Alternatively, the cell broth can be diluted and directly micofluidized to produce cell homogenate without a hold step.

In certain embodiments, the cell pasting option is used. The homogenate is then clarified using a disc-stack centrifuge, followed by depth filtration using the X0HC membrane in tandem with 0.2 μm filtration. The material is then kept frozen as a hold step and then thawed and loaded to the TMAE HiCap capture column. Eluted material is passed through a 0.2 μm filter and then directly loaded to the Ceramic Hydroxyapatite Type I (CHT) column. CHT column eluate is then subjected to 0.2 μm filtration and mild-reduction treatment while being held at ambient temperature. The material post mild-reduction treatment is then buffer exchanged by TFF and 0.2 μm filtered and stored frozen at −80° C.

In embodiments, the purified rCSP obtained using the methods of the invention has greater than 90% purity as determined by SDS-PAGE (SDS-CGE), less than 10% dimer as determined by SE-HPLC, no detectable higher molecular weight (HMW) aggregates as determined by SE-HPLC, less than 5% fragments detectable by LC/MS, and less than 100 EU/mg endotoxin. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Purification process steps were identified and tested for use in the methods of the present invention. SDS-CGE analysis was used to evaluate protein yields and purity. Protein samples were analyzed by HTP microchip SDS capillary gel electrophoresis using a LabChip GXII instrument (Caliper LifeSciences, Hopkinton, Mass.) with a HT Protein Express v2 chip and corresponding reagents (part numbers 760499 and 760328, respectively, Caliper LifeSciences). Samples were prepared following the manufacturer's protocol (Protein User Guide Document No. 450589, Rev. 3).

Protein concentrations of purified rCSP samples were routinely determined by absorbance at 280 nm ($A_{280}$ for 1 mg/ml=0.61 AU as determined by Vector NTI Invitrogen) using an Eppendorf BioPhotometer (Eppendorf, Hamburg, Germany).

Cell paste batches used in process development and assay development were prepared from bacterial host cells engineered to recombinantly express CSP using methods described herein. The CSP nucleotide sequence expressed by the *P. fluorescens* strains that were used to prepare the batches of cell paste comprised the optimized nucleotide sequence set forth in SEQ ID NO: 5 (corresponding amino acid sequence set forth in SEQ ID NO: 3). Strain CS533-129 is *P. fluorescens* DC469 (ΔpyrF, lacI$^Q$, ΔhtpX) containing an expression vector encoding CSP (SEQ ID NO: 3) fused to the LAO secretion leader. Strain CS533-211 is *P. fluorescens* DC488 (degP2 deletion) containing an expression vector encoding CSP (SEQ ID NO: 3) fused to the CupA2 leader.

Examples

Example 1

Preferential Reduction of Recombinantly Produced *Plasmodium Falciparum* Circumsporozoite Protein Conversion of rCSP Dimer to Monomer This Example describes experiments carried out to identify preferential reducing conditions useful for selectively reducing the intermolecular disulfide bonds of dimerized rCSP, while preserving the C-terminal region intramolecular disulfide bonds and native structural state needed for CSP immunogenicity.

As discussed, rCSP readily dimerizes during purification due to an N-terminal region free cysteine that is available to form an intermolecular disulfide bond. The dimer can then form higher molecular weight aggregates dependent on time, concentration, and temperature. Recombinant CSP further contains two disulfide bonds in its C-terminal region that are believed to be important for CSP potency. To increase the recovery of monomer rCSP, we investigated conditions that would reduce the intermolecular disulfide bond and convert the dimer to monomer. Conditions were desired that did not reduce the C-terminal region intramolecular disulfides.

Dithiothreitol (DTT) was tested as a reducing agent and was added to 1 mL samples of dimerized rCSP from Butyl 650S chromatography fractions in varying concentrations. The samples were stirred overnight on a magnetic stirplate at ambient temperature. The samples were then analyzed for the monomer and dimer content by RP-HPLC (FIG. 4). Panel A shows the results corresponding to DTT concentrations of 0.5 mM (represented by the lowest monomer peak and the second-highest dimer peak), 0.1 mM (second-highest monomer peak overlapping with 0.03 peak, second-lowest dimer peak), 0.03 mM (second-highest monomer peak overlapping with 0.03 peak, lowest dimer peak), and no DTT (highest monomer peak, highest dimer peak). Panel B shows the results corresponding to DTT concentrations of 0.01 mM (highest monomer peak, lowest dimer peak) 0.003 mM (middle monomer peak, middle dimer peak), and no DTT (lowest monomer peak, highest dimer peak).

Figure 4A:
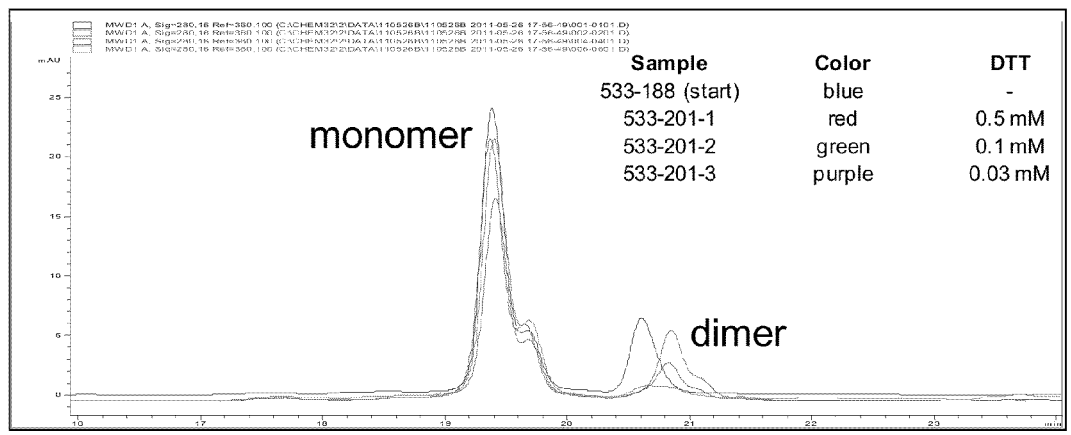
FIG. 4. RP-HPLC Analysis of Dimer rCSP After Addition of Varying Amounts of Reductant. A. DTT concentration of 0.5 mM, 0.1 mM, 0.03 mM, and no DTT. B. DTT concentration of 0.01 mM, 0.003 mM, and no DTT.
Figure 4B:
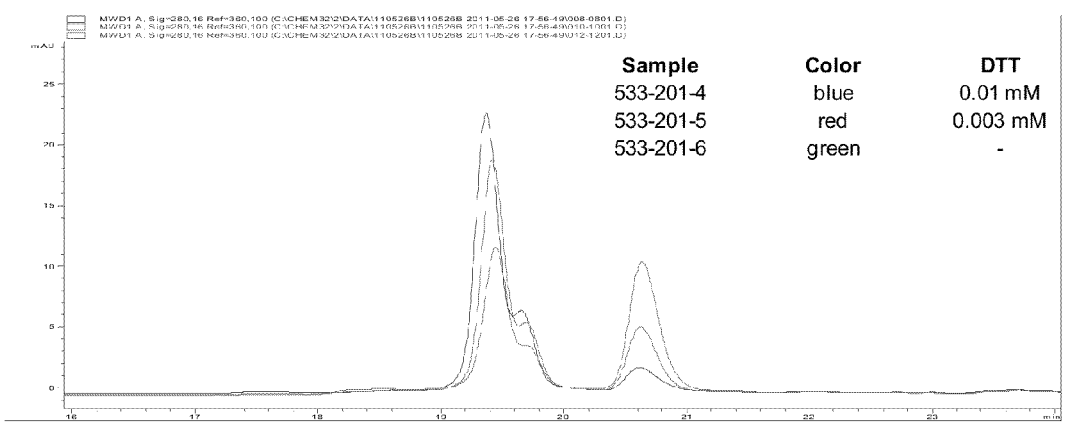

There are three features to the RP-HPLC chromatogram that are routinely observed when analyzing rCSP: the main rCSP in monomeric form, a trailing shoulder peak off the main rCSP peak, and a peak that elutes 1.4 minutes later than the main peak, which is the dimer form of rCSP. As shown in FIG. 4, DTT addition generally decreased the concentration of the dimer and increased the concentration of the monomer peak; however, if the DTT concentration was too high (0.5 mM, in FIG. 4A) or too low (0.003 mM in FIG. 4B) the conversion of dimer to monomer was minimal. The best preferential reducing concentration range of DTT for conversion was determined to be from 0.010 to 0.030 mM DTT.

Figure 5A:
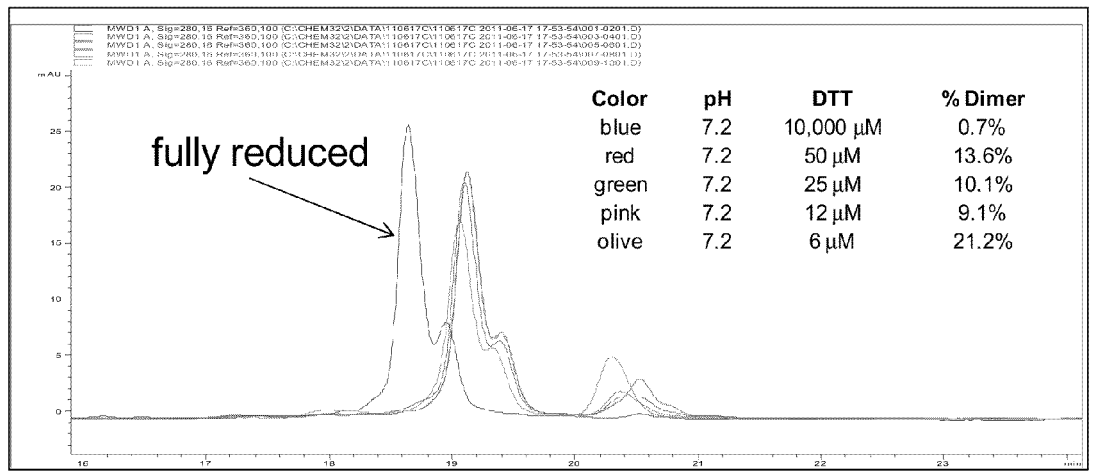
FIG. 5. RP-HPLC Analysis of Disaggregated rCSP. A. Treatment with 2M urea and varying amounts of DTT at pH 7.2. B. Treatment with 2M urea and varying amounts of DTT at pH 8.0.
Figure 5B:
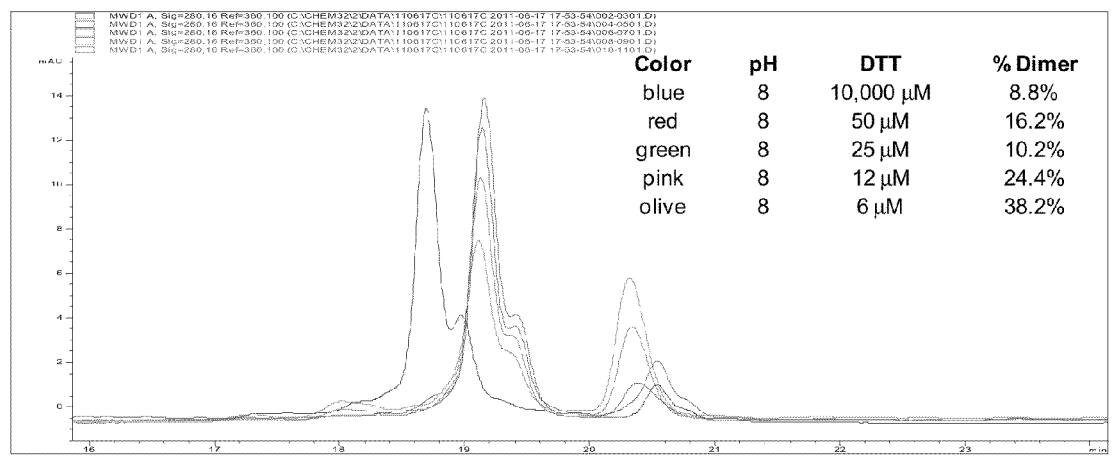

The experiment was repeated using a batch of rCSP (533-128) that contained dimer and HMW aggregates of dimer. Approximately 3 g of batch 533-128 was produced using a small-scale purification process in multiple cycles to >90% purity as determined by SDS-PAGE. Batch 533-128 later was determined to be aggregated. Addition of 2 M urea was observed to disrupt the HMW aggregates, breaking them down to the dimer form (data not shown). DTT was added to one mL samples of 533-128 containing 2 M urea with varying concentrations of DTT at pH 7.2 and pH 8.0 and incubated for 6 h at ambient temperature. Samples were stirred for 6 h on a magnetic stirplate at ambient temperature. The RP-HPLC analysis of the samples is shown in FIG. 5. The DTT concentrations used for the experiment in FIG. 5A and FIG. 5B are shown in Table 5 and Table 6, respectively.

TABLE 5

RP-HPLC at pH 7.2 at Varying Concentrations of DTT

| Fully Reduced Peak 1 height (1-5 highest to lowest) | Peak 2 height (1-5 highest to lowest) | DTT concentration µM | % Dimer |
|---|---|---|---|
| 1 | 5 | 10,000 | 0.7 |
| 4 | 2 | 50 | 13.6 |
| 2/3 | 4 | 25 | 10.1 |
| 2/3 | 3 | 12 | 9.1 |
| 5 | 1 | 6 | 21.2 |

TABLE 6

RP-HPLC at pH 8.0 at Varying Concentrations of DTT

| Fully Reduced Peak 1 height (1-5 highest to lowest) | Peak 2 height (1-5 highest to lowest) | DTT concentration µM | % Dimer |
|---|---|---|---|
| 2 | 5 | 10,000 | 8.8 |
| 3 | 3 | 50 | 16.2 |
| 1 | 4 | 25 | 10.2 |
| 4 | 2 | 12 | 24.4 |
| 5 | 1 | 6 | 38.2 |

At pH 7.2, the best DTT concentrations determined to be 12 µM and 25 µM for conversion, and for pH 8.0 the best concentration was 25 µM. The highest concentration of DTT (10 mM) decreased the dimer peak completely for both pH 7.2 and pH 8.0 samples, and caused a retention time shift to the left (shorter retention time) which is likely the fully reduced form of rCSP.

Based on the experiments performed, the optimal concentration of DTT used in the mild reduction process was determined to be 20 µM. Performing the reduction step overnight (16-18 h) had no negative impact on the quality of rCSP, so this step was used as a hold point prior to starting the final UF/DF buffer exchange.

Figure 6A:
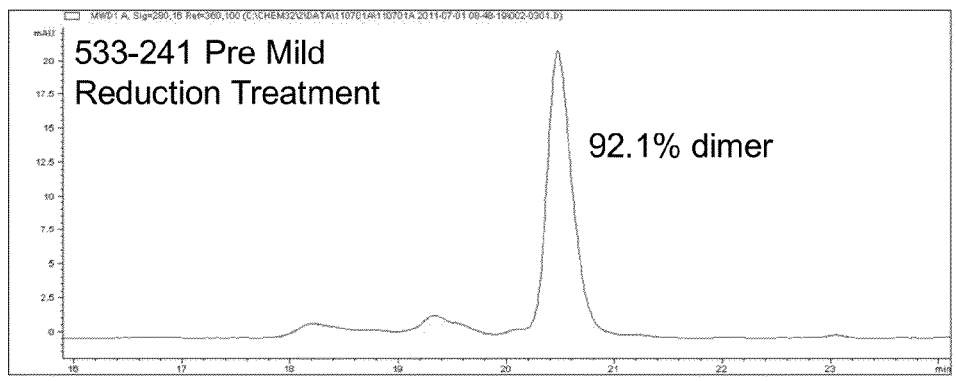
FIG. 6. RP-HPLC Analysis of rCSP Pre and Post Mild Reduction Treatment and Final Buffer Exchange. A. RP-HPLC analysis of batch 533-241 before mild reduction treatment. B. RP-HPLC analysis of batch 533-241 after mild reduction treatment and final TFF buffer exchange. C. RP-HPLC of internal reference standard 533-191.
Figure 6B:
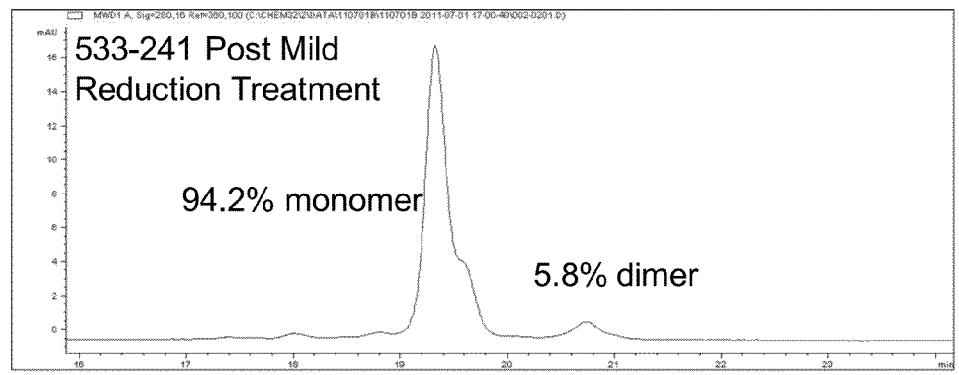
Figure 6C:
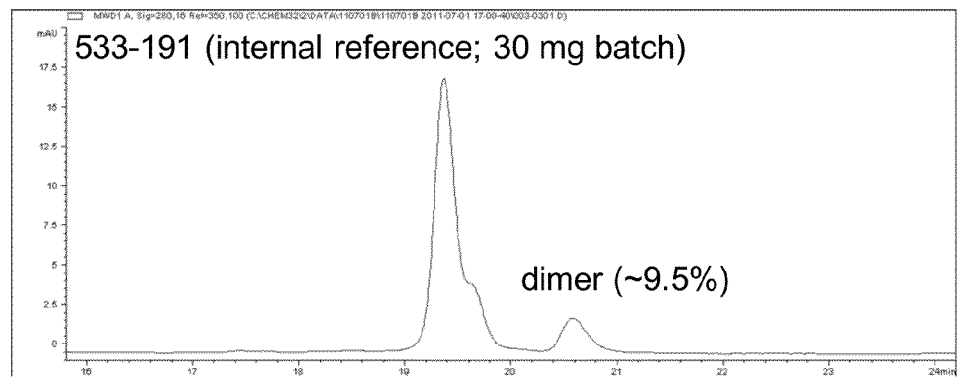
Figure 7A:
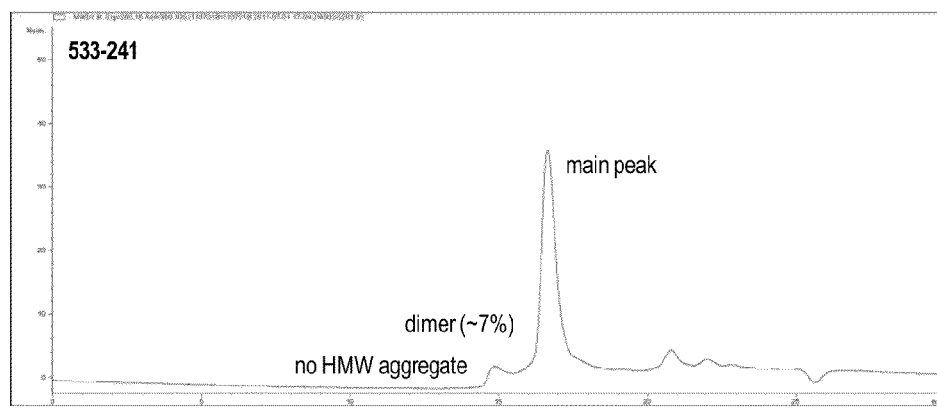
FIG. 7. SE-HPLC Analysis of rCSP Post Mild Reduction Treatment and Final Buffer Exchange. A. SE-HPLC analysis of batch 533-241 after mild reduction treatment and final TFF buffer exchange. B. SE-HPLC of internal reference standard 533-191.
Figure 7B:
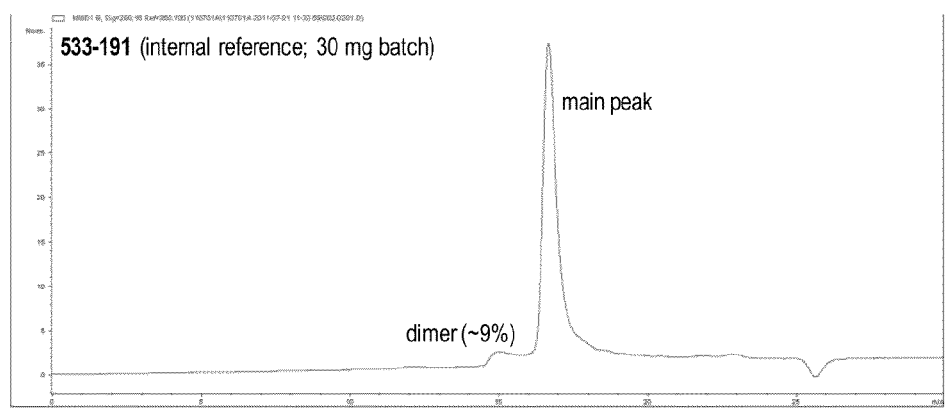
Figure 8A:
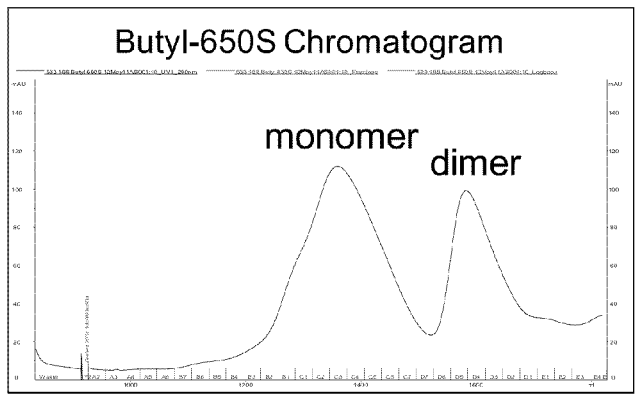
FIG. 8. In Process RP-HPLC Detection of Dimeric Form of rCSP. A. Separation of rCSP monomer and dimer by hydrophobic interaction chromatography. B. SDS-CGE analysis (reduced) of monomer and dimer rCSP fractions. C. SDS-CGE analysis (non-reduced) of monomer and dimer rCSP fractions. D. RP-HPLC analysis of monomer and dimer rCSP pools.
Figure 8B:
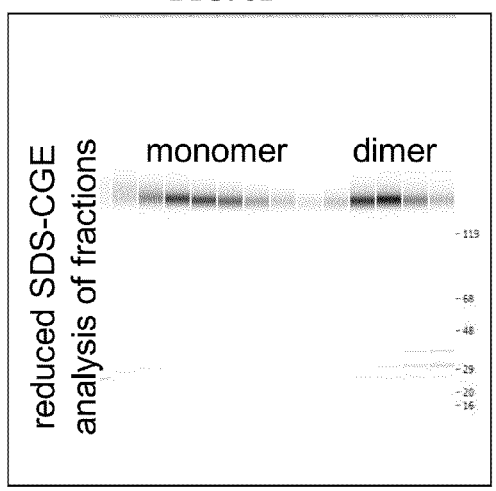
Figure 8C:
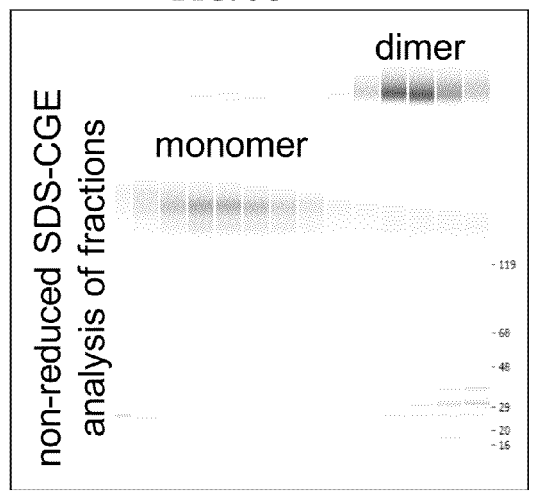
Figure 8D:
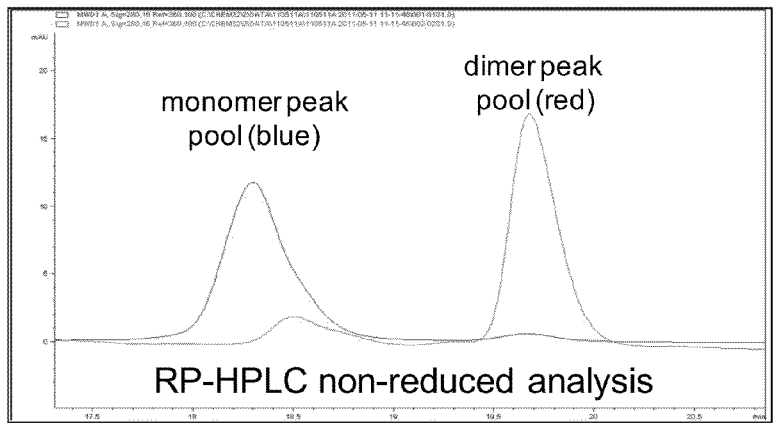

FIG. 6 shows an example where ~120 mg of dimeric rCSP from Butyl 650S chromatography (rCSP batch 533-241) was treated for 16 h with 20 µM DTT and mixing. The batch prior to treatment contained 92.1% dimer by RP-HPLC analysis (FIG. 6A) and post-treatment with final buffer exchange by TFF contained 94.2% monomer (FIG. 6B). The final buffer-exchanged material was analyzed by SE-HPLC and no HMW aggregates observed (FIG. 7). The mild-reduction method appeared to be very robust, and not impacted by small differences in base buffer composition. Recombinant CSP dimer fractions eluting from ceramic hydroxyapatite chromatography also were subjected to mild reduction treatment successfully as discussed below.

As described in detail herein, batches of rCSP that were subjected to the mild reduction treatment were analyzed by LC/MS and peptide mapping to demonstrate that the N-terminal cysteine was free and the C-terminal disulfides were intact.

Example 2

Development of Assays for Analyzing Preferentially Reduced Recombinant Plasmodium Falciparum Circumsporozoite Protein In-process and final product analytical methods were developed for evaluating recombinant *Plasmodium falciparum* circumsporozoite protein. These methods are contemplated for use in evaluating rCSP obtained using the preferential reduction conditions described in Example 1, or by any other method.

1. Purification of rCSP Internal Reference Standard

Purification of rCSP (batch 533-191) for use as an internal reference was performed as follows.

Preparation of Lysates for Purification

Frozen cell pastes (~70 g) from cultured CS533-129 cells were thawed and resuspended in 20 mM Tris, pH 8.0 buffer (one molar stock solution, pH 8.0 diluted 50-fold with Milli-Q water prepared using 1M TRIS stock, catalog number T1080, Teknova, Hollister, Calif.) without protease inhibitors and homogenized by passing once through a Microfluidics Microfluidizer M-110Y at 15,000 psi. Lysates were centrifuged at 12,000 g for 60 min and filtered by passing through a Sartorius Sartobran P 0.45/0.2 µm filter capsule (catalog number 5235307H8-O-A, Sartorius-Stedim, Bohemia, N.Y.). Filtered lysates were adjusted to 2.0 M urea using an 8.0 M urea stock solution (catalog number 4203-08, JT Baker, Phillipsburg, N.J.).

Chromatography

Fast protein liquid chromatography (FPLC) operations were performed using ÄKTAexplorer 100 chromatography systems (GE Healthcare) equipped with Frac-950 fraction collectors. Conditions for the purification run used in the preparation of 30 mg of purified CSP are summarized in Table 7 below. Materials used: Q-Sepharose FF (catalog number 17-0510-01, GE Healthcare, Piscataway, N.J.); AK26/20 columns (part number 28-9889-48, GE Healthcare); Butyl-650S (catalog number 14701, TosohUSA, Flemington, N.J.); NaCl (catalog number 13423, Sigma/Riedel de Haen, St. Louis, Mo.); NaOH (catalog number 5674-03, JT Baker, Phillipsburg, N.J.); ammonium sulfate (catalog number BDH9001, VWR, West Chester, Pa.); and urea (catalog number 4203-08, JT Baker, Phillipsburg, N.J.).

Conversion of rCSP Dimer to Monomer

Hydrophobic interaction chromatography elution fractions containing dimerized CSP in buffer [elution buffer: 2 M urea, 200-600 mM ammonium sulfate, and 20 mM Tris, pH 8.0] were pooled to a final volume of 200-600 mL. The pool was subjected to selective reduction by addition of dithiothreitol reductant (JT Baker, part number JT-F780-2, Phillipsburg, N.J.) to a final concentration of 20 µM and stirred rapidly with a magnetic stir bar and stir plate for 12-24 hours at room temperature. Alternatively, aggregated rCSP in PBS (e.g., batch 533-128) was subjected to the same process by first adding 2 M urea to the material before undergoing selective reduction.

Final Buffer-Exchange

The mildly reduced rCSP pool was exchanged into 1×PBS buffer by desalting chromatography (PD-10 column, catalog number 17-0851-01, GE Healthcare). For larger preparations, the preferentially reduced rCSP pool was diafiltered with 1×PBS (Teknova, P0191, 20× concentrate) via tangential-flow filtration. Pellicon XL (10 kDa, 50 cm$^2$) and Pellicon 2 (5 kDa, 0.1 m$^2$ and 10 kDa, 50 cm$^2$ and 0.1 m$^2$) regenerated cellulose membranes (EMD Millipore, Billerica, Mass.) were used to retain CSP during the buffer exchange. FilterTec and SciPres (Scilog, Inc., Madison, Wis.) units were used to collect transmembrane pressure (TMP) and permeate mass data from a balance. FilterTec or Masterflex L/S (Cole Parmer, Vernon Hills, Ill.) peristaltic pumps were used for retentate recirculation. Polypropylene and PETG containers were used as mixing and recirculation vessels. Tygon (Cole Parmer) and platinum-cured silicone (Cole Parmer; AdvantaPure, Southampton, Pa.) tubing was used to direct fluid streams. The load (mildly reduced CSP) and retentate (diafiltered load) were filtered with a Millipak Durapore® (EMD Millipore) or Sartobran® P (Aubagne, France) sterilizing 0.22 µm membranes.

Membranes were equilibrated with 1×PBS prior to product introduction. Preferentially reduced CSP was recirculated across the membranes at 324 liters per square meter per hour (LMH) and 648 LMH at room temperature (21-23° C.). TMPs of 10-15 psi and 21-24 psi were applied to retentate while over the 10 kDa and 5 kDa membranes, respectively. Constant volume diafiltration was carried out for six retentate volumes (diavolumes). Mass load ratios (target÷membrane area) were 2.6-14.6 g/m$^2$. In one experiment, after three diavolumes, the

TABLE 7

Purification Run Conditions

| Column | Column Size | Residence time | Running Conditions |
|---|---|---|---|
| Capture step Q Sepharose FF | 2.6 cm diameter × 12.7 cm height volume: 67 mL | 5.1 min | Equil Buffer (EQ): 20 mM Tris, 2.0M urea, pH 8.0<br>Load: filtered lysate adjusted to 2.0M urea<br>Wash: 3 CV EQ buffer<br>Elute: linear gradient elution over 15 CV of 0-40% B1 (20 mM Tris, 1.0M NaCl, 2.0M urea, pH 8.0), and 3 CV step elution with 100% B1<br>Strip: 3 CV 0.5N NaOH |
| Polishing Butyl-650S | 2.6 cm diameter × 11.1 cm height volume: 59 mL | 4.0 min | Equil Buffer (EO): 20 mM Tris, 2.0M urea, 1.0M ammonium sulfate, pH 8.0<br>Load: Q-FF elution pool, with addition of granular ammonium sulfate to 1.0M<br>Wash: 5 CV EQ buffer<br>Elute: linear gradient elution over 20 CV of 0-100% B1 (20 mM Tris, 2.0M urea, pH 8.0), and 2 CV step elution with 100% B1<br>Strip: 3 CV 0.5N NaOH | retentate was concentrated 2× and diafiltered for another three diavolumes. The retentate was mixed with a magnetic stir bar and a stir plate. Membranes were cleaned by recirculating 0.1 N NaOH at room temperature for ≥60 minutes. Regeneration of the membrane was verified by normalized water permeability measurements.

Various reworked batches of this material were analyzed as methods were developed and is discussed in multiple sections below.

2. HPLC

Reversed Phase HPLC (RP-HPLC)

Reverse Phase HPLC (RP-HPLC) methods were developed to evaluate rCSP monomer and dimer content, fragmentation, deamidation, and oxidation.

Separations were carried out on an Agilent 1100 Series liquid chromatography system (Agilent Technologies, Inc., Palo Alto, Calif.) equipped with an autosampler, quaternary pump, and multiple wavelength (UV-vis) detection modules. Mobile phase reagents were of analytical grade or best available. Acetonitrile used was HPLC grade (J. T. Baker, 'Baker Analyzed' ® HPLC solvent, ≥99.9%, catalog number 9017-33). TFA (trifluoreacetic acid) was obtained from Pierce (catalog number 28904). Deionized water was obtained using a Milli-Q system (Millipore, Bedford, Mass.) and filtered prior to use with a PES Filter Unit, 1000 ml, 90 mm, 0.2 μm filter-sterilization apparatus (Nalgene, catalog number 567-0020). Mobile phase A contained 0.1% TFA in water (v/v); solvent B contained 0.1% TFA in acetonitrile (v/v). Samples were diluted with PBS, pH 7.2 (catalog number 14200, GIBCO, Carlsbad, Calif.) and 30-60 μl injected onto a Jupiter $C_4$ (Phenomenex, Part No. 00G-4167-E0) column (300 Å pore, 5 μm particle size, 4.6×250 mm) equipped with a guard cartridge (Security Guard, 4×3 mm, catalog number KJO-4282). Gradient conditions were 22%-32% Mobile B in 20 min. The column temperature was 50° C. Flow rate was 1 ml/min. Detection was 214 nm and 280 nm.

Shown in FIG. 8 is analysis of in-process samples for determining dimer and monomeric forms of rCSP. Preparative hydrophobic chromatography resolved monomer and dimer forms of rCSP, determined by reducing and non-reducing SDS-CGE analysis (FIGS. 8A-C). Analysis of the isolated forms by RP-HPLC showed single peaks with different retention times consistent with the retention times for mixtures of monomer and dimer described above (FIG. 8D).

Size Exclusion HPLC (SE-HPLC)

SE-HPLC methods were developed to identify aggregated species and analyze globular structure of rCSP.

Size exclusion chromatography was carried out on a TSK-gel G3000SW$_{XL}$, 7.8 mm ID×300 mm, 5 micron (Tosoh, catalog number 8541) with a Guard TSKgel SW$_{XL}$ (Tosoh, catalog number 8543) equipped to an Agilent 1100 Series liquid chromatography system (Agilent Technologies, Inc.). The mobile phase was phosphate buffered saline (PBS), pH 7.4, diluted from 10× (Mediatech, catalog number 46-013-CM) with MilliQ water, and filtered prior to use with a PES Filter Unit, 1000 ml, 90 mm, 0.2 μm filter-sterilization apparatus (Nalgene, catalog number 567-0020). Flow rate was 0.5 ml·min$^{-1}$; injection volume was 50-100 4 and absorbance was monitored at 280 nm.

Figure 9A:
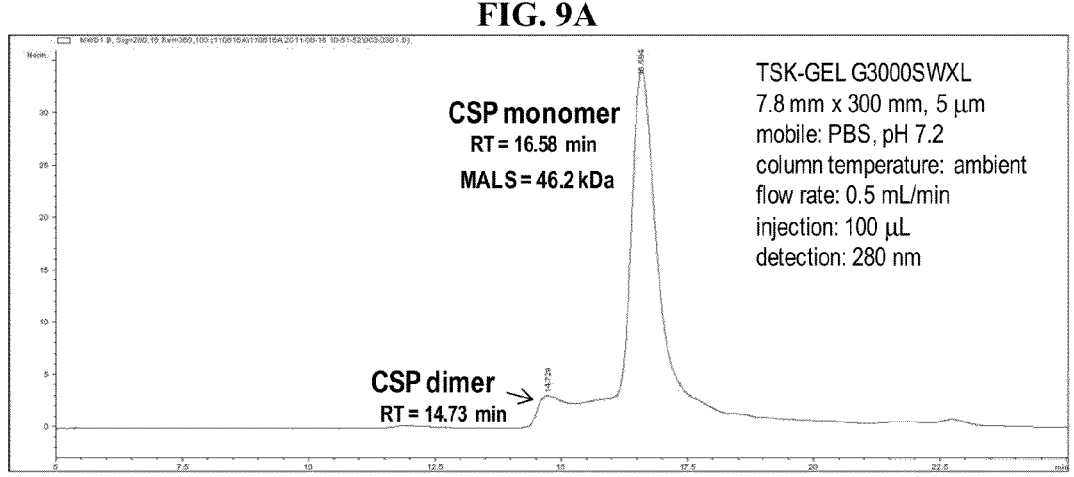
FIG. 9. Size Exclusion HPLC Method with Multi-Angle Laser Light Scattering for rCSP. A. SE-HPLC chromatogram of rCSP internal reference standard (batch 533-191) with MALS detection. B. SE-HPLC chromatogram of Bovine Serum Albumin (BSA) standard with MALS detection.
Figure 9B:
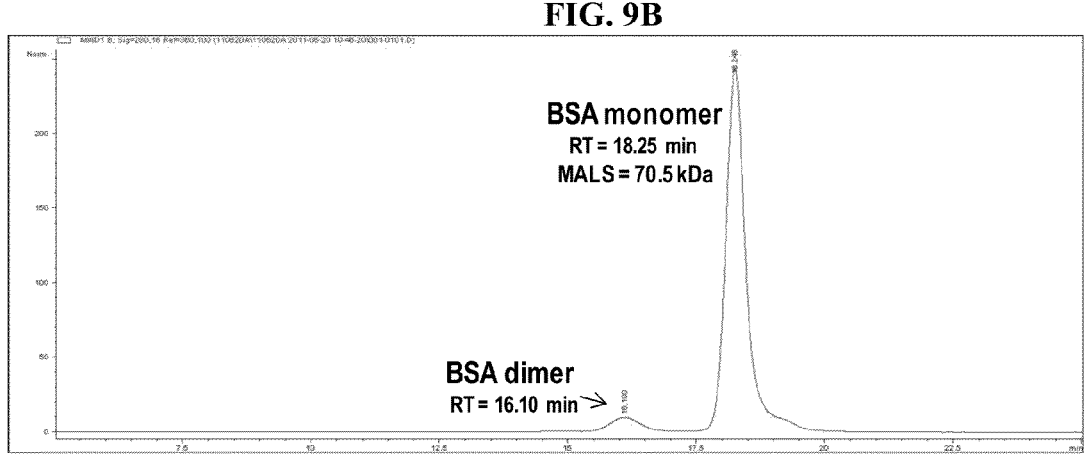

FIG. 9A shows a SE chromatogram of rCSP (533-191) where a TSK-GEL G3000SWXL column, which provided the best performance, was used. Size exclusion separates proteins based on size with larger proteins eluting earlier than smaller ones. Based on the molecular weight of rCSP (~38 kDa), the retention time should be longer than what is observed. For example, chromatographing a calibration standard such as BSA on the same column, which has a molecular weight of ~67 kDa (~1.8× larger in size than rCSP), elutes at a retention time 1.66 min later than rCSP FIG. 11B. One explanation for this is the highly extended, non-globular structure of CSP, which can be misleading for sizing by SE-HPLC. The molecular weight of rCSP was measured by multiangle laser light scattering (MALS) detection coupled to SE-HPLC and was determined to be 42-46 kDa, which is close to its actual molecular weight (not shown). The size of BSA measured by MALS was 70.5 kDa, which is also close to its molecular weight.

Figure 10A:
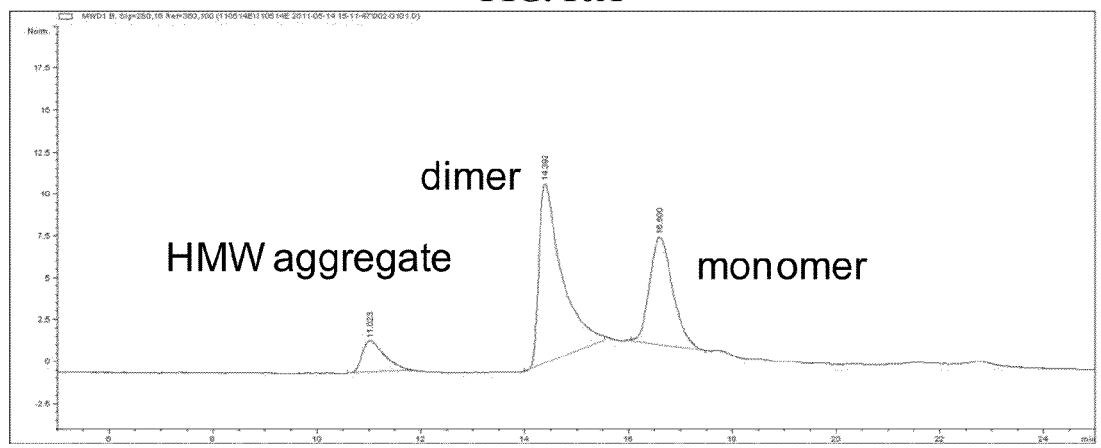
FIG. 10. Size Exclusion HPLC Analysis of Aggregated and Dimer Forms of rCSP.
Figure 10B:
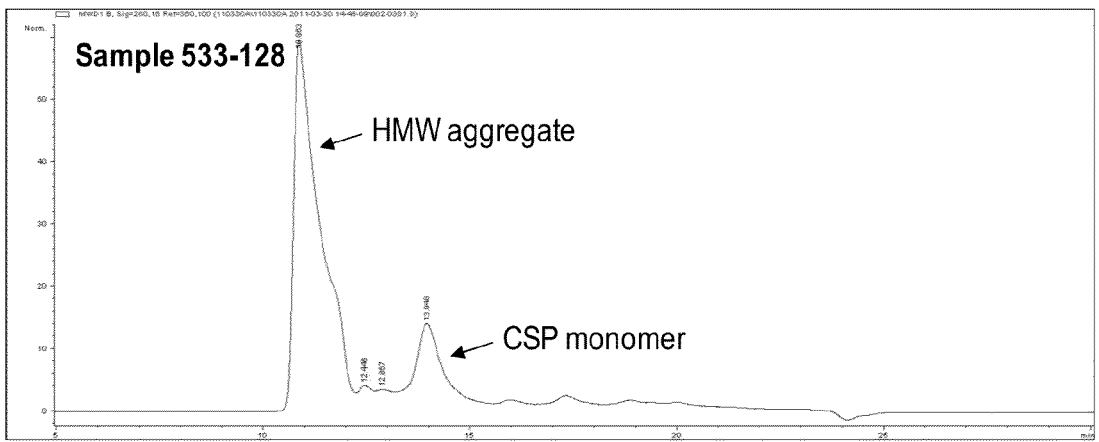

Forced degradation studies of rCSP were analyzed by SE-HPLC, along with samples that were determined by other methods to be of compromised quality. Aggregated forms of rCSP were analyzed as shown in FIG. 10. FIG. 10A shows a sample that was concentrated using a centrifugal concentration device that, in the case for rCSP, produces dimer and high molecular weight (HMW) aggregates. FIG. 10B shows SE-HPLC analysis of rCSP batch 533-128 which was found to be highly aggregated.

3. SDS-PAGE

An SDS-PAGE method was developed to analyze rCSP purity and degradation fragments. Samples were diluted 1:1 with Laemmli Sample Buffer (Bio-Rad, catalog number 161-0737) and then heated for 5 minutes at 95° C. in a thermocycler. The samples were allowed to reach room temperature and then loaded to a 18-well Bio-Rad 10% Bis-Tris gels (Bio-Rad, catalog number 345-0112) and electrophoresed at 100V for 20 minutes, followed by 200V for 60 minutes, in 1×MOPS running buffer (Bio-Rad, catalog number 161-0788). Running buffers were chilled to 10° C. during PAGE separation. After separation the gel was stained with GelCode Blue Stain (Pierce, catalog number 24592), destained, and imaged using a digital imaging instrument.

4. Western Blot

A Western Blotting method was developed to monitor rCSP purity degradation fragments.

Proteins were transferred from SDS-PAGE gels at 100V for 60 minutes onto a 0.20 m nitrocellulose membrane (Bio-Rad, catalog number 162-0232) using 1× NuPAGE Transfer Buffer (Invitrogen, catalog number NP0006-1) with 20% methanol. Some samples were subjected to alkylation prior to SDS-PAGE. For this analysis, iodoacetamide (Sigma, p/n 16125) was added in excess to reduced samples to a final concentration of 5 mM, and incubated for 30 min. at room temperature. in the dark. Membranes were blocked for 1 hour at room temperature in Blocker™ Casein in PBS (Pierce, 37528). For detection, the diluents were poured off and more was added containing a 1:2000 dilution of a monoclonal anti-PfCSP. The blots were incubated with rocking overnight at 4° C. The blots were washed three times with PBS-Tween for 5 minutes each, and were then incubated in more diluent containing a 1:5,000 dilution of anti-Mouse IgG (γ chain specific)-peroxidase, derived in goat (Southern Biotech, 1030-05) at room temperature for 1 hour. The blots were washed three times with PBS-Tween (Sigma, P3563) for 5 minutes each, before color development using Immunopure Metal Enhanced DAB substrate (Pierce, 34065) for 1 minute at room temperature. Imaging was performed with an Alpha Innotech FluorImager.

5. Biolayer Interferometry (BLI)

Binding assays for rCSP were developed using biolayer interferometry (BLI) as the detection method. BLI can be used to monitor folding and functionality by the ability of rCSP to bind to conformation-specific antibodies and/or heparin. Functional binding assays therefore are useful for detecting differences in rCSP conformation and can be employed as activity assays. Three strategies were developed: one involving heparin, where CSP binds heparin as part of its function to bind to hepatocyte heparin sulfate proteoglycans, and two others involving conformation-specific monoclonal antibodies.

Method: Monoclonal anti-CSP antibody IG12 or 4C2 (described by Plassmeyer, et al., 2009, referenced above, which also describes methods for isolating antibodies that recognize CSP) was biotinylated using the method described in ForteBio (Menlo Park, Calif.) Technical Note: "Biotinylation of Protein for Immobilization onto Streptavidin Sensors" using NHS-LC-LC-biotin (Pierce, catalog number 21343) at a molar ratio over antibody of 2.5:1. Heparin, from Calbiochem (catalog number 375095, Calbiochem is a division of EMD Chemicals, Gibbstown, N.J.), was biotinylated as above. The biosensors (Streptavidin Biosensors, ForteBio, catalog number 18-0009) were hydrated in 1× kinetics buffer (10-fold dilution of 10× Kinetics Buffer, ForteBio, catalog number 18-5032 into PBS) for at least 10 minutes. The sensors were loaded with 10 µg/ml biotinylated substrate diluted into sample diluent (ForteBio, catalog number 18-5028) for 90 minutes at room temperature and 1000 rpm on a Sidekick™ (ForteBio) shaker/mixer or overnight without mixing at 4° C.

Samples were diluted into either sample diluent or 1× kinetics buffer. Samples and standards were loaded at a volume of 100 µl into half area plates (E&K Scientific, catalog number EK-78076) or 200 µl into standard size 96-well plates (E&K Scientific, catalog number EK-25209). The sensors were soaked in 1× kinetics buffer for ~5 minutes, and then pre-equilibrated for 40 minutes at 1000 rpm on a Sidekick™ shaker/mixer in a dilution of null soluble fraction at approximate total protein concentration of test samples. The sample plate was pre-equilibrated at 30° C. in the Octet BLI instrument for 10 minutes prior to initiating the assay. The samples were read at 1000 rpm, 30° C., for 180 sec, and quantitation was calculated from a standard curve of substrate at 64, 32, 16, 8, 4, 2, 1, and 0.5 µg/ml.

Results: Shown in FIG. 11A is the biosensor configuration using heparin for rCSP binding. Three preparations of rCSP, each prepared from cells expressing the rCSP set forth in SEQ ID NO: 3, were assayed for heparin binding: batch 533-036; batch 533-191 which was purified as an internal reference standard; and batch 533-128. Shown in FIG. 11B are the results of the binding rates for these preparations at varying concentrations. The rates for each sample concentration were quite different from one another (FIGS. 11B and C).

6. Capillary Isoelectric Focusing (cIEF)

A Capillary Isoelectric Focusing analytical method was developed to monitor rCSP charge heterogeneity.

Sample preparation: Sample were reduced by incubating for 2 h in 2M urea (JT Baker, catalog number 4203-08) and 10 mM DTT and then concentrating to >1.5 mg/mL using a 10 kDa Millipore Microcon centrifugal concentrator (catalog number 42407). Thirty microliters of sample was then mixed with 5 µl of 40% Pharmalytes pH 2.5-5 (GE Healthcare, catalog number 17-0451-01), 5 µl of 40% Pharmalytes pH 5-8 (GE Healthcare, catalog number 17-0453-01), 35 µl of 1% methylcellulose (ProteinSimple, catalog number 101876), 25 µl of 8M urea, and pI markers 4.22 and 6.14 (ProteinSimple, catalog numbers 102350 and 102220, respectively).

Method: Acquisition and analysis were performed on an iCE280 Analyzer (Convergent Bioscience, Toronto, Canada, S/N 1348) equipped with CFR Software Version 2.3.6, a cIEF cartridge-FC coating (Convergent Bioscience, catalog number 101700), and a PrinCE MicroInjector (Convergent Bioscience, s/n 54-20-07-4-048). The following analyzer settings were used: Focus Period 1=1500 V for 1.0 mM; Focus Period 2=3000V for 7.0 min; Sample Transfer Time=135 sec; Wash Duration=0 sec; Scans Averaged=16; Exposure Time=73 msec; Desalt Current=101 µAMP; Transfer Time Delay=0.0 min; Detection=280 nm.

Calibration of pI markers was performed by the iCE software followed by the conversion and processing of data by ChromPerfect version 5.5.6. Electrolytic tank reagents included 0.08% phosphoric acid in 0.1% methylcellulose, and 0.1 M sodium hydroxide in 0.1% methylcellulose (both reagents part of SimpleProtein Kit, part number 102506).

A method to analyze charge heterogeneity of rCSP was developed using cIEF and results are shown in FIG. 12. The internal reference rCSP batch 533-191 showed main peaks at pI 5.20 and pI 5.76 and smaller peaks at pI 4.99, 5.08 and 5.52 (FIG. 12A). The calculated pI based on the primary amino acid sequence was pI 5.21. The lower pI peaks were likely due to deamidation of asparagines residues in rCSP which created negative charge and lowered the pI.

7. Circular Dichroism and Intrinsic Fluorescence

A circular dichroism (CD) method was developed for rCSP. The far UV-CD region from 185-250 nm monitors secondary structural differences (i.e., α-helices, β-sheets, and random coils). Intrinsic fluorescence was evaluated for monitoring tertiary structural differences.

Method: Far-UV CD spectroscopy (240-190 nm) was carried out on a Jasco J-815 spectropolarimeter (JASCO) with bandwidth set to 1 nm and scanning speed of 100 nm/min, Digital Integration Time (DIT)=1 sec, with 5× accumulations, using 0.1 mm path length cuvettes. Samples were analyzed at 20° C. in ×5 mM tris (Sigma, catalog number T7818-250G)/16.7 mM sodium sulfate (Sigma, catalog number S9627-500G) pH, 7.5 buffer.

Results: FIG. 13A shows the CD line spectrum for the rCSP reference material at 0.37 mg/mL in phosphate buffered saline. The CD spectrum exhibited a minimum at 200 nm with no other distinguishing minima or maxima. These features suggest a low percentage of alpha helix. Analysis was performed using K2D2 software, yielding results of 8% alpha helix and 29% beta strand FIG. 16B. The maximum error was 0.23. These values are consistent with those reported in the literature (5% alpha helix and 27% beta strand, e.g., in Plassmeyer, M. L. et al., 2009, Structure of the *Plasmodium falciparum* Circumsporozoite Protein, a Leading Malaria Vaccine Candidate, JBC 284 (39): 26951-26963).

The fluorescence spectrum of rCSP was determined for reference standard 533-191. The initial temperature setting for analysis was 20° C., followed by stepwise increases to 40 and 75° C., followed by a return to 20° C. The fluorescence spectrum was read at each temperature setting. The emission maximum was 340 nm and did not shift significantly as the temperature increased. However, the baseline did increase for reasons that are not clear. The intensity of emission at the maximum was significantly decreased at 75° C. upon denaturation. Upon return to 20° C., the emission intensity returned to a higher level than the initial reading; this may be due to the upward shift in the baseline.

8. Mass Spectrometry Analysis

Intact Mass Analysis by LC-MS

Method: Preparation 533-191 was subjected to intact mass analysis. Intact mass analysis is useful for monitoring proteolytic clipping, e.g., at the N-terminus, deamidation, oxidation, and fragmentation. This sample was analyzed by LC-MS under non-reduced and reduced conditions.

Results: For reduced analysis, purified 533 samples were mixed with an equal volume of UTD buffer (7.2 M urea, 100 mM Tris pH 7, 100 mM DTT). The reduced sample was then heated at 37° C. for 30 min. prior to analysis. For non-reduced analysis, samples were run neat. For alkylated samples, see below. Samples (10 μg) were subjected to LC-MS analysis using an interconnected autosampler, column heater, UV detector, and HPLC (Agilent 1100) coupled to a Q-T of micro mass spectrometer (Waters) with an electrospray interface. Prior to a run, the mass spectrometer was calibrated from 600-2600 m/z using NaCsI. A CN column (Zorbax 5 μm, 300SB-CN, 2.1×150 mm, Agilent, P/N 883750-905) fitted with a guard column (Zorbax 5 μm, 300SB-CN, 4.6×12.5 mm, Agilent, P/N 820950-923) was used for separation at 50° C. The HPLC buffers used were buffer A (0.1% formic acid) and buffer B (90% acetonitrile 0.1% formic acid). In new method developed, after sample injection at 5% B, the column was immediately developed with a 17 min. gradient from 5% to 30% B, and then brought to 100% B for 5 min., ending with 5% B for 5 min. The flow rate was 0.3 ml/min, and the flow was diverted to waste using the MS switching valve for the first 10 min. to allow for sample desalting. 533 target protein (CSP) eluted at ~17.9 min.

UV absorbance was collected from 180-500 nm, prior to MS. The ESI-MS source was used in positive mode at 2.5 kV. MS scans were carried out using a range of 600-2600 m/z at 2 scans per second. MS and UV data were analyzed using MassLynx software (Waters). UV chromatograms and MS total ion current (TIC) chromatograms were generated. The MS spectra of the target peak were summed. The summed spectrum was deconvoluted using MaxEnt 1 (Waters) scanning for a molecular weight range of 10,000-80,000, with resolution of 1 Da per channel, and a Gaussian width of 0.25 Da. The theoretical MW of fully processed 533 was determined to be 38,725.0 Da and 38,721.0 Da for reduced and non-reduced, respectively.

The difference between the observed and theoretical MW (delta MW) was 1 and 4 Da for the reduced and non-reduced samples, respectively. This is within the expected mass accuracy of 4 Da+/−4 Da, for the analysis of a protein of this size using an instrument with a resolution of 5,000. Due to the mass accuracy limitation of the instrument, it is not possible to determine the status of disulfide bond formation by intact mass analysis alone. The results of this analysis are shown in FIG. 14.

Cysteine Alkylation Followed by Intact Mass Analysis

To investigate the status of disulfide bond formation, preparation 533-191 was subjected to a cysteine alkylation experiment.

Method: Purified 533-191 samples were subjected to alkylation for the analysis of free cysteine(s) in the native protein. For this analysis, iodacetamide (Sigma, p/n I6125) was added to native non-reduced 533 samples to a final concentration of 5 mM, and incubated for 30 min. at R.T. in the dark. The reaction was subsequently desalted into PBS for intact mass analysis or into 25 mM $NH_4HCO_3$ for digestion using a size-exclusion spin column (0.7 ml, Pierce, p/n 89849).

Purified 533-191 samples were also subjected to alkylation of all cysteines after denaturation and complete reduction of all disulfide bonds. For the alkylation of denatured and reduced samples, urea was added to 2 M final concentration, DTT was added to 10 mM final concentration, and samples were incubated at 37° C. for 30 min. Subsequently, iodacetamide was added to a final concentration of 30 mM, and was incubated for 30 min. at room temperature in the dark. Samples were then desalted as above for intact mass analysis or digestion.

Figure 15A:
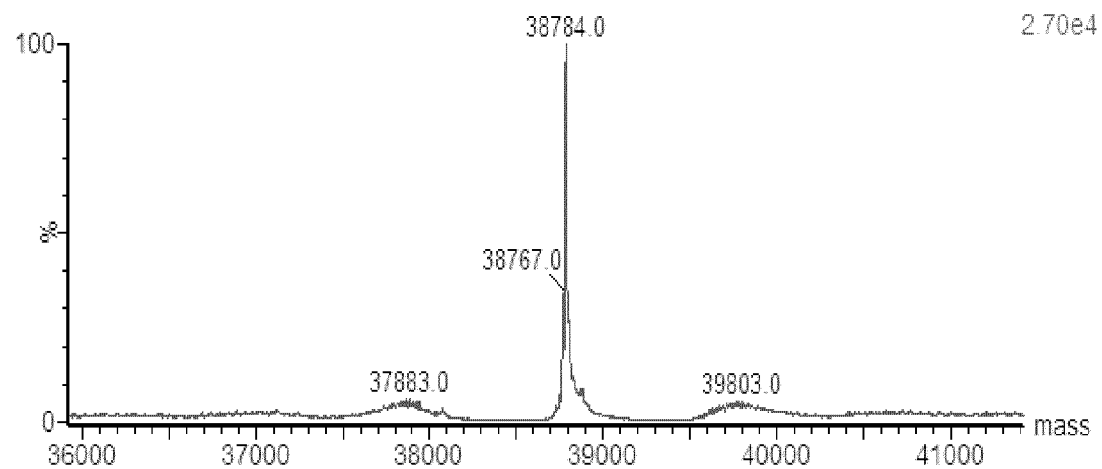
Figure 15B:
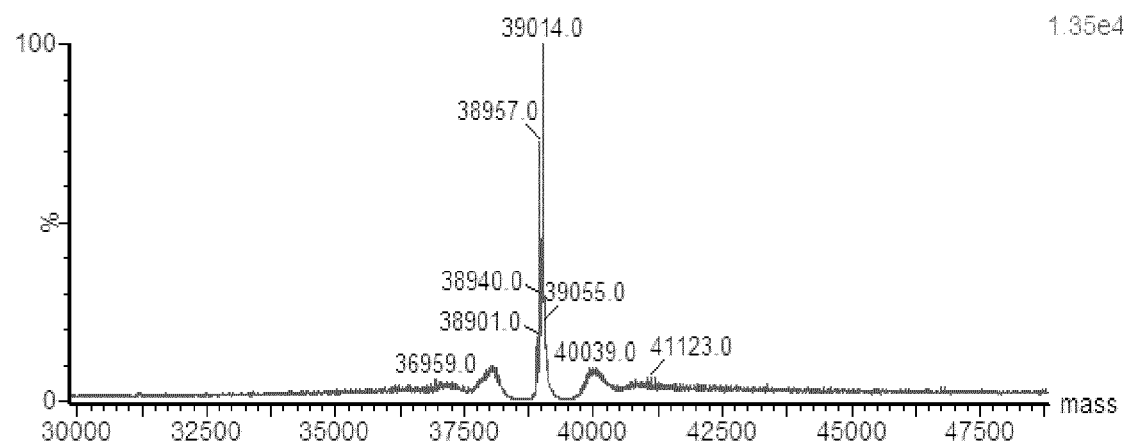

Results: Iodoacetamide was added to both non-reduced and reduced samples as described above. These samples were subjected to intact mass analysis by LC-MS, and the results are shown in FIG. 15. For the non-reduced and alkylated sample, the observed mass was consistent with 533-191 containing one cysteine alkylation FIG. 15A. It is assumed that the N-terminal cysteine is being alkylated, though this experiment did not identify which cysteine is actually alkylated. Analysis of the reduced and alkylated sample showed that all five cysteines were alkylated when 533-191 was fully reduced FIG. 15B.

Alkylated non-reduced 533-191 was observed to have a delta of 6.0 Da compared to the theoretical MW of 533 with one cysteine alkylation. Reduced and alkylated 533-191 was observed to have a delta of 3.9 Da compared to the theoretical MW of 533 with five cysteine alkylations. There was an additional species that correlates with 533 containing four cysteine alkylations, and was present at ~43% total abundance. This observation was most likely due to incomplete alkylation.

Identification of the Free N-terminal Cysteine by Alkylation and Peptide Mapping A peptide mapping analytical method was developed to evaluate rCSP microheterogeneity and identify the available cysteine in the N-terminal region of rCSP.

Method: Native, non-reduced-alkylated, and reduced-alkyled 533 samples were desalted into 25 mM $NH_4HCO_3$ as described above. For individual digests, 5-20 μg of desalted sample was digested with different proteases. For trypsin (Sigma, proteomics grade, p/n T6567) and Glu-C (Roche, sequencing grade, p/n 11420399001) digests, each protease was added at 1:50 (wt:wt), enzyme:substrate, and incubated overnight at 37° C. A double digest of trypsin and elastase was also carried out. First, samples were digested with trypsin as above. After trypsin digestion, elastase (Sigma, Type IV, p/n E0258) was added at different ratios, 1:20, 1:100, and 1:500, and incubated at 37° C. for 7 hrs. All of the above digests were stopped with the addition of formic acid to a final concentration of 1-5% (vol:vol).

Two μg of each digest was subjected to LC-MS/MS as described below. Prior to a run, the mass spectrometer was calibrated from 200-2000 m/z using NaCsI. The above LC-MS set-up was used for the analysis of the digests, except that a $C_{18}$ column (Zorbax 300SB $C_{18}$, 2.1×250 mm, 5 μm, Agilent, part number 881750-902) was used for separation. The column was developed with the following LC segments: 10 min. at 5% B, a gradient of 5-40% B over 50 min., a gradient of 40-60% B over 20 min., 100% B for 5 min., and 5% B for 5 min.; run at 0.3 ml·min$^{-1}$ and 50° C. UV absorbance was collected from 180-500 nm, prior to MS. The MS source was used in positive mode at 2.5 kV. An MS/MS scan strategy was used, which includes a survey MS scan followed by a data-independent MS/MS scan. Scans were carried out using a range of 100-2000 m/z and a scan time of 0.5 sec; survey scans were at a collision energy of 6 V and data-independent MS/MS scans were at 28V. Post acquisition, each raw file was lock-mass calibrated using certain peptides, previously observed, at particular retention times.

BiopharmaLynx (Waters) was used to analyze the LC-MS/MS results. For individual trypsin Asp-N, and Glu-C digests the following parameters were used: 60 ppm mass tolerance, two missed-cleavages allowed, and semi-specificity (one end of peptide allowed to be non-specific); Asp-N and Glu-C were allowed to have cleavage at both Asp and Glu (in terms of specificity). For measuring sequence coverage, a 2% intensity filter was used (i.e., to count as an identification, a peptide ion had to be greater than 2% the intensity of the most intense identified peptide ion); additionally, deamidation at N and Q was searched for variably. For non-reduced digests, expected disulfide bonds of 533 ($C_{314}$-$C_{349}$ and $C_{318}$-$C_{354}$) were used for the searches of monomer preparations; and for instances of looking for dimerization, two copies of the 533 sequence were added, the above disulfide bonds were used, plus a $C_5$-$C_5$ intermolecular disulfide bond was added to the method file. For the reduced and alkylated digests, a fixed modification at Cys (carbamidomethyl-Cys) was used for the searches, without any disulfide bonds in the protein sequence. For non-reduced and alkylated samples, variable alkylation at Cys was used for the searches, without any disulfide bonds in the protein sequence. For the double-digest (trypsin and elastase) samples, 100 ppm and no enzyme specificity was used for the search. A nonspecific search of the entire protein sequence with two disulfide bonds would have taken an extraordinary amount of time to finish, making it impractical. Thus, only three short segments of the 533 sequence containing the four cysteines making up the two disulfide bonds were used. These sequences consisted of amino acids 303-325, 348-350, and 354-362, and are the peptide sequences that make up the tryptic disulfide-bonded tripeptide. These sequences were added as separate protein sequences in the method file, and the correct disulfide bonds mentioned above were used.

Results: Peptide mapping was implemented to determine which cysteine was alkylated in the aforementioned alkylated, non-reduced 533-191 sample. Glu-C was the protease used, because of the appropriately sized near-N-terminal peptide (E2) produced. This peptide contains the first cysteine ($C_5$), the expected free cysteine. The digested sample was subjected to LC-MS/MS analysis. The alkylated E2 peptide was identified using BiopharmaLynx software as described in the methods section FIG. 16A. This peptide is one of the most intense peptides identified and had 22 b- and y-ions identified (data not shown). The Glu-C digest can also produce two other highly visible peptides, E18 containing the second and third cysteine ($C_{314}$ and $C_{318}$), and E23 containing the fifth cysteine ($C_{354}$). These two peptides can be observed, at high intensities, in completely reduced and alkylated samples (data not shown). However, these peptides were not identified at significant levels in the aforementioned analysis of non-reduced, alkylated sample 533-191. This suggests that the cysteines within these peptides are primarily involved in disulfide bonds. Lastly, we attempted to identify an intermolecular disulfide bond between $C_5$ and $C_5$ in the same sample. BiopharmaLynx was used to search the same data, but allowing for a disulfide bond between two copies of 533 via C1. This disulfide-bonded dipeptide, E1-E2:E1-E2, was identified in this search FIG. 16B. E1-E2 signifies a missed cleavage at a glutamic acid residue within the peptide. In this instance, the missed cleavage may be due to restricted access for the protease caused by the adjacent disulfide bond. This was a low intensity ion, agreeing with other data (e.g. RP-HPLC, SE-HPLC) that the dimer in this preparation was a minor component compared to the monomer. Altogether, the Glu-C analysis of non-reduced, alkylated 533-191 suggested that the near-N-terminal cysteine ($C_5$) was the only free cysteine, and that this was the primary form of 533-191. Thus, the selective reduction method appeared to reduce only the $C_5$-$C_5$ intermolecular disulfide bond and not the intramolecular disulfide bonds.

Disulfide Bond Analysis by Peptide Mapping

The nature of the disulfide bonds in Pfenex-produced 533 was analyzed by peptide mapping. 533-128 was subjected to a sequential double digest, first with trypsin, then with elastase. The elastase digestion was tested at three different enzyme:substrate ratios. All double digests were analyzed by LC-MS/MS, and the resulting data was processed using BiopharmaLynx. First the expected disulfide bonds ($C_{314}$-$C_{349}$ and $C_{318}$-$C_{354}$) were included in the search parameters. As a result, multiple disulfide-bonded dipeptides were identified in all three double digests. Two of these dipeptides, making up both disulfide bonds, are shown in Table 8. As a negative control procedure, the same data was also processed using a method file containing the inverse of the above (or incorrect) disulfide bonds, $C_{314}$-$C_{354}$ and $C_{318}$-$C_{349}$. From this search, some disulfide-bonded dipeptides were identified. However, these identifications were of significant poorer quality in terms of ion intensity, delta mass, and b/y fragment ions found compared to the previous search using the correct disulfide bonds (data not shown). Altogether, the data from the double digests suggest that the major form, or possibly the only form, of 533-128 contains the expected disulfide bonds $C_{314}$-$C_{349}$ and $C_{318}$-$C_{354}$.

TABLE 8

Disulfide Bond Analysis by Peptide Mapping

| Disulfide Bond | Dipeptide | Δ Mass (ppm) | b/y Ions Found |
|---|---|---|---|
| C2-C4 | IQNSLSTEWSPCS=ICK | 28.9 | 8 |
| C3-C5 | TCGNGIQVR=CSSV | 22.3 | 9 |

Full Amino Acid Sequence Coverage

Figure 17C:
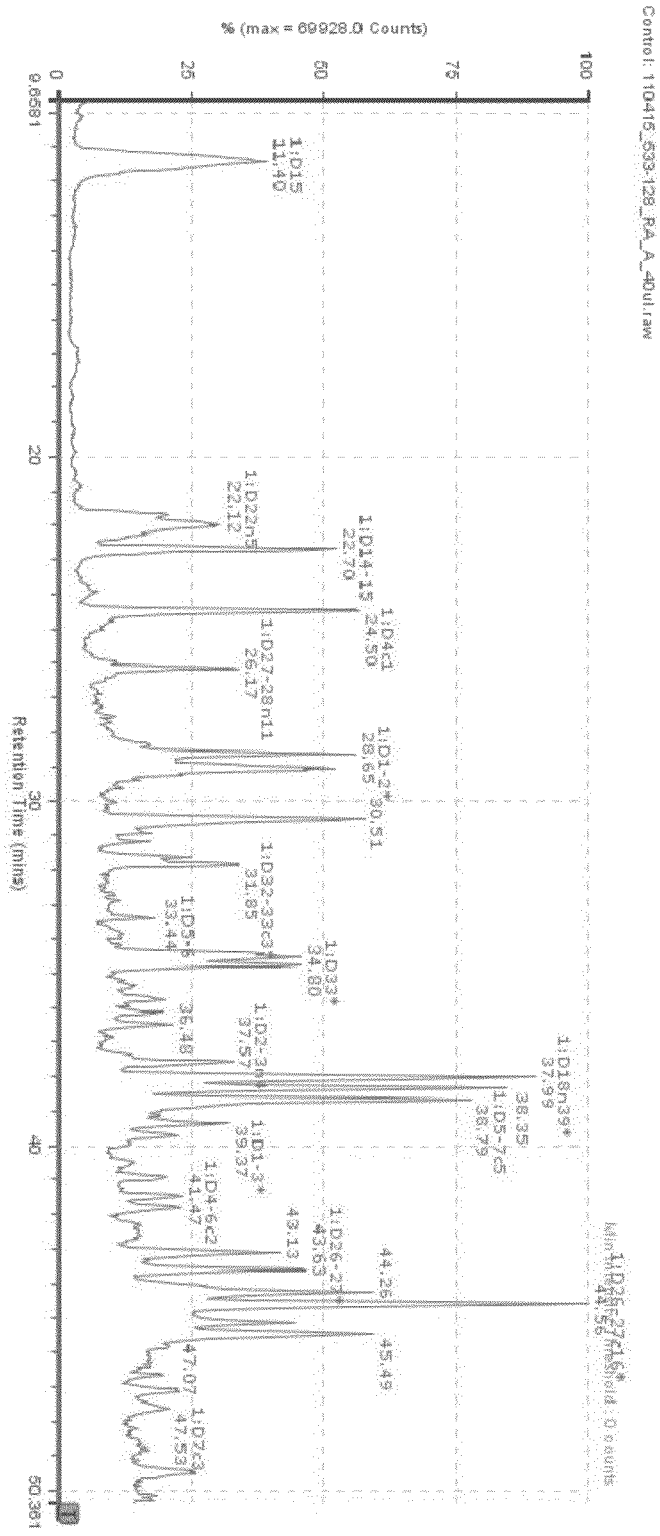
Figure 17D:
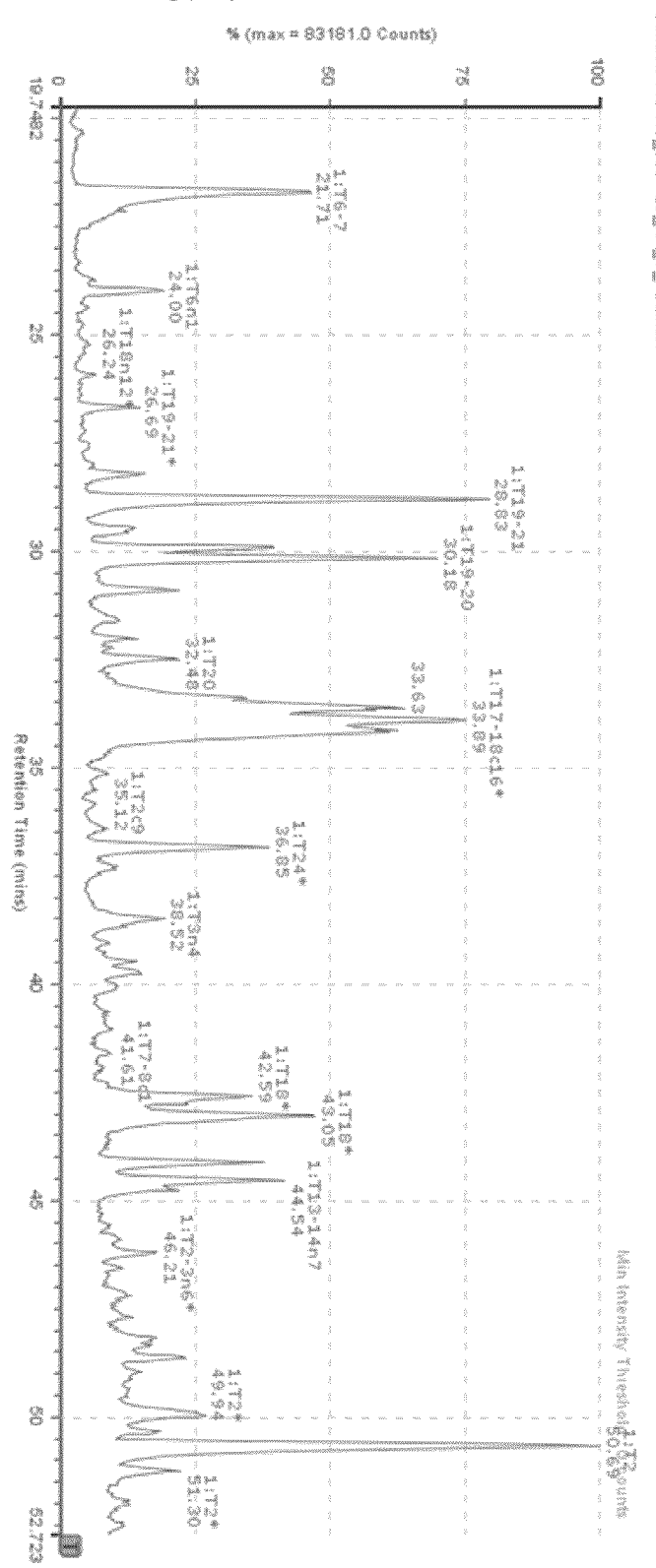

For full amino acid sequence coverage by peptide mapping, multiple proteases were tested on a reduced and alkylated sample (533-128). Each digest was subjected to LC-MS/MS and analyzed by BiopharmaLynx. Combining the data from Asp-N and trypsin (or Lys-C) digests gave the best results. Shown in FIG. 17A, the sequence coverage achieved with Asp-N was 75.4%. For trypsin, shown in FIG. 17B, the sequence coverage achieved was 56.9%. The peptides identified in each of these analyses are shown in Table 9 and 10, respectively. The associated LC-MS chromatograms for the Asp-N and trypsin digests are shown in FIGS. 17C and 17D, respectively. The sequence coverage for Lys-C was 66.9% (data not shown). The sequence coverage achieved by combining the results from the Asp-N and trypsin/Lys-C digests is less than 100%. This is due to the inability of BiopharmaLynx to identify large peptides. Due to the large repeat region of 533, two peptides expected from Asp-N are a.a. 107-178 and 179-267. The theoretical molecular weights for these two peptides are 7,178.2 Da and 8,971.2 Da, respectively. By manually examining the raw data, we observed both of the peptides in the chromatogram of the Asp-N digest. These peptides were identified by mass (using MaxEnt1), and eluted at 30.5 and 29.1 min., respectively. The deconvoluted spectra from the respective peaks are shown in FIG. 18. Altogether, by combining automated processing using BiopharmaLynx and manual processing, Asp-N plus trypsin/Lys-C protein digests allowed for 100% sequence coverage.

TABLE 9

Peptides Identified by Asp-N Digestion of 533-128

| Peptide | Fragment Number | Start | End | Modifiers | Control RT (Min) | Control Intensity (Counts) | Control Mass Error (ppm) |
|---|---|---|---|---|---|---|---|
| QEYQCYGSSSNTRVLN | 1:D001-002* | 1 | 16 | Cathamidomethyl C(1) | 28.65 | 156656 | 4.8 |
| QEYQCYGSSSNTRVLNELNY | 1:D001-003* | 1 | 20 | Cathamidomethyl C(1) | 39.37 | 85989 | 12.7 |
| YGSSSNTRVLNELNY | 1:D002-003n4 | 6 | 20 | | 37.57 | 9254 | 10.8 |
| NTRVLNELNYDNAGTNLYN | 1:D002-004n9 | 11 | 29 | | 50.16 | 12691 | 32.6 |
| ELNY | 1:D003 | 17 | 20 | | 21.71 | 149477 | 4.8 |
| ELN | 1:D003c1 | 17 | 19 | | 5.32 | 16893 | 0.5 |
| NYDNAGTNLYN | 1:D003-004n2* | 19 | 29 | Deamidation N(3) | 22.7 | 39561 | 0.2 |
| NYDNAGTNLYN | 1:D003-004n2* | 19 | 29 | Deamidation N(3) | 37.99 | 12770 | 31 |
| DNAGTNLY | 1:D004c1 | 21 | 28 | | 24.5 | 150878 | 2.9 |
| DNAGTNLYNEL | 1:D004-005 | 21 | 31 | | 38 | 86383 | 9.5 |
| DNAGTNLYNELMNYYG | 1:D004-006c2 | 21 | 37 | | 41.47 | 51418 | 20.5 |
| DNAGTNLYNELMNYY | 1:D004-006c3* | 21 | 36 | Deamidation N(3) | 31.84 | 10893 | 12.4 |
| TNLYN | 1:D004n4* | 25 | 29 | Deamidation N(2) | 2.54 | 132024 | -22.2 |
| NELEMNYYGKQ | 1:D004-006n8 | 29 | 39 | | 31.63 | 25600 | 6.6 |
| ELEMNYYGKQENWYSLKKN | 1:D005-007c5 | 30 | 48 | | 38.79 | 8428 | 12 |
| EMNYYGKQENWYSLKKNSRSLGEN | 1:D006-008 | 32 | 55 | | 34.42 | 94905 | 9.1 |
| EMNYYGKQENWY | 1:D006-007c10 | 32 | 43 | | 36.48 | 28164 | 7.9 |
| GKQENWYSLKKNSRSLG | 1:D006-007n5 | 37 | 53 | | 45.07 | 17480 | 56.6 |
| GKQENWYSLKKNSRSLGEN | 1:D006-008n5 | 37 | 55 | | 28.9 | 8719 | 8 |
| ENWYSLKKNSRSLGEND | 1:D007-009 | 40 | 56 | | 31.16 | 23689 | 7.4 |
| ENWYSLKKNSRSLGEN | 1:D007-008 | 40 | 55 | | 30.98 | 22273 | 5.4 |
| ENWYSLKKNSR | 1:D007c3 | 40 | 50 | | 43.42 | 13018 | 44 |
| ENWYSLKKNSRSLGEN | 1:D007-008* | 40 | 55 | Deamidation N(3) | 28.65 | 12460 | -30.8 |
| ENWYSLKKNSR | 1:D007c3 | 40 | 50 | | 47.53 | 9928 | -0.5 |
| SLKKNSRSLGEND | 1:D007-009n4 | 44 | 56 | | 3.02 | 19034 | 5.9 |
| SLKKNSRSLGEN | 1:D007-008n4 | 44 | 55 | | 2.89 | 14807 | 7.2 |
| SLKKNSRSLGEN | 1:D007-008n4 | 44 | 55 | | 34.62 | 8635 | -9.8 |
| SRSLGEND | 1:D007-009n9* | 49 | 56 | Deamidation N(1) | 11.42 | 48611 | -47.6 |
| DNEKLRKPKHKKLKQPA | 1:D012-013 | 62 | 78 | | 2.72 | 80488 | 6.3 |
| DGNPDPNANPNV | 1:D014-015 | 79 | 90 | | 22.7 | 216445 | 0.3 |
| DPNANPNV | 1:D015 | 83 | 90 | | 11.4 | 418052 | 1.9 |
| DPNANPN | 1:D015/b7 | 83 | 89 | | 11.42 | 9817 | 2.4 |

TABLE 9-continued

Peptides Identified by Asp-N Digestion of 533-128

| Peptide | Fragment Number | Start | End | Modifiers | Control RT (Min) | Control Intensity (Counts) | Control Mass Error (ppm) |
|---|---|---|---|---|---|---|---|
| DPNANPNVDPNANPNANPNA | 1:D017-018c60* | 99 | 118 | Deamidation N(1) | 9.09 | 115535 | -1 |
| ANPNANPNANPNANPNANPNANPNANPNV | 1:D018n39* | 146 | 178 | Deamidation N(7) | 37.99 | 152472 | 57.4 |
| NPNANPNANPNANPNANPNKNNQGNGQGHNMPN | 1:D019n56* | 235 | 267 | Deamidation N(6) | 35.77 | 12795 | 56.8 |
| ANPNANPNANPNKNNQGNGQGHNMPNDPNRNV | 1:D019-020n63* | 242 | 273 | Oxidation M(1) | 38.08 | 145409 | 25.8 |
| ANPNANPNANPNKNNQGNGQGHNMPNDPNRNV | 1:D019-020n63* | 242 | 273 | Deamidation N(1), Oxidation M(1) | 38.91 | 11171 | 29 |
| NGQGHNMPN | 1:D019n80* | 259 | 267 | Deamidation N(1) | 3.22 | 15921 | -1.1 |
| DPNRNV | 1:D020 | 268 | 273 | | 2.94 | 95085 | 1.8 |
| DPNRNVDEN | 1:D020-022c12* | 268 | 276 | Deamidation N(3) | 36.53 | 16005 | 25.6 |
| DPNRNVDENANANSAVKN | 1:D020-022c3* | 268 | 285 | Deamidation N(2) | 28.65 | 8377 | -26.8 |
| DENANANSA | 1:D021-022c6 | 274 | 282 | | 24.5 | 14743 | -15.4 |
| DENANAN | 1:D021-022c8* | 274 | 280 | Deamidation N(1) | 2.83 | 13967 | -34.7 |
| ENANANSAVKNN | 1:D022c2 | 275 | 286 | | 22.7 | 25933 | -50.9 |
| ENANANSAVKNN | 1:D022c2 | 275 | 286 | | 38 | 10106 | -26.9 |
| SAVKNNNN | 1:D022n6* | 281 | 288 | Deamidation N(2) | 11.43 | 15975 | -20.2 |
| EPSDKHIKEYLNK | 1:D024-026c7 | 290 | 302 | | 37.59 | 14357 | 22.6 |
| EPSDKHIKEYLNKIQNSLST | 1:D024-026* | 290 | 309 | Deamidation N(2) | 39.47 | 10462 | 13 |
| DKHIKEYLNKIQNSLSTEWSPCSVTCG | 1:D025-027c16* | 293 | 319 | Cathamidomethyl C(2) | 45.44 | 43612 | 14.1 |
| DKHIKEYLNKIQNSLS | 1:D025-026c1 | 293 | 308 | | 37.58 | 36342 | 10.8 |
| DKHIKEYLNKIQNSLSTEWSPCSVTCGNGIQVRIKPGSANKPK | 1:D025-027* | 293 | 335 | Deamidation N(1), Cathamidomethyl C(2) | 44.27 | 17896 | 0.3 |
| DKHIKEYLNKIQNSLSTEWSPCSVTCGN | 1:D025-027c15* | 293 | 320 | Deamidation N(2), Cathamidomethyl C(2) | 35.71 | 13119 | -11.9 |
| KHIKEYLNKIQNSLSTEWSPCSVTCGNGIQVRIKPGSANKPK | 1:D025-027n1* | 294 | 335 | Cathamidomethyl C(2) | 45.15 | 36065 | -5.4 |
| KHIKEYLNKIQNSLST | 1:D025-026n1* | 294 | 309 | Deamidation N(1) | 38.61 | 12232 | 25.8 |
| EYLNKIQNSLSTEWSPCSVTCGNGIQVRIKPGSANKPK | 1:D026-027* | 298 | 335 | Deamidation N(1), Cathamidomethyl C(2) | 43.63 | 83604 | 7.2 |

Table 9 discloses SEQ ID NOS 29-34, 34-48, 47-50, 50-59, 59-66 and 66-76, respectively, in order of appearance.

TABLE 10

Peptides Identified by Trypsin Digestion of 533-128

| Peptide | Fragment Number | Start | End | Modifiers | Control RT (Min) | Control Intensity (Counts) | Control Mass Error (ppm) |
|---|---|---|---|---|---|---|---|
| QEYQCYGSSSNTR | 1:T001* | 1 | 13 | Carbamidomethyl C(1) | 15.98 | 57587 | 7.6 |
| VLNELNYDNAGTNLYNELEMNYYGK | 1:T002 | 14 | 38 | | 50.69 | 583021 | 9 |
| VLNELNYDNAGTNLYNELEMNYYGK | 1:T002* | 14 | 38 | Oxidation M(1) | 49.94 | 98974 | 6.2 |
| VLNELNYDNAGTNLYNELEMNYYGK | 1:T002* | 14 | 38 | Deamidation N(1) | 50.31 | 24563 | 12.6 |
| VLNELNYDNAGTNLYNELEMNYYGKQ | 1:T002-003c7 | 14 | 39 | | 48.65 | 21116 | 21 |
| VLNELNYDNAGTNLYNELEMNYYGK | 1:T002 | 14 | 38 | Deamidation N(1) | 51.3 | 13665 | 13.1 |
| ELNYDNAGTNLYNELEMNYYGK | 1:T002n3 | 17 | 38 | | 48.39 | 12990 | 11 |
| LNYDNAGTNLYNELEMNYYGK | 1:T002n4* | 18 | 38 | Deamidation N(1) | 44.54 | 14186 | 25.5 |
| LNYDNAGTNLYNELEMNYYGK | 1:T002n4 | 18 | 38 | | 44.13 | 11839 | 20.4 |
| YDNAGTNLYNELEMNYYGKQENWYSLK | 1:T002-003n6* | 20 | 46 | Deamidation N(3) | 46.21 | 22882 | 34.8 |
| TNLYNELEMNYYGKQENWYSLK | 1:T002-003n11* | 25 | 46 | Deamidation N(3), Deamidation Q(1), Oxidation M(1) | 30.17 | 11786 | -48 |
| YNELEMNYYGKQENWYSLKK | 1:T002-004n14* | 28 | 47 | Oxidation M(1) | 43.05 | 30770 | 2.3 |
| QENWYSLK | 1:T003 | 39 | 46 | | 34.21 | 276972 | 9 |
| QENWYSLKK | 1:T003-004 | 39 | 47 | | 29.94 | 179253 | 0.8 |
| QENWYSLKK | 1:T003-004* | 39 | 47 | Deamidation N(1) | 33.38 | 14607 | -9.6 |
| SLGENDDGNNEDNEKLR | 1:T006-007 | 51 | 67 | | 21.71 | 245881 | 2.3 |
| SLGENDDGNNEDNEK | 1:T006 | 51 | 65 | | 3.36 | 142740 | 6.1 |
| LGENDDGNNEDNEK | 1:T006n1 | 52 | 65 | | 24 | 58530 | 0.8 |
| DNEKLRKPK | 1:T006-008n11* | 62 | 70 | Deamidation N(1) | 29.5 | 17038 | -29.4 |
| LKQPADGNPDPNANPNVDPNANPNVD | 1:T011-012c155 | 74 | 99 | | 29.86 | 11983 | 8.2 |
| PNANPNANPNKNNQGNGQGHNMPNDPNR | 1:T012-013n168* | 244 | 271 | Oxidation M(1) | 48.63 | 21238 | 26 |
| PNANPNKNNQGNGQGHNMPNDPNR | 1:T012-013n172* | 248 | 271 | Oxidation M(1) | 42.59 | 14992 | 31.1 |
| NNQGNGQGHNMPNDPNR | 1:T013* | 255 | 271 | Deamidation N(1) | 3.59 | 79962 | 9.2 |
| NNQGNGQGHNMPNDPNR | 1:T013 | 255 | 271 | | 3.22 | 16516 | 10.8 |
| NNQGNGQGHNMPN | 1:T013c4* | 255 | 267 | Deamidation N(2) | 7.67 | 12541 | 46.7 |
| GHNMPNDPNRNVDENANANSAVK | 1:T013-014n7 | 262 | 284 | | 44.54 | 173876 | 22 |

TABLE 10-continued

Peptides Identified by Trypsin Digestion of 533-128

| Peptide | Fragment Number | Start | End | Modifiers | Control RT (Min) | Control Intensity (Counts) | Control Mass Error (ppm) |
|---|---|---|---|---|---|---|---|
| NVDENANANSAVK | 1:T014 | 272 | 284 | | 7.69 | 272740 | 1.1 |
| NVDENANANSAVKNNNNE | 1:T014-015c5* | 272 | 289 | Deamidation N(3) | 48.18 | 22174 | 56.2 |
| NNNNEEPSDK | 1:T015 | 285 | 294 | | 2.72 | 16507 | 3.4 |
| HIKEYLNKIQNSLSTEW | 1:T016-018c14 | 295 | 311 | | 42.98 | 20256 | 44.8 |
| HIK | 1:T016 | 295 | 297 | | 2.65 | 14221 | 6.8 |
| EYLNK | 1:T017 | 298 | 302 | | 5.47 | 85875 | 8.3 |
| EYLNK | 1:T017-H2O | 298 | 302 | | 5.48 | 32286 | 0.3 |
| IQNSLSTEWSPCSVTCGNGIQVR | 1:T018* | 303 | 325 | Deamidation N(1), Carbamidomethyl C(2) | 43.05 | 214747 | 10.7 |
| IQNSLSTEWSPCSVTCGNGIQVR | 1:T018* | 303 | 325 | Carbamidomethyl C(2) | 42.59 | 127446 | 12 |
| IQNSLSTEWSPCSVTCGNGIQVRIKPG | 1:T018-019c6* | 303 | 329 | Deamidation N(2), Deamidation Q(2), Carbamidomethyl C(2) | 50.69 | 32319 | -22.8 |
| IQNSLSTEWSPCSVTCGNGIQVRIKPG | 1:T018-019c6* | 303 | 329 | Deamidation N(2), Deamidation Q(2), Carbamidomethyl C(2) | 49.94 | 11828 | -11.4 |
| IKPGSANKPKDELDYANDIEKK | 1:T019-021 | 326 | 347 | | 28.83 | 384069 | 10.2 |
| IKPGSANKPKDELDYANDIEK | 1:T019-020 | 326 | 346 | | 30.18 | 304498 | 3.9 |
| IKPGSANKPKDELDYANDIEKK | 1:T019-021* | 326 | 347 | Deamidation N(1) | 26.69 | 22585 | 11.8 |
| IKPGSANKPKDELDYANDIEK | 1:T019-020* | 326 | 346 | Deamidation N(1) | 28.2 | 13388 | 5.1 |
| DELDYANDIEK | 1:T020 | 336 | 346 | | 32.48 | 71581 | 1.6 |
| DELDYANDIEKK | 1:T020-021 | 336 | 347 | | 30.92 | 68525 | -1.7 |
| CSSVFNVVN | 1:T024* | 354 | 362 | Carbamidomethyl C(1) | 36.85 | 157656 | 4 |
| CSSVFNVV | 1:T024*/b8 | 354 | 361 | Carbamidomethyl C(1) | 36.85 | 15354 | 7.6 |

Table 10 discloses SEQ ID NOS 77-78, 78, 78-79, 78, 80-81, 81-86, 86-94, 94-101, 101-102, 102-103, 103-105 and 104-109, respectively, in order of appearance.

9. Host Cell Analyses

Host-Cell Protein (HCP) Assay

The host cell protein (HCP) ELISA was performed using the "Immunoenzymetric Assay for the Measurement of *Pseudomonas fluorescens* Host Cell Proteins" kit from Cygnus Technologies, Inc., catalog number F450. The assay was performed using the manufacturer's protocol.

Q-PCR Host-Cell DNA Assay

To analyze host cell DNA, oligonucleotide primers against the DNA Polymerase I gene and expression plasmid backbone sequences were designed for the detection of *P. fluorescens* DNA by real-time quantitative PCR. The primers were synthesized by Integrated DNA Technologies, Inc. Real-time PCR was performed with a DNA Engine Opticon System PTC-200 DNA Engine Cycler (MJ Research, CFD-3200 Opticon).

10. Endotoxin Assay

The endotoxin in the elution fractions was analyzed using an Endosafe-PTS portable endotoxin analyzer (Charles River Laboratories (CHL)) following manufacturer-supplied operating procedures, using cartridges with sensitivity ranges of 1-0.01 EU/mL (CHL, part number PTS2001F) and 10-0.1 EU/mL (CHL, part number PTS201F).

Example 3

Purification of rCSP and Preferential Reduction of rCSP Dimer

Purified recombinant CSP was obtained using a method identified based on the results described in Example 2 wherein the purified rCSP dimer was subjected to preferential reducing conditions and separated into monomers. Overall process yields of 36% were obtained for all experiments and 0% degraded species were observed by LC-MS.

Overview:

The *Pseudomonas fluorescens* fermentation whole broth (10 liters) was transferred to a harvest vessel for primary recovery. The fermentation whole broth was first diluted with 3.1 M urea, 31 mM Tris, pH 8.2 to achieve a homogenization feed that was ≤20% solids. The diluted fermentation broth was lysed by microfluidization, generating cell lysate. The lysate was diluted 1:1 with 2 M urea, 20 mM Tris, pH 8.2, creating a 10% solids lysate. The *P. fluorescens* solids in the lysate were separated from the rCSP-containing buffer by disk-stack centrifugation and depth filtration. The rCSP-containing buffer was then further 0.2-1 μm filtered and frozen. A portion of the rCSP clarified cell extract once thawed, was purified by anion exchange chromatography (AEX). The rCSP-containing AEX eluate was collected and further purified by hydroxyapatite chromatography (HA). The rCSP-containing HA eluate was collected and stored at 2-8° C. Once the HA eluate was brought back to ambient temperature and 0.2-1 μm filtered, the rCSP was subjected to preferential reducing conditions. Chromatography elution fractions containing dimerized CSP in buffer were pooled to a final volume of 200-600 mL. The pool was subjected to preferential reduction by addition of dithiothreitol reductant (JT Baker, part number JT-F780-2, Phillipsburg, N.J.) to a final concentration of 20 μM and stirred rapidly with a magnetic stir bar and stir plate for 12-24 hours at room temperature. Alternatively, aggregated rCSP in PBS (e.g., batch 533-128) was subjected to the same process by first adding 2 M urea to the material before undergoing selective reduction.

After being subjected to preferential reducing conditions, the rCSP was concentrated and diafiltered into formulation buffer by TFF. The diafiltered rCSP was then passed through a final 0.2-μm filter to yield the bulk drug substance.

Purification summaries for the two integrated purifications are presented in Table 11. The primary recovery steps were performed on 500 g of frozen cell paste and processed through depth filtration with a recovery yield of approximately 85% with a purity of 8%. This material was then chromatographed over the TMAE column (run 533-402 and run 533-404) with an average recovery of 83% and purity of 78% (FIGS. 19 and 20). The TMAE pools were then passed over Ceramic Hydroxyapatite Type I (run 533-403 and run 533-405) with an average recovery of 69% and a purity of 96% by SDS-CGE (FIGS. 21 and 22). The CHT material was then subjected to the mild-reduction process and the buffer exchanged into PBS by TFF with a yield of ~75% and final purity of 96% by SDS-CGE. The rCSP concentrations were determined to be 1.0 mg/ml and 1.2 mg/ml by absorbance at 280 nm for batches 533-406 and 533-407, respectively (Table 11). The purified rCSP (batches 533-406 and 533-407) was then aliquoted and stored at −80° C. for additional analysis and characterization, as discussed below. The overall purification yield for both integrated runs was approximately 36%, representing an approximate 10-fold improvement over the earlier stage purification processes. For example, an earlier stage process involving anion exchange followed by hydrophobic interaction chromatography and carried out at small scale (with less than 0.5 g rCSP in starting material) resulted in a 3.2% overall process yield for CS533-129, a 6.5% overall process yield for CS533-211, and a 3.1% overall process yield for CS533-249 (expressing the rCSP of SEQ ID NO: 3 fused to a pbp leader).

As shown in FIG. 23, the purified material was analyzed by SDS-PAGE and the purity determined to be consistent with SDS-CGE (>95% purity). Western blot analysis confirmed identity and showed low fragmentation (FIG. 24). A conformation-specific antibody (4C2) that is sensitive to the C-terminal domain containing two disulfides showed a strong signal (2). Reduced and alkylated samples showed loss of signal, suggesting that the purified rCSP had the correct disulfide structure (FIG. 24). Endotoxin was <10 EU/mg for both batches (Table 11). HCP-ELISA measured host cell protein at ~4000 ppm for both purifications (Table 11) which is consistent with 96% purity measured by SDS-CGE. Host DNA (genomic) was measured to be 78-98 pg/mg by Q-PCR (Table 11). Analysis by SE-HPLC showed <5% dimer for both preparations and no HMW aggregates (FIG. 25 and Table 11). RP-HPLC showed 11% dimer for both preparations (Table 11) and a peak profile consistent with the 533-191 reference (FIG. 26). Intact mass was consistent with the theoretical molecular weight for both 533-406 and 533-407, with no detectable clipping at the N-terminus (FIG. 27). Peptide mapping analysis using Glu-C proteolysis for both preparations was compared to the 533-191 reference (FIG. 28). This analysis demonstrated that the cysteine near the N-terminus was free and that the disulfide bonds were intact (not shown).

Figure 30A:
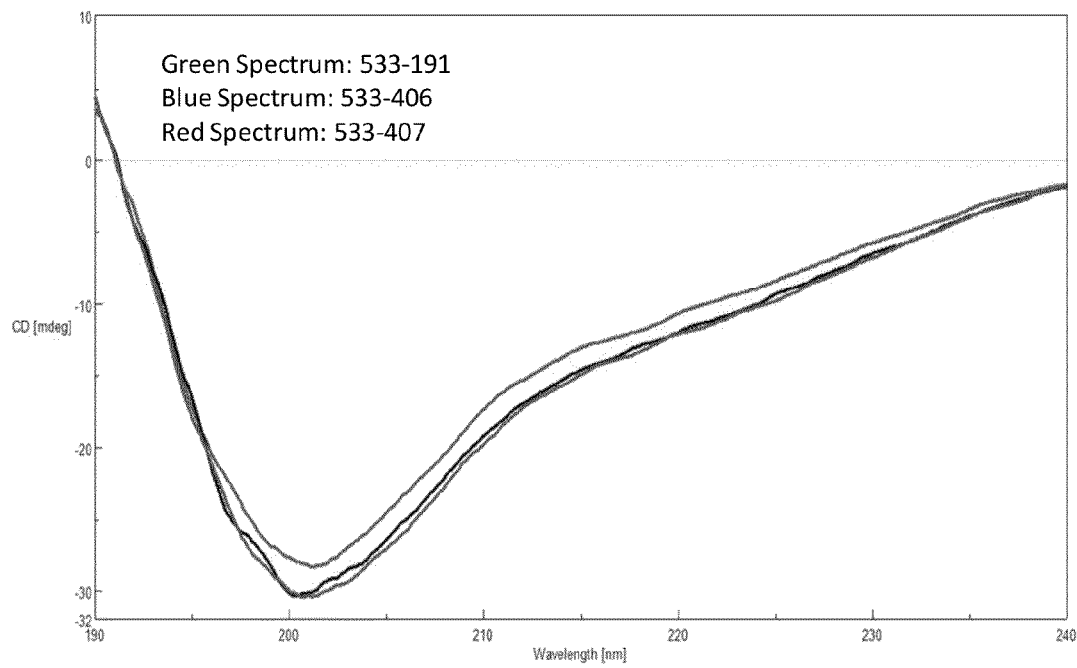
Figure 30B:
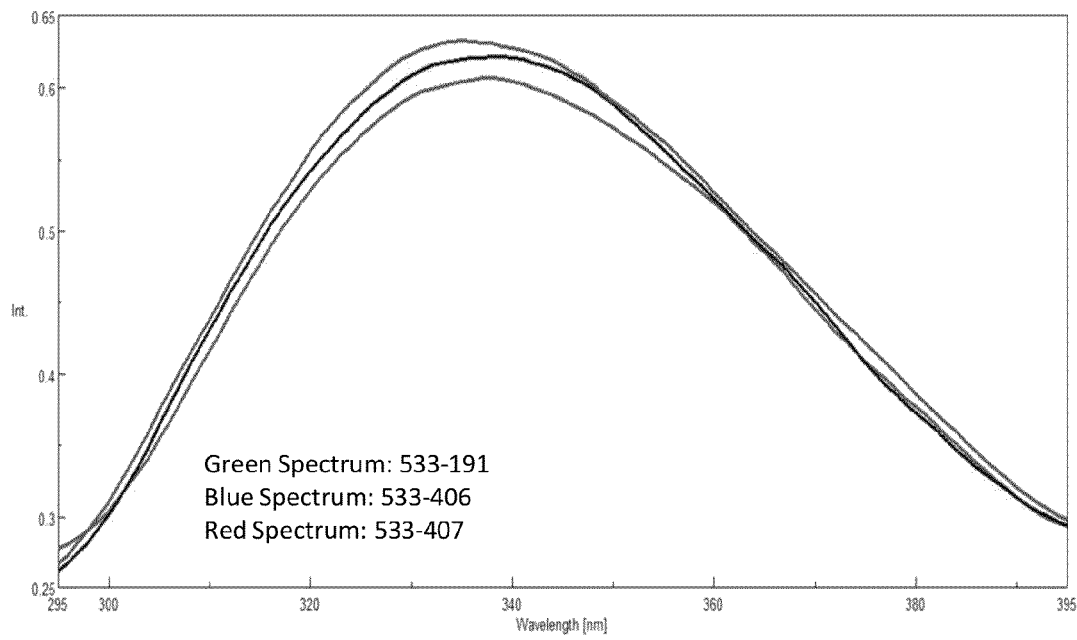

Charge heterogeneity for the preparations matched the 533-191 internal reference profile (FIG. 29). Slight differences in the intensities of the pI peaks were observed due to differences in the sample concentrations. Far UV-CD analysis for both preparations was similar to the reference material (FIG. 30A). Analysis using K2D2 software calculated the 10.45% α-helix and 29.09% β-strand for batch 533-406, and 10.45% α-helix and 29.09% β-strand for batch 533-407 and 10.04% α-helix and 29.65% β-strand for the 533-191 reference. Intrinsic fluorescence spectra for both preparations matched the reference material (FIG. 30B).

In summary, batches 533-406 and 533-407 from the integrated purification runs are of high quality and purity, and met all of the analytical specifications for this stage of the project. Comparative analysis showed minimal differences between the preparations as well as with the 533-191 reference standard.

TABLE 11A

Purification Summary for Integrated Purification Run (batch 533-406)

| | Harvest/Clarification | TMAE HiCap | Ceramic HA | Reduction & UF/DF |
|---|---|---|---|---|
| Protocol Number | 533-387 (533-252 paste) | 533-402 | 533-403 | 533-406 |
| Scale | 500 g | 151 mL CV | 85 mL CV | 160 mL |
| Load (mg) | | 518 | 340 | 224 |
| Yield (mg) | 3240 | 453 | 238 | 168 |
| Step Recovery | 85% | 81% | 70% | 75% |
| Overall Recovery | 85% | 69% | 48% | 36% |
| CGE Purity | 8% | 79% | 96% | 96% |
| CGE Conc (mg/ml) | 0.37 | 0.6 | 0.75 | 0.8 |
| Q-Page Conc (mg/ml) | 0.81 | 1.0 | 1.4 | 0.9 |
| Concentration by A280 | | | 1.5 | 1.0 |
| HPLC-SEC (% Dimer) | | | | 2.5 |
| RP (% Dimer) | | | 77% | 11% |
| Mass Spec (% clipped) | | 4.1% | 0% | 0% |
| HCP ELISA (ppm) | | | | 4123 |
| Host Genomic DNA (pg/mg) | | | | 98.0 |
| Host Plasmid DNA (pg/mg) | | | | 7.4 |
| Endotoxin (EU/mg) | | n/a | | 4.3 |
| Western Blot | | | | Positive band; no fragments |
| Peptide Mapping | | | | N-terminal cysteine free |
| cIEF | | | | pI peaks at 4.94, 5.02, 5.16, 5.31; additional minor peaks |
| CD | | | | α helix = 10.45%; β strand = 29.09% |
| Intrinsic Fluorescence | | | | consistent with standard |

TABLE 11B

Purification Summary for Integrated Purification Run (batch 533-407)

| | Harvest/Clarification | TMAE HiCap | Ceramic HA | Reduction & UF/DF |
|---|---|---|---|---|
| Protocol Number | 533-387 (533-252 paste) | 533-404 | 533-405 | 533-407 |
| Scale | 500 g | 151 mL CV | 85 mL CV | 150 mL |
| Load (mg) | | 644 | 408 | 255 |
| Yield (mg) | 3240 | 544 | 272 | 190 |
| Step Recovery | 85% | 84% | 67% | 75% |
| Overall Recovery | 85% | 71% | 48% | 36% |
| CGE Purity | 9% | 76% | 96% | 96% |
| CGE Conc (mg/ml) | 0.4 | 0.6 | 0.9 | 1.0 |
| Q-Page Conc (mg/ml) | 0.8 | 1.2 | 1.7 | 1.2 |
| Concentration by A280 | | | 1.8 | 1.2 |
| HPLC-SEC (% Dimer) | | | | 4.2 |
| RP (% Dimer) | | | 67% | 11% |
| Mass Spec (% clipped) | | | | 0% |
| HCP ELISA (ppm) | | | | 4093 |
| Host Genomic DNA (pg/mg) | | | | 76.0 |
| Host Plasmid DNA (pg/mg) | | | | 4.5 |
| Endotoxin (EU/mg) | | | | 6.5 |
| Western Blot | | | | Positive band; no fragments |
| Peptide Mapping | | | | N-terminal cysteine free |
| cIEF | | | | pI peaks at 4.93, 5.03, 5.16, 5.32; additional minor peaks |
| CD | | | | α helix = 10.45%; β strand = 29.09% |
| Intrinsic Fluorescence | | | | consistent with standard |

Example 4

Purification of rCSP from a Five Liter Fermentation

A purification method of the present invention, as described in Example 43 was used to obtain purified rCSP from a 5 liter fermentation culture of a *P. fluorescens* expression strain having an expression vector comprising SEQ ID NO: 5. Degradation of the N-terminus was determined to be 5.1%. The overall process yield was 60%.

Example 5

Purification of rCSP Encoded by SEQ ID NO: 6

A purification method of the present invention, as used in Example 3, was used to obtain rCSP from a culture of a *P. fluorescens* expression strain having an expression vector comprising SEQ ID NO: 6. SEQ ID NO: 6 is an optimized CSP nucleotide sequence that encodes the rCSP as set forth in SEQ ID NO: 3. The CSP gene was fused to the pbp secretion leader coding sequence.

Example 6

Optimization of Reducing Agent Concentrations for Use in Preferential Reducing Buffers Following the general strategy described in Example 1, other reducing agents are tested as done with DTT to identify an optimal concentration for preferentially reducing rCSP dimers to monomeric form without denaturing the protein. The other reducing agents tested include DTT, cysteine, glutathione, monothioglycerol, thioglycolate, dithothiothreitol, dithioerythritol, acetylcysteine, 2-Mercaptoethanol (B-mercaptoethanol), TCEP-HCl (pure, crystalline Tris(2-carboxyethyl)phosphine hydrochloride), or 2-Mercaptoethylamine-HCl (2-MEA).

Example 7

Evaluation of Monothioglycerol as a Reducing Agent

Other reducing agents/conditions were evaluated to optimize the production of rCSP monomer. This included testing buffer formulations and procedures to further enhance the stability of rCSP in liquid form. Reagents were evaluated for their ability to preserve rCSP as an active monomer based on their effects on degradation, dimerization, and aggregation of rCSP. These studies demonstrated that rCSP can be maintained at >85% monomer content, in a PBS buffer containing monothioglycerol and arginine at 4° C., for up to 23 days.

The stabilizing effect of arginine was demonstrated in experiments in which arginine alone and arginine with the reducing agent monothioglycerol were spiked into rCSP samples in PBS, pH 7.2. Further studies measured 80 percent rCSP monomer content following buffer exchange by ultrafiltration/diafiltration into PBS containing monothioglycerol and arginine. This level of stability was demonstrated with rCSP at concentrations from 1 mg/mL to >5 mg/mL. On the other hand, Tris and histidine buffers containing mannitol, monothioglycerol, and arginine exhibited aggregate formation of approximately 11% of total rCSP.

Reversed phase-HPLC elution fractions were analyzed by liquid chromatography/mass spectroscopy (LC/MS) and SDS-PAGE to determine molecular weight and differences in chemical structure. These studies showed that a fraction of the RP-HPLC eluate contained rCSP possessing a pyroglutamate moiety. Studies comparing recombinant CSP stability in PBS containing 1 mM monothioglycerol and 10% w/v arginine at three pH levels showed that the pyroglutamate-containing fraction increased over time as the fraction of native rCSP, which did not contain pyroglutamate, decreased. Stability levels for total rCSP at 4° C. and pH 6.4 after 21 and 23 days were comparable to stability at pH 7.0; at 25° C., stability decreased significantly over the same period.

These studies were carried out using rCSP prepared from strain CS533-129 using the method described for internal reference standard preparation in Example 2. All methods are as described in Example 2 unless otherwise specified.

Spiking Studies

To stabilize rCSP as an active monomer, a number of formulation buffer excipients were evaluated for their ability to decrease or prevent dimerization, aggregation, and overall degradation of rCSP.

Spiking Experiment 1: Effect of Reducing Agents and Arginine on rCSP Stability

A panel of reducing agents was tested for effectiveness in preventing rCSP dimer formation. Reducing agents tested were monothioglycerol (MTG), L-cysteine, acetylcysteine, glutathione, and thioglycolate. Arginine was tested in combination with each reducing agent as a means for decreasing the rate of rCSP aggregation. The reagents were used in a small-scale stability experiment in which individual samples of rCSP (1 mg/mL in PBS, pH 7.2) each were spiked with one of the six reducing agents in the presence and absence of 1% arginine.

Samples were kept at room temperature (25° C.) for 3, 6, or 14 days then analyzed by SE-HPLC. HPLC was carried out as described in Example 2. Four distinct peak regions were observed: The first region contained high molecular weight (HMW) rCSP aggregates; the second peak region contained rCSP dimers; the third peak region contained rCSP monomer; the last eluting peak region contained low molecular weight degradation products.

The rCSP samples held in PBS spiked with monothioglycerol (MTG), cysteine, or acetylcysteine had the highest percentage of protein in the main (monomer) peak and lowest percentages in the high molecular weight (aggregate) and low molecular weight (degradation product) peaks at 6 and 14 days compared to samples stored for the same periods in the other excipients (Tables 12A-C). The "Main peak" columns indicate rCSP monomer percentages.

TABLE 12A

Spiking Experiment 1: SE-HPLC of rCSP Stored for 3 Days

| | | Day 3 (02162B) | | | | | | | |
|---|---|---|---|---|---|---|---|---|---|
| | | HMW peak | | Dimer peak | | Main peak | | LMW peaks | |
| ID | Sample | Area | % | Area | % | Area | % | Area | % |
| 533-462-1 | Acetylcysteine (1 mM) | 223 | 10 | 0 | 0 | 1809 | 78 | 292 | 13 |
| 533-462-2 | Cysteine (1 mM) | 365 | 11 | 0 | 0 | 2438 | 75 | 430 | 13 |
| 533-462-3 | Monothioglycerol (1 mM) | 385 | 13 | 0 | 0 | 2509 | 85 | 69 | 2 |
| 533-462-4 | Glutathione (1 mM) | 432 | 14 | 0 | 0 | 2470 | 80 | 170 | 6 |
| 533-462-5 | Thioglycolate (1 mM) | 769 | 22 | 0 | 0 | 2270 | 66 | 387 | 1 |
| 533-462-6 | Acetylcysteine (1 mM) + Arginine (1%) | 268 | 10 | 0 | 0 | 2205 | 82 | 215 | 8 |
| 533-462-7 | Cysteine (1 mM) + Arginine (1%) | 316 | 11 | 0 | 0 | 2240 | 81 | 202 | 7 |
| 533-462-8 | Monothioglycerol (1 mM) + Arginine (1%) | 259 | 10 | 0 | 0 | 2190 | 85 | 117 | 5 |
| 533-462-9 | Glutathione (1 mM) + Arginine (1%) | 300 | 10 | 0 | 0 | 2322 | 79 | 317 | 11 |
| 533-462-10 | Thioglycolate (1 mM) + Arginine (1%) | 585 | 19 | 0 | 0 | 1967 | 65 | 472 | 16 |

TABLE 12A-continued

Spiking Experiment 1: SE-HPLC of rCSP Stored for 3 Days

| | | Day 3 (02162B) | | | | | | | |
|---|---|---|---|---|---|---|---|---|---|
| | | HMW peak | | Dimer peak | | Main peak | | LMW peaks | |
| ID | Sample | Area | % | Area | % | Area | % | Area | % |
| 533-462-11 | Arginine (1%) | 506 | 18 | 112 | 4 | 2049 | 73 | 128 | 5 |
| 533-462-12 | PBS alone | 606 | 25 | 75 | 3 | 1693 | 70 | 43 | 2 |

TABLE 12B

Spiking Experiment 1: SE-HPLC of rCSP Stored for 6 Days

| | | Day 6 (02202B) | | | | | | | |
|---|---|---|---|---|---|---|---|---|---|
| | | HMW peak | | Dimer peak | | Main peak | | LMW peaks | |
| ID | Sample | Area | % | Area | % | Area | % | Area | % |
| 533-462-1 | Acetylcysteine (1 mM) | 77 | 4 | 0 | 0 | 1837 | 86 | 227 | 11 |
| 533-462-2 | Cysteine (1 mM) | 282 | 10 | 0 | 0 | 2218 | 76 | 431 | 15 |
| 533-462-3 | Monothioglycerol (1 mM) | 373 | 13 | 0 | 0 | 2397 | 81 | 177 | 6 |
| 533-462-4 | Glutathione (1 mM) | 524 | 17 | 0 | 0 | 2196 | 66 | 391 | 12 |
| 533-462-5 | Thioglycolate (1 mM) | 728 | 22 | 0 | 0 | 2196 | 66 | 391 | 12 |
| 533-462-6 | Acetylcysteine (1 mM) + Arginine (1%) | 212 | 9 | 0 | 0 | 1881 | 84 | 147 | 7 |
| 533-462-7 | Cysteine (1 mM) + Arginine (1%) | 334 | 12 | 0 | 0 | 2090 | 75 | 375 | 13 |
| 533-462-8 | Monothioglycerol (1 mM) + Arginine (1%) | 213 | 9 | 0 | 0 | 1909 | 82 | 204 | 9 |
| 533-462-9 | Glutathione (1 mM) + Arginine (1%) | 258 | 10 | 0 | 0 | 2102 | 79 | 317 | 12 |
| 533-462-10 | Thioglycolate (1 mM) + Arginine (1%) | 572 | 19 | 0 | 0 | 1928 | 63 | 562 | 18 |
| 533-462-11 | Arginine (1%) | 659 | 27 | 131 | 5 | 1452 | 59 | 207 | 8 |
| 533-462-12 | PBS alone | 972 | 40 | 107 | 4 | 1288 | 53 | 53 | 2 |

TABLE 12C

Spiking Experiment 1: SE-HPLC of rCSP Stored for 14 Days

| | | Day 14 (02282B) | | | | | | | |
|---|---|---|---|---|---|---|---|---|---|
| | | HMW peak | | Dimer peak | | Main peak | | LMW peaks | |
| ID | Sample | Area | % | Area | % | Area | % | Area | % |
| 533-462-1 | Acetylcysteine (1 mM) | 519 | 23 | 0 | 0 | 1349 | 60 | 386 | 17 |
| 533-462-2 | Cysteine (1 mM) | 597 | 20 | 0 | 0 | 1886 | 64 | 449 | 15 |
| 533-462-3 | Monothioglycerol (1 mM) | 680 | 25 | 0 | 0 | 1716 | 63 | 346 | 13 |
| 533-462-4 | Glutathione (1 mM) | 901 | 27 | 0 | 0 | 1739 | 50 | 708 | 21 |
| 533-462-5 | Thioglycolate (1 mM) | 793 | 24 | 0 | 0 | 1648 | 50 | 869 | 26 |
| 533-462-6 | Acetylcysteine (1 mM) + Arginine (1%) | 326 | 14 | 0 | 0 | 1621 | 68 | 427 | 18 |
| 533-462-7 | Cysteine (1 mM) + Arginine (1%) | 395 | 15 | 0 | 0 | 1927 | 71 | 384 | 14 |
| 533-462-8 | Monothioglycerol (1 mM) + Arginine (1%) | 283 | 12 | 0 | 0 | 1737 | 73 | 344 | 15 |
| 533-462-9 | Glutathione (1 mM) + Arginine (1%) | 342 | 12 | 0 | 0 | 1731 | 61 | 768 | 27 |
| 533-462-10 | Thioglycolate (1 mM) + Arginine (1%) | 588 | 20 | 0 | 0 | 1641 | 56 | 676 | 23 |
| 533-462-11 | Arginine (1%) | 1156 | 44 | 277 | 11 | 927 | 36 | 251 | 10 |
| 533-462-12 | PBS alone | 1427 | 57 | 137 | 5 | 813 | 32 | 140 | 6 |

Samples spiked only with 1% arginine showed increases in the sizes of the dimer peak and the high molecular weight aggregate peak, along with a decrease in the size of the monomer peak, from 3 days to 14 days. The combination of arginine with other excipients also was evaluated.

progressively lower percentage in the high MW peak, indicating an inhibitory effect of arginine on aggregate formation. All samples in MTG showed no material in the dimer peak; only the sample kept in PBS alone displayed dimerization (Table 13A and B).

TABLE 13A

Spiking Experiment 2: SE-HPLC of rCSP Stored for 3 Days

| | | Day 3 (02202C) | | | | | | | |
|---|---|---|---|---|---|---|---|---|---|
| | Samples | HMW peak | | Dimer peak | | Main peak | | LMW peaks | |
| ID | Excipients | Area | % | Area | % | Area | % | Area | % |
| 533-468-1 | Monothioglycerol (1 mM) | 296 | 15 | 0 | 0 | 1645 | 85 | 0 | 0 |
| 533-468-2 | Monothioglycerol (1 mM) + 1% Arginine | 238 | 13 | 0 | 0 | 1624 | 87 | 94 | 5 |
| 533-468-3 | Monothioglycerol (1 mM) + 5% Arginine | 155 | 8 | 0 | 0 | 1829 | 92 | 232 | 10 |
| 533-468-4 | Monothioglycerol (1 mM) + 10% Arginine | 120 | 6 | 0 | 0 | 1891 | 94 | 328 | 14 |
| 533-468-5 | Monothioglycerol (1 mM) + 20% Arginine | 67 | 3 | 0 | 0 | 1911 | 97 | 528 | 21 |
| 533-468-6 | PBS Alone | 435 | 28 | 0 | 0 | 1093 | 72 | 0 | 0 |

TABLE 13B

Spiking Experiment 2: SE-HPLC of rCSP Stored for 12 Days

| | | Day 12 (02292A) | | | | | | | |
|---|---|---|---|---|---|---|---|---|---|
| | Samples | HMW peak | | Dimer peak | | Main peak | | LMW peaks | |
| ID | Excipients | Area | % | Area | % | Area | % | Area | % |
| 533-468-1 | Monothioglycerol (1 mM) | 390 | 23 | 0 | 0 | 1296 | 77 | 473 | 22 |
| 533-468-2 | Monothioglycerol (1 mM) + 1% Arginine | 247 | 16 | 0 | 0 | 1289 | 84 | 258 | 14 |
| 533-468-3 | Monothioglycerol (1 mM) + 5% Arginine | 137 | 8 | 0 | 0 | 1660 | 92 | 430 | 19 |
| 533-468-4 | Monothioglycerol (1 mM) + 10% Arginine | 102 | 5 | 0 | 0 | 1762 | 95 | 435 | 19 |
| 533-468-5 | Monothioglycerol (1 mM) + 20% Arginine | 56 | 3 | 0 | 0 | 1578 | 97 | 628 | 28 |
| 533-468-6 | PBS Alone | 859 | 53 | 109 | 7 | 657 | 40 | 0 | 0 |

The addition of arginine had a small effect on the proportion of monomer at 3 and 6 days, but at 14 days, reducing agent plus arginine resulted in a 9% to 23% higher amount of monomer than reducing agent alone. Monothioglycerol plus arginine maintained a 2% higher amount of material in the main peak than cysteine plus arginine and a 5% higher amount than acetylcysteine plus arginine.

Spiking Experiment 2: Effect of Monothioglycerol and Arginine on rCSP Stability

A set of experiments was conducted to evaluate rCSP stability in PBS, pH 7.2, spiked with MTG and a wider range of concentrations of arginine. Samples were held for 3 or 12 days in PBS alone, 1 mM MTG alone, or 1 mM MTG plus 1, 5, 10, or 20% arginine. Protein stability was analyzed by SE-HPLC. In MTG alone, the main monomer peak decreased in relative size as the low molecular weight peak increased in relative size from day 3 to day 12. Increasing concentrations of arginine resulted in increasing percentages of total protein in the main (monomer) peak. Increasing concentrations of arginine also resulted in a progressively higher percentage of each sample in the low molecular weight (MW) peak and a Monothioglycerol with 10% arginine was selected for use in subsequent concentration and pH stability experiments. The formulation containing 20% arginine gave slightly better stability results. SE-HPLC data for the excipient formulations tested is summarized in Table 13. None of the samples from Spiking Experiments 1 and 2 exhibited significant fragmentation in SDS-CGE and all showed the major band at the expected MW for rCSP.

Concentration Study

The stability of rCSP concentrated to 5 mg/mL in 1 mM MTG plus 10% arginine was evaluated. Samples of rCSP in PBS with 1 mM MTG and 10% arginine or in PBS alone were concentrated 8-fold on a centrifugal concentrator. SE-HPLC was performed on samples at the starting concentration of 0.8 mg/mL and at 6.4 mg/mL with or without a holding step of 16 hours at 4° C. In PBS alone, the monomer decreased from 86% to 50% following 8-fold concentration; with the addition of a 16 hour hold following concentration, the monomer peak decreased to 29%. Samples of rCSP in 1 mM MTG with 10% arginine displayed much more stability. The main monomer peak decreased from 86% to 80% with 8-fold concentration, and did not decrease at all with a 16-hour hold. Relative peak size data is summarized in Table 14. These data confirmed the results of the spiking studies and showed that concentration to 5 mg/mL could be attained without a drastic decrease in rCSP monomer.

TABLE 14

Relative SE-HPLC Peak Sizes for Concentrated Sample

| Conditions | HMW peak % | Dimer peak % | Main peak % |
|---|---|---|---|
| Starting with PBS | 14 | — | 86 |
| Concentrated 8X to approx 6.4 mg/mL | 49 | 1 | 50 |
| Concentrated 8X to approx 6.4 mg/mL, held 16 hr at 4° C. | 71 | — | 29 |
| Starting with PBS + 1 mM MTG + 10% Arginine | 14 | — | 86 |
| PBS + 1 mM MTG + 10% Arginine, Conc. 8X to approx 6.4 mg/mL | 16 | 4 | 80 |
| PBS + 1 mM MTG + 10% Arginine, Conc. 8X to approx 6.4 mg/mL, held 16 hr at 4° C. | 17 | 3 | 80 |

Buffer Exchange Using Non-PBS Buffers

Formulations containing 4.2% mannitol, 2% arginine, 1 mM MTG, and 10 μM ethylenediaminetetraacetic acid (EDTA) were tested in Tris and Histidine buffers (Table 15). These experiments were carried out to test the stabilizing effects of the buffer systems on rCSP. Stability was assessed following buffer exchange by ultrafiltration/diafiltration (UF/DF).

TABLE 15

Non-PBS Buffer Formulations

| Experiment Number | Formulation | Starting Material |
|---|---|---|
| A | 10 mM Tris base, 4.2% Mannitol, 2% Arginine-HCl, 100 μM EDTA, 1 mM MTG, pH 7.5 | CHT Eluate + 20 μM DTT, 0.27 mg/mL |
| B | 10 mM Histidine, 4.2% Mannitol, 2% Arginine-HCl, 100 μM EDTA, 1 mM MTG, pH 7.0 | CHT Eluate + 20 μM DTT, 0.27 mg/mL |

In both experiments A and B, eluate from the ceramic hydroxyapatite (CHT) column was subjected to mild reduction, and then exchanged into the test excipient buffers by UF/DF. For the UF/DF process, mildly reduced CHT eluate was concentrated by ultrafiltration to 1.0 mg/mL and diafiltered against six diavolumes of the specified formulation. The retentate was further concentrated to ~5.0 mg/mL before being recovered from the system and subjected to 0.22 μm filtration. Analysis by SE-HPLC showed that for both excipient formulations, samples held for two days or longer exhibited 11% aggregate formation. The SE-HPLC data carried out on protein in mildly reduced CHT eluate exchanged into 10 mM Tris base, 4.2% mannitol, 2% arginine-HCl, 100 μM EDTA, 1 mM monothioglycerol, pH 7.5, are summarized in Table 16 (UF 1=0.0 hours to ~1.0 hours; DF=1.0 hours to 4.5 hours; UF 2=4.5 hours to 5.0 hours).

The SE-HPLC data carried out on protein in mildly reduced CHT eluate exchanged into 10 mM histidine, 4.2% mannitol, 2% arginine-HCl, 100 μM EDTA, 1 mM monothioglycerol, pH 7.0, are summarized in Table 17 (UF 1=0.0 hours to 1.0 hours; DF=1.0 hour to 4.5 hours; UF 2=4.5 hours to 5.0 hours).

TABLE 16

Buffer Exchange into Tris Buffer by Tangential Flow Filtration (UF/DF) (533-536).

| 533-536 | Aggregate % | Dimer % | Monomer % | LMW % |
|---|---|---|---|---|
| Post-reduction, 0.43 g/L | — | — | 96 | 4 |
| | — | — | 100 (CSP only) | — |
| Post-reduction, t = 24 hr | 5 | — | 95 | — |
| End UF 1, 1 mg/ml | — | 1 | 95 | 4 |
| | — | 0.5 (CSP only) | 99.5 (CSP only) | — |
| End UF 1, 1 mg/ml, t = 24 hr, RT | — | 2 | 98 | — |
| End DF, 1 mg/ml | 1.0 | — | 96 | 3 |
| | 0.7 (CSP only) | — | 99.3 (CSP only) | — |
| End DF, 1 mg/ml, t = 24 hr, RT | 4 | 0.5 | 96 | — |
| End DF, 1 mg/ml, t = 48 hr | 1.6 | — | 98.4 | — |
| End UF 2, 5 mg/ml | 2.4 | — | 94 | 3.5 |
| | 2.2 (CSP only) | — | 97.8 (CSP only) | — |
| End UF 2, 5 mg/ml, freeze/thaw | 4.7 | — | 95.3 | — |
| End UF 2, 5 mg/ml, t = 24 hr, RT | 7 | — | 93 | — |
| End UF 2, 5 mg/ml, t = 48 hr | 11 | — | 89 | — |

TABLE 17

Buffer Exchange into Histidine Buffer by Tangential Flow Filtration (UF/DF) (533-538).

| 533-538 | Aggregate % | Dimer % | Monomer % | LMW % |
|---|---|---|---|---|
| Post-reduction, 0.43 mg/mL | — | 1 | 99 | — |
| End UF 1, 1 mg/mL | — | 1 | 99 | — |
| End DF, 0.9 mg/mL | 1.5 | — | 98.5 | — |
| End DF, 0.9 mg/mL, t = 24 hr | 2 | — | 98 | — |
| End UF 2, 5 mg/mL | — | 4 | 96 | — |
| End UF 2, 5.6 mg/mL, t = 24 hr | 11 | — | 89 | — |
| End UF 2, Freeze/Thaw | — | 6 | 94 | — | pH Stability Study

The formulation buffer containing 1×PBS, 0.5M arginine, and 1 mM monothioglycerol was tested at three different pH levels for 21 days at 2-8° C. and ambient temperature (~25° C.). A frozen control at −70° C. also was analyzed at each time point. Samples were buffer exchanged by tangential flow filtration. The rCSP was then concentrated to 1 and 5 mg/mL by UF/DF and the pH was adjusted to 6.44 with 6N HCl and QS'd to 1 L (Batch 1, 533-551), to pH 7.0 with 10N NaOH and QS'd to 1 L (Batch 2, 533-550), or to pH 7.5 with 10N NaOH and QS'd to 1 L (Batch 3, 533-549). Time points were analyzed by RP-HPLC at 214 nm and by SE-HPLC at 280 nm. The SE-HPLC samples were analyzed immediately at the ending time points. The RP-HPLC samples were frozen at −80° C. at their ending time points, then thawed and analyzed. Data were not available for pH 7.0, 25° C., 21 days.

RP-HPLC was performed on rCSP pH stability study samples at three pH levels: 6.4, 7.0, and 7.5. The samples analyzed in these experiments exhibited a main peak containing native rCSP with a shoulder eluting slightly later consisting of rCSP with the pyroglutamate moiety discussed above. Together the areas of the native CSP peak and the pyroglutamate-containing shoulder made up the chromatogram area representing total rCSP. Three other groups of peaks were observed: Group 1 at approximately 10 minutes, Group 2 just ahead of the main peak, and Group 3 just after the pyroglutamate-containing shoulder. FIG. 31 shows the relative positions of Groups 1-3 peaks observed in a T0 control stability sample of 1 mg/ml rCSP stored at 4° C., pH 7.5.

Samples at pH 7.5 (Batch 3) containing rCSP at either 1 mg/mL or 5 mg/mL were analyzed by RP-HPLC at T=0, or stored at either 4° C. or 25° C. and analyzed at 5 days, 14 days, or 21 days. Time course analysis was performed in the same way for samples at pH 7.0 (Batch 2) and pH 6.4 (Batch 1). At all three pH levels, the material in the native CSP fraction decreased over time while the material in the pyroglutamate-containing fraction increased over time; this was seen to a markedly greater extent in samples held at 25° C. than in those held at 4° C.

Side-by-side stability data comparisons were made of the three pH levels over time at 1 and mg/mL and at 4° C. and 25° C. using either the total CSP fraction or material eluting only in the native (main) RP-HPLC peak, which excluded the pyroglutamate-containing shoulder (Tables 18-20). For 1 mg/mL and 5 mg/mL samples at 4° C., buffers at pH 6.4 and pH 7.0 provided higher levels of stability at 14/15 days and 21/23 days than did buffer at pH 7.5. RP-HPLC analysis showed a difference in stability of approximately 2% between pH 6.4 and pH 7.0 at 21/23 days for native rCSP at 1 mg/mL and 1.6% at 5 mg/mL. For native and total CSP samples at both concentrations at 25° C., pH 6.4 and 7.0 provided higher levels of stability than pH 7.5 at 5/6 days and comparable levels at 14/15 days and 21/23 days. Samples at 5 mg/mL which were kept at pH 7.5 showed a greater increase in material in the group 1 peaks at 21 days than did samples held in pH 6.4 and pH 7.0 buffers.

Samples containing either 5 mg/mL or 1 mg/mL rCSP were held in buffer at pH 6.4, 7.0, or 7.5 at either 4° C. or 25° C. and analyzed by SE-HPLC at 1/3 days, 5/6 days, 14/15 days and 21/23 days (Tables 21 and 22). An increase in peak tailing was observed that was more pronounced in samples held at 25° C. for the same amount of time. The trend was similar for 1 mg/mL samples held at 4° C. and at 25° C.

Side-by-side data comparisons were performed of the three pH levels at 4° C. and 25° C. with samples of 1 mg/mL and 5 mg/mL at 1/3 days, 5/6 days, 14/15 days and 21/23 days. The most stable samples were those in buffer of pH 7.0 at both 4° C. and 25° C. and at both 1 mg/mL and 5 mg/mL. Similarly to RP-HPLC, SE-HPLC indicates slightly higher stability of the 5 mg/mL sample at 25° C. with pH 6.4 buffer than with pH 7.0 at 1, 5, and 14 days. At the 21 day endpoint, somewhat higher stability was measured for pH 7.0 than for pH 6.4.

TABLE 18

RP-HPLC relative areas of pH 7.5 liquid formulation (533-549) at 4° C. and 25° C., and 1 mg/mL and 5 mg/mL rCSP, up to 28 days.

| Formulated rCSP Concentration (mg/mL) | Temperature held (° C.) | Duration Held as Liquid (days) | % Area Native rCSP | % Area pE-rCSP | Total rCSP (% Area Native rCSP + % Area pE-rCSP) |
|---|---|---|---|---|---|
| 1 | n/a | 0 | 62.2 | 21.2 | 83.3 |
| 1 | 4 | 0.92 | 63.2 | 20.1 | 83.3 |
| 1 | 4 | 4 | 59.6 | 23.3 | 82.9 |
| 1 | 4 | 5 | 59.9 | 22.8 | 82.7 |
| 1 | 4 | 14 | 56.0 | 24.1 | 80.1 |
| 1 | 4 | 21 | 51.4 | 27.5 | 79.0 |
| 1 | 4 | 28 | 49.7 | 27.7 | 77.4 |
| 1 | 25 | 0.92 | 61.9 | 21.0 | 82.9 |
| 1 | 25 | 4 | 49.8 | 28.6 | 78.4 |
| 1 | 25 | 5 | 48.0 | 30.7 | 78.6 |
| 1 | 25 | 14 | 37.4 | 32.3 | 69.7 |
| 1 | 25 | 21 | 34.4 | 28.9 | 63.3 |
| 1 | 25 | 28 | 31.4 | 27.1 | 58.5 |
| 5 | n/a | 0 | 62.1 | 20.3 | 82.4 |
| 5 | 4 | 0.92 | 60.9 | 18.9 | 79.9 |
| 5 | 4 | 4 | 57.1 | 22.3 | 79.3 |
| 5 | 4 | 5 | 55.3 | 20.6 | 76.0 |
| 5 | 4 | 14 | 54.3 | 22.2 | 76.5 |
| 5 | 4 | 21 | 49.8 | 24.8 | 74.6 |
| 5 | 4 | 28 | 47.6 | 26.3 | 73.9 |
| 5 | 25 | 0.92 | 57.2 | 22.0 | 79.2 |
| 5 | 25 | 4 | 51.0 | 25.4 | 76.4 |
| 5 | 25 | 5 | 46.2 | 29.8 | 76.0 |
| 5 | 25 | 14 | 37.8 | 28.7 | 66.5 |
| 5 | 25 | 21 | 33.7 | 27.2 | 60.9 |
| 5 | 25 | 28 | 31.6 | 25.3 | 56.9 |

All RP-HPLC samples listed in Table 18 were frozen at −80° C. until analysis. Native rCSP does not contain pyroglutamate. pE-CSP is a pyroglutamate species.

TABLE 19

RP-HPLC relative areas of pH 7.0 liquid formulation (533-550) at 4° C. and 25° C., and 1 mg/mL and 5 mg/mL rCSP, up to 21 days.

| Formulated rCSP Concentration (mg/mL) | Temperature held (° C.) | Duration Held as Liquid (days) | % Area Native rCSP | % Area pE-rCSP | Total rCSP (% Area Native rCSP + % Area pE-rCSP) |
|---|---|---|---|---|---|
| 1 | n/a | 0 | 62.8 | 20.1 | 82.9 |
| 1 | 4 | 3 | 63.3 | 20.9 | 84.2 |
| 1 | 4 | 5 | 62.3 | 21.9 | 84.1 |
| 1 | 4 | 14 | 60.6 | 21.9 | 82.5 |
| 1 | 4 | 21 | 58.0 | 23.3 | 81.3 |
| 1 | 25 | 3 | 55.0 | 26.5 | 81.4 |
| 1 | 25 | 5 | 49.8 | 30.5 | 80.2 |
| 1 | 25 | 14 | 39.9 | 34.7 | 74.6 |
| 1 | 25 | 21 | No data | No data | No data |
| 5 | n/a | 0 | 62.3 | 19.2 | 81.4 |
| 5 | 4 | 3 | 62.8 | 18.8 | 81.6 |
| 5 | 4 | 5 | 59.4 | 19.1 | 78.5 |
| 5 | 4 | 14 | 56.6 | 22.6 | 79.2 |
| 5 | 4 | 21 | 54.7 | 23.9 | 78.6 |
| 5 | 25 | 3 | 53.7 | 25.7 | 79.4 |
| 5 | 25 | 5 | 50.3 | 27.6 | 77.8 |
| 5 | 25 | 14 | 36.1 | 29.0 | 65.1 |
| 5 | 25 | 21 | No data | No data | No data |

All RP-HPLC samples listed in Table 19 were frozen at −80° C. until analysis.

TABLE 20

RP-HPLC relative areas of pH 6.4 liquid formulation (533-551) at 4° C. and 25° C. for concentrations of rCSP of 1 mg/mL and 5 mg/mL, up to 28 days.

| Formulated rCSP Concentration (mg/mL) | Temperature held (° C.) | Duration Held as Liquid (days) | % Area Native rCSP | % Area pE-rCSP | Total rCSP (% Area Native rCSP + % Area pE-rCSP) |
|---|---|---|---|---|---|
| 1 | n/a | 0 | 64.5 | 18.8 | 83.3 |
| 1 | 4 | 1 | 61.2 | 20.3 | 81.5 |
| 1 | 4 | 2 | 62.3 | 20.5 | 82.7 |
| 1 | 4 | 6 | 61.9 | 20.3 | 82.2 |
| 1 | 4 | 15 | 62.1 | 20.3 | 82.4 |
| 1 | 4 | 23 | 60.3 | 21.3 | 81.6 |
| 1 | 4 | 28 | 49.7 | 27.7 | 77.4 |
| 1 | 25 | 1 | 60.7 | 23.3 | 84.0 |
| 1 | 25 | 2 | 58.4 | 24.5 | 82.8 |
| 1 | 25 | 6 | 51.2 | 29.4 | 80.6 |
| 1 | 25 | 15 | 36.8 | 39.5 | 76.4 |
| 1 | 25 | 23 | 35.3 | 37.4 | 72.7 |
| 5 | n/a | 0 | 63.3 | 18.1 | 81.4 |
| 5 | 4 | 1 | 62.7 | 20.8 | 83.5 |
| 5 | 4 | 2 | 62.7 | 19.5 | 82.2 |
| 5 | 4 | 6 | 63.4 | 18.3 | 81.8 |
| 5 | 4 | 15 | 60.2 | 20.4 | 80.6 |
| 5 | 4 | 23 | 56.3 | 22.8 | 79.2 |
| 5 | 4 | 28 | 47.6 | 26.3 | 73.9 |
| 5 | 25 | 1 | 60.9 | 21.7 | 82.6 |
| 5 | 25 | 2 | 60.8 | 20.4 | 81.2 |
| 5 | 25 | 6 | 51.5 | 26.8 | 78.3 |
| 5 | 25 | 15 | 35.2 | 37.2 | 72.4 |
| 5 | 25 | 23 | 32.7 | 27.8 | 60.5 |

All RP-HPLC samples listed in Table 20 were frozen at −80° C. until analysis.

TABLE 21

SE-HPLC relative monomer area of liquid formulation of 1 mg/mL rCSP (533-549-550-551) at 4° C. and 25° C., and pH 6.4, 7.0, 7.5 for up to 28 days.

| Formulated rCSP Concentration (mg/mL) | Formulated rCSP pH | Temperature held (° C.) | Duration Held as Liquid (days) | % Monomer Area rCSP |
|---|---|---|---|---|
| *1* | *6.4* | *−80* | *0* | *90.4* |
| *1* | *7.0* | *−80* | *0* | *90.4* |
| *1* | *7.5* | *−80* | *0* | *89.0* |
| 1 | 6.4 | 4 | 1 | 89.5 |
| 1 | 6.4 | 4 | 2 | 90.7 |
| 1 | 6.4 | 4 | 6 | 88.4 |
| 1 | 6.4 | 4 | 15 | 88.3 |
| 1 | 6.4 | 4 | 23 | 87.1 |
| 1 | 7.0 | 4 | 3 | 90.0 |
| 1 | 7.0 | 4 | 5 | 90.7 |
| 1 | 7.0 | 4 | 14 | 90.1 |
| 1 | 7.0 | 4 | 21 | 88.0 |
| 1 | 7.5 | 4 | 1 | 88.2 |
| 1 | 7.5 | 4 | 4 | 88.7 |
| 1 | 7.5 | 4 | 5 | 87.3 |
| 1 | 7.5 | 4 | 14 | 89.6 |
| 1 | 7.5 | 4 | 21 | 87.7 |
| 1 | 7.5 | 4 | 28 | 83.5 |
| 1 | 6.4 | 25 | 0 | 87.8 |
| 1 | 6.4 | 25 | 1 | 88.8 |
| 1 | 6.4 | 25 | 2 | 85.5 |
| 1 | 6.4 | 25 | 6 | 85.3 |
| 1 | 6.4 | 25 | 15 | 82.0 |
| 1 | 6.4 | 25 | 23 | 80.9 |
| 1 | 7.0 | 25 | 0 | 90.0 |
| 1 | 7.0 | 25 | 3 | 89.4 |
| 1 | 7.0 | 25 | 5 | 89.6 |
| 1 | 7.0 | 25 | 14 | 87.0 |
| 1 | 7.0 | 25 | 21 | 83.1 |
| 1 | 7.5 | 25 | 1 | 89.2 |
| 1 | 7.5 | 25 | 4 | 87.8 |
| 1 | 7.5 | 25 | 5 | 82.9 |
| 1 | 7.5 | 25 | 14 | 75.8 |
| 1 | 7.5 | 25 | 21 | 69.9 |
| 1 | 7.5 | 25 | 28 | 62.5 |

Samples listed in italics in Table 21 were frozen at −80° C. at 0 days. All other samples were held liquid (unfrozen) until time of analysis.

TABLE 22

SE-HPLC relative monomer area of liquid formulation of 5 mg/mL rCSP (533-549-550-551) at 4° C. and 25° C., and pH 6.4, 7.0, 7.5 for up to 28 days.

| Formulated rCSP Concentration (mg/mL) | Formulated rCSP pH | Temperature held (° C.) | Duration Held as Liquid (days) | % Monomer Area rCSP |
|---|---|---|---|---|
| *5* | *6.4* | *−80* | *0* | *90.0* |
| *5* | *7.0* | *−80* | *0* | *91.0* |
| *5* | *7.5* | *−80* | *0* | *89.0* |
| 5 | 6.4 | 4 | 1 | 89.8 |
| 5 | 6.4 | 4 | 2 | 90.1 |
| 5 | 6.4 | 4 | 6 | 87.6 |
| 5 | 6.4 | 4 | 15 | 86.8 |
| 5 | 6.4 | 4 | 23 | 86.4 |
| 5 | 7.0 | 4 | 3 | 88.3 |
| 5 | 7.0 | 4 | 5 | 87.5 |
| 5 | 7.0 | 4 | 14 | 90.2 |
| 5 | 7.0 | 4 | 21 | 87.7 |
| 5 | 7.5 | 4 | 1 | 88.7 |
| 5 | 7.5 | 4 | 4 | 87.2 |
| 5 | 7.5 | 4 | 5 | 87.0 |
| 5 | 7.5 | 4 | 14 | 87.5 |
| 5 | 7.5 | 4 | 21 | 84.9 |
| 5 | 7.5 | 4 | 28 | 88.7 |
| 5 | 6.4 | 25 | 0 | 90.1 |
| 5 | 6.4 | 25 | 1 | 88.8 |
| 5 | 6.4 | 25 | 2 | 87.5 |
| 5 | 6.4 | 25 | 6 | 86.8 |
| 5 | 6.4 | 25 | 15 | 84.2 |
| 5 | 6.4 | 25 | 23 | 79.4 |
| 5 | 6.4 | 25 | 28 | 60.3 |
| 5 | 7.0 | 25 | 0 | 90.1 |
| 5 | 7.0 | 25 | 3 | 87.0 |
| 5 | 7.0 | 25 | 5 | 86.9 |
| 5 | 7.0 | 25 | 14 | 82.5 |
| 5 | 7.0 | 25 | 21 | 81.4 |
| 5 | 7.5 | 25 | 1 | 86.3 |
| 5 | 7.5 | 25 | 4 | 85.1 |
| 5 | 7.5 | 25 | 5 | 84.4 |
| 5 | 7.5 | 25 | 14 | 70.3 |
| 5 | 7.5 | 25 | 21 | 66.5 |
| 5 | 7.5 | 25 | 28 | 60.3 |

Samples listed in italics in Table 22 were frozen at −80° C. at 0 days. All other samples were held liquid (unfrozen) until time of analysis.

Conclusions

The stability studies show that preparations of recombinant CSP produced as described herein maintained a monomer content of >85% for up to 23 days at 4° C. when kept at a pH of 6.4 to 7.0 in an excipient buffer of PBS containing 1 mM monothioglycerol and 0.5M arginine. In the PBS, 1 mM MTG, 10% arginine buffer rCSP consisting of 80% monomer was maintained for 16 hours at 4° C. following concentration to 5 mg/mL, while concentrated samples in PBS alone contained 29% monomer after 16 hours at 4° C. By RP-HPLC and SE-HPLC analyses, rCSP in buffer at pH 7.5 demonstrated less stability at nearly all time points than rCSP in buffer at either pH 6.4 or 7.0.

Additional stability studies confirmed and improved upon the above results, showing an increase of about 10% total rCSP on average. The host cell proteins in the rCSP preparation used for these studies was reduced by the use of hydrophobic interaction chromatography as described in Example 9 herein.

Example 8

Engineering Runs

Four engineering runs were carried out to test scaling of the process described in Example 3 to larger quantities.

The inocula for the fermentor cultures were generated by inoculating shake flasks containing 600 mL of a chemically-defined medium supplemented with yeast extract and glycerol with a frozen culture stock of the selected strain. After approximately 21 hours incubation with shaking at 32° C., a shake flask culture was aseptically transferred to a 20 L bioreactor (New Brunswick Scientific, IF-20 L) containing a chemically defined medium designed to support high biomass. Dissolved oxygen was maintained at a positive level in the liquid culture by regulating the sparged flow of compressed atmospheric air as well as the agitation rate. The pH was controlled at the desired set-point through the addition of aqueous ammonia. The fed-batch high cell density fermentation process was divided into an initial growth phase, followed by a gene expression (induction) phase in which 0.38 g of IPTG was added (for a concentration of 0.2 mM in the broth based on an estimated 8 L volume at induction) to initiate recombinant gene expression. The cells were grown at 27-32° C. at pH 6.85 to 7.2. The induction phase of the fermentation was then allowed to proceed for 24 hours. At time points during this phase, samples were withdrawn from the fermentor to determine cell density and 100 μL aliquots were then frozen at −20° C. for later determination of target gene expression. At the final time point of 24 hours, the whole fermentation broth, approximately 10 L for each 20 L bioreactor, was harvested in 1 L aliquots by centrifugation (Beckman Coulter, Avanti J-20) at 15,900×g for 90 min. The cell paste was frozen at −80° C. For all four runs, the previously frozen cell paste was thawed in 2M urea, 20 mM tris, pH 8.0 at 20% concentration (cell paste/L solution), resuspended into a homogeneous solution, and microfluidized.

Engineering Run 1: In this run, TMAE was carried out on fresh (not previously frozen) lysate. Following harvest, microfluidization, disk-stack centrifugation, and 0.2 μm filtration, 9.9 g of crude rCSP was recovered and the overall yield from 20% cell lysate was 81%. 10 g of CSP were loaded on the TMAE column at a concentration of 0.31 mg/mL and purity of 7% as measured by SDS-CGE. 3 g of CSP protein was eluted at a concentration of 0.05 mg/mL and purity of 40%.

Polishing chromatography on ceramic hydroxyapatite (CHT) was performed on the TMAE eluate. Purity of the TMAE eluate loaded on the CHT column was 45% and purity of the CHT eluate was 75% by SDS-CGE. Concentration of CHT eluate was 0.04 mg/ml (from 0.05 ng/ml TMAE eluate). The yield was 81%, all in the elution. The calculated CSP balance was 96% (the remainder of CSP, not collected in the elution, could be accounted for in fractions other than the eluate).

Recovery from the Engineering Run 1 TMAE column was 27% by SDS-PAGE. Studies were undertaken to determine the causes for the low yield and purity of material obtained in this run as compared to the (10 liter) runs described above in Example 3.

Resin (conditioned vs. new resin), resin loading, lysate paste (proven paste from a successful run-through vs. Engineering Run 1 paste), conductivity, resin loading, and linear flow rate (residence time) combined, and repetition of all conditions from a successful run, including use of frozen lysate.

SDS-CGE of fresh lysate and frozen/thawed lysate samples revealed "laddering" of high molecular weight bands above the main rCSP band in all fresh lysate samples. All lysate samples exhibiting laddering gave unacceptable yield and purity on TMAE. Frozen samples that were thawed and immediately analyzed by electrophoresis also showed laddering; however, frozen samples that were thawed and held at RT for 6 hours before analysis showed no laddering. Filtration and hold time after freezing were evaluated for effect on laddering. Filtering was found to not significantly affect laddering, while a hold time after freezing of 6 hours significantly reduced laddering (FIG. 32). Post-freeze/thaw hold times of 1 h, 3 h, 6 h, 7.5 h, and 14 h were evaluated. Samples dissolved in 4 M urea were found to exhibit significantly less laddering than samples in 2 M urea at the same hold times. Further, increasing hold times up to 6 hours directly reduced laddering in both 2 M and 4 M urea samples; beyond 6 hours, hold time showed no discernible effect on laddering in 4 M urea samples, but did reduce laddering in 2 M urea samples.

In summary, a strong association was measured between presence of aggregates in samples loaded onto the TMAE column, as evidenced by "laddering" of high MW bands in SDS-CGE, and poor anion exchange chromatography results. Upon elimination of a number of possible process variables, hold time after freezing and thawing was determined to be the primary parameter affecting detection of aggregates in the lysate samples. The results suggested that a six hour hold time after freezing and thawing greatly would reduce aggregate formation. The other factors evaluated—conductivity, resin loading, linear flow rate, differences in cell paste between the engineering runs and process run-throughs, and whether resin was new or conditioned—were ruled out as causes for the poor anion exchange chromatography results.

Engineering Run 2: In this run, a freeze/thaw cycle with a 6-hour hold of the lysate between depth filtration and TMAE chromatography was carried out, with good results. Primary recovery measured by Q-PAGE following depth filtration was 12.8 g rCSP; the overall yield from 20% cell lysate was 91%. The anion-exchange capture column was loaded with lysate at a concentration of 0.30 mg/mL and purity of 5% as measured by SDS-CGE. rCSP was eluted at a concentration of 0.58 mg/mL and purity of 78%. The TMAE column showed some signs of fouling, but performance was not affected. Precipitation was detected in the loaded lysate, which had not been filtered. TMAE eluate was filtered at 0.2 μm and the filtrate subjected to polishing chromatography by CHT. Purity of the HA (CHT) load after 0.2 μm filtration of TMAE eluate was 82%. CHT eluate purity was 97%, concentration was 0.75 mg/ml, and yield was 113% as measured by SDS-CGE.

Following 0.2 μm filtration of the CHT eluate (533-511) and a RT hold of 12 hrs, mild reduction by DTT was carried out (533-512). Ten mM DTT was spiked into the filtered eluate for a final concentration of 20 µM. The eluate was then recirculated for 19 hours at 1.5-2.5 L/min in a 20 L bag with a peristaltic pump (16.6 L CHT eluate @ 0.72 g/L CSP in bag). Recovery from this step was 102%. Size exclusion-HPLC chromatography analysis of CHT eluate pre- and post-reduction showed a clear increase in monomer content, from 85% to 100%.

Buffer exchange by tangential flow filtration (TFF) was performed on the mildly reduced material to remove salts, urea, and DTT. CSP monomer was diafiltered with 1×PBS. 5 kDa molecular weight cutoff, 0.1 m2 regenerated cellulose membrane was used to retain CSP. Recovery from the buffer exchange step was 86.2% with 7.3% of CSP in the permeate and 0.4% hold-up volume within the system. Analysis of the final product showed 0.66 g/L at $A_{280}$, an endotoxin level of 10.3 EU/mL, 4700 ppm host cell proteins by HCP-ELISA, and 97% purity by SDS-CGE. LC/MS revealed 5.1% of rCSP was N-terminal clipped. RP-HPLC retention times were consistent with CSP standard. 10.6 g of CSP was recovered after UF/DF and frozen at −80° C. Size-exclusion chromatography of post-UF/DF bulk drug substance (533-513) showed low levels of dimerization and aggregation of rCSP during this step compared to the control (533-407), resulting in content that was 90% monomer, 7% dimer, and 3% aggregate.

This run confirmed that purified rCSP conforming to targeted levels of purity, yield, concentration, monomer content, clipping, and endotoxin could be produced at scale using the fermentation and integrated purification processes described.

Engineering Run 3: In this run, harvest, cell disruption, and clarification of lysate were carried out according to the same protocol as Engineering Run 2. The lysate was kept at −80° C. for six hours and held at room temperature for six hours before being loaded onto the TMAE column, but incomplete freezing of the lysate was observed. Primary recovery measured by Q-PAGE following depth filtration was 14.8 g CSP, and the overall yield was 98% from 20% cell lysate. Heavy precipitation was observed in the thawed lysate and heavy column fouling observed early in the loading process and became increasingly worse as the run progressed. Purity and yield for Engineering Run 3 were noticeably reduced compared to Engineering Run 2. By SDS-CGE, the rCSP balance for ER3 was 41%, with 23% in the elution, 4% in the wash, and 13% in the flow-through. Polishing chromatography and buffer exchange were not performed.

Engineering Run 4: In this run, harvest, cell disruption, and clarification of lysate again were carried out according to the same protocol as Engineering Run 2, but low-temperature buffers were used for the TMAE chromatography.

Primary recovery measured by quantitative SDS-PAGE (Q-PAGE) following depth filtration was 13.7 g CSP; the overall yield from 20% cell lysate was 81%. After thawing, precipitation was observed and the lysate was filtered by 0.45 µm filtration before loading onto the TMAE column. Fouling of the column was not observed. Buffers used in this column run were 6-12° C. when used. Purity was 65% by SDS-CGE. Concentration of loaded lysate was 0.34 ng/mL and 0.24 ng/mL for the elution. Yield was 54% in the elution, 4% in the wash, 1% in the flow-through, and 3% in the strip. CSP mass balance was 62%. These results are significantly lower than those for Engineering Run 2 and are believed to have resulted from use of low-temperature buffers.

Polishing chromatography on CHT was conducted. The TMAE eluate loaded was 65% pure by SDS-CGE and the CHT elution purity was 94%. Concentration of the loaded material was 0.25 mg/mL; elution was 0.27 mg/mL. Yield by SDS-CGE was 112%, with all protein coming off in the elution. 7.2 g of CHT eluate was recovered and stored at −80° C. The most probable cause for slightly lower purity than ER2 was potentially lower TMAE eluate concentration and purity.

Conclusion

The fermentation and purification process successfully produced multi-gram quantities of rCSP that meet or exceed target values for purity, yield, monomer content, N-terminal clipping, and endotoxin. Engineering run 2 produced 10.6 g of purified CSP bulk drug substance. Engineering run 4 produced 7.2 g of CHT eluate. The purity of the material produced by both of these engineering runs met targeted values by HPLC-SEC and RP-HPLC. Precipitation observed in the larger runs was potentially due to the additional time required for the larger quantities of lysate to freeze, which may have resulted in some portions of the lysate not freezing, or resulting in a shorter freezing time required for disaggregation.

Example 9

Methods for Host Cell Protein Removal

Methods for further eliminating host cell proteins were developed. Two size exclusion resins and five hydrophobic interaction resins were evaluated for use in a third chromatography step to reduce the amount of host cell protein in the bulk drug substance. Hydrophobic interaction chromatography using Toyo Hexyl-650C was found to reduce host cell protein to less than 100 ppm with excellent rCSP purity, concentration, yield and intact mass. The use of MTG in the mild reducing conditions further improved output.

A full-scale engineering run utilizing the improved process procedures, including a 4.56 L Hexyl-650C third chromatography step, was carried out. This run produced 7.6 g of bulk drug substance in the final excipient buffer formulation described in Example 7, with monomer content of 96.3% and host cell proteins of 152 ppm.

Evaluation of Methods for Removing Host Cell Protein

Analytical separation methods for HCP reduction were evaluated. SE-HPLC was used to resolve away rCSP from HCPs and collected (microfractionated) for analysis by SDS-PAGE and HCP-ELISA. SE-HPLC analysis of 533-407 (an internal rCSP reference standard prepared from strain 533-129 using methods described in Example 2) showed a greatly reduced level of HCPs in the main SE-HPLC fraction by ELISA: 350 ppm for the SE-HPLC peak versus 4100 ppm pre-SE-HPLC. When analyzed by SDS-PAGE, no HCP bands were apparent in the main rCSP peak sample from 533-407 following SE-HPLC.

Evaluation of Preparative Hydrophobic Interaction Chromatography for HCP Reduction Hexyl 650 C, Phenyl HP, Butyl HP, and PPG 600M were evaluated for third column purification by hydrophobic interaction chromatography (HIC). The relative binding strengths and retention times of the tested hydrophobic interaction resins from strongest (longest retention) to weakest (shortest retention) are: Hexyl 650 C>Butyl HP>Phenyl HP>PPG 600M. Bench scale runs using 5.13 mL columns were performed for all the resins tested. CHT eluate samples reduced with MTG (533-565 and 533-563) and DTT (533-523) were compared, using 20 CV elution gradients from 1.0M to 0M ammonium sulfate. Fast protein liquid chromatography (FPLC) operations were performed using ÄKTAexplorer 100 chromatography systems (GE Healthcare) equipped with Frac-950 fraction collector. Materials used: Tosoh resin Hexyl 650C (Lot-no 65HECB501N0); HEPES acid (catalog number 4018-06, JT Baker, Phillipsburg, N.J.); Hepes Na salt (catalog number 4153-05, JT Baker, Phillipsburg, N.J.); NaCl (catalog number 13423, Sigma/Riedel de Haen, St. Louis, Mo.); Ammonium sulfate (catalog number BDH8001-12 Kg, BDH); urea (catalog number 4203-60, JT Baker, Phillipsburg, N.J.); Monothioglycerol (MP Biomedicals catalog number 155727); Hexyl 650C and PPG 600M (catalog number 21399, Tosoh USA, Flemington, N.J.) GE Healthcare, Piscataway, N.J.); Phenyl HP (GE, 17-5195-01); Butyl HP (GE, 28-4110-01).

Of the column resins tested for the third column, Hexyl 650-C produced the lowest levels of HCPs (<100 ppm) along with low N-terminal clipping and high levels of purity, yield, and separation of monomer from dimer. Hexyl-650C was optimized at an intermediate scale using a 112.5 mL column in order to provide sufficient predictability of performance at the much larger manufacturing scale. The chromatography parameters are shown in Table 23.

higher levels of HCP than later fractions, and all fractions were well below 100 ppm. Some rCSP monomer and nearly all of the dimer eluted in the column water strip. The same sample material (CHT eluate 533-565) used for 533-597 was loaded to obtain eluate 533-594 and eluted under the same conditions. SDS-CGE analysis of 533-594 revealed that fractions eluting just ahead of the peak rCSP fractions exhibited double-banding, indicating presence of HCPs, while the peak rCSP elution fraction did not show double bands on SDS-CGE. Most significantly, the amount of HCP in the peak fraction, as measured by ELISA, was 50 ppm. Electropherograms of selected fractions showed single peaks in those fractions near the center of the elution range. Analysis by RP-HPLC of 533-594 showed that the F2 fraction, which displayed two bands in SDS-CGE, was enriched in group 2

TABLE 23

Chromatograpby parameters for integrated purification runs

| Column | Column Size | Running Conditions |
|---|---|---|
| Hexyl 650C (TOSOH) Step elution | Hexyl-650C_0.66 cm diameter × 15 cm height Volume: 5.13 mL | Load: Reduced CHT eluate adjusted to contain 0.5M ammonium sulfate + 1 mM MTG in 20 mM Hepes, 2M Urea, 0.5M Ammonium sulfate; pH 7.5 Adjust buffer: 20 mM Hepes, 2M Urea, 3M Ammonium sulfate + 1 mM MTG; pH 7.5 Pre eq: 20 mM Hepes, 2M Urea + 1 mM MTG pH 7.5 Equil Buffer (EQ): 20 mM Hepes, 2M Urea, 0.5M Ammonium sulfate + 1 mM MTG; pH 7.5 Step elution buffer: 20 mM Hepes, 2M Urea + 100 mM Ammonium sulfate + 1 mM MTG; pH 7.5 Wash 2: 20 mM Hepes, 2M Urea + 1 mM MTG; pH 7.5 |
| Hexyl 650C (TOSOH) 15 CV gradient | Hexyl-650C_0.66 cm diameter × 15 cm height Volume: 5.13 mL | Load: Reduced CHT Eluate in 20 mM Hepes, 2M Urea, 0.5M Ammonium sulfate + 1 mM MTG pH 7.5 Adjust buffer: 20 mM Hepes, 2M Urea, 3M Ammonium sulfate + 1 mM MTG pH 7.5 Pre eq: 20 mM Hepes, 2M Urea + 1 mM MTG pH 7.5 Equil Buffer (EQ): 20 mM Hepes, 2M Urea, 0.5M Ammonium sulfate + 1 mM MTG pH 7.5 Elution: linear gradient elution over 15 CV of 0-100% B (20 mM Hepes, 2M Urea + 1 mM MTG pH 7.5 ), and 3 CV with 100% B |
| Hexyl 650C (TOSOH) 15 CV gradient | Hexyl-650C_3.2 cm diameter × 14 cm height Volume: 112.5 mL | Load: Reduced CHT eluate in 20 mM Hepes, 2M Urea, 0.5M Ammonium sulfate + 1 mM MTG pH 7.5 Adjust buffer: 20 mM Hepes, 2M Urea, 3M Ammonium sulfate + 1 mM MTG pH 7.5 Pre eq: 20 mM Hepes, 2M Urea + 1 mM MTG pH 7.5 Equil Buffer (EQ): 20 mM Hepes, 2M Urea, 0.5M Ammonium sulfate + 1 mM MTG pH 7.5 Elution: linear gradient elution over 15 CV of 0-100% B (20 mM Hepes, 2M Urea + 1 mM MTG pH 7.5) and 3 CV with 100% B |
| Hexyl 650C (TOSOH) 15 CV gradient | Hexyl-650C_20 cm diameter × 14.5 cm height Volume: 4.56 L | Load: Reduced CHT Eluate adjusted to contain 0.5M Ammonium Sulfate, pH 7.5 + 1 mM MTG Adjust buffer: 20 mM Hepes, 2M Urea, 3M Ammonium sulfate + 1 mM MTG pH 7.5 Pre eq Buffer: 20 mM Hepes, 2M Urea + 1 mM MTG pH 7.5 Equil Buffer (EQ): 20 mM Hepes, 2M Urea, 0.5M Ammonium sulfate + 1 mM MTG pH 7.5. Elution: linear gradient elution over 15 CV of 0-100% B (20 mM Hepes, 2M Urea + 1 mM MTG pH 7.5) and 3 CV with 100% B. |

Bench Scale Hexyl-650C Runs

1. Bench Scale Hexyl-650C Runs: 1.0M to 0M Ammonium Sulfate Gradient with MTG (533-597 & 533-594)

A Toyo-Hexyl 650-C column (0.66 cm diameter×15 cm height) was run with 1 mM MTG-reduced CHT eluate (533-565) and eluted with a 15 column volume (CV) gradient of 1M to 0 M ammonium sulfate with 1 mM MTG followed by 3 CVs at 0M ammonium sulfate with 1 mM MTG. The column eluate was designated 533-597. SDS-CGE was performed on the eluted fractions and HCP levels determined by HCP-ELISA. Early fractions of the elution peak exhibited impurities which eluted ahead of the main CSP peak. The tailing shoulder of the main CSP peak, designated "fraction #2" (see Example 7), contained rCSP species having intact mass measurements consistent with N-terminal pyroglutamate. Elution fraction 7, near the center of the elution peak, showed very little pyroglutamate-CSP; fraction F12, also near the center of the peak, displayed more pyroglutamate-CSP and less of the group 2 impurities than F7. The column strip contained a greater amount of pE-CSP and group 3 dimer than any part of the elution gradient. Table 24 compares the RP-HPLC runs of the Hexyl 650-C elution peak 533-594 fractions, showing the relative enrichments of the 3 RP peak groups among the fractions. The analyzed fraction is indicated in the Sample column. Groups 1, 2, and 3 peaks are as described in Example 7. Intact mass analysis by LC/MS measured 2% clipping in the reduced Hexyl G2 fraction.

TABLE 24

Reversed Phase-HPLC Analysis of Toyo Hexyl-650C Eluate Fractions (533-594)

| Sample | Area % | | | | |
|---|---|---|---|---|---|
| | Group 1 | Group 2 | Group 3 | Native CSP | Total CSP |
| 533-594 e12 | 0.0 | 71.9 | 2.3 | 19.2 | 25.8 |
| 533-594 f1 | 0.0 | 68.8 | 1.9 | 22.8 | 29.3 |
| 533-594 f3 | 4.9 | 51.1 | 1.1 | 36.2 | 42.9 |
| 533-594 f7 | 5.7 | 14.3 | 1.6 | 69.3 | 78.3 |
| 533-594 f12 | 3.8 | 5.2 | 2.1 | 72.7 | 88.9 |
| 533-594 g2 | 2.6 | 4.2 | 3.7 | 69.8 | 89.5 |
| 533-594 g5 | 2.1 | 3.7 | 2.9 | 65.0 | 91.4 |
| 533-595 strip | 0.0 | 3.3 | 10.4 | 56.6 | 86.3 |
| 533-565 control | 3.0 | 10.7 | 6.6 | 57.4 | 79.7 |

2. Bench Scale Hexyl-650C Runs: 0.5M to 0M Ammonium Sulfate Gradient with MTG and Step Elutions Further gradient-eluted Hexyl 650-C column runs 3-6 utilized an elution gradient of 0.5M to 0M ammonium sulfate. The narrower gradient range allowed better resolution within the rCSP elution range. Runs 3 & 4 compared CHT eluates reduced with 1 mM MTG (533-606) with those reduced with 100 mM DTT (533-610) on columns eluted with a gradient of 0.5M to 0M ammonium sulfate. Comparison of HCP levels of individual eluate fractions and fraction pools from 533-610 indicated higher HCP concentration near the elution peak, but much lower HCP levels of approximately 900 ppm compared to 7000 ppm in the loaded material (533-523). Clipping in the loaded material was 15%, while clipping for the main peak fractions of the Hexyl eluate (fractions E2-F2) was 6.2%. Runs 5 & 6 each used a 3 CV step elution of 0.1M ammonium sulfate with CHT eluates reduced with MTG (533-607 and 533-611). SDS-CGE analysis showed that the gradient elution achieved significantly better separation of monomer from dimer and HCPs than did the step elution. Table 25 shows the analytical data from these column runs. The lowest HCP level along with low clipping and high purity was achieved with 533-606; therefore, 1 mM MTG reduction followed by Hexyl-650C chromatography with a 0.5 to 0M ammonium sulfate gradient was chosen for the subsequent intermediate- and full-scale runs.

Intermediate-Scale Hexyl-650C Run (533-615) and Bulk Drug Substance (533-616)

Based on the results obtained from the bench-scale Hexyl gradient columns, a large-scale Hexyl 650-C preparative column with a column volume of 112.6 mL was loaded with MTG-reduced CHT eluate (533-563) and eluted with a gradient of 0.5M to 0M ammonium sulfate; eluate was designated 533-615 (Run 7). HCP by ELISA from 533-615 was 152 ppm and purity of rCSP was 99.2%. Data for purity by SDS-CGE, total protein concentration by absorbance at 280 nm, amino acid clipping by LC/MS, and host cell protein level by ELISA for 533-615 along with 533-606, -610, -607, and -611 are summarized in Table 25. Total CSP (native plus pyroglutamate forms) as measured by reversed-phase HPLC increased from 82.4% after CHT to 91.5% after Hexyl 650C.

TABLE 25

Analytical Data for Pre- and Post-Hexyl Purification

| Experiment Protocol Number | | 533-606 15CV Gradient | 533-610 15CV Gradient | 533-607 Step Elution | 533-611 Step Elution | 533-615 15CV Gradient |
|---|---|---|---|---|---|---|
| Loaded Sample | | 533-563 | 533-523 | 533-563 | 533-523 | 533-563 |
| Reducing Agent | | MTG | DTT | MTG | MTG | MTG |
| % Purity (CGE) | Pre 3$^{rd}$ column | 97.5% | 94% | 97.5% | 94% | 97.5% |
| | Post 3$^{rd}$ column | 99.3% | 99.88% | 99.4% | >99% | 99.2% |
| Concentration (A280 nm) mg/ml | Pre 3$^{rd}$ column | 0.84 | 0.42 | 0.84 | 0.42 | 0.84 |
| | Post 3$^{rd}$ column | 0.239 | 0.17 | 0.847 | 0.637 | 0.173 |
| CLIPPING (LC-MS) | Pre 3$^{rd}$ column | 15% | 15.2% | 15% | 15.2% | 15% |
| | Post 3$^{rd}$ column | N0 | 6.2% | N0 | 5.4% | 1.6 (non-reduced) 1.1 (reduced) |
| HCP(ppm) | Pre 3$^{rd}$ column | 2515 | ~7223 | 2515 | ~7223 | 2515 |
| | Post 3$^{rd}$ column | 30 | 1007.8 | N0 | 673 | 152 |

UF/DF Buffer Exchange (533-616)

The 533-616 Hexyl elution pool was concentrated by tangential flow filtration and diafiltered into the final excipient buffer consisting of 1×PBS, 0.5M arginine-HCl, 1 mM monothioglycerol, pH 6.7.

Membranes were equilibrated with 1×PBS prior to product introduction. 1×PBS, 10% (w/v) arginine-HCl (0.5M arginine-HCl for 533-616) (J. T. Baker, part number 2067), 1 mM monothioglycerol (MP BIOMEDICALS catalog number 155727), pH 6.4 was recirculated across the membranes at 324 LMH at room temperature (21-23° C.). TMPs of 10-15 psi and 21-24 psi were applied to the retentate while over the 5 kDa membranes. The hold-up volume was calculated with the buffer at 60.2 mL. For 533-616, concentration of the eluate was from an original volume of 1532 mL at 0.173 mg/ml to a volume of 189.3 mL at 1.4 mg/mL. After concentrating, constant volume diafiltration was carried out for eight retentate volumes: 189.3 mL×8=1514.4 mL. It was then concentrated to a volume of 163.4 mL and diluted to a final volume of 221.9 mL (209.5 mL for 533-616) at 1.0 mg/mL. Membranes were flushed with 52.3 mL of buffer and cleaned by recirculating 0.1 N NaOH at room temperature for ≥60 minutes. Regeneration of the membranes was verified by normalized water permeability measurements. The final purified CSP was stored frozen at −80° C.

Recovery from the buffer exchange step was 87.6%; purity by SDS-CGE was 99.8%. SDS-PAGE showed a decrease in the amount of dimer after exchange into the final buffer; monomer was 97.6% by SEC-HPLC. N-terminal clipping after reduction was 2.7% by LC/MS and rCSP was 90.3% by RP-HPLC. Analysis of the final product showed 1.05 mg/mL at $A_{280}$, an endotoxin level of 4 EU/mg, and a host cell protein level of 216 ppm by HCP-ELISA. The analytical data is summarized in Table 26.

TABLE 26

| Final Bulk Drug Substance: Summary of Measured Analytical Data | |
|---|---|
| Sample Name | 533-563 |
| % Purity (SDS-CGE) | 99.8% |
| Concentration ($A_{280}$) | 1.05 mg/mL |
| (LC-MS) N-Terminal Clipping | Non-reduced: 3.5% |
| | Reduced: 2.7% |
| Host Cell Protein | 216 ppm |
| Endotoxin | 4 EU/mg |
| SEC-HPLC | 97.6% monomer |
| RP-HPLC | 90.3% CSP |
| Yield after UF/DF | 87.6% |
| Final Buffer | 1X PBS, 0.5M Arginine, 1 mM MTG, pH 6.7 |

Production at Scale Using a 20 Cm Hexyl-650C Third Column (533-618)

With the achievement of satisfactory HCP and dimer reduction results using Hexyl-650C at bench scale and at the 112 mL scale, a full-scale technology transfer production run was attempted using a 20 cm, 4.56 L Hexyl-650C column. Centrate material which had been frozen at −80° C. was thawed 14 days later and purified by TMAE and CHT. Reduction with 1 mM MTG began the same day as the TMAE and CHT purification reduction. Hexyl-650C purification began the following day (Hexyl eluate: 533-617). The next day the 533-617 Hexyl-650C eluate was transferred to bulk buffer consisting of 1×PBS with 1 mM MTG, 0.5M arginine, pH 6.7 by UF/DF and designated 533-618. The $A_{280}$ chromatogram of 533-617 shows a peak of small molecules coming off the column in the flow-through. Analysis of the 533-618 BDS from the 20 cm column showed key performance criteria all falling within specifications (Table 27).

TABLE 27

| Bulk Drug Substance Release Test Results for 533-618, Hexyl-650C 20 cm Column Run | | |
|---|---|---|
| Endotoxin (LAL-PTS) | | 4.1 EU/mL |
| Intact Mass (reduced) | | 7.1% |
| Intact Mass (non-reduced) | | 7.7% |
| | Area % | |
| SEC | HMW aggregates | 3.04 |
| | Dimer | 0.33 |
| | Monomer | 96.23 |
| | Low MW | 0.40 |
| | Area % | |
| RP-HPLC | Group 1: | 5.28 |
| | Group 2: | 3.6 |
| | Group 3: | 1.9 |
| | CSP: | 72.11 |
| | P-CSP: | 16.75 |
| | CSP + P-CSP | 88.86 |
| Concentration | 1.02 g/L by $A_{280}$ | |
| Yield (pre-fill) | 7.6 g | |
| Yield (post-fill) | 7.1 g | |
| HCP | 653 ppm | |
| Overall Purification Yield | ~23% | |

Conclusion: Host cell proteins were identified by mass spectrometry peptide database analysis. None of the identified host cell proteins were identified as toxic. An immunogenicity study comparing 'high' (2-column purification) and 'low' (3-column purification) amounts of HCP-containing rCSP batches did not indicate a difference in rCSP immunogenicity resulting from different levels of HCPs in rCSP preparations.

The level of HCPs in the bulk drug substance was reduced by a third chromatography step. The lowest HCP level along with low clipping and high purity was achieved using mild reducing conditions comprising 1 mM MTG, followed by Hexyl-650C chromatography with a 0.5 to 0M ammonium sulfate gradient.

Example 11

Methods for Reducing Precipitation in Lysate

Methods for reducing precipitation in the lysate prior to anion-exchange chromatography were evaluated for their effect on rCSP yield and purity.

As described, freezing and thawing of lysate prior to loading on the TMAE anion-exchange column can enhance rCSP purity, concentration, and yield. Freezing of lysate in 2 L bottles was evaluated as an alternative to larger containers due to their higher surface-area-to-volume ratio. Ten percent lysate was prepared by the process described for the Engineering Runs. One 2 L PETG bottle containing 10% lysate supernatant (533-555, prepared from cell paste 533-446) and 5×2 L PETG bottles containing deionized water were placed in a Revco −80° C. freezer. Table 28 outlines the progress of the freezing over time.

TABLE 28

Progression of Lysate Freezing in 1 L PETG Bottles

| Time | Estimated % solid | Description | Freezer Temp (° C.) |
| --- | --- | --- | --- |
| T = 4.5 hrs | 25-30% | DI water appeared 20% frozen. | −72° C. |
| T = 7 hrs | 65-70% | Lysate appeared solid; pink-orange color. Region of liquid still visible in DI water-filled bottles. | −72° C. |
| T = 18.3 hrs | 100% | Frozen lysate appeared yellowish, much lighter tint than at 7 hrs. | (Not recorded) |

To establish an expected time for thawing, the 2 L PETG bottle containing 10% frozen lysate (533-555), along with 6×2 L PETG bottles containing DI water and various 1 L and 500 mL PETG bottles containing frozen liquid at ≤−76° C. (totaling 24 L of frozen liquid) were placed in a Precision 270 (Thermo Scientific) water bath set to 25° C., and the water bath temperature never dropped below 22° C. After 3.25 hours, with several gentle mixes of the bottles, the 10% frozen lysate was completely thawed at 22-23° C.

To further reduce precipitation, filtration of thawed lysate that had been thoroughly frozen was evaluated. Ten percent lysate (533-558) made from the same cell paste used to prepare the lysate for Engineering Run 3 (533-485) was prepared by the described process, frozen in 2 L PETG bottles, and thawed as described above in 2 hours 35 minutes. In light of the possibility of increased N-terminal clipping during the additional time required for centrifugation, filtration without centrifugation was considered desirable if it was found to adequately reduce the amount of precipitant. In order to determine the length of time and force required for centrifugation, filtration of thawed lysate through the Sartobran P (0.45 μm/0.2 μm) membrane filter was evaluated under three different conditions: no centrifugation, 15 minutes at 15,000×g, and 30 minutes at 30,000×g. $V_{max}$ methodology was followed to determine filter capacities. $V_{75}$ values were considered to be practical capacity limits because the flow rate at 75% percent plugging was approximately 25% of initial flow rates. Membrane filtration without centrifugation was found to produce $V_{75}$ values adequate for manufacturing (Table 29). With filtration at 0.45 μm (a size small enough to prevent fouling of the TMAE resin) determined to be practical without centrifugation, TMAE chromatography was carried out with filtration but not centrifugation of frozen/thawed lysate. The larger filtration area required for non-centrifuged versus centrifuged lysate was justified when weighed against the potential for increased proteolytic clipping. There was no apparent decrease in rCSP concentration at the filter throughputs required for non-centrifuged sample.

TABLE 29

Thawed Lysate 533-558 Filtered with Sartobran P (0.45 μm/0.2 μm) Membrane Filters

| Thawed 533-558 Lysate Condition | Load OD600 | Filtrate OD600 | $V_{75}(L/m^2)$ | $V_{max}(L/m^2)$ | Recommended Sartobran P (0.45 μm/0.2 μm) Filter Area at $V_{75}$ |
| --- | --- | --- | --- | --- | --- |
| No centrifugation | 0.224-0.242 | 0.183-0.212 | 18.2 | 36.4 | 1.3 m² |
| 15 min, 15,000 g, supernatant | 0.207 | 0.177 | 22.5 | 45.0 | 1.1 m² |
| 30 min, 15,000 g, supernatant | 0.166 | 0.126 | 29.6 | 59.2 | 0.8 m² |

A 0.65 μm/0.45 μm membrane filter, a size combination known to provide adequate particulate removal to protect the TMAE column from fouling, was used. Throughput of 25 L/m² was achieved with uncentrifuged lysate, and no TMAE column fouling occurred.

The results indicate the use of 0.2/0.45 μm or 0.65 μm/0.45 μm membrane filtration, without centrifugation, following freeze-thaw of the lysate in 2 L bottles. This additional step reduced precipitation to allow successful chromatography, and resulted in a low level of N-terminal clipping of rCSP related to the shortened processing time.

What is claimed is:

1. A process for purifying recombinant P. falciparum circumsporozoite protein (rCSP), said process comprising:
   (a) obtaining a bacterial cell lysate preparation comprising recombinant P. falciparum circumsporozoite protein dimer;
   (b) separating the bacterial cell lysate preparation of step (a) into a soluble fraction comprising the recombinant P. falciparum circumsporozoite protein dimer, and an insoluble fraction;
   (c) separating the recombinant P. falciparum circumsporozoite protein dimer in the soluble fraction of step (b) from host cell proteins in the soluble fraction; and
   (d) subjecting the recombinant P. falciparum circumsporozoite protein dimer obtained in step (c) to preferential reducing conditions, wherein the preferential reducing conditions reduce intermolecular disulfide bonds and preserve intramolecular disulfide bonds in the rCSP;
   thereby obtaining purified recombinant rCSP, without a denaturation or refolding step, wherein the recombinant P. falciparum circumsporozoite protein obtained includes the most N-terminal cysteine, said most N-terminal cysteine corresponding to the cysteine at position 25 as set forth in SEQ ID NO: 1, and wherein not more than about 10% of the purified recombinant P. falciparum circumsporozoite protein obtained is dimerized, and not more than about 10% of the purified recombinant P. falciparum circumsporozoite protein obtained is present as high molecular weight aggregates.

2. The process of claim 1, further comprising:
(e) separating the recombinant P. falciparum circumsporozoite protein obtained (d) from host cell proteins.

3. The method of claim 1, wherein the purified recombinant P. falciparum circumsporozoite protein is obtained at an overall purification yield of about 10% to about 75%.

4. The process of claim 1, wherein not more than about 10% of the purified recombinant P. falciparum circumsporozoite protein obtained is degraded at the N-terminus.

5. The process of claim 1, wherein not more than about 5% of the purified recombinant P. falciparum circumsporozoite protein obtained is dimerized.

6. The process of claim 1, wherein not more than about 5% of the purified recombinant P. falciparum circumsporozoite protein obtained is present as high molecular weight aggregates.

7. The process of claim 1, wherein not more than about 10% of the purified recombinant P. falciparum circumsporozoite protein obtained is denatured.

8. The process of claim 1, wherein the purified recombinant P. falciparum circumsporozoite protein obtained comprises at least about 90% P. falciparum circumsporozoite protein monomer.

9. The process of claim 1, wherein the bacterial cell lysate is a Pseudomonad cell lysate.

10. The process of claim 9, wherein the Pseudomonad cells are Pseudomonas cells.

11. The process of claim 10, wherein the Pseudomonas cells are Pseudomonas fluorescens.

12. The process of claim 1, wherein the separating of step (b) comprises disk-stack centrifugation.

13. The process of claim 1, wherein the separating of step (b) comprises depth filtration.

14. The process of claim 1, wherein the separating of step (c) comprises chromatography, and wherein the chromatography comprises anion-exchange chromatography and mixed mode chromatography.

15. The process of claim 14, wherein the separating of step (c) comprises mixed mode chromatography, and wherein the mixed mode chromatography is hydroxyapatite chromatography.

16. The process of claim 2, wherein the separating of step (e) comprises hydrophobic interaction chromatography.

17. The process of claim 1, wherein the preferential reducing conditions comprise a mild reducing agent.

18. The process of claim 17, wherein the mild reducing agent is dithiothreitol (DTT), cysteine, acetylcysteine, glutathione, monothioglycerol (MTG), thioglycolate, dithioerythritol, 2-Mercaptoethanol (B-mercaptoethanol), TCEP-HCl (pure, crystalline Tris(2-carboxyethyl)phosphine hydrochloride), or 2-Mercaptoethylamine-HCl (2-MEA).

19. The process of claim 18, wherein the mild reducing agent is DTT, MTG, acetylcysteine, glutathione, thioglycolate, or cysteine.

20. The process of claim 19, wherein the mild reducing agent is DTT at a concentration of about 0.01 to about 0.03 mM, or MTG at a concentration of about 0.5 mM to about 1.5 mM.

21. The process of claim 17, wherein the preferential reducing conditions further comprise a disaggregating agent.

22. The process of claim 21, wherein the disaggregating agent is urea, arginine, guanidine HCl, or a detergent.

23. The process of claim 22, wherein the disaggregating agent is about 1.5 to about 2.5M urea.

24. The process of claim 1, wherein the preferential reducing conditions comprise about 0.05 to about 1 mM MTG and about 2M urea.

25. The process of claim 2, further comprising preparing a stable liquid P. falciparum circumsporozoite protein formulation, comprising diafiltering about 1 mg/ml to about 50 mg/ml purified recombinant P. falciparum circumsporozoite protein into a formulation buffer comprising about 0.5 mM to about 1.5 mM MTG and about 10% to about 20% arginine.

26. The process of claim 25, wherein the formulation buffer comprises 0.5× or 1×PBS.

27. The process of claim 25, wherein the formulation buffer has a pH of about 6.0 to about 7.5.

28. The process of claim 26, wherein the formulation buffer has a pH of about 6.0 to about 7.5.

29. The process of claim 25, further comprising storing the stable liquid P. falciparum circumsporozoite protein formulation at a storage temperature of about 4° C. to about 15° C.

30. The process of claim 26, further comprising storing the stable liquid P. falciparum circumsporozoite protein formulation at a storage temperature of about 4° C. to about 15° C.

31. The process of claim 27, further comprising storing the stable liquid P. falciparum circumsporozoite protein formulation at a storage temperature of about 4° C. to about 15° C.

32. The process of claim 28, further comprising storing the stable liquid P. falciparum circumsporozoite protein formulation at a storage temperature of about 4° C. to about 15° C.

33. The process of claim 25, wherein the formulation buffer comprises about 1.0 mM MTG, about 10% to about 20% arginine, 1×PBS, has a pH of about 6.4 to about 6.0, and further comprising storing the stable liquid P. falciparum circumsporozoite protein formulation at a storage temperature of about 4° C. to about 6° C.

34. The process of claim 25, wherein the stable liquid P. falciparum circumsporozoite protein formulation contains at least one of the following: not more than about 10% P. falciparum circumsporozoite protein dimer; not more than about 10% high P. falciparum circumsporozoite protein molecular weight aggregates; not more than about 10% denatured P. falciparum circumsporozoite protein; and, not more than about 10% P. falciparum circumsporozoite protein degradation products.

35. The process of claim 1, wherein the process is scalable to a bacterial cell lysate preparation comprising about 1 gram to about 2000 grams rCSP.

36. The process of claim 1, wherein the amount of rCSP in the bacterial lysate preparation is about 1 gram to about 2000 grams.

37. The process of claim 1, wherein the bacterial cell lysate is prepared from host cells transformed with an expression vector comprising a nucleic acid sequence encoding the recombinant P. falciparum circumsporozoite protein.

38. The process of claim 37, wherein the Pseudomonad cells are Pseudomonas cells.

39. The process of claim 38, wherein the Pseudomonas cells are Pseudomonas fluorescens.

40. The process of claim 37, wherein the recombinant P. falciparum circumsporozoite protein encoded by the nucleic acid sequence has an amino acid sequence as set forth in SEQ ID NO: 3, or an amino acid sequence having at least 90% identity to the amino acid sequence set forth in SEQ ID NO: 3.

41. The process of claim 39, wherein the P. fluorescens cells are a PyrF production host strain comprising ΔpyrF, lacIQ, and ΔhtpX.

42. The process of claim 40, wherein the nucleic acid sequence encoding the recombinant *P. falciparum* circumsporozoite protein is fused to a periplasmic secretion signal sequence.

43. The process of claim 42, wherein the periplasmic secretion signal sequence is a *P. fluorescens* secretion signal sequence.

44. The process of claim 43, wherein the *P. fluorescens* periplasmic secretion signal sequence is LAO, pbp, pbpA20V, or cupA2.

45. The process of claim 44, wherein the *P. fluorescens* periplasmic secretion signal sequence is LAO.

46. The process of claim 1, further comprising stably maintaining the purified recombinant *P. falciparum* circumsporozoite protein in a stable liquid formulation, the method comprising providing a formulation comprising about 1 to about 50 mg/ml purified rCSP, about 0.5 to about 1.5 mM MTG and about 1% to about 20% arginine in 0.5× or 1×PBS at a pH of about 6.0 to about 7.5, wherein the rCSP is stably maintained at a temperature of about 3° C. to about 25° C., for at least about 7 days.

47. The process of claim 2, further comprising stably maintaining the purified recombinant *P. falciparum* circumsporozoite protein in a stable liquid formulation, the method comprising providing a formulation comprising about 50 mg/ml purified rCSP, about 0.5 to about 1.5 mM MTG and about 10% to about 20% arginine in 1×PBS at a pH of about 6.4 to about 7.2, wherein the rCSP is stably maintained at a temperature of about 3° C. to about 25° C., for at least about 7 days.

48. The process of claim 16, further comprising stably maintaining the purified recombinant *P. falciparum* circumsporozoite protein in a stable liquid formulation, the method comprising providing a formulation comprising about 1 to about 50 mg/ml purified rCSP, about 0.5 to about 1.5 mM MTG and about 10% to about 20% arginine in 1×PBS at a pH of about 6.4 to about 7.0, wherein the rCSP is stably maintained at a temperature of about 3° C. to about 25° C., for at least about 7 days.

49. The process of claim 48, wherein the formulation comprises about 1.0 mM MTG and about 10% arginine in 1×PBS at a pH of about 6.4 to 7.0, at a temperature of about 3° C. to 5° C., wherein the rCSP is stably maintained for at least about 7 days.

50. The process of claim 1, wherein the N-terminus of the purified recombinant *P. falciparum* circumsporozoite protein obtained includes the glutamine corresponding to the glutamine at position 24 as set forth in SEQ ID NO: 1.

51. The process of claim 1, wherein the N-terminus of the purified recombinant *P. falciparum* circumsporozoite protein obtained includes the tyrosine corresponding to the tyrosine at position 23 as set forth in SEQ ID NO: 1.

52. The process of claim 1, wherein the N-terminus of the purified recombinant *P. falciparum* circumsporozoite protein obtained includes the glutamic acid corresponding to the glutamic acid at position 22 as set forth in SEQ ID NO: 1.

53. The process of claim 1, wherein the N-terminus of the purified recombinant *P. falciparum* circumsporozoite protein obtained includes the glutamine corresponding to the glutamine at position 21 as set forth in SEQ ID NO: 1.

* * * * *